United States Patent
Flyer et al.

(10) Patent No.: US 10,202,400 B2
(45) Date of Patent: *Feb. 12, 2019

(54) CORTISTATIN ANALOGUES AND SYNTHESES THEREOF

(71) Applicant: President and Fellows of Harvard College, Cambridge, MA (US)

(72) Inventors: Alec Nathanson Flyer, Boston, MA (US); Hong Myung Lee, Cambridge, MA (US); Andrew G. Myers, Boston, MA (US); Cristina Montserrat Nieto-Oberhuber, Cambridge, MA (US); Matthew D. Shair, Lexington, MA (US); Chong Si, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/658,201

(22) Filed: Jul. 24, 2017

(65) Prior Publication Data

US 2017/0320886 A1 Nov. 9, 2017

Related U.S. Application Data

(63) Continuation of application No. 14/848,086, filed on Sep. 8, 2015, now Pat. No. 9,714,255, which is a continuation of application No. 14/293,743, filed on Jun. 2, 2014, now Pat. No. 9,127,019, which is a continuation of application No. 13/061,318, filed as application No. PCT/US2009/004911 on Aug. 28, 2009, now abandoned.

(60) Provisional application No. 61/115,395, filed on Nov. 17, 2008, provisional application No. 61/092,492, filed on Aug. 28, 2008.

(51) Int. Cl.
*A61K 31/34* (2006.01)
*C07D 493/08* (2006.01)
*A61K 31/4725* (2006.01)

(52) U.S. Cl.
CPC ............ *C07D 493/08* (2013.01); *A61K 31/34* (2013.01); *A61K 31/4725* (2013.01)

(58) Field of Classification Search
CPC ............................. A61K 31/34; C07D 493/08
See application file for complete search history.

(56) References Cited

U.S. PATENT DOCUMENTS

| | | | |
|---|---|---|---|
| 2,886,589 A | 5/1959 | Novello et al. | |
| 4,853,224 A | 8/1989 | Wong | |
| 4,863,457 A | 9/1989 | Lee | |
| 4,997,652 A | 3/1991 | Wong | |
| 5,098,443 A | 3/1992 | Parel et al. | |
| 5,185,152 A | 2/1993 | Peyman | |
| 5,378,475 A | 1/1995 | Smith et al. | |
| 5,410,016 A | 4/1995 | Hubbell et al. | |
| 5,443,505 A | 8/1995 | Wong et al. | |
| 5,554,187 A | 9/1996 | Rizzo, III | |
| 5,710,182 A | 1/1998 | Reunamaki et al. | |
| 5,725,493 A | 3/1998 | Avery et al. | |
| 6,177,095 B1 | 1/2001 | Sawhney et al. | |
| 6,632,457 B1 | 10/2003 | Sawhney | |
| 6,803,031 B2 | 10/2004 | Rabinowitz et al. | |
| 9,127,019 B2 | 9/2015 | Flyer et al. | |
| 2003/0060425 A1 | 3/2003 | Ahlem et al. | |
| 2003/0149287 A1 | 8/2003 | Zasloff et al. | |
| 2004/0220161 A1 | 11/2004 | Ahlem et al. | |
| 2005/0014737 A1 | 1/2005 | Agoston et al. | |
| 2006/0014727 A1 | 1/2006 | Karsan et al. | |
| 2006/0094696 A1 | 5/2006 | Leese et al. | |
| 2007/0004689 A1 | 1/2007 | Agoston et al. | |
| 2007/0225256 A1 | 9/2007 | Leese et al. | |
| 2009/0023666 A1 | 1/2009 | Gardiner et al. | |

(Continued)

FOREIGN PATENT DOCUMENTS

EP 0562849 A2 9/1993
WO WO 97/43417 A1 11/1997

(Continued)

OTHER PUBLICATIONS

Diabetic-retinopathy, 2017, https://www.mayoclinic.org/diseases-conditions/diabetic-retinopathy/diagnosis-treatment/drc-20371617.*
MacularDegeneration, 2017, https://www.brightfocus.org/macular/wet-macular-degeneration/treatments.*
Ra, 2017, http://www.jrheum.org/content/29/5/890.*
Aoki et al., J. Am. Chem. Soc. 2006, 128, 3148-3149.*
Rosen, Cancer J., Nov.-Dec. 2001(abstract only).*
Park et al., PLOS One, Nov. 23, 2015, 19 pages.*
Abushanab et al., 9(10 leads to 19)abeo steriods. Total synthesis of abeo-estradiol, abeo-estradiol 3-methyl ether, and 17 alpha-ethynyl abeo-estradiol-3-methyl ether. JOC Apr. 30, 1976;41(9):1601-3.

(Continued)

*Primary Examiner* — Sun Jae Yoo
(74) *Attorney, Agent, or Firm* — Knowles Intellectual Property Strategies, LLC

(57) ABSTRACT

The present invention relates to analogs of cortistatin A, J, K, and L, having the general formula:

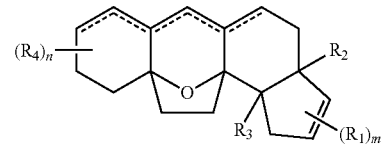

and salts thereof, wherein $R_1$, $R_2$, $R_3$, $R_4$, n, and m are as defined herein; processes for preparing such compounds and intermediates thereto; pharmaceutical compositions comprising such compounds; methods for treating a proliferative disease; methods for treating a disease associated with aberrant angiogenesis; methods for inhibiting angiogenesis; and processes for preparing cortistatin A, J, K, and L, and analogs thereof.

21 Claims, 1 Drawing Sheet

(56) References Cited

U.S. PATENT DOCUMENTS

2011/0190323 A1 4/2011 Flyer et al.
2012/0190659 A1 7/2012 Corey et al.

FOREIGN PATENT DOCUMENTS

| WO | WO 98/29438 | A2 | 7/1998 |
|---|---|---|---|
| WO | WO 00/41545 | A2 | 7/2000 |
| WO | WO 00/66611 | A1 | 11/2000 |
| WO | WO 01/023405 | A2 | 4/2001 |
| WO | WO 01/027135 | A2 | 4/2001 |
| WO | WO 01/030802 | A2 | 5/2001 |
| WO | WO 03/004518 | A2 | 1/2003 |
| WO | WO 06/093993 | A1 | 9/2006 |
| WO | WO 07/082980 | A1 | 7/2007 |
| WO | WO 07/103162 | A2 | 9/2007 |
| WO | WO 08/064425 | A1 | 6/2008 |
| WO | WO 2010/024930 | A1 | 3/2010 |
| WO | WO 10/123545 | A2 | 10/2010 |

OTHER PUBLICATIONS

Aguayo et al. Angiogenesis in acute and chronic leukemias and myelodysplastic syndromes. Blood. 3002 Sep. 15;96(6):2240-5.
Amice et al., Enol Silyl Ethers and their Use for the Synthesis of a-Halo-a,B-unsaturated Carbonyl Compounds. Synthesis. 1976:196-97.
Aoki et al., Cortistatins A, B, C, and D, anti-angiogenic steroidal alkaloids, from the marine sponge *Corticum simplex*. JACS Mar. 15, 2006;128(10):3148-9.
Aoki et al., Cortistatins J, K, L, novel abeo-0(10-19)-androstane-type steroidal alkaloids with isoquinoline unit, from marine sponge *Carticium simplex*. Tetrahedron Lett. 2007;48(26)4485-88.
Aoki et al., Structure-activity relationship and biological property of cortistatins, anti-angiogenic spongean steoidal alkaloids. Bioorg. Med. Chem. Nov. 1, 2007;15(21):6758-62. Epub Aug. 21, 2007.
Atta et al., New Steroidal Alkaloids from the Roots of Buxus sempervirens. J. Nat. Prod. 1999; 62(5):665-69.
Berge et al., Pharmaceutical salts. J. Pharm. Sci. Jan. 1977;66(1):1-19.
Boekman et al., The Dess-Martin Periodinane: 1,1,1-Triacetoxy-1,1-Dihydro-1,2-Benziodoxol-3(1H)-One. J. Org. Synth. 2000p 77:141-52.
Brown, The Pomeranz-Fritsch Reaction, Isoquinoline vs Oxazoles. J. Org. Chem. 1977;42:3208-09.
Chen et al., Eryhtropoietin deficiency decreases vascular stability in mice. J. Clin. Invest. Feb. 2008.p. 118(2):526-33.
Cheson et al., National Cancer Institute-sponsored Working Group guidelines for chronic lymphocytic leukemia:revised guidelines for diagnosis and treatment. Blood. Jun. 15, 1996;87(12):4990-7.
Coulson et al., 23. Tetrakis(Triphenylphosphine)Palladium(0). Inorg. Synth. 1972;13:121-24.
De Marino et al.,A new steroidal alkaloid from a marine sponge *Corticium* sp. Tetrahedron Lett. 1998;39(41):7611-14.
Du Bois et al. Nitrogen Transfer from Nitrodomanganese (v) Complex: Amination of Silyl Enol Ethers. JACS 1996;118(4)915-16.
Duboudin et al., Evidence for [2+2] and [4+2] cycloadditions of allylic Grignard-reagents to benzyne. J. Chem. Soc-Chem Commun. 1977;13:454-55.
Eder et al., Synthese von (−)-Des-A-Steroiden. Chem Ber. 1975; 108:2673-79—Abstract Only.
Evans et al., New silicon-phosphorous reagents in organic synthesis-carbonyl and conjugate addition-reactions of silicon phosphate esters and related systems. JACS 1978;100(11):3467-77.
Extended European Search Report for EP 09810384.9, dated Mar. 30, 2012.
Extended European Search Report for EP 10767413.7, dated Apr. 10, 2013.
Ferrara, Vascular endothelial growth factor as a target for anticancer therapy. Oncologist. 2004;9 Suppl 1:2-10.
Folkman, Angiogenesis: an organizing principle for drug discovery? Nat. Rev. Drug Discov. Apr. 2007;6(4):273-86.
Folkman, Antiangiogenesis in cancer therapy—endostatin and its mechanisms of action. Exp. Cell Res. Mar. 10, 2006;312(5):594-607. Epub Dec. 22, 2005.
Folkman, Tumor angiogenesis: therapeutic implicaitons. N. Engl. J. Med. Nov. 18, 1971;285(21):1182-6.
Furrow et al., Practical procedures for the preperation of N-tert-butyldimethylsilylhydrazones and their use in modified Wolff-Kishner reductions and in the synthesis of vinyl halides and gem-dihalides. JACS May 5, 2004;126(17):5436.
Gerber et al., The role of VEGF in normal and neoplastic hematopoiesis. J. Mol. Med. Jan. 2003;81(1):20-31. Epub Dec. 14, 2002.
Grant et al., Matrigel induces thymosin beta 4 gene in differentiating endothelial cells. J. Cell Sci. Dec. 1995;108(Pt 12):3685-94.
Greene et al., Urinary matrix metalloproteinases and their endogenous inhibitors predict hepatic regeneration after murine partial hepatectomy. Transplantation. Oct. 27, 2004;78(8):1139-44.
Hajos et al., Synthesis and Conversion of 2-Methyl-2-(3oxobutyl)-1,3-cyclopentanedione to the Isomeric Racemic Ketols of the [3.2.1]Bicyclooctane and of the Perhydroindan Series. J. Org. Chem. 1974;39:1612-15.
Hajos et al., Total Synthesis of (+−)-17B-Hydroxy-d9(10)-des-A-Androsten-5-one-[(+−)-2,3,4a,4,5,7,8,9,9aB,9ba-Decahydro-3B-hydroxy-3aB,6-dimethyl-1H-benz[e]inden=7-one]. J. Org. Chem. 1967;32:3008-10.
Hanahan et al., Patterns and emerging mechanisms of the angiogenic switch during tumorigenesis. Cell. Aug. 9, 1996;86(3):353-64.
Hatada et al., Preperation of PMMA macromers by ortho-vinylbenzylmagnesium chloride and their polymerization. Polymer Bulletin. 1988;19(3):231-37.
Huang et al., Control of cyclin D1, p27(Kipl), and cell cycle progression in human capillary endothelial cells by cell shape and cytoskeletal tension. Mol. Biol. Cell. Nov. 9, 1998(11):3179-93.
Hurwitz et al., Bevacizumab plus irinotecan, fluorouracil, and leucoviorin for metastatic colorectal cancer. N. Engl. J. Med. Jun. 3, 2004;350(23):2335-42.
Hussong et al., Evidence of increased angiogenesis in patients with acute myeloid leukemia. Blood. Jan. 1, 2000;95(1):309-13.
International Preliminary Report on Patentability for PCT/US2009/004911, dated Nov. 3, 2011.
International Preliminary Report on Patentability for PCT/US2010/001121, dated Nov. 3, 2011.
International Search Report and Written Opinion for PCT/US2009/004911, dated May 4, 2010.
International Search Report and Written Opinion for PCT/US2010/001121, dated Dec. 8, 2010.
Isaacs et al., Synthesis of an Enantiomerically Pure Intermediate Containing the CD Substructure of Taxol. J. Org. Chem. 1993;58:3938-41.
Jain, Normalizing tumor vaculature with anti-angiogenic therapy:a new paradigm for combination therapy. Nat. Med. Sep. 2001;7(9):987-9.
Kerbel et al., Clinical translation of angiogenesis inhibitors. Nat. Rev. Cancer. Oct. 2002;2(10):727-39.
Khurana et al., Angiogenesis-dependent and independent phases of intimal hyperplasia. Circulation. Oct. 19, 2004;110(16):2436-43. Epub Oct. 11, 2004.
Klagsbrun et al., Molecular angiogenesis. Chem. Biol. Aug. 1999;6(8):R127-24.
Kohen et al., Solvolysis of 19-substituted androstane derivaties. J. Org. Chem. Jul. 1970;35(7):2272-5.
Kolb et al., Catalytic Asymmetric Dihydroxylation. J. Chem. Rev. 1994;94:2483-547.
Kolonin et al., Reversal of obesity by targeted ablation of adipose tissue. Nat. Med. Jun. 2004;10(6);625-32. Epub May 9, 2004.
Kozikowiski et al., Phosphoniosilyation—an efficient and practical method for the beta-functionalization of enones. J. Org. Chem. 1986;51(17):3400-02.
Kunding, Low temperature Grignard reactions with pure MG slurries. Trapping of cyclopropylmethyl and benzocyclobutenylmethyl Grignard reagents with CO2. Helvetica Chimica Acta. 1981;64(8):2606-13.

(56) References Cited

OTHER PUBLICATIONS

Kupchan et al., Buxus alkaloids. 13. A synthetic approach to the 9(10-19) abeo-pregnane system. JACS. Nov. 22, 1967;89(24):6327-32.

Lee et al., Entantioselective synthesis of (+)-cortistatin A, a potent and selective inhibitor of endothelial cell proliferation. JACS Dec. 17, 2008;130(50):16864-6.

Liu et al., 5-(Trimethylstannyl)-2H-pyran-2-one and 3-(Trimethylstannyl)-2H-pyran-2-one: New 2H-Pyran-2-one Synthons. JOC Sep. 20, 1996;61(19):6693-6699.

Magnus et al., Oxidative addition of azide anion to triisopropylsilyl enol ethers: Synthesis of [alpha]-azido ketones and 2-amino(methoxycarbonyl)alk-2-en-1-ones. Tetrahedron 1995;51(41):11075-86.

Mammoto et al., A mechanosensitivie transcriptional mechanism that controls angiogenesis. Nature. Feb. 26, 2009;457(7233)1103-8.

Mayer, Two steps forward in the treatment of colorectal cancer. N. Engl. J. Med. Jun. 3, 2004;350(23):2406-8.

Molica et al., Prognostic value of enhanced bone marrow angiogenesis in early B-cell chronic lymphocytic leukemia. Blood. Nov. 1, 2002;100(9):3344-51.

Moses, The regulation of neovascularization of matrix metalloproteinases and their inhibitors. Stem Cells. 1997;15(3):180-9.

Moulton et al., Angiogenesis inhibitors endostatin or TNP-470 reduce intimal neovascularization and plaque growth in apolipoprotein E-deficient mice. Circulation. Apr. 6, 1999;99(13):1726-32.

Neef et al., A radical approach to the synthesis of 9(10-19)abeosteroids. Tetrahedron. 1993;49(4):833-40.

Neef et al., New steroids by Simmons-Smith methylenation and subsequent rearrangement. J. Org. Chem. 1987;52(18):4143-46.

Nicolaou et al., Total synthesis of (+)-cortistatin A. (Supportive Information) Angew. Chem. Int. Ed. Engl. 2008;47(38):1-57.

Nicolaou et al., Total synthesis of (+)-cortistatin A. Angew. Chem. Int. Ed. Engl. 2008;47(38):7310-3.

Ohtani et al., Blockade of vascular endothelial growth factor suppresses experimental restenosis after intraluminal injury by inhibiting recruitment of monocye lineage cells. Circulation. Oct. 19, 2004;110(16):2444-52. Epub Oct. 11, 2004.

Ottow et al., Highly diastereoselective synthesis of 11 beta, 17 beta-diaryl-18a-homo-19-nor steroids. Journal Fur Praktishche Chemie-Chemiker-Zeitung. 1997;339(4):365-70.

Peacock et al., Angiogenesis inhibition suppresses collagen arthritis. J. Exp. Med. Apr. 1, 1992;175(4):1135-8.

Perez-Atayde et al., Spectrum of tumor angiogenesis in the bone marrow of children with acute lymphoblastic leukemia. Am. J. Pathol. Mar. 1997;150(3):815-21.

Puckett et al., The structure of buxenine-G. Tetrahedron Lett. 1966;7(32):3815-18.

Ranieri et al., Vascular endothelial growth factor (VEGF) as a target of bevacizumab in cancer: from the biology to the clinic. Curr. Med. Chem. 2006;13(16):1845-57.

Rastinejad et al., Regulation of the activity of a new inhibitor of angiogenesis by a cancer suppressor gene. Cell. Feb. 10, 1989;56(3):345-55.

Rigby et al., Agneral approach to the synthesis of C8-Oxygenated Guaianolides. JOC. 1987;52:34-44.

Schenone et al., Antiangiogenic agents: an update on small molecule VEGFR inhibitors. Curr. Med. Chem. 2007; 14(23):2495-516.

Shenvi et al., Synthesis of (+)-cortistatin A (Supporting Information). JACS Jun. 11, 2008; 130(23):SI-1-SI-12. Epub May 14, 2008.

Shenvi et al., Synthesis of (+)-cortistatin A JACS Jun. 11, 2008; 130(23):7241-3. Epub May 14, 2008.

Shih et al., Selective stimulation of VEGFR-1 prevents oxygen-induced retinal vascular degeneration in retinopathy of prematurity. J. Clin. Invest. Jul. 2003;112(1):50-7.

Shimizu et al., ABL2/ARG tyrosine kinase mediates SEMA3F-induced RhoA inactivation and cytoskeleton collapse in human glioma cells. J. Biol. Chem. Oct. 3, 2008;283(40):27230-8. Epub Jul. 25, 2008.

Shojima et al., The role of vascular endothelial growth factor in restenosis: the controversy continues. Circulation. Oct. 19, 2004;110(16):2283-6.

Smith et al., A new protocol for construction of the indole nucleus. Tetrahedron. 1986;42:2957.

Still et al., Rapid Chromatographic Technique for Perparative Seperations with Moderate Resolution. J. Org. Chem. 1978;43:2923-25.

Street et al., Vascular endothelial growth factor stimulates bone repair by promoting angiogenesis and bone turnover. Proc. Natl. Acad. Sci. USA. Jul. 23, 2002;99(15):9656-61. Epub Jul. 12, 2002.

Tamao et al., (Diisopropoxymethylsilyl)methyl Grignard Reagent: A New, Practically Useful Nucleophilic Hydroxymethylating Agent. J. Org. Chem. 1983;48:2120-22.

Teicher et al., Antiangiogenic agents can increase tumor oxygenation and response to radiation therapy. Radiat. Oncol. Investig. 1994;2(6):269-276.

Teicher, A systems approach to cancer therapy. (Antioncogenics + standard cytotoxics→mechanism(s) of interaction). Cancer Metastasis Rev. Jun. 1996;15(2):247-72.

Vacca et al., Bone marrow angiogenesis and progression in multiple myeloma. Br. J. Haematol. Jul. 1994;87(3):503-8.

Watanabe et al., Cortistatins E, F, G, and H, four novel steroidal alkaloids from marine sponge *Corticium simplex.* Tetrahedron. 2007;63(19):4074-79.

Williams et al., Isocyanide addition to pyridinium salts. Efficient entry into substituted nicotinonitrile derivatives. Org. Lett. Dec. 7, 2006;8(25):5789-92.

U.S. Pat. No. 9,127,019, B2, U.S. Appl. No. 14/293,743, Flyer et al., Sep. 8, 2015.

U.S. Pat. No. 9,714,255, B2, U.S. Appl. No. 14/848,086, Flyer et al., Jul. 25, 2017.

US, 2017-0029435, A1, U.S. Appl. No. 15/192,629, Shair et al., Feb. 2, 2017.

* cited by examiner

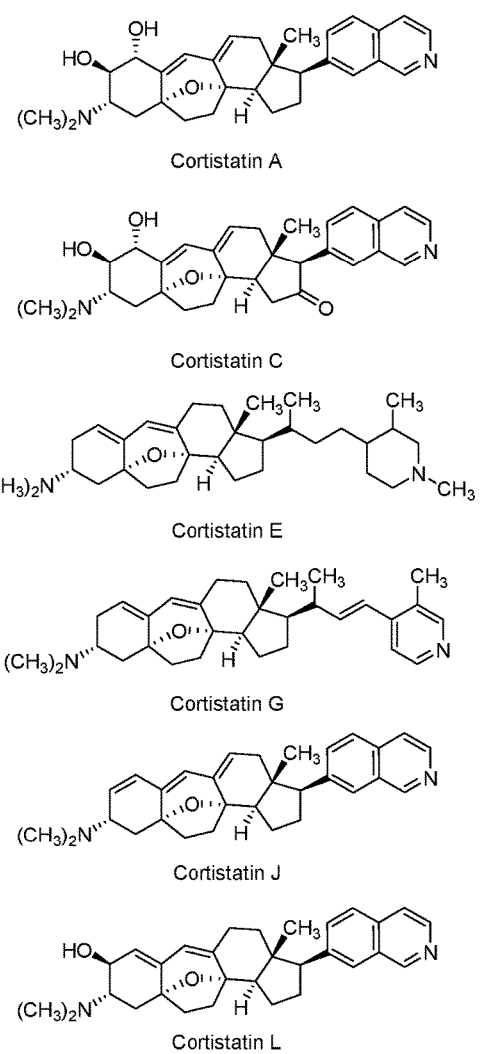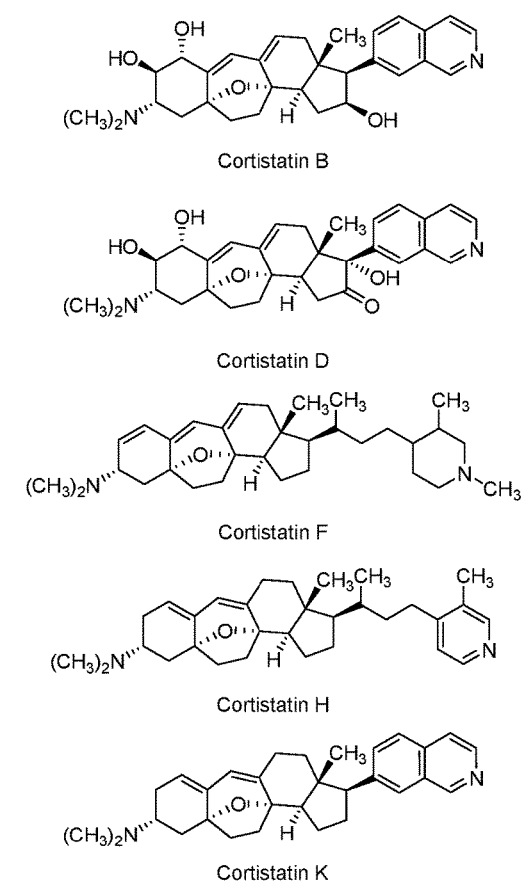

CORTISTATIN ANALOGUES AND SYNTHESES THEREOF

RELATED APPLICATIONS

The present application is a continuation of and claims priority under 35 U.S.C. § 120 to U.S. Application, U.S. Ser. No. 14/848,086, filed Sep. 8, 2015, which is a continuation of U.S. Application, U.S. Ser. No. 14/293,743, filed Jun. 2, 2014, which is a continuation of U.S. Application, U.S. Ser. No. 13/061,318, filed Apr. 26, 2011, which is a national stage filing under 35 U.S.C. § 371 of international PCT application, PCT/US2009/004911, which claims priority under 35 U.S.C. § 119(e) to U.S. provisional patent applications, U.S. Ser. No. 61/092,492, filed Aug. 28, 2008, and U.S. Ser. No. 61/115,395, filed Nov. 17, 2008, each of which is incorporated herein by reference.

BACKGROUND OF THE INVENTION

Angiogenesis is the process of generating new capillary blood vessels from the pre-existing vasculature. After birth, angiogenesis contributes to organ growth, but in adulthood it is strictly regulated and occurs only during wound healing and in the female reproductive cycle. See Klagsbrun et al., Molecular angiogenesis. *Chemistry & Biology* 1999, 6 (8), R217-R224. Under normal physiological conditions, angiogenesis is tightly controlled by a series of pro-angiogenic and anti-angiogenic factors, which allow vascular growth for controlled periods of time. Ferrara, Vascular Endothelial Growth Factor as a Target for Anticancer Therapy. *The Oncologist* 2004, 9:2-10. Persistent, unregulated angiogenesis has been implicated in a wide range of diseases, including rheumatoid arthritis, macular degeneration, atherosclerosis, obesity, benign neoplasms, and cancers. See Moulton et al., Angiogenesis inhibitors endostatin or TNP-470 reduce intimal neovascularization and plaque growth in apolipoprotein E-deficient mice. *Circulation* 1999, 99, (13), 1726-1732; and Hanahan et al., The hallmarks of cancer. *Cell* 2000, 100, (1), 57-70. That these pathological states are unified by their status as "angiogenesis-dependent diseases" but are otherwise unrelated has led Folkman to propose the concept of angiogenesis as an "organizing principle" in biology, by which many types of seemingly dissimilar phenomena may be connected. See Folkman, Opinion-Angiogenesis: an organizing principle for drug discovery? *Nature Reviews Drug Discovery* 2007, 6(4):273-286.

A current principle focus of angiogenesis research concerns its role in cancer. Tumor growth depends heavily on neovascularization-tumors are marked by a state of constant hypoxia, and in order to grow beyond 1-2 mm in size they require new capillaries to supply nutrients, remove metabolic waste, and also to metastasize. See Hanahan et al., Patterns and emerging mechanisms of the angiogenic switch during tumorigenesis. *Cell* 1996, 86, (3), 353-364. Cancer cells begin to promote angiogenesis early in tumorigenesis; this "angiogenic switch" is marked by oncogene-driven expression of pro-angiogenic factors such as vascular endothelial growth factor (VEGF), basic fibroblast growth factor (bFGF), angiopoietin 2 (ANGPT2), and platelet-derived growth factor (PDGF). Kerbel et al., Clinical translation of angiogenesis inhibitors. *Nature Reviews Cancer* 2002, 2, (10), 727-739. The best characterized pathway is that of VEGF and its receptors. VEGF has been shown to induce endothelial cell proliferation; furthermore, activation of the receptor VEGF2 has been associated with the production of matrix metalloproteinases (MMPs) which degrade the extracellular matrix (ECM), thus allowing migration of cells and further mobilizing pro-angiogenic proteins from the stroma. Ferrara, Vascular Endothelial Growth Factor as a Target for Anticancer Therapy. *The Oncologist* 2004, 9, 2-10; and Moses, The regulation of neovascularization by matrix metalloproteinases and their inhibitors. *Stem Cells* 1997, 15, (3), 180-189. Several of the pro-angiogenic proteins upregulate endothelial integrins and are thought to sustain endothelial cell viability during the detachments that are required as the cell migrates towards the tumor. Tumors also promote blood vessel growth by down-regulating endogenous angiogenesis inhibitors such as thrombospondin. Rastinej ad et al., Regulation of the activity of a new inhibitor of angiogenesis by a cancer suppressor gene. *Cell* 1989, 56, (3), 345-355.

Since Folkman first presented his hypothesis in 1971 that angiogenesis inhibitors could be used in the treatment of cancer, enormous effort has been directed toward the discovery and investigation of anti-angiogenic factors. The first to be identified was interferon-α/β in 1980, and over the past 27 years many more endogenous angiogenesis inhibitors have been isolated, thirty-three in the Folkman lab alone. See Folkman et al., Tumor angiogenesis—therapeutic implications. *New England Journal of Medicine* 1971, 285, (21), 1182-1186; and Folkman, J., Opinion—Angiogenesis: an organizing principle for drug discovery? *Nature Reviews Drug Discovery* 2007, 6, (4), 273-286. Extensive effort has also been expended to develop artificial angiogenesis inhibitors. These compounds are generally divided into two classes: direct and indirect inhibitors. Direct inhibitors of angiogenesis either neutralize VEGF in the blood plasma, such as the antibody Bevacizumab (AVASTIN) or prevent endothelial cell growth in response to VEGF or other angiogenic factor stimulation, such as the kinase inhibitor sunitinib malate (SUTENT). Indirect inhibitors, such as the small molecule gefitinib (IRESSA), block tumor cell production of VEGF or other pro-angiogenic factors. Direct angiogenesis inhibitors are less likely to induce acquired resistance because they target genetically stable endothelial cells instead of mutating tumor cells. Kerbel, Inhibition of tumor angiogenesis as a strategy to circumvent acquired-resistance to anticancer therapeutic agents. *Bioessays* 1991, 13, (1), 31-36.

Although when administered as single agents angiogenesis inhibitors have not provided long-term survival benefits, when given in combination with existing treatments these agents have shown utility in enhancing traditional chemotherapy or radiation therapy. Mayer, Two steps forward in the treatment of colorectal cancer. *New England Journal of Medicine* 2004, 350, (23), 2406-2408; Hurwitz et al., Bevacizumab plus irinotecan, fluorouracil, and leucovorin for metastatic colorectal cancer. *New England Journal of Medicine* 2004, 350, (23), 2335-2342; Teicher et al., Antiangiogenic agents can increase tumor oxygenation and response to radiation therapy. *Radiation Oncology Investigations* 1994, 2, (6), 269-276. It is known that tumor vasculature is "leaky", being characterized by aberrant morphology, absent or loosely attached pericytes, an abnormal basement membrane, and high interstitial pressure. Jain, Normalizing tumor vasculature with anti-angiogenic therapy: A New Paradigm for Combination Therapy. *Nature Medicine* 2001, 7, (9), 987-989. Synergistic effects in combination therapy have been observed, supporting the predictions of Teicher that simultaneous targeting of both cancer cells and their supporting vasculature would provide maximal benefit. Jain, Normalizing tumor vasculature with anti-angiogenic therapy: A new paradigm for combination therapy. *Nature*

Medicine 2001, 7, (9), 987-989. One current hypothesis is that the anti-angiogenic drug "normalizes" the tumor vasculature, decreasing leakage and allowing the chemotherapeutic agent more efficient access to the cancerous tissue. Teicher, A systems approach to cancer therapy (antiangiogenics plus standard cytotoxics, mechanism(s) of interaction). *Cancer and Metastasis Reviews* 1996, 15, (2), 247-272. Angiogenesis inhibition also decreases tumoral interstitial pressure, raising oxygen content in the tumor and increasing sensitivity to ionizing radiation. Teicher et al., Antiangiogenic agents can increase tumor oxygenation and response to radiation therapy. *Radiation Oncology Investigations* 1994, 2, (6), 269-276.

In addition to cancerous tissue, genotypically normal cells may also have tissue mass regulated by the endothelial microvasculature. Gerber et al., The role of VEGF in normal and neoplastic hematopoiesis. *Journal of Molecular Medicine* 2003, 81, (1), 20-31. Rats that have undergone hepatectomy to remove 70% of their liver regenerate the lost mass in approximately 10 days. If an angiogenic protein, such as VEGF, is administered systemically, the liver continues to grow beyond its normal size. In contrast, if an angiogenesis inhibitor is administered, liver regeneration is prevented; discontinuation of the inhibitor is followed by immediate liver regeneration. Folkman, Opinion-Angiogenesis: an organizing principle for drug discovery? *Nature Reviews Drug Discovery* 2007, 6, (4), 273-286; Greene et al., Urinary matrix metalloproteinases and their endogenous inhibitors predict hepatic regeneration after murine partial hepatectomy. *Transplantation* 2004, 78, (8), 1139-1144. Both bone growth and adipocyte enlargement are also under endothelial control, raising the possibility that in the future specific endothelial inhibitors may be used to control obesity and other tissue overgrowth. Street et al., Vascular endothelial growth factor stimulates bone repair by promoting angiogenesis and bone turnover. *Proceedings of the National Academy of Sciences of the United States of America* 2002, 99, (15), 9656-9661; Kolonin et al., Reversal of obesity by targeted ablation of adipose tissue. *Nature Medicine* 2004, 10, (6), 625-632.

Due to the fundamental role that angiogenesis plays in numerous pathological states, anti-angiogenic pharmaceutical agents have become targets of intensive research. Schenone et al., Antiangiogenic agents: an update on small molecule VEGFR inhibitors. *Current Medicinal Chemistry* 2007, 14, (23), 2495-2516. Currently, ten drugs that have an anti-angiogenic effect have been approved by the FDA, and 30 more are in Phase II or Phase III clinical trials. See Folkman, Opinion—Angiogenesis: an organizing principle for drug discovery?*Nature Reviews Drug Discovery* 2007, 6, (4), 273-286. Furthermore, drugs that have gained approval for the treatment of cancer are also being evaluated for the treatment of other angiogenesis-dependent diseases. In 2006, Ranibizumab, a fragment of the monoclonal antibody therapy Bevacizumab (approved in 2004 for colorectal cancer), was approved for direct injection into the eye to treat age-related macular degeneration. Ranieri et al., Vascular endothelial growth factor (VEGF) as a target of bevacizumab in cancer: From the biology to the clinic. *Current Medicinal Chemistry* 2006, 13, (16), 1845-1857. There is certainly a need for additional innovation in the field; angiogenesis is a highly complex process regulated by a host of factors, and it is believed that inhibition of multiple factors in combination may lead to enhanced patient outcome. See Folkman, Antiangiogenesis in cancer therapy—endostatin and its mechanisms of action. *Experimental Cell Research* 2006, 312, (5), 594-607. Furthermore, several of the currently available drugs are biologics and suffer the drawbacks of high production costs and required parenteral administration.

SUMMARY OF THE INVENTION

Several members of a new family of anti-angiogenic alkaloids known as the cortistatins have been isolated from the marine sponge Corticium simplex (See FIG. 1). The structure of cortistatin A is unusual among natural products and includes a rearranged steroid in the form of a 9(10-19)-abeo-androstane skeleton, an ether bridge connecting C5 and C8, and a C17 isoquinoline substituent. The structure of cortistatin A was confirmed by X-ray crystallography, while its absolute configuration was determined using circular dichroism. Aoki et al., Cortistatins A, B, C, and D, anti-angiogenic steroidal alkaloids, from the marine sponge Corticium simplex. *Journal of the American Chemical Society* 2006, 128, (10), 3148-3149; Aoki et al, Cortistatins J, K, L, novel abeo-9(10-19)-androstane-type steroidal alkaloids with isoquinoline unit, from marine sponge Corticium simplex. *Tetrahedron Letters* 2007, 48, (26), 4485-4488; and Watanabe et al., Cortistatins E, F, G, and H, four novel steroidal alkaloids from marine sponge Corticium simplex. *Tetrahedron* 2007, 63, (19), 4074-4079. Several of the cortistatins exhibit extremely potent (2-40 nM) and selective cytostatic activity against human umbilical vein endothelial cells (HUVECs) with markedly less potency against a panel of human cancer cell lines (including KB3-1, Neuro2A, K562, and NHDF). Cortistatin A in particular exhibits in HUVECs, a $GI_{50}$=180 pM, while the $GI_{50}$=6-7 µM in several human and murine cancer cell lines and one normal human dermal fibroblast cell line. Cortistatin A exhibits a selectivity index ranging from 3,000 to 4,000 for the endothelial cell line, making it a valuable lead in the development of novel anti-angiogenic agents.

Aoki and coworkers have demonstrated that cortistatin A and several other members of the cortistatin family are direct and highly selective angiogenesis inhibitors. They have presented evidence for a cytostatic, and not cytotoxic, mechanism of action, and they have demonstrated that cortistatin A inhibits tubular formation in HUVECs and also inhibits HUVEC cellular migration. Aoki and coworkers postulate that cortistatin A acts by inhibiting the phosphorylation of an unidentified 110 kDa protein that is normally phosphorylated upon VEGF stimulation, and they further propose that this protein may be involved in the PI3 kinase/AKT pathway for angiogenic factor-induced signal transduction. Aoki et al, Structure-activity relationship and biological property of cortistatins, anti-angiogenic spongean steroidal alkaloids. *Bioorganic & Medicinal Chemistry* 2007, 15, (21), 6758-6762.

Aoki and coworkers conducted preliminary structure-activity relationship studies by comparing the activities and selectivities of the eleven naturally occurring cortistatins they had isolated (see FIG. 1). Their analysis concluded that the D ring isoquinoline unit was required for activity and that the A ring anti diol was not.

IC$_{50}$ Values Against HUVECs for Selected Cortistatins

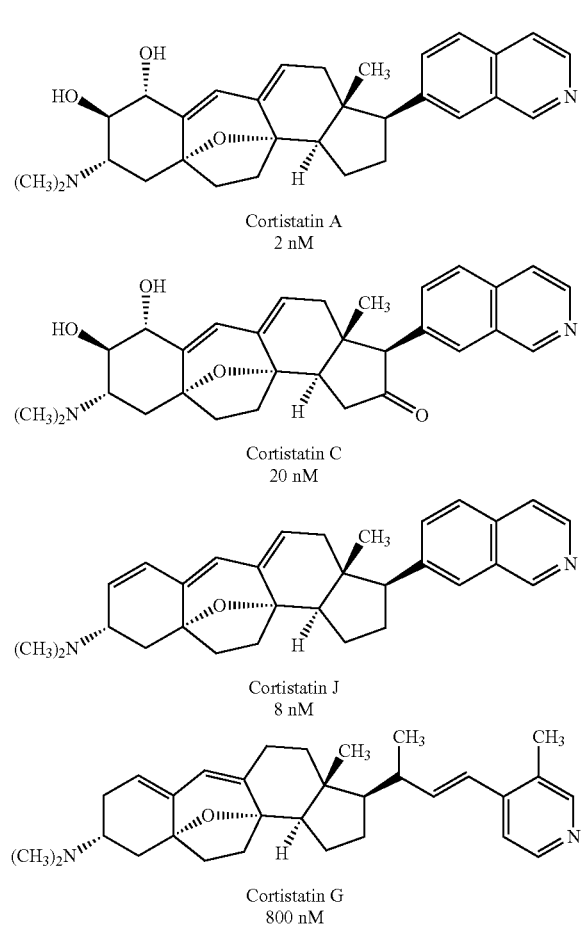

Cortistatin A
2 nM

Cortistatin C
20 nM

Cortistatin J
8 nM

Cortistatin G
800 nM

Several B-ring homosteroid natural products have been previously described in the literature; however, none contain the unique C$_5$-C$_8$ oxabridge featured in the cortistatins. Kupchan and coworkers isolated the first B-ring homosteroid, buxenine G, from *Buxus sempervirens* and elucidated its structure in 1966. Puckett et al., The structure of buxenine-G. *Tetrahedron Letters* 1966, 7, (32), 3815-3818. The *Buxus* genus of plants has yielded several more compounds of this structural class, including buxamine F, described in 1999 by Raman and coworkers. Atta et al., New Steroidal Alkaloids from the Roots of *Buxus sempervirens*. *Journal of Natural Products* 1999, 62, (5), 665-669). The first B-ring homosteroid to be isolated from a marine source was the unnamed compound depicted below, identified by Zollo and coworkers in 1998. De Marino et al., A new steroidal alkaloid from a marine sponge Corticium sp. *Tetrahedron Letters* 1998, 39, (41), 7611-7614. Both buxenine G and the latter compound showed significant cytotoxicity in human nasopharynx carcinoma (KB) cells, with an ED$_{50}$ of 0.4 µg/mL for buxenine G. It is unclear whether any of these compounds were screened against HUVECs.

Selected Structurally Related Naturally Occurring Alkaloids

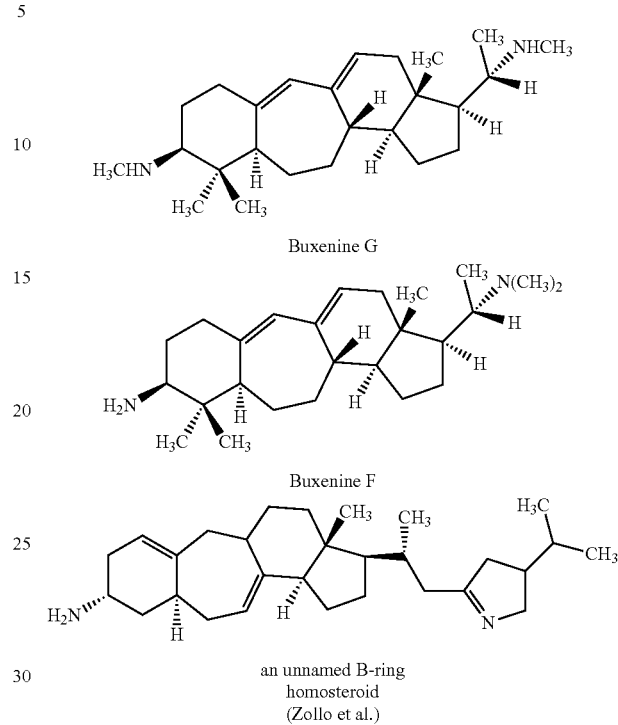

Buxenine G

Buxenine F an unnamed B-ring homosteroid (Zollo et al.)

There have been several previous syntheses of the B(9a)-homo-19-norsteroid skeleton, some of which have resulted in very efficient construction of the carbon framework (see the schemes below). Neef et al., New steroids by Simmons-Smith methylenation and subsequent rearrangement. *Journal of Organic Chemistry* 1987, 52, (18), 4143-4146; Neef et al., A radical approach to the synthesis of 9(10-19) abeosteroids. *Tetrahedron* 1993, 49, (4), 833-840; Kupchan et al., Buxus alkaloids 13. A synthetic approach to 9(10-19) abeo-pregnane system. *Journal of the American Chemical Society* 1967, 89, (24), 6327-6332; Abushanab et al., 9(10-19) abeosteroids—total synthesis of abeo-estradiol, abeo-estradiol 3-methyl ether, and 17-alpha-ethynyl abeo-estradiol 3-methyl ether. *Journal of Organic Chemistry* 1976, 41, (9), 1601-1603; and Kohen et al., Solvolysis of 19-substituted androstane derivatives. *Journal of Organic Chemistry* 1970, 35, (7), 2272-2275. With the exception of the acid-mediated cyclization by Abushanab and coworkers (Abushanab et al, 9(10-19) abeosteroids—total synthesis of abeo-estradiol, abeo-estradiol 3-methyl ether, and 17-alpha-ethynyl abeo-estradiol 3-methyl ether. *Journal of Organic Chemistry* 1976, 41, (9), 1601-1603), all of these routes commenced from an advanced steroidal intermediate. None of these approaches could be easily adapted to incorporate the C8-α oxygenation necessary for the construction of the B-ring oxabridge of cortistatin A or its analogs.

Previous Approaches to the B-Ring Homosteroid Skeleton

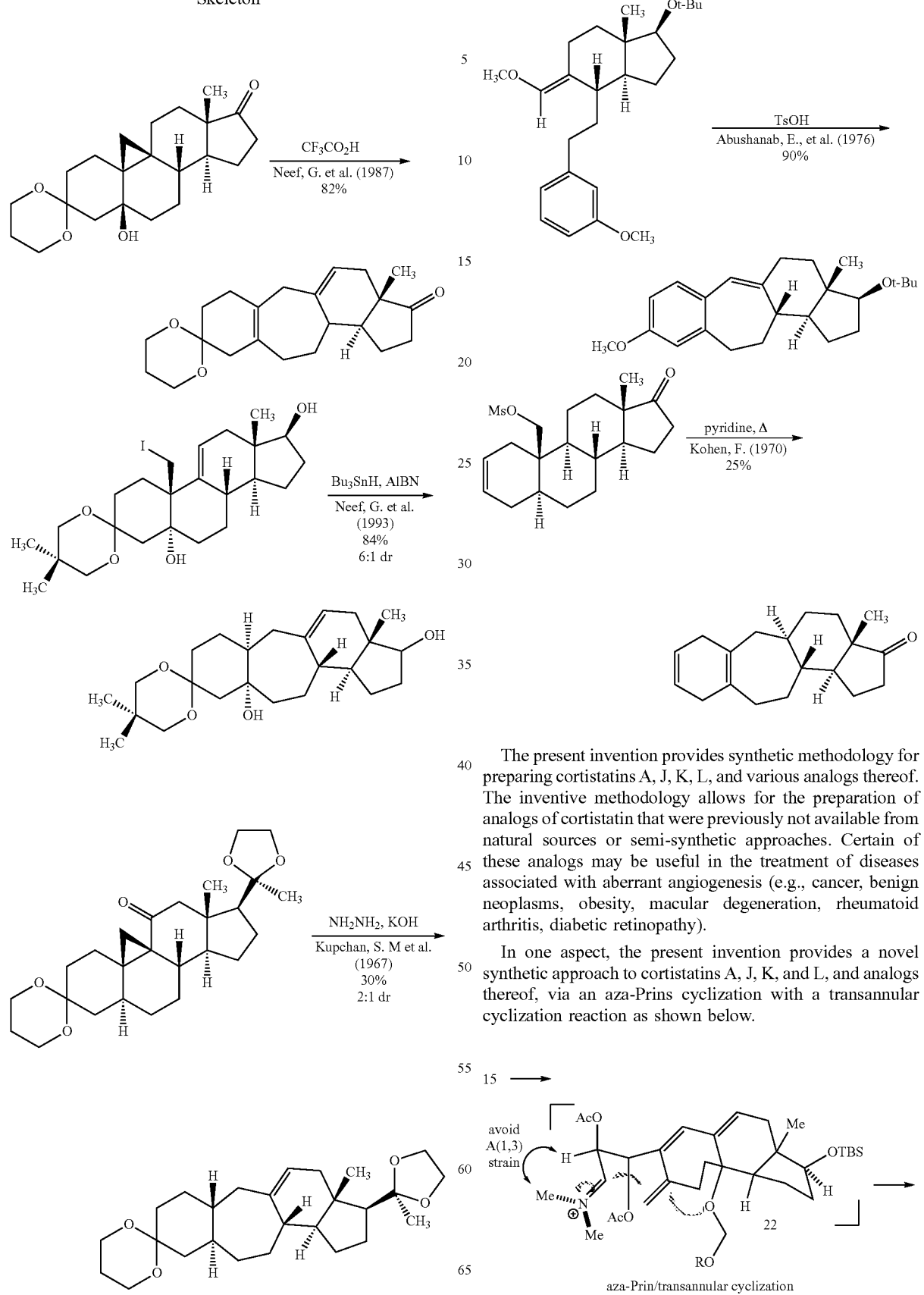

The present invention provides synthetic methodology for preparing cortistatins A, J, K, L, and various analogs thereof. The inventive methodology allows for the preparation of analogs of cortistatin that were previously not available from natural sources or semi-synthetic approaches. Certain of these analogs may be useful in the treatment of diseases associated with aberrant angiogenesis (e.g., cancer, benign neoplasms, obesity, macular degeneration, rheumatoid arthritis, diabetic retinopathy).

In one aspect, the present invention provides a novel synthetic approach to cortistatins A, J, K, and L, and analogs thereof, via an aza-Prins cyclization with a transannular cyclization reaction as shown below.

-continued

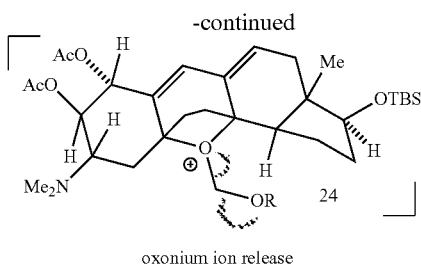

oxonium ion release

In another aspect, the present invention provides several novel synthetic approaches to cortistatin A, J, K, and L, and analogs thereof, as described herein. In certain embodiments, the invention provides a synthetic approach that involves an oxidative dearomatization reaction with intramolecular hydroxyl trapping to form the $C_5$-$C_8$ oxa-bridge in preparing Intermediate 2 as depicted below.

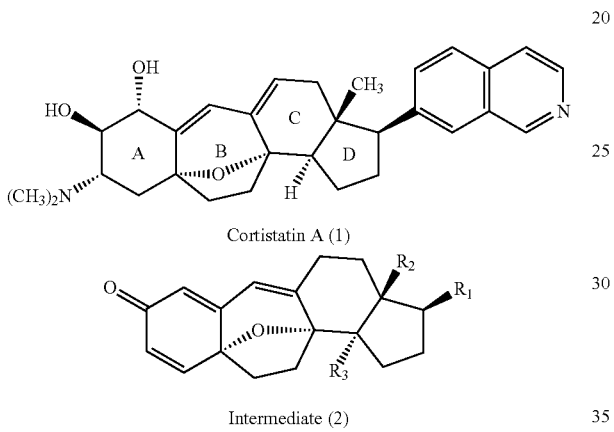

In another embodiment, the present invention provides a novel synthetic approach to intermediate 2 and to cortistatins A, J, K, and L and analogs thereof, via intramolecular oxidative coupling and the formation of cyclohexyldieneone derivatives as shown below.

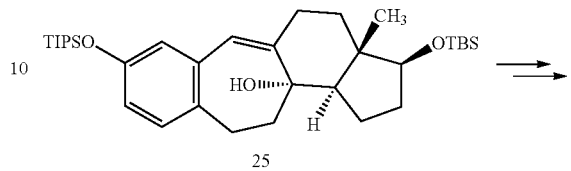

In still another embodiment, the present invention provides further synthetic approach to precursors of cortistatins A, J, K, and L, and analogs thereof, from intermediate 2, via a multistep sequence comprising reductive c-halogenation, allylic epoxidation, azide formation, protecting group manipulations, and reductive amination as shown below.

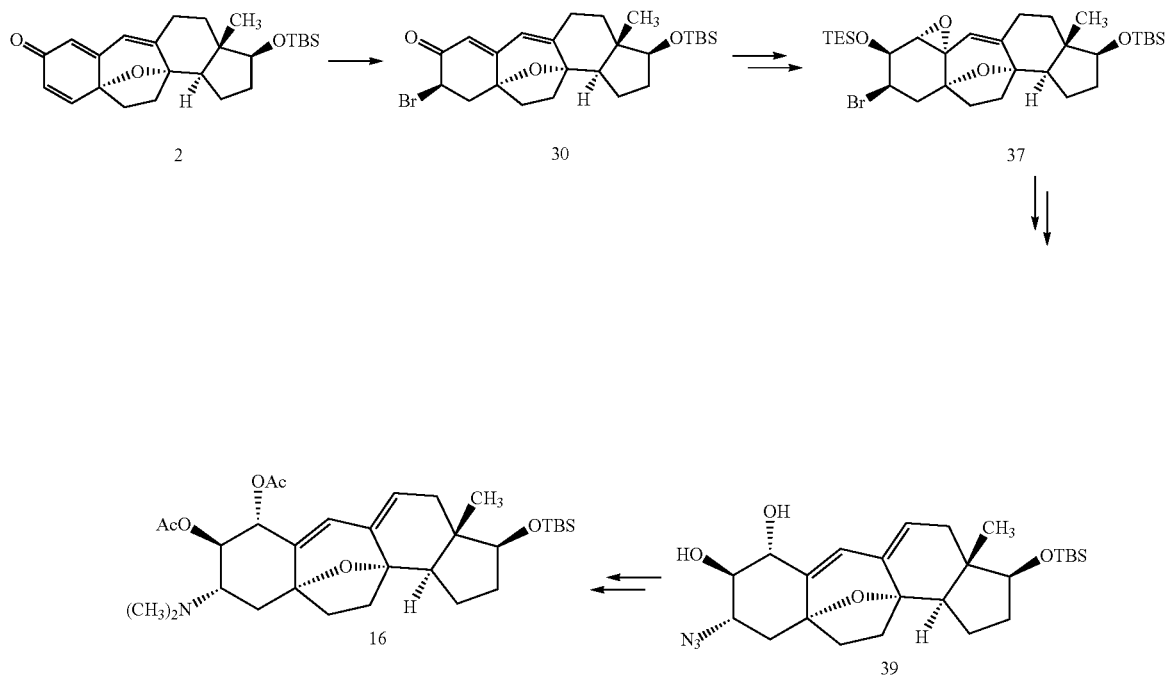

In another embodiment, the present invention provides synthetic approaches by which cortistatins A, J, K, and L, and analogs thereof, may be derivatized with biological probes or labels such as biotin or biotin derivatives via a multistep sequence comprising the reduction of an azide to a primary amine, which can be protected and/or converted to the corresponding biotinylated amide derivative as shown below.

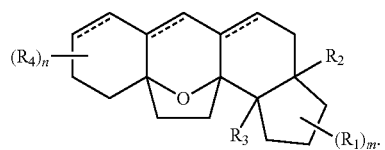

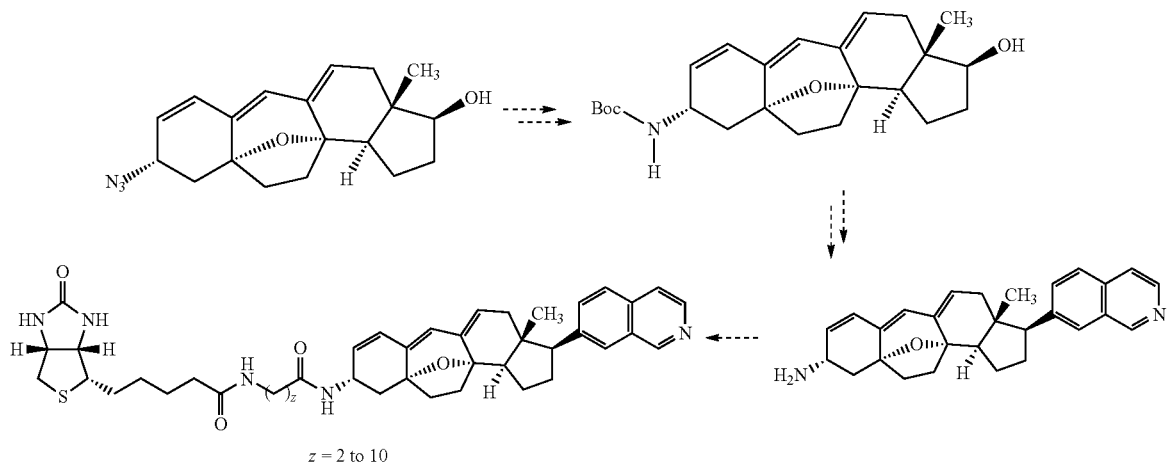

$z = 2$ to $10$

In another aspect, the present invention provides novel cortistatin analogs. The compounds provided by the inventive synthetic approached described herein may be useful as anti-angiogenic agents for use in treatment of cancer, benign tumors, diabetic retinopathy, rheumatoid arthritis, macular degeneration, obesity, atherosclerosis, and other diseases associated with aberrant angiogenesis. In certain embodiments, the invention provides compounds of the general formula:

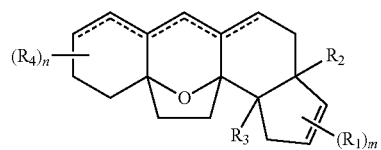

and pharmaceutically acceptable salts thereof, wherein dashed lines, $R_1$, $R_2$, $R_3$, $R_4$, n, and m are as defined herein. In certain embodiments, the invention provides compounds of the general formula:

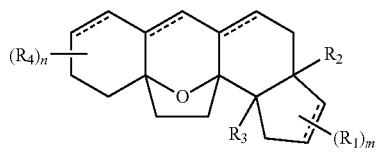

In certain embodiments, the invention provides compound of the formula:

In certain embodiments, the invention provides compound of the formula:

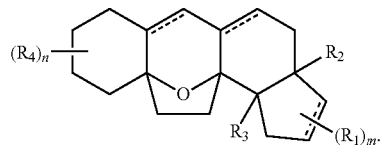

In certain embodiments, the invention provides compounds of the general formula:

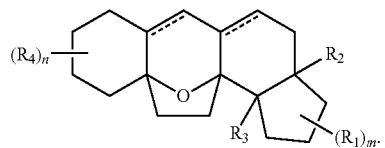

In certain embodiments, the invention provides compounds of the general formula:

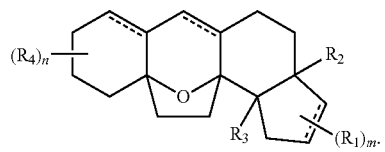

In certain embodiments, the invention provides compounds of the general formula:

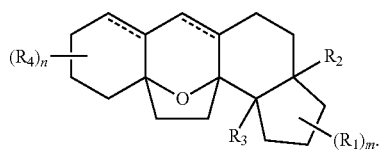

In certain embodiments, the invention provides truncated cortistatin analogs of the formula:

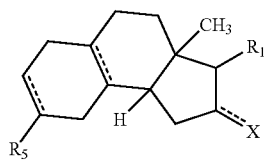

and pharmaceutically acceptable salts thereof, wherein dashed lines, X, $R_1$, and $R_5$ are as defined herein. In certain other embodiments, the invention provides truncated cortistatin analogs of the formula:

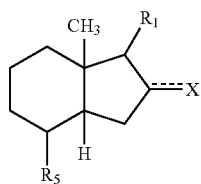

and pharmaceutically acceptable salts thereof, wherein dashed line, X, $R_1$, and $R_5$ are as defined herein. Such analogs may also be useful intermediates in the synthesis of cortistatin analogs. In certain embodiments, the invention also provides compounds with a modified carbon skeleton of the formula:

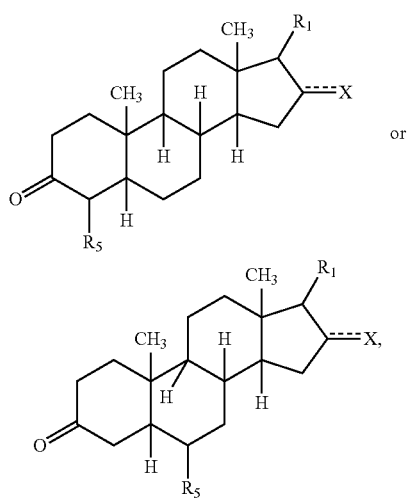

and pharmaceutically acceptable salts thereof, wherein dashed line, X, $R_1$, and $R_5$ are as defined herein.

Certain compounds of the present invention and pharmaceutically acceptable salts thereof are useful for treating a variety of diseases, disorders, or conditions, associated with angiogenesis. In some embodiments, the diseases, disorders, and conditions associated with undesired angiogensis include many types of cancer, benign tumors, diabetic retinopathy, rheumatoid arthritis, macular degeneration, obesity, and atherosclerosis. In another aspect, the invention provides a method of treating a proliferative disease by administering an effective amount of an inventive compound to a subject. In certain embodiments, the invention provides a method of inhibiting angiogenesis by administering an effective amount of an inventive compound to a subject. In certain embodiments, the invention provides a method of inhibiting the proliferation of endothelial cells by contacting endothelial cells with an effective amount of an inventive compound.

The present invention provides pharmaceutical compositions comprising the inventive compounds. In certain embodiments, the pharmaceutical composition comprises an amount of the inventive compound effective to inhibit angiogenesis in a subject and optionally a therapeutically acceptable excipient. A compound of the invention is typically combined with a pharmaceutically acceptable excipient to form a pharmaceutical composition for administration to a subject. In certain embodiments, the present invention provides methods of using an inventive compound or pharmaceutical composition thereof to treat diseases associated with angiogenesis. Methods of treating a disease associated with angiogenesis, including many types of cancer, benign neoplasms, diabetic retinopathy, rheumatoid arthritis, macular degeneration, obesity, and atherosclerosis, are provided wherein a therapeutically effective amount of an inventive compound is administered to a subject. In certain embodiments, the present invention also provides a pharmaceutical pack or kit comprising one or more containers filled with one or more pharmaceutical composition of the invention. In certain embodiments, the kit or pack includes multiple dosage units (e.g., multiple tablets with each containing a specified amount of an inventive compound). In certain embodiments, the pack or kit includes an additional therapeutic agent for use in a combination therapy. In certain embodiments, the pack or kit includes instructions for use and/or prescribing.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkylp-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "alkylthio" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of alkylthio include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into five classes: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; c) colored, luminescent, phosphorescent, or fluorescent dyes; d) photoaffinity labels; and e) ligands with known binding partners (such as biotin-streptavidin, FK506-FKBP, etc.). It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of compound in vivo. Due to isotope effects, enzymatic degradation of the deuterated compounds may be slowed thereby increasing the half-life of the compound in vivo. In other embodiments such as in the identification of the biological target(s) of a natural product or derivative thereof, the compound is labeled with a radioactive isotope, preferably an isotope which emits detectable particles, such as 1 particles. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid. In other embodiments, biotin labeling is utilized.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In certain embodiments, the esters are cleaved by enzymes such as esterases.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, the term "biological probe" comprises modifications of the compounds of the invention to include substituents, such as biotin or biotin derivatives, which have high affinities for known biological targets, such as avidin (also streptavidin and neutravidin). The attachment of a biotin or a biotin derivative to compounds of the invention is referred to herein as "biotinylation." The attachment of biological probes to compounds of the invention, including the biotinylation of compounds of the invention, can be used to study the biological basis of diseases including protein localization, protein interactions, transcription, translation, and replication, or the mechanism of action of a compound (e.g., cortistatin or an analog thereof). In certain embodiments, biological probe is synonymous with the term label.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Effective amount": In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a compound with anti-angiogenic activity is the amount that results in a sufficient concentration to inhibit the growth of blood vessels or the proliferation of endothelial cells.

BRIEF DESCRIPTION OF THE DRAWING

FIG. 1 depicts various exemplary cortistatins.

DETAILED DESCRIPTION OF CERTAIN EMBODIMENTS OF THE INVENTION

The present invention is based upon the synthetic approaches described herein for preparing cortistatins A, J, K, L, cortistatin analogs, and other inventive compounds. The cortistatins have unique structural features and potent anti-angiogenesis activity. The relative paucity of data concerning both their structure-activity relationships and biological target(s) has made these compounds particularly interesting and important in designing novel anti-angiogenic agents. Thus, the present invention provides the synthesis of cortistatins A, J, K, L, and cortistatin analogs, for the purpose of developing cortistatin analogs with improved anti-angiogenic biological activity and/or improving its pharmacological properties. Such compounds may find use in the treatment of diseases associated with aberrant angiogenesis.

I. Compounds

In one aspect, the present invention provides novel compounds. The inventive compounds are cortistatin analogs or intermediates useful in the synthesis of cortistatins A, J, K, L, or analogs thereof. The various inventive compounds are described herein. The inventive analogs may be prepared by the synthetic methods described herein. Such compounds may have anti-angiogenic activity, making them useful in the treatment of diseases associated with angiogenesis.

In certain embodiments, the present invention provides compounds of the formula:

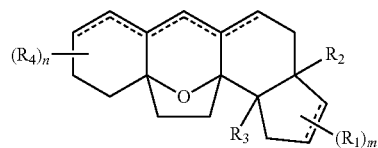

wherein:

each of the dashed lines independently represents the presence or absence of a bond;

m is an integer between 0 and 6, inclusive;

n is an integer between 0 and 8, inclusive;

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_A$; $-C(=O)R_A$; $-CO_2R_A$; $-CN$; $-SCN$; $-SR_A$; $-SOR_A$; $-SO_2R_A$; $-NO_2$; $-N_3$; $=O$; $=N(R_A)$; $=S$; $-N(R_A)_2$; $-NHC(=O)R_A$; $-NR_AC(=O)N(R_A)_2$; $-OC(=O)OR_A$; $-OC(=O)R_A$; $-OC(=O)N(R_A)_2$; $-NR_AC(=O)OR_A$; or $-C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic;

each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_D$; $-C(=O)R_D$; $-CO_2R_D$; $-CN$; $-SCN$; $-SR_D$; $-SOR_D$; $-SO_2R_D$; $-NO_2$; $-N_3$; $=O$; $=N(R_D)$; $=S$; $-N(R_D)_2$; $-NHC(=O)R_D$; $-NR_AC(=O)N(R_D)_2$; $-OC(=O)OR_D$; $-OC(=O)R_D$; $-OC(=O)N(R_D)_2$; $-NR_DC(=O)OR_D$; or $-C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

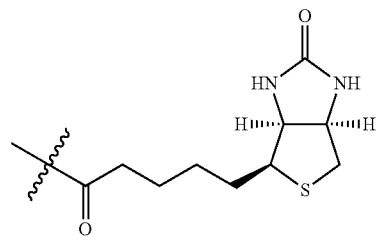 [SMILES: *C(=O)CCCC[C@@H]1SC[C@@H]2NC(=O)N[C@@H]21]

moiety; or a moiety wherein z is an integer between 2 and 10, inclusive; provided that the compound is not any of the following formulae:

Cortistatin A

Cortistatin B

Cortistatin C

Cortistatin D

Cortistatin E

Cortistatin F

Cortistatin G

Cortistatin H

Cortistatin J

Cortistatin K

Cortistatin L

Didehydrocortistatin A and pharmaceutically acceptable salts thereof. In certain embodiments, the inventive compound is not a naturally occurring cortistatin analogs. In certain embodiments, the inventive compound is not a previously isolated and characterized, naturally occurring cortistatin analog. In certain embodiments, the inventive compound is not any of the compounds, cortistatin A-L, or didehydrocortistatin A.

In certain embodiments, the invention provides compounds of the general formula:

In certain embodiments, the invention provides compound of the formula:

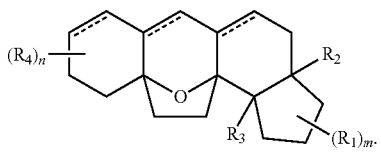

In certain embodiments, the invention provides compound of the formula:

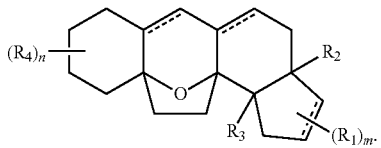

In certain embodiments, the invention provides compounds of the general formula:

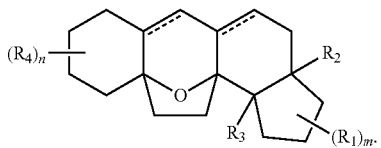

In certain embodiments, the invention provides compounds of the general formula:

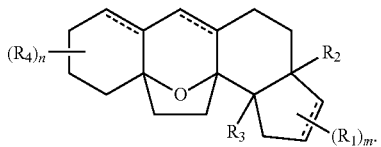

In certain embodiments, the invention provides compounds of the general formula:

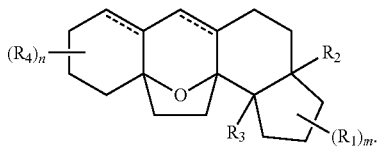

In certain embodiments, the present invention provides compounds of the formula:

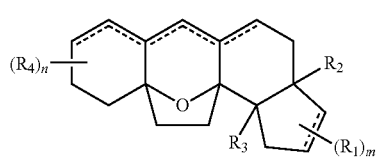

wherein:
each of the dashed lines independently represents the presence or absence of a bond;

m is an integer between 0 and 6, inclusive;
n is an integer between 0 and 8, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_A$; $-C(=O)R_A$; $-CO_2R_A$; $-CN$; $-SCN$; $-SR_A$; $-SOR_A$; $-SO_2R_A$; $-NO_2$; $-N_3$; $=O$; $=N(R_A)$; $=S$; $-N(R_A)_2$; $-NHC(=O)R_A$; $-NR_AC(=O)N(R_A)_2$; $-OC(=O)OR_A$; $-OC(=O)R_A$; $-OC(=O)N(R_A)_2$; $-NR_AC(=O)OR_A$; or $-C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;
$R_3$ is hydrogen or $C_1$-$C_6$ aliphatic;
each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_D$; $-C(=O)R_D$; $-CO_2R_D$; $-CN$; $-SCN$; $-SR_D$; $-SOR_D$; $-SO_2R_D$; $-NO_2$; $-N_3$; $=O$; $=N(R_D)$; $=S$; $-N(R_D)_2$; $-NHC(=O)R_D$; $-NR_AC(=O)N(R_D)_2$; $-OC(=O)OR_D$; $-OC(=O)R_D$; $-OC(=O)N(R_D)_2$; $-NR_DC(=O)OR_D$; or $-C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

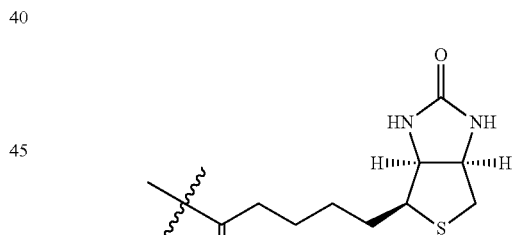

moiety; or a

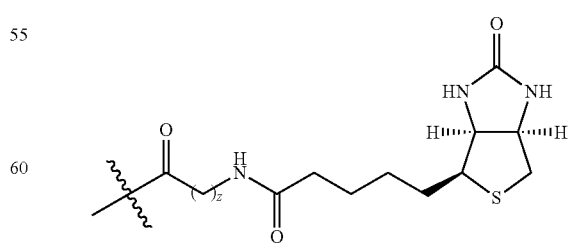

moiety wherein z is an integer between 2 and 10, inclusive;
provided that the compound is not any of the following formulae:

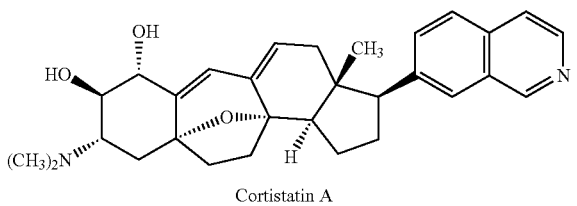

Cortistatin A

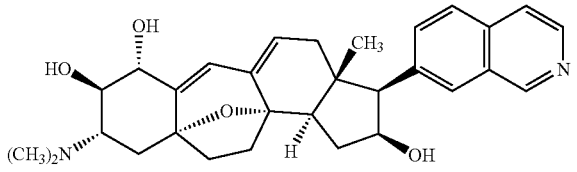

Cortistatin B

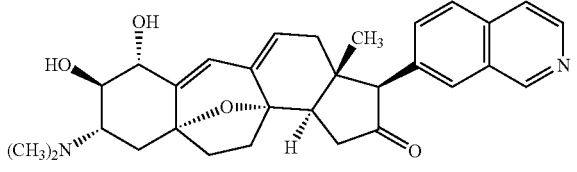

Cortistatin C

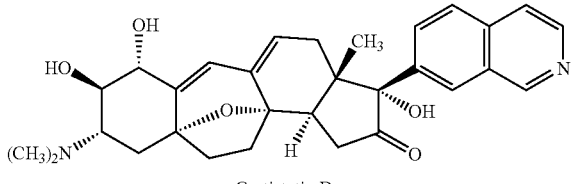

Cortistatin D

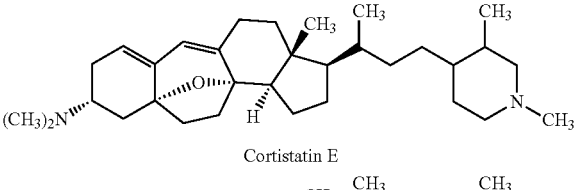

Cortistatin E

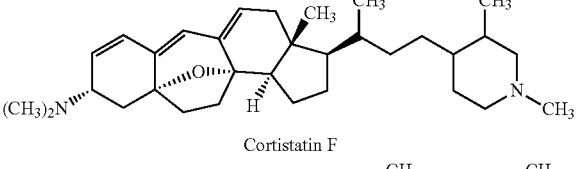

Cortistatin F

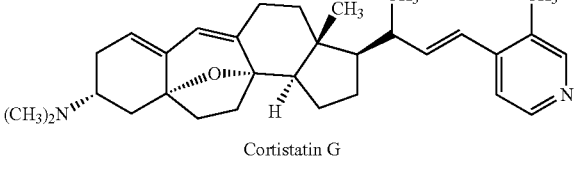

Cortistatin G

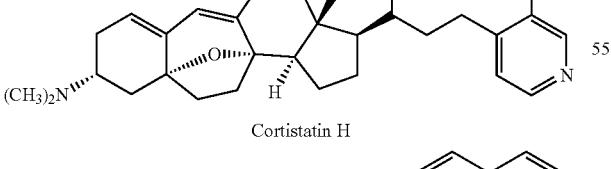

Cortistatin H

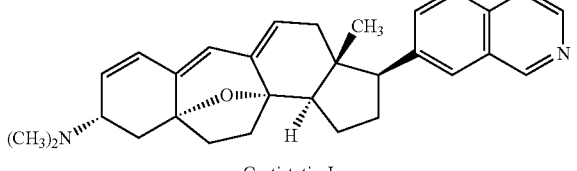

Cortistatin J

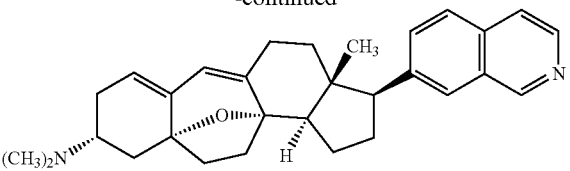

Cortistatin K

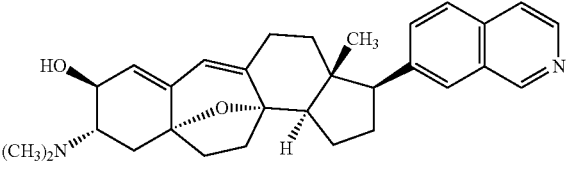

Cortistatin L and pharmaceutically acceptable salts thereof. In certain embodiments, the inventive compound is not a naturally occurring cortistatin analogs. In certain embodiments, the inventive compound is not a previously isolated and characterized, naturally occurring cortistatin analog. In certain embodiments, the inventive compound is not any of the compounds, cortistatin A-L.

In certain embodiments, the inventive compound is of the formula:

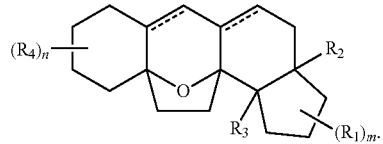

In certain embodiments, the inventive compound is of the formula:

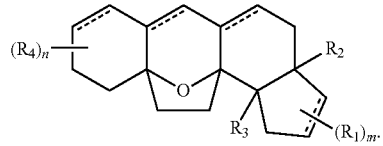

In certain embodiments, the inventive compound is of the formula:

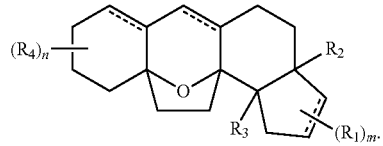

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

In certain embodiments, at least one $R_1$ is hydrogen. In certain embodiments, at least one $R_1$ is halogen. In certain embodiments, at least one $R_1$ is fluorine. In certain embodiments, at least one $R_1$ is substituted or unsubstituted aliphatic. In some embodiments, at least one $R_1$ is substituted or unsubstituted alkyl. In certain embodiments, at least one $R_1$ is $C_1$-$C_6$ alkyl. In certain embodiments, at least one $R_1$ is methyl. In certain embodiments, at least one $R_1$ is ethyl. In certain embodiments, at least one $R_1$ is propyl. In certain embodiments, at least one $R_1$ is substituted or unsubstituted aryl. In certain embodiments, at least one $R_1$ is substituted or unsubstituted phenyl. In certain embodiments, at least one $R_1$ is substituted phenyl. In certain embodiments, at least one $R_1$ is unsubstituted phenyl. In certain embodiments, at least one $R_1$ is substituted or unsubstituted naphthyl. In certain embodiments, at least one $R_1$ is substituted naphthyl. In certain embodiments, at least one $R_1$ is unsubstituted naphthyl. In certain embodiments, at least one $R_1$ is substituted or unsubstituted heteroaryl. In certain embodiments, at least one $R_1$ is substituted or unsubstituted isoquinolinyl. In certain embodiments, at least one $R_1$ is substituted isoquinolinyl. In certain embodiments, at least one $R_1$ is unsubstituted isoquinolinyl. In certain embodiments, at least one $R_1$ is unsubstituted 5-isoquinolinyl. In certain embodiments, at least one $R_1$ is unsubstituted 6-isoquinolinyl. In certain embodiments, at least one $R_1$ is substituted or unsubstituted indolyl. In certain embodiments, at least one $R_1$ is substituted or unsubstituted isoindolyl. In certain embodiments, at least one $R_1$ is substituted or unsubstituted benzothienyl. In certain embodiments, at least one $R_1$ is substituted or unsubstituted benzofuranyl. In certain embodiments, at least one $R_1$ is substituted or unsubstituted dibenzofuranyl. In certain embodiments, at least one $R_1$ is substituted or unsubstituted indazolyl. In certain embodiments, at least one $R_1$ is substituted or unsubstituted benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, $R_2$ is hydrogen. In certain embodiments, $R_2$ is or $C_1$-$C_6$ aliphatic. In some embodiments, $R_2$ is substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, $R_2$ is hydrogen or methyl, and $R_3$ is hydrogen or methyl. In certain embodiments, $R_2$ is methyl, and $R_3$ is hydrogen. In certain embodiments, $R_2$ is hydrogen, and $R_3$ is methyl. In certain embodiments, both $R_2$ and $R_3$ are hydrogen. In certain embodiments, both $R_2$ and $R_3$ are methyl.

In certain embodiments, at least one $R_4$ is hydrogen. In certain embodiments, at least one $R_4$ is halogen. In certain embodiments, at least one $R_4$ is fluorine. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ is $C_1$-$C_6$ alkyl substituted with an aryl group. In certain embodiments, at least one $R_4$ comprises biotin or a biotin derivative. In certain embodiments, at least one $R_4$ is a

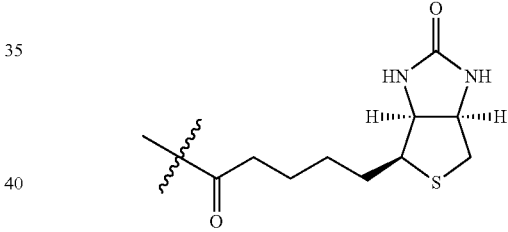

moiety. In certain embodiments, at least one $R_4$ is a

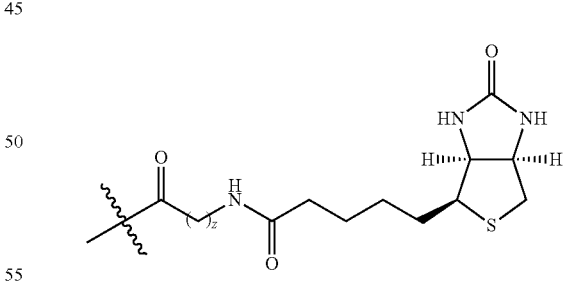

moiety wherein z is an integer between 2 and 10, inclusive. In certain embodiments, at least one $R_4$ is a benzyl group. In certain embodiments, at least one $R_4$ is —$OR_D$ wherein $R_D$ is hydrogen. In certain embodiments, at least one $R_4$ is —$OR_D$ wherein $R_D$ is $C_1$-$C_6$ alkyl. In certain embodiments, at least one $R_4$ wherein z is an integer methyl. In certain embodiments, at least one $R_4$ is —$OR_D$ wherein $R_D$ is ethyl. In certain embodiments, at least one $R_4$ is —$OR_D$ wherein $R_D$ is propyl. In certain embodiments, at least one $R_4$ is —$N(R_D)_2$, wherein each $R_D$ is hydrogen or $C_1$-$C_6$ alkyl. In certain embodiments, at least one $R_4$ is —$N(R_D)_2$, wherein each $R_D$ is $C_1$-$C_6$ alkyl. In certain embodiments, at least one $R_4$ is —N($R_D$)$_2$, wherein each $R_D$ is methyl. In certain embodiments, at least one $R_4$ is —N($R_D$)$_2$, wherein each $R_D$ is ethyl. In certain embodiments, at least one $R_4$ is —N($R_D$)$_2$, wherein each $R_D$ is propyl. In certain embodiments, at least one $R_4$ is —N($R_D$)$_2$, wherein each $R_D$ is butyl. In certain embodiments, at least one $R_4$ is —N($R_D$)$_2$, wherein each $R_D$ is pentyl. In certain embodiments, at least one $R_4$ is —N($R_D$)$_2$, wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, the compound is of formula:

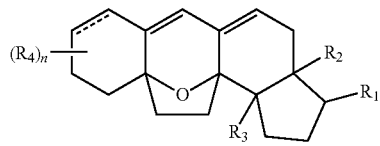

wherein $R_1$, $R_2$, $R_3$, $R_4$, and n are as defined herein.

In certain embodiments, the compound is of formula:

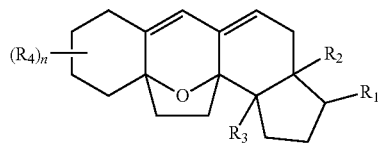

wherein $R_1$, $R_2$, $R_3$, $R_4$, and n are as defined herein.

In certain embodiments, the compound is of formula:

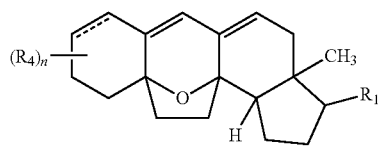

wherein $R_1$, $R_4$, and n are as defined herein.

In certain embodiments, the compound is of formula:

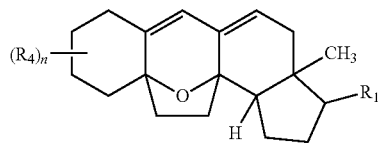

wherein $R_1$, $R_4$, and n are as defined herein.

In certain embodiments, the compound is of formula:

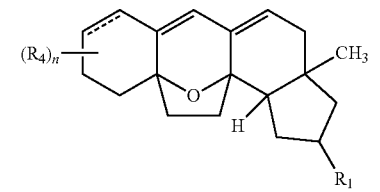

wherein $R_1$, $R_4$, and n are as defined herein.

In certain embodiments, the compound is of formula:

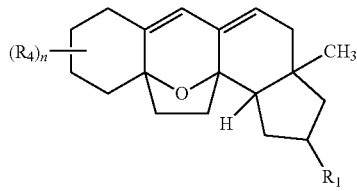

wherein $R_1$, $R_4$, and n are as defined herein.

In certain embodiments, the compound is of formula:

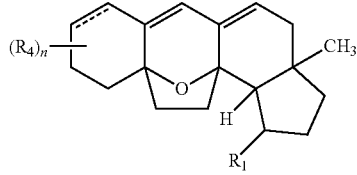

wherein $R_1$, $R_4$, and n are as defined herein.

In certain embodiments, the compound is of formula:

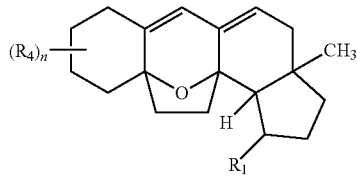

wherein $R_1$, $R_4$, and n are as defined herein.

In certain embodiments, the compound is of formula:

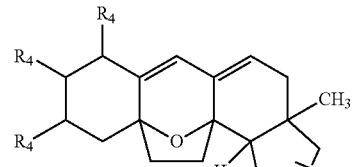

wherein $R_1$ and $R_4$ are as defined herein.

In certain embodiments, the compound is of formula:

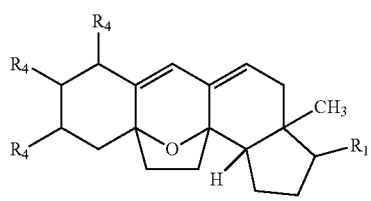

wherein $R_1$ and $R_4$ are as defined herein.

In certain embodiments, the compound is of formula:

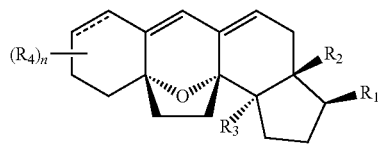

wherein $R_1$, $R_2$, $R_3$, $R_4$, and n are as defined herein.

In certain embodiments, the compound is of formula:

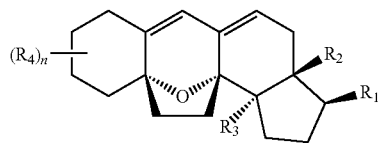

wherein $R_1$, $R_2$, $R_3$, $R_4$, and n are as defined herein.

In certain embodiments, the compound is of formula:

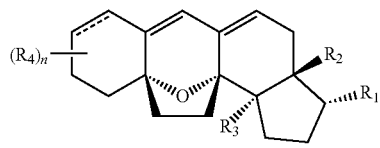

wherein $R_1$, $R_2$, $R_3$, $R_4$, and n are as defined herein.

In certain embodiments, the compound is of formula:

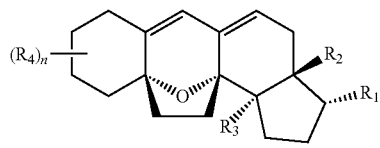

wherein $R_1$, $R_2$, $R_3$, $R_4$, and n are as defined herein.

In certain embodiments, the compound is of formula:

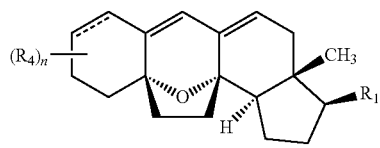

wherein $R_1$, $R_4$, and n are as defined herein.

In certain embodiments, the compound is of formula:

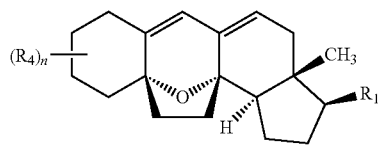

wherein $R_1$, $R_4$, and n are as defined herein.

In certain embodiments, the compound is of formula:

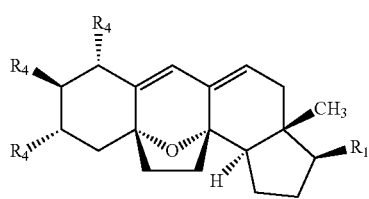

wherein $R_1$ and $R_4$ are as defined herein.

In certain embodiments, the compound is of formula:

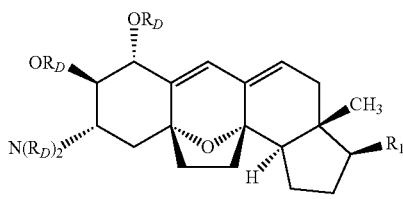

wherein $R_1$ and $R_D$ are as defined herein.

In certain embodiments, the compound is of formula:

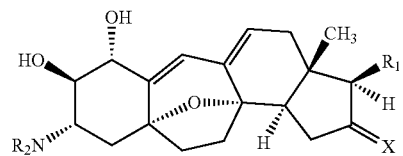

wherein $R_1$ and $R_2$ are as defined herein; and X is =O, =NR, =NOH, or =NSO$_2$R. In certain embodiments, X is =O.

In certain embodiments, the compound is of formula:

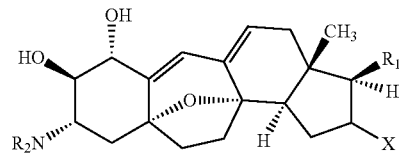

wherein $R_1$ and $R_2$ are as defined herein; and X is —R, —Ar, —NR$_2$, or —OR. In certain embodiments, X is —OR. In certain embodiments, X is —OH.

In certain embodiments, the compound is of formula:

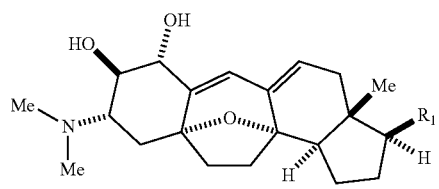

wherein $R_1$ is as defined herein.

In certain embodiments, the compound is of formula:

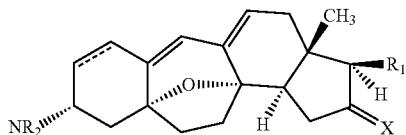

wherein $R_1$ and $R_2$ are as defined herein; and X is =O, =NR, =NOH, or =NSO$_2$R. In certain embodiments, X is =O.

In certain embodiments, the compound is of formula:

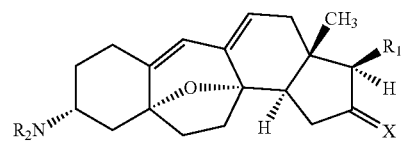

wherein $R_1$ and $R_2$ are as defined herein; and X is =O, =NR, =NOH, or =NSO$_2$R. In certain embodiments, X is =O.

In certain embodiments, the compound is of formula:

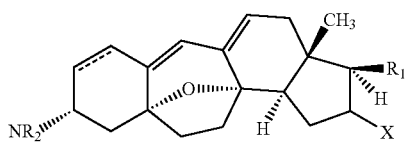

wherein $R_1$ and $R_2$ are as defined herein; and X is —R, —Ar, —NR$_2$, or —OR. In certain embodiments, X is —OH.

In certain embodiments, the compound is of formula:

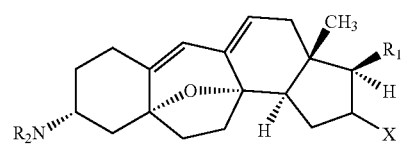

wherein $R_1$ and $R_2$ are as defined herein; and X is —R, —Ar, —NR$_2$, or —OR. In certain embodiments, X is —OH.

Below are exemplary cortistatin analogs with different substituents provided on the A- and/or D-ring.

| Potential Analogs Varying A-Ring Substituents |
|---|
| 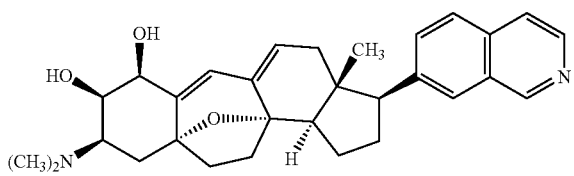 |

| Potential Analogs Varying D-Ring Appendage |
|---|
| 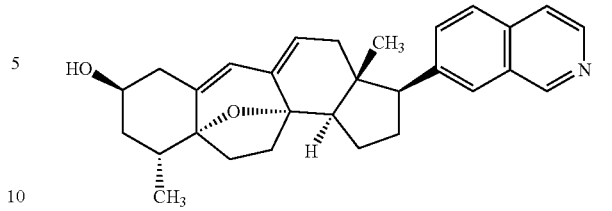 |
| 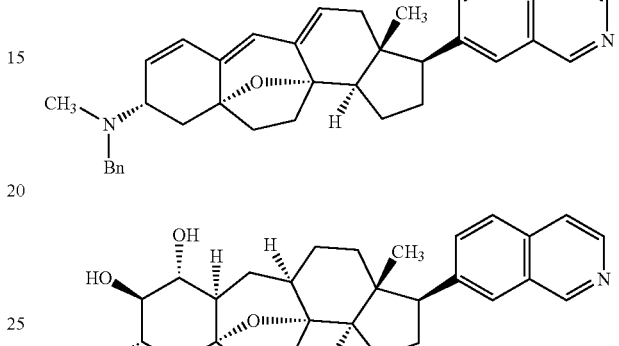 |
| 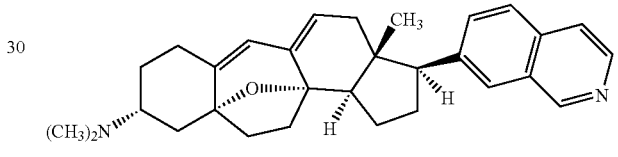 |
| 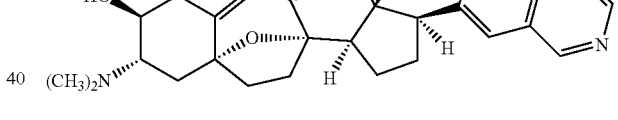 |
| 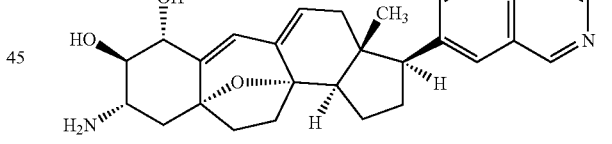 |
| 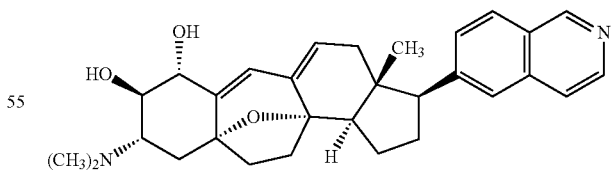 |
| 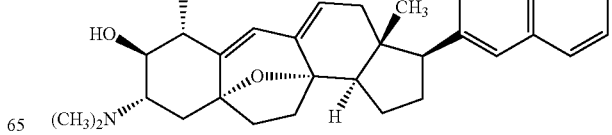 |

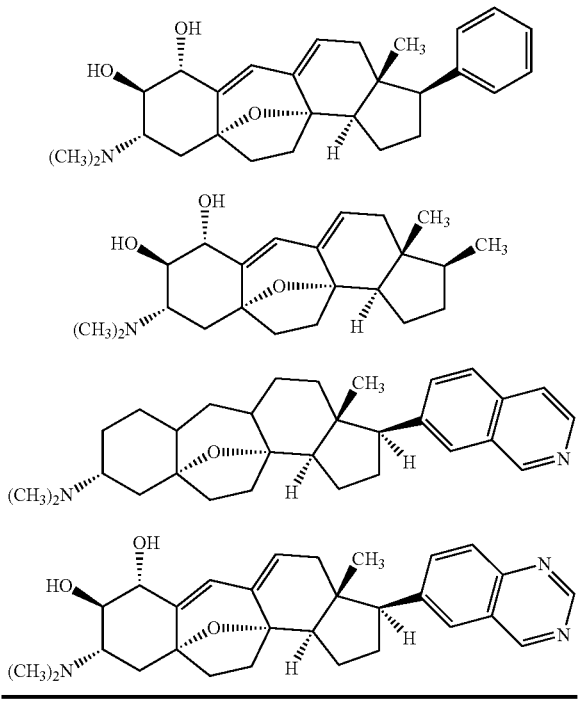

One of ordinary skill in the art would understand that various substituents on the A-ring can be combined with various substituents on the D-ring. Not only the substituents depicted above but also the substituents as defined by $R_1$ and $R_4$ may be combined to produce inventive compounds. As would be appreciated by one skilled in the art, any combination of substituents is considered to be within the scope of the present invention.

The present invention also provides truncated cortistatin analogues. Such analogues may include bicyclic, tricyclic, or four cyclic moieties of the cortistatin skeleton. The analogs may contain any subset of contiguous rings of the cortistatin skeleton (e.g., A-B, B-C, C-D, A-B-C, or B-C-D)

(a) 6-5 Fused Ring System Compounds

In certain embodiments, the compound of the invention includes the C-D ring system (i.e., a 6-5 fused ring system) of the cortistatin skeleton.

In certain embodiments, the compound is of formula:

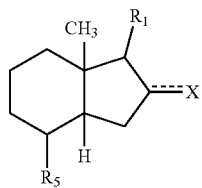

wherein
the dashed line independently represents the presence or absence of a bond;
when X is present with a single bond, then X is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_y$; —C(=O)$R_y$; —$CO_2R_y$; —CN; —SCN; —$SR_y$; —$SOR_y$; —$SO_2R_y$; —$NSO_2R_y$; —$NO_2$; —$N_3$; —NH($R_y$); —N($R_y$)$_2$; —NHC(=O)$R_y$; —$NR_yC$(=O)N ($R_y$)$_2$; —OC(=O)$OR_y$; —OC(=O)$R_y$; —OC(=O)N($R_y$)$_2$; —$NR_yC$(=O)$OR_y$; or —C($R_y$)$_3$; wherein each occurrence of $R_y$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

when X is present with a double bond, then X is =O, =S, =$NR_y$, =N($OR_y$), or =$NSO_2R_y$, wherein $R_y$ is independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl.

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; =O; =N($R_A$); =S; —N($R_A$)$_2$; —NHC(=O)$R_A$; —$NR_AC$(=O)N($R_A$)$_2$; —OC(=O)$OR_A$; —OC(=O)$R_A$; —OC(=O)N($R_A$)$_2$; —$NR_AC$(=O)$OR_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and each occurrence of $R_5$ is independently selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —C(=O)$R_E$; —C(=O)$OR_E$; —C(=O)N($R_E$)$_2$; —$SO_2R_E$; —$SO_2NR_E$; wherein each occurrence of $R_E$ is independently a hydrogen, a protecting group, a substituted or unsubstituted, branched or unbranched moiety selected from an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

In certain embodiments, the dashed line is absent to form a single bond with X. In certain embodiments, when X is present with a single bond, then X is —$OR_y$, wherein $R_y$ is hydrogen or $C_{1-6}$ alkyl. In certain embodiments, when X is present with a single bond, then X is —OH. In certain embodiments, when X is present with a single bond, then X is substituted or unsubstituted aliphatic. Exemplary aliphatic groups include hydrogen or $C_{1-6}$ alkyl. In certain embodiments, when X is present with a single bond, then X is —N($R_y$)$_2$. Exemplary $R_y$ groups include hydrogen to form X as —$NH_2$, or methyl to form X as —$NHCH_3$ or —N($CH_3$)$_2$. In certain embodiments, when X is present with a single bond, then X is a substituted or unsubstituted aryl.

In certain embodiments, the dashed line is present to form a double bond with X. In certain embodiments, when X is present with a double bond, then X is =O. In certain embodiments, when X is present with a double bond, then X is =S. In certain embodiments, when X is present with a double bond, then X is =NR$_y$, wherein R$_y$ is hydrogen or C$_{1-6}$ alkyl. In certain embodiments, when X is present with a double bond, then X is =N(OR$_y$), wherein R$_y$ is hydrogen or C$_{1-6}$ alkyl. In certain embodiments, when X is present with a double bond, then X is =NSO$_2$R$_y$, wherein R$_y$ is hydrogen or C$_{1-6}$ alkyl.

In certain embodiments, at least one R$_1$ is hydrogen. In certain embodiments, at least one R$_1$ is halogen. In certain embodiments, at least one R$_1$ is fluorine. In certain embodiments, at least one R$_1$ is substituted or unsubstituted aliphatic. In some embodiments, at least one R$_1$ is substituted or unsubstituted alkyl. In certain embodiments, at least one R$_1$ is C$_1$-C$_6$ alkyl. In certain embodiments, at least one R$_1$ is methyl. In certain embodiments, at least one R$_1$ is ethyl. In certain embodiments, at least one R$_1$ is propyl. In certain embodiments, at least one R$_1$ is substituted or unsubstituted aryl. In certain embodiments, at least one R$_1$ is substituted or unsubstituted phenyl. In certain embodiments, at least one R$_1$ is substituted phenyl. In certain embodiments, at least one R$_1$ is unsubstituted phenyl. In certain embodiments, at least one R$_1$ is substituted or unsubstituted naphthyl. In certain embodiments, at least one R$_1$ is substituted naphthyl. In certain embodiments, at least one R$_1$ is unsubstituted naphthyl. In certain embodiments, at least one R$_1$ is substituted or unsubstituted heteroaryl. In certain embodiments, at least one R$_1$ is substituted or unsubstituted isoquinolinyl. In certain embodiments, at least one R$_1$ is substituted isoquinolinyl. In certain embodiments, at least one R$_1$ is unsubstituted isoquinolinyl. In certain embodiments, at least one R$_1$ is unsubstituted 5-isoquinolinyl. In certain embodiments, at least one R$_1$ is unsubstituted 6-isoquinolinyl.

In certain embodiments, at least one R$_1$ is substituted or unsubstituted indolyl. In certain embodiments, at least one R$_1$ is substituted or unsubstituted isoindolyl. In certain embodiments, at least one R$_1$ is substituted or unsubstituted benzothienyl. In certain embodiments, at least one R$_1$ is substituted or unsubstituted benzofuranyl. In certain embodiments, at least one R$_1$ is substituted or unsubstituted dibenzofuranyl. In certain embodiments, at least one R$_1$ is substituted or unsubstituted indazolyl. In certain embodiments, at least one R$_1$ is substituted or unsubstituted benzimidazolyl. In certain embodiments, at least one R$_1$ is substituted or unsubstituted benzthiazolyl. In certain embodiments, at least one R$_1$ is substituted or unsubstituted quinolyl. In certain embodiments, at least one R$_1$ is substituted or unsubstituted isoquinolyl. In certain embodiments, at least one R$_1$ is substituted or unsubstituted cinnolinyl. In certain embodiments, at least one R$_1$ is substituted or unsubstituted phthalazinyl. In certain embodiments, at least one R$_1$ is substituted or unsubstituted quinazolinyl. In certain embodiments, at least one R$_1$ is substituted or unsubstituted quinoxalinyl. In certain embodiments, at least one R$_1$ is substituted or unsubstituted 4H-quinolizinyl. In certain embodiments, at least one R$_1$ is substituted or unsubstituted carbazolyl. In certain embodiments, at least one R$_1$ is substituted or unsubstituted acridinyl. In certain embodiments, at least one R$_1$ is substituted or unsubstituted phenazinyl. In certain embodiments, at least one R$_1$ is substituted or unsubstituted phenothiazinyl. In certain embodiments, at least one R$_1$ is substituted or unsubstituted phenoxazinyl. In certain embodiments, at least one R$_1$ is substituted or unsubstituted tetrahydroquinolinyl. In certain embodiments, at least one R$_1$ is substituted or unsubstituted tetrahydroisoquinolinyl. In certain embodiments, at least one R$_1$ is substituted or unsubstituted pyrido[2,3-b]-1,4-oxazin-3(4H)-one.

In certain embodiments, R$_5$ is substituted or unsubstituted, branched or unbranched aliphatic. In certain embodiments, R$_5$ is C$_{1-6}$ alkyl. In certain embodiments, R$_5$ is —N(R$_E$)$_2$, wherein R$_E$ is hydrogen or C$_{1-6}$ alkyl. In certain embodiments, R$_5$ is —(C$_{1-3}$ alkyl)-N(R$_E$)$_2$, wherein R$_E$ is hydrogen or C$_{1-6}$ alkyl. In certain embodiments, R$_5$ is —C(=O)R$_E$, wherein R$_E$ is hydrogen or C$_{1-6}$ alkyl. In certain embodiments, R$_5$ is —C(=O)OR$_E$, wherein R$_E$ is hydrogen or C$_{1-6}$ alkyl. In certain embodiments, R$_5$ is —C(=O)N(R$_E$)$_2$, wherein R$_E$ is hydrogen or C$_{1-6}$ alkyl. In certain embodiments, R$_5$ is —SO$_2$R$_E$, wherein R$_E$ is hydrogen or C$_{1-6}$ alkyl. In certain embodiments, R$_5$ is —SO$_2$NR$_E$, wherein R$_E$ is hydrogen or C$_{1-6}$ alkyl.

In certain embodiments, the compound has the stereochemistry as shown in the formula below:

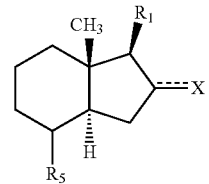

wherein the dashed line, X, R$_1$, and R$_5$ are as defined herein.

In certain embodiments, the compound has the stereochemistry as shown in the formula below:

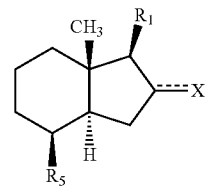

wherein the dashed line, X, R$_1$, and R$_5$ are as defined herein.

In certain embodiments, the compound has the stereochemistry as shown in the formula below:

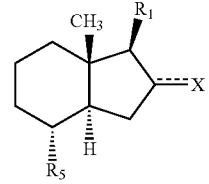

wherein the dashed line, X, R$_1$, and R$_5$ are as defined herein.

Such compounds may be useful not only as cortistatin analogs but also as intermediate in the synthesis of cortistatin analogs. In certain embodiments, the compounds may have anti-angiogenic activity. In certain embodiments, the compounds may not have anti-angiogenic activity.

In certain embodiments, when X is connected to the carbon skeleton through a double bond, the compound is of formula:

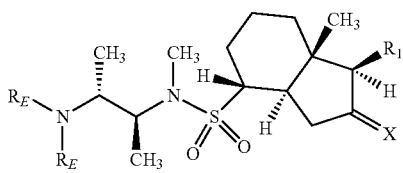

wherein X, $R_1$, and $R_E$ are as defined herein.

In certain embodiments, when X is connected to the carbon skeleton through a single bond, the compound is of formula:

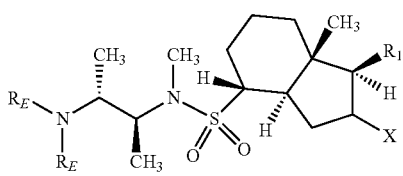

wherein X, $R_1$, and $R_E$ are as defined herein.

In certain embodiments, when X is hydrogen, the compound is of formula:

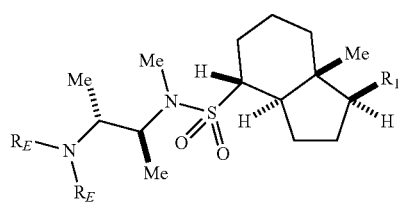

wherein $R_1$ and $R_E$ are as defined herein.

In certain embodiments, when $R_1$ is a quinolinyl and X is hydrogen, the compound is of formula:

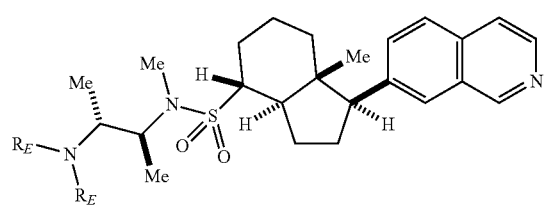

wherein $R_E$ is as defined herein.

In certain embodiments, when X is hydrogen, the compound is of formula:

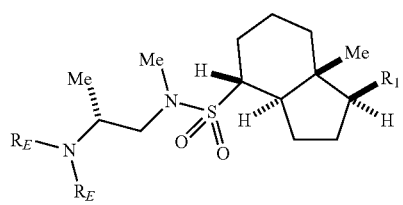

wherein $R_1$ and $R_E$ are as defined herein.

In certain embodiments, when X is hydrogen, the compound is of formula:

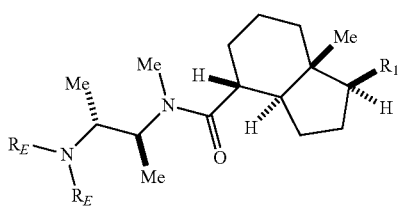

wherein $R_1$ and $R_E$ are as defined herein.

In certain embodiments, when X is hydrogen, and $R_1$ is a quinolinyl, the compound is of formula:

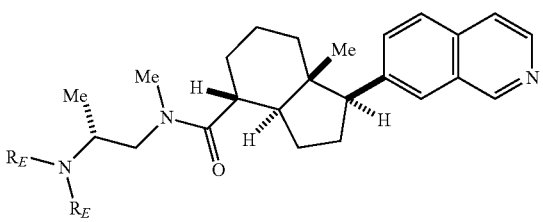

wherein $R_E$ is as defined herein.

In certain embodiments, when X is hydrogen and $R_1$ is a quinolinyl, the compound is of formula:

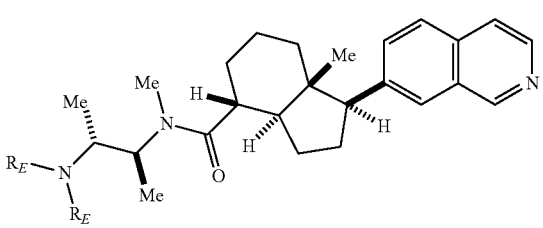

wherein $R_E$ is as defined herein.

In certain embodiments, when X is connected to the carbon skeleton through a double bond, the compound is of formula:

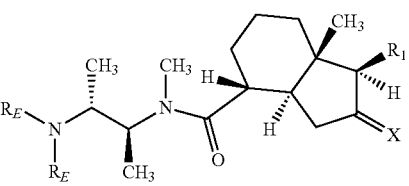

wherein X, $R_1$, and $R_E$ are as defined herein.

In certain embodiments, when X is connected to the carbon skeleton through a single bond, the compound is of formula:

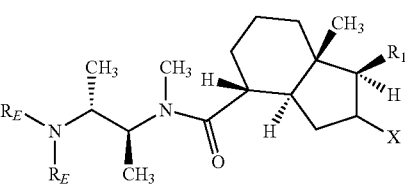

wherein X, $R_1$, and $R_E$ are as defined herein.

(b) 6-6-5 Fused Ring System Compounds

The present invention also provides compounds that include the 6-6-5 fused ring system when X is connected to the carbon skeleton through either a single bond or a double bond, as shown in the formula:

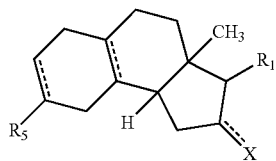

wherein each of the dashed lines independently represents the presence or absence of a bond;

when X is present with a single bond, then X is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_y$; —$C(=O)R_y$; —$CO_2R_y$; —CN; —SCN; —$SR_y$; —$SOR_y$; —$SO_2R_y$; —$NSO_2R_y$; —$NO_2$; —$N_3$; —$NH(R_y)$; —$N(R_y)_2$; —$NHC(=O)R_y$; —$NR_yC(=O)N(R_y)_2$; —$OC(=O)OR_y$; —$OC(=O)R_y$; —$OC(=O)N(R_y)_2$; —$NR_yC(=O)OR_y$; or —$C(R_y)_3$; wherein each occurrence of $R_y$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

when X is present with a double bond, then X is =O, =S, =$NR_y$, =$N(OR_y)$, or =$NSO_2R_y$, wherein $R_y$ is independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl.

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and each occurrence of $R_5$ is independently selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —$C(=O)R_E$; —$C(=O)OR_E$; —$C(=O)N(R_E)_2$; —$SO_2R_E$; —$SO_2NR_E$; wherein each occurrence of $R_E$ is independently a hydrogen, a protecting group, a substituted or unsubstituted, branched or unbranched moiety selected from an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, the dashed line is absent to form a single bond with X. In certain embodiments, when X is present with a single bond, then X is —$OR_y$, wherein $R_y$ is hydrogen or $C_{1-6}$ alkyl. In certain embodiments, when X is present with a single bond, then X is —OH. In certain embodiments, when X is present with a single bond, then X is substituted or unsubstituted aliphatic. Exemplary aliphatic groups include hydrogen or $C_{1-6}$ alkyl. In certain embodiments, when X is present with a single bond, then X is —$N(R_y)_2$. Exemplary $R_y$ groups include hydrogen to form X as —$NH_2$, or methyl to form X as —$NHCH_3$ or —$NH(CH_3)_2$. In certain embodiments, when X is present with a single bond, then X is substituted or unsubstituted aryl.

In certain embodiments, the dashed line represents a bond to form a double bond with X. In certain embodiments, when X is present with a double bond, then X is =O. In certain embodiments, when X is present with a double bond, then X is =S. In certain embodiments, when X is present with a double bond, then X is =$NR_y$, wherein $R_y$ is hydrogen or $C_{1-6}$ alkyl. In certain embodiments, when X is present with a double bond, then X is =$N(OR_y)$, wherein $R_y$ is hydrogen or $C_{1-6}$ alkyl. In certain embodiments, when X is present with a double bond, then X is =$NSO_2R_y$, wherein $R_y$ is hydrogen or $C_{1-6}$ alkyl.

In certain embodiments, at least one $R_1$ is hydrogen. In certain embodiments, at least one $R_1$ is halogen. In certain embodiments, at least one $R_1$ is fluorine. In certain embodiments, at least one $R_1$ is substituted or unsubstituted aliphatic. In some embodiments, at least one $R_1$ is substituted or unsubstituted alkyl. In certain embodiments, at least one $R_1$ is $C_1$-$C_6$ alkyl. In certain embodiments, at least one $R_1$ is methyl. In certain embodiments, at least one $R_1$ is ethyl. In certain embodiments, at least one $R_1$ is propyl. In certain embodiments, at least one $R_1$ is substituted or unsubstituted aryl. In certain embodiments, at least one $R_1$ is substituted or unsubstituted phenyl. In certain embodiments, at least one $R_1$ is substituted phenyl. In certain embodiments, at least one $R_1$ is unsubstituted phenyl. In certain embodiments, at least one $R_1$ is substituted or unsubstituted naphthyl. In certain embodiments, at least one $R_1$ is substituted naphthyl. In certain embodiments, at least one $R_1$ is unsubstituted naphthyl. In certain embodiments, at least one $R_1$ is substituted or unsubstituted heteroaryl. In certain embodiments, at least one $R_1$ is substituted or unsubstituted isoquinolinyl. In certain embodiments, at least one $R_1$ is substituted isoquinolinyl. In certain embodiments, at least one $R_1$ is unsubstituted isoquinolinyl. In certain embodiments, at least one $R_1$ is unsubstituted 5-isoquinolinyl. In certain embodiments, at least one $R_1$ is unsubstituted 6-isoquinolinyl. In certain embodiments, at least one $R_1$ is substituted or unsubstituted indolyl. In certain embodiments, at least one $R_1$ is substituted or unsubstituted isoindolyl. In certain embodiments, at least one $R_1$ is substituted or unsubstituted benzothienyl. In certain embodiments, at least one $R_1$ is substituted or unsubstituted benzofuranyl. In certain embodiments, at least one $R_1$ is substituted or unsubstituted dibenzofuranyl. In certain embodiments, at least one $R_1$ is substituted or unsubstituted indazolyl. In certain embodiments, at least one $R_1$ is substituted or unsubstituted benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, $R_5$ is substituted or unsubstituted, branched or unbranched aliphatic. In certain embodiments, $R_5$ is $C_{1-6}$ alkyl. In certain embodiments, $R_5$ is $-N(R_E)_2$, wherein $R_E$ is hydrogen or $C_{1-6}$ alkyl. In certain embodiments, $R_5$ is $-(C_{1-3}alkyl)-N(R_E)_2$, wherein $R_E$ is hydrogen or $C_{1-6}$ alkyl. In certain embodiments, $R_5$ is $-C(=O)R_E$, wherein $R_E$ is hydrogen or $C_{1-6}$ alkyl. In certain embodiments, $R_5$ is $-C(=O)OR_E$, wherein $R_E$ is hydrogen or $C_{1-6}$ alkyl. In certain embodiments, $R_5$ is $-C(=O)N(R_E)_2$, wherein $R_E$ is hydrogen or $C_{1-6}$ alkyl. In certain embodiments, $R_5$ is $-SO_2R_E$, wherein $R_E$ is hydrogen or $C_{1-6}$alkyl. In certain embodiments, $R_5$ is $-SO_2NR_E$, wherein $R_E$ is hydrogen or $C_{1-6}$alkyl.

In certain embodiments, when X is connected to the carbon skeleton through a single bond, $R_1$ is an optionally substituted heterocyclic moiety, and $R_4$ is a substituted aliphatic moiety, the compound is of formula:

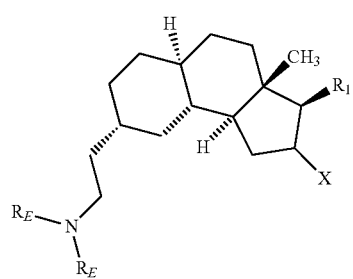

wherein X, $R_1$, and $R_E$ are as defined herein.
In certain embodiments, the compound is of formula:

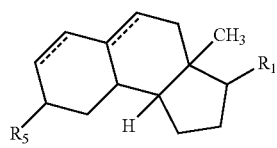

wherein $R_1$, and $R_5$ are as defined herein.

In certain embodiments, when $R_1$ is an optionally substituted heterocyclic moiety and $R_4$ is a substituted aliphatic moiety, the compound is of formula:

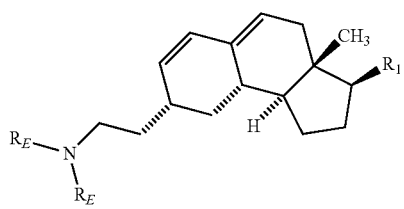

wherein $R_1$ and $R_E$ are as defined herein.

(c) 6-6-6-5 Fused Ring System Compounds

The present invention also provides compounds that include the 6-6-6-5 fused ring system, as shown in the formula:

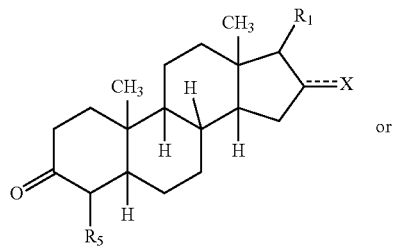

or

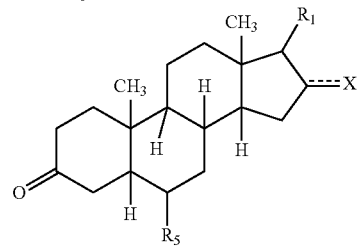

wherein
the dashed line independently represents the presence or absence of a bond;
when X is present with a single bond, then X is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_y$; $-C(=O)R_y$; $-CO_2R_y$; $-CN$; $-SCN$; $-SR_y$; $-SOR_y$; $-SO_2R_y$; $-NSO_2R_y$; $-NO_2$; $-N_3$; $-NH(R_y)$; $-N(R_y)_2$; $-NHC(=O)R_y$; $-NR_yC(=O)N(R_y)_2$; $-OC(=O)OR_y$; $-OC(=O)R_y$; $-OC(=O)N(R_y)_2$; $-NR_yC(=O)OR_y$; or $-C(R_y)_3$; wherein each occurrence of $R_y$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
when X is present with a double bond, then X is $=O$, $=S$, $=NR_y$, $=N(OR_y)$, or $=NSO_2R_y$, wherein $R_y$ is independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl;

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and each occurrence of $R_5$ is independently selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —$C(=O)R_E$; —$C(=O)OR_E$; —$C(=O)N(R_E)_2$; —$SO_2R_E$; —$SO_2NR_E$; wherein each occurrence of $R_E$ is independently a hydrogen, a protecting group, a substituted or unsubstituted, branched or unbranched moiety selected from an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts thereof.

In certain embodiments, the dashed line is absent to form a single bond with X. In certain embodiments, when X is present with a single bond, then X is —$OR_y$, wherein $R_y$ is hydrogen or $C_{1-6}$ alkyl. In certain embodiments, when X is present with a single bond, then X is —OH. In certain embodiments, when X is present with a single bond, then X is substituted or unsubstituted aliphatic. Exemplary aliphatic groups include hydrogen or $C_{1-6}$ alkyl. In certain embodiments, when X is present with a single bond, then X is —$N(R_y)_2$. Exemplary $R_y$ groups include hydrogen to form X as —$NH_2$, or methyl to form X as —$NHCH_3$ or —$NH(CH_3)_2$. In certain embodiments, when X is present with a single bond, then X is a substituted or unsubstituted aryl.

In certain embodiments, the dashed line is present to form a double bond with X. In certain embodiments, when X is present with a double bond, then X is =O. In certain embodiments, when X is present with a double bond, then X is =S. In certain embodiments, when X is present with a double bond, then X is =$NR_y$, wherein $R_y$ is hydrogen or $C_{1-6}$ alkyl. In certain embodiments, when X is present with a double bond, then X is =$N(OR_y)$, wherein $R_y$ is hydrogen or $C_{1-6}$ alkyl. In certain embodiments, when X is present with a double bond, then X is =$NSO_2R_y$, wherein $R_y$ is hydrogen or $C_{1-6}$ alkyl.

In certain embodiments, at least one $R_1$ is hydrogen. In certain embodiments, at least one $R_1$ is halogen. In certain embodiments, at least one $R_1$ is fluorine. In certain embodiments, at least one $R_1$ is substituted or unsubstituted aliphatic. In some embodiments, at least one $R_1$ is substituted or unsubstituted alkyl. In certain embodiments, at least one $R_1$ is $C_1$-$C_6$ alkyl. In certain embodiments, at least one $R_1$ is methyl. In certain embodiments, at least one $R_1$ is ethyl. In certain embodiments, at least one $R_1$ is propyl. In certain embodiments, at least one $R_1$ is substituted or unsubstituted aryl. In certain embodiments, at least one $R_1$ is substituted or unsubstituted phenyl. In certain embodiments, at least one $R_1$ is substituted phenyl. In certain embodiments, at least one $R_1$ is unsubstituted phenyl. In certain embodiments, at least one $R_1$ is substituted or unsubstituted naphthyl. In certain embodiments, at least one $R_1$ is substituted naphthyl. In certain embodiments, at least one $R_1$ is unsubstituted naphthyl. In certain embodiments, at least one $R_1$ is substituted or unsubstituted heteroaryl. In certain embodiments, at least one $R_1$ is substituted or unsubstituted isoquinolinyl. In certain embodiments, at least one $R_1$ is substituted isoquinolinyl. In certain embodiments, at least one $R_1$ is unsubstituted isoquinolinyl. In certain embodiments, at least one $R_1$ is unsubstituted 5-isoquinolinyl. In certain embodiments, at least one $R_1$ is unsubstituted 6-isoquinolinyl. In certain embodiments, at least one $R_1$ is substituted or unsubstituted indolyl. In certain embodiments, at least one $R_1$ is substituted or unsubstituted isoindolyl. In certain embodiments, at least one $R_1$ is substituted or unsubstituted benzothienyl. In certain embodiments, at least one $R_1$ is substituted or unsubstituted benzofuranyl. In certain embodiments, at least one $R_1$ is substituted or unsubstituted dibenzofuranyl. In certain embodiments, at least one $R_1$ is substituted or unsubstituted indazolyl. In certain embodiments, at least one $R_1$ is substituted or unsubstituted benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, $R_5$ is substituted or unsubstituted, branched or unbranched aliphatic. In certain embodiments, $R_5$ is $C_{1-6}$ alkyl. In certain embodiments, $R_5$ is —$N(R_E)_2$, wherein $R_E$ is hydrogen or $C_{1-6}$ alkyl. In certain embodiments, $R_5$ is —($C_{1-3}$ alkyl)-$N(R_E)_2$, wherein $R_E$ is hydrogen or $C_{1-6}$ alkyl. In certain embodiments, $R_5$ is —$C(=O)R_E$, wherein $R_E$ is hydrogen or $C_{1-6}$ alkyl. In certain embodiments, $R_5$ is —$C(=O)OR_E$, wherein $R_E$ is hydrogen or $C_{1-6}$ alkyl. In certain embodiments, $R_5$ is —$C(=O)N(R_E)_2$, wherein $R_E$ is hydrogen or $C_{1-6}$ alkyl. In certain embodiments, $R_5$ is —$SO_2R_E$, wherein $R_E$ is hydrogen or $C_{1-6}$ alkyl. In certain embodiments, $R_5$ is —$SO_2NR_E$, wherein $R_E$ is hydrogen or $C_{1-6}$ alkyl.

In certain embodiments, the compound is of formula:

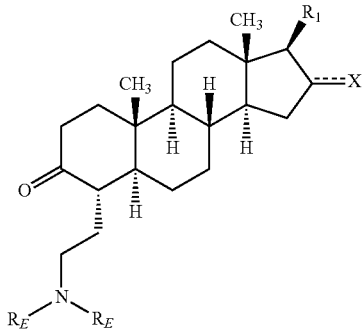

wherein X, $R_1$, and $R_E$ are as defined herein.

In certain embodiments, the compound is of formula:

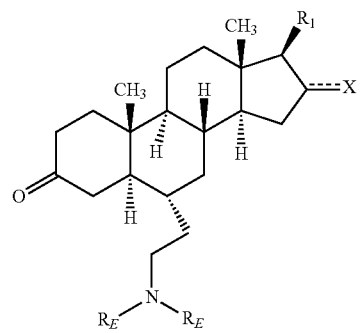

wherein X, $R_1$, and $R_E$ are as defined herein.

In certain embodiments, when X is not present, the compound is of formula:

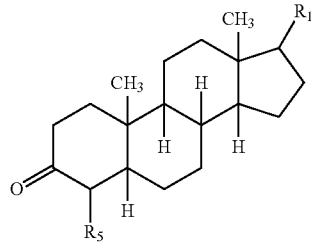

wherein $R_1$ and $R_5$ are as defined herein.

In certain embodiments, when X is not present, the compound is of formula:

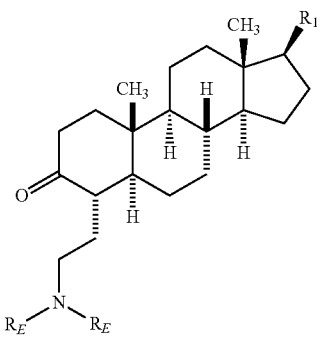

wherein $R_1$ and $R_E$ are as defined herein.

II. Methods of Synthesis

The present invention provides methods of preparing cortistatins A, J, K, L, and cortistatin analogs. In certain embodiments, the present invention provides methods of synthesizing an inventive compound. In other embodiments, the present invention provides methods of synthesizing a cortistatin natural product (e.g., cortistatin A, cortistatin B, cortistatin C, cortistatin J, cortistatin K, cortistatin L, etc.). As would be appreciated by one of skill in the art, the synthetic methods described herein may be modified without departing from the scope of the present invention. For example, different starting materials and/or different reagents may be used in the inventive synthetic methods.

In certain embodiments, the inventive compounds are prepared via a route that goes through the epoxide depicted below (see exemplary Route I or Route II as described below), followed by conversion to Intermediate 2. Intermediate 2 is then converted to cortistatin A or a cortistatin analog.

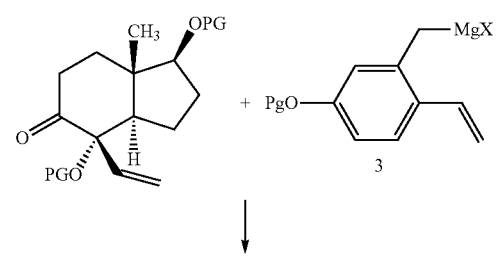

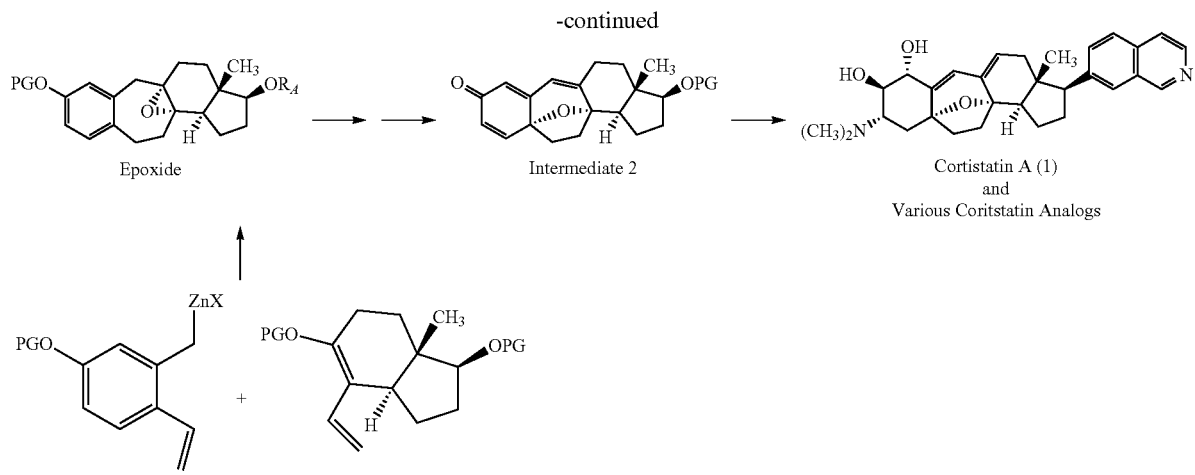

Epoxide → Intermediate 2 → Cortistatin A (1) and Various Coritstatin Analogs

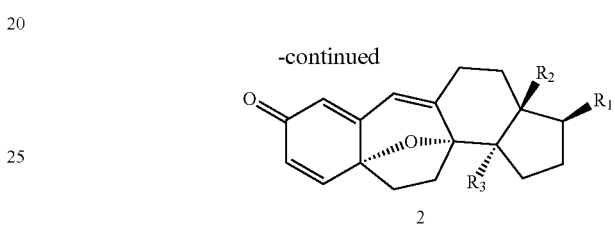

General Methods

Provided below are two general methods for preparing Intermediate 2 (Route I and Route II).

Route I Synthesis of Intermediate 2

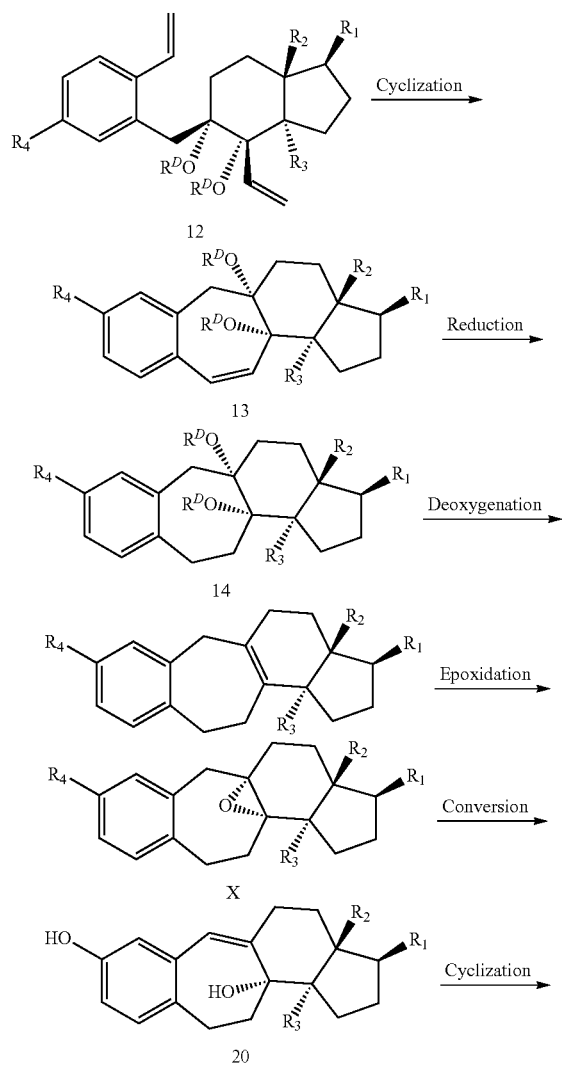

The present invention provides a process for preparing intermediate 2 according to the steps depicted in the scheme above. In the scheme, $R_1$, $R_2$, $R_3$, $R_4$, and $R_D$ are as defined herein. To begin, a compound of formula 12 is cyclized under suitable conditions in the presence of an olefin metathesis catalyst to form a compound of formula 13. In certain embodiments, the olefin metathesis catalyst is a Grubbs catalyst. In certain embodiments, the olefin metathesis catalyst is a Grubbs III catalyst. In certain embodiments, the catalyst is a ruthenium-based catalyst. In certain embodiments, approximately 5 mol % of the catalyst is used. In certain embodiments, approximately 10 mol % of the catalyst is used. In certain embodiments, approximately 15 mol % of the catalyst is used. In certain embodiments, the ring closing metathesis reaction is performed in a suitable solvent. In certain embodiments, the suitable solvent is a hydrocarbon solvent. In certain embodiments, toluene is used as the solvent.

In the following step, a compound of formula 13 is reduced using a suitable reducing agent to form a compound of formula 14. For example, reduction of the double bond is achieved by catalytic reduction with Pd(OH)$_2$ under a hydrogen atmosphere. Other suitable reductive conditions may also be used. In an alternative method, the reduction step may be performed using other methods known to one of ordinary skill in the art.

In the following step, the compound of formula 14 is deoxygenated under suitable conditions to form an alkene as shown in the scheme above. In certain embodiments, the suitable conditions include the presence of HC(OEt)$_3$. In certain embodiments, the deoxygenation step is done in the presence of a suitable solvent. In certain embodiments, the solvent is a halogenated hydrocarbon solvent. In certain embodiments, the halogenated hydrocarbon solvent is 1,2-dichlorobenzene. In certain embodiments, the deoxygenation step is performed in the presence of an organic acid. In certain embodiments, the organic acid is acetic acid.

In the following step, the alkene is epoxidized under suitable conditions to form an epoxide. In certain embodiments, the epoxidizing agent is a peroxycarboxylic acid. In certain embodiments, the epoxidizing agent is meta-chloroperoxybenzoic acid (mCPBA). In certain embodiments, the epoxidizing agent is DMDO. Other epoxidizing reagents may also be used.

In the following conversion step, a compound of formula X, wherein $R_4$ is a suitably protected hydroxyl group, is deprotected to form a compound 20. One skilled in the art will appreciate that the protecting group of $R_4$ can be exchanged with a different protecting group prior to deprotection and the epoxide ring opening to form compound 20. In some embodiments, the protecting group is a silyl protecting group. In other embodiments, the suitable protecting group is triisopropylsilyl (to form a TIPSO group). In some embodiments, the deprotecting agent is a suitable quaternary ammonium salt. In certain embodiments, the deprotecting agent is TBAF.

In the final step, a compound of formula 20 is cyclized under suitable conditions in the presence of a suitable Vargolis hypervalent iodine reagent, to form Intermediate 2. In certain embodiments, the hypervalent iodine reagent is $PhI(OCOCF_3)_2$. In certain embodiments, the cyclizing step is typically done in the presence of a suitable solvent and a suitable buffer. Exemplary solvents include dichloromethane. An exemplary buffer includes 2,6-lutidine.

In each of the above described steps, the $R_1$, $R_2$, $R_3$, $R_4$, and $R_D$ groups of the various formulae are as described herein.

In some embodiments, the $R_D$ groups of formulae 12 and 13 optionally include a suitable oxygen protecting groups. Suitable hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Exemplary $R_D$ groups of formulae 12 and 13 include benzyl, TIPS, TBS, PMB, TES, and the like.

Route II as depicted below provides an alternative approach for preparing Intermediate 2.

Route II Synthesis of Intermediate 2

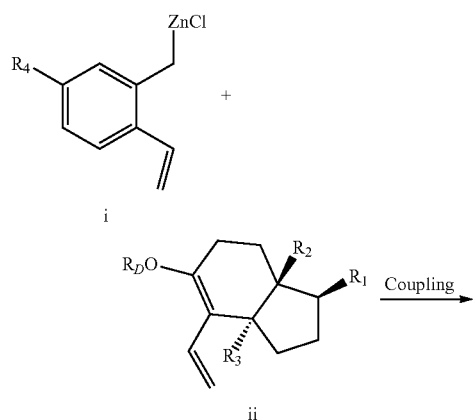

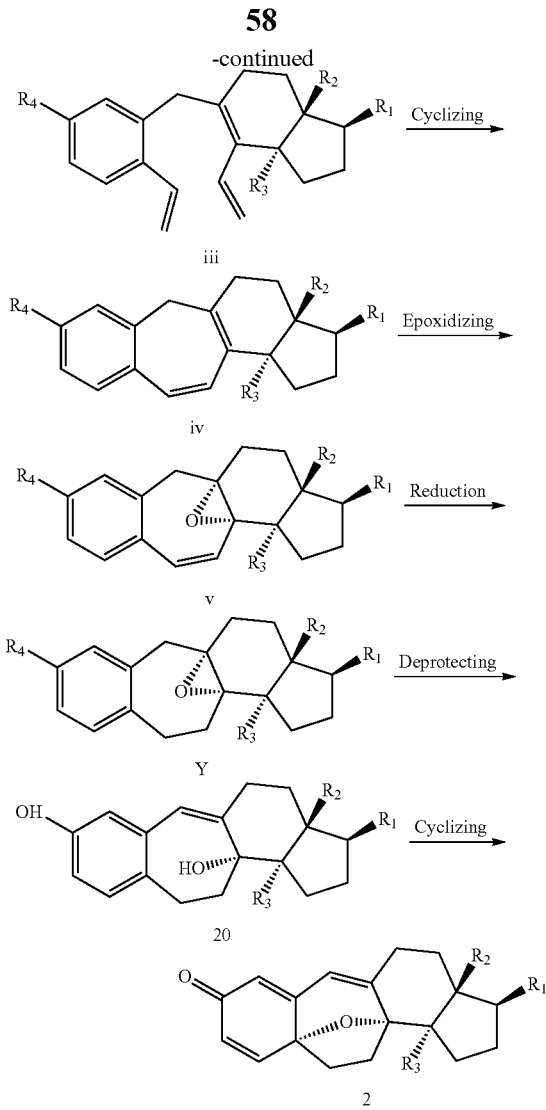

The present invention provides a process for preparing compound 2 according to the steps depicted in the scheme above. A compound of formula i is coupled to a compound of formula ii in the presence of an appropriate coupling reagent to form a compound of formula iii. In certain embodiments, the coupling reagent is a palladium-containing coupling reagent. In certain embodiments, the coupling reagent is $Pd_2dba_3$. The coupling step is typically performed in the presence of a suitable organophosphorous compound. An exemplary organophosphorus compound is S-Phos. The coupling reaction is typically performed in a suitable solvent. In certain embodiments, the suitable solvent is a mixture of polar, aprotic solvents. In certain embodiments, the polar, aprotic solvents include NMP and THF.

In the following step, the compound of formula iii is cyclized under suitable conditions in the presence of an olefin metathesis catalyst to form a compound of formula iv. In certain embodiments, the olefin metathesis catalyst is a Grubbs III catalyst. In certain embodiments, approximately 5 mol % of the catalyst is used. In certain embodiments, approximately 10 mol % of the catalyst is used. In certain embodiments, approximately 15 mol % of the catalyst is used. In other embodiments, the cyclization reaction is done in a suitable solvent. In certain embodiments, the solvent is a hydrocarbon solvent. Exemplary solvents include toluene.

In the following step, the compound of formula iv is epoxidized under suitable conditions in the presence of a suitable oxidizing agent to form an epoxide-containing compound of formula v. In certain embodiments, the oxidizing agent is a peroxycarboxylic acid. In some embodiments, the oxidizing agent is meta-chloroperoxybenzoic acid (mCPBA). In other embodiments, the oxidizing agent is DMDO.

In the following step, the compound of formula v is reduced using a suitable reducing agent to form a compound of formula Y, followed by the removal of the $R_4$ protecting In certain embodiments, the $R_D$ group of formulae 12 and 13 is a suitable hydroxyl protecting group. Suitable hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Exemplary $R^D$ groups of formulae 12 and 13 include benzyl, TIPS, TBS, PMB, TES, Tf, and the like.

Conversion of Intermediate 2 to Protected Precursors of Cortistatin A

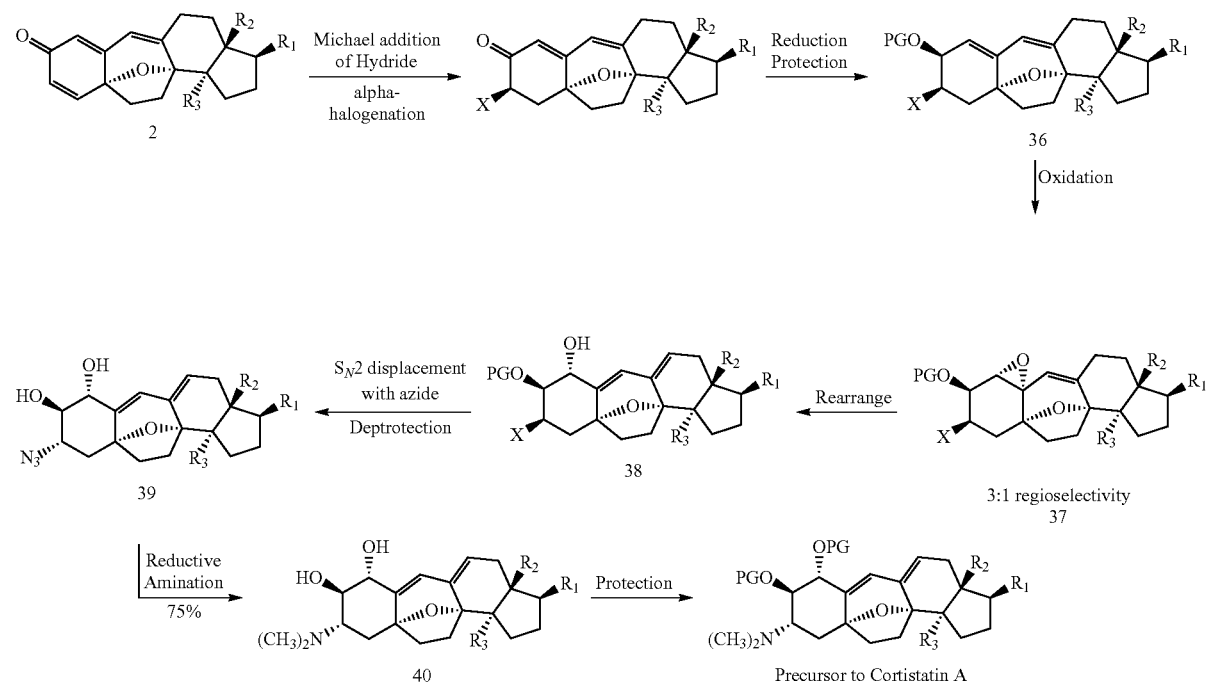

group of formula Y using a suitable deprotecting agent to afford the compound of formula 20. In certain embodiments, the reduction of the double bond of compound v is achieved using Pd/BaSO$_4$ and hydrogen in a suitable solvent. An exemplary solvent is ethyl acetate. Alternatively, the reduction of the double bond is achieved using nBSH in the presence of N(Et$_3$) in a suitable solvent. An exemplary solvent is DCM. In some embodiments, the protecting group is a silyl protecting group. In other embodiments, the protecting group is a triisopropylsilyl protecting group. In some embodiments, the deprotecting agent is a suitable quaternary ammonium salt. In certain embodiments, the deprotecting agent is TBAF.

In the final step, a compound of formula 20 is cyclized under suitable conditions in the presence of a suitable Vargolis hypervalent iodine reagent, to form Intermediate 2. In certain embodiments, the hypervalent iodine reagent is PhI(OCOCF$_3$)$_2$. In certain embodiments, the cyclizing step is typically done in the presence of a suitable solvent and a suitable buffer. Exemplary solvents include dichloromethane. An exemplary buffer includes 2,6-lutidine.

In the above-described steps, the $R_1$, $R_2$, $R_3$, $R_4$, and $R_D$ groups of the various formulae are as described herein.

The present invention provides a process for preparing cortistatins, including cortistatin A, or analogs thereof, from intermediate 2 according to the steps depicted in the scheme above. Cyclohexyldienone 2 is initially subjected to a Michael addition of hydride, and the intermediate is quenched by an electrophilic halogen source as depicted above. Reduction of the ketone and protection of the resulting alcohol yields diene 36. In some embodiments, reduction is accomplished with tributoxylithium aluminum hydride. Allylic oxidation yields epoxide 37. In some embodiments, oxidation is accomplished with dimethyldioxirane. Rearrangement yields alcohol 38. Stereoselective S$_N$2 displacement of X is accomplished with azide. Deprotection, reduction of azide 39 to the primary amine, and reductive amination to dimethylamine 40 is followed by protection of the hydroxyl groups to yield protected precursor 16, which can be converted to (+)-cortistatin A according to the methods described herein. In some embodiments, protection of the hydroxyl groups is accomplished with acetyl esters.

Conversion of Intermediate 2 to Cortistatin A

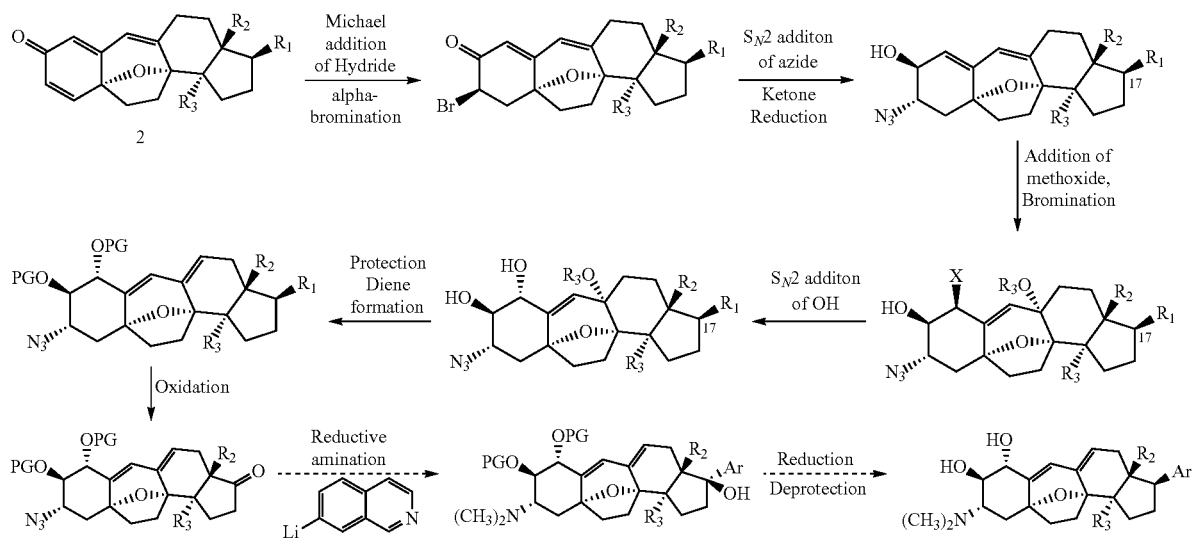

The present invention provides alternative processes for preparing cortistatins, including cortistatin A, or analogs thereof, from intermediate 2 according to the steps depicted in the scheme above. In the scheme, $R_1$, $R_2$, $R_3$, and PG are as defined herein. To begin, cyclohexyldienone 2 is subjected to a transition metal-catalyzed Michael addition of hydride. In some embodiments, the transition metal catalyst is rhodium. Quenching a proposed enol intermediate with an electrophilic halogen source stereoselectively yields the α-halide product shown. In some embodiments, the electrophilic halogen source is N-bromosuccinimide (NBS). $S_N2$ displacement of the α-halide substituent with azide and reduction of the ketone yield the azidohydroxydiene derivative shown. In some embodiments, $S_N2$ displacement is accomplished with tetramethylguanidinium azide (TMGA).

acidic conditions. In some embodiments, $S_N2$ displacement is accomplished with Crown ether and potassium superoxide in polar aprotic solvent. The diol functionality is protected before an oxidation sequence yields the corresponding cyclopentanone structure shown above. In some embodiments, oxidation is accomplished with Dess-Martin periodinane. Stereoselective 1,2-addition of 7-lithioisoquinoline to the cyclopentanone results in the tertiary alcohol shown, which is reduced with inversion of configuration. In some embodiments, reduction is accomplished with tributyltin hydride and AIBN. Deprotection of the diol functionality furnishes cortistatin A.

Conversion of Intermediate 2 to Cortistatin Analogs

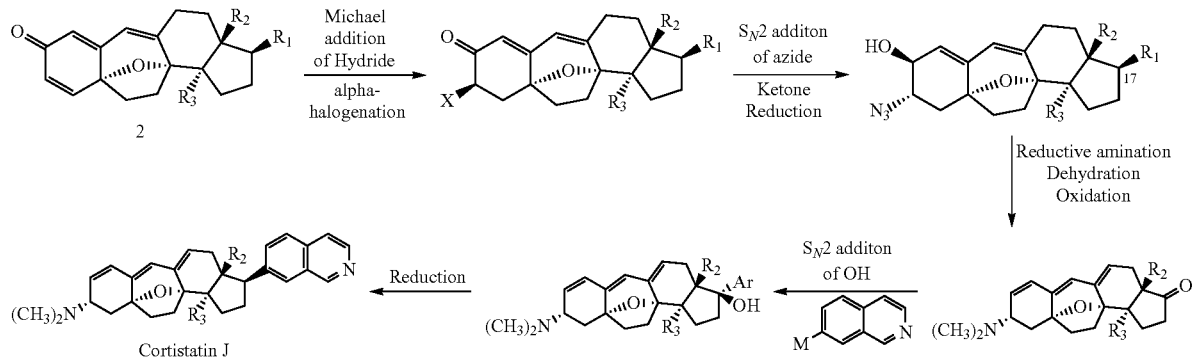

In some embodiments, reduction is accomplished by hydroboration. An electrophilic reagent in alcohol solvent stereoselectively adds alkoxide and an electrophile (X) across the diene functionality. In some embodiments, the electrophilic reagent is NBS. In some embodiments, the solvent is an alcohol (e.g., methanol, ethanol, or propanol). $S_N2$ displacement of substituent X yields the diol shown which is subsequently converted to the corresponding diene under The present invention provides another process for preparing cortistatin analogs and isomers, including cortistatin J, from intermediate 2 according to the steps depicted in the scheme above. As described above, intermediate 2 is converted to a hydroxyazide intermediate. Reductive amination of the hydroxyazide intermediate, followed by dehydration under acidic conditions yield the dimethylaminotriene shown above. In some embodiments, dehydration is accomplished with a strong acid, such as concentrated HCl, in an organic solvent, such as chloroform. Oxidation to the corresponding cyclopentanone is accomplished with reagents such as the Dess-Martin periodinane. Stereoselective 1,2-addition of 7-lithioisoquinoline to the cyclopentanone results in the tertiary alcohol shown, which is derivatized and deoxygenated to the corresponding hydrocarbon with inversion of configuration to furnish cortistatin J. In some embodiments, derivatization yields a trifluoroacetate ester and deoxygenation is accomplished with tributyltin hydride and AIBN.

The present invention also provides yet another approach for preparing cortistatin A and analogs thereof as depicted below.

Synthesis for Cortistatin Analogs

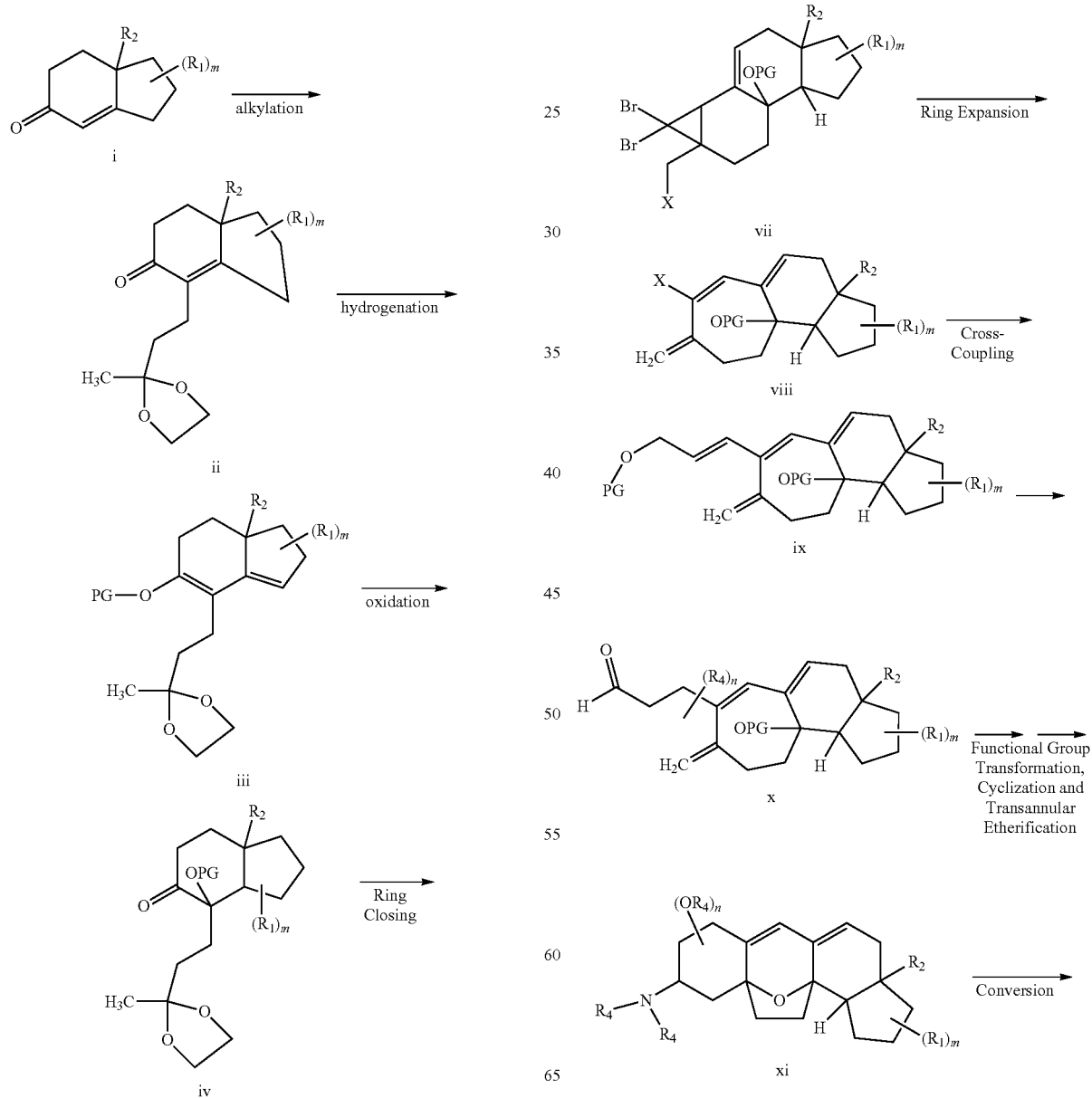

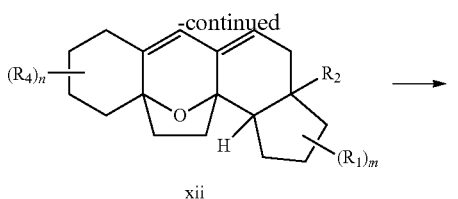

xii

Cortistatin A
and Various
Cortistatin Analogs

The present invention provides a process for preparing cortistatin A and various cortistatin analogs according to the steps depicted in the scheme above. In the scheme, $R_1$, $R_2$, $R_4$, m, and n are as defined herein. To begin, a compound of formula vii is converted under suitable conditions in the presence of a fluoride source to form a compound of formula viii. Any fluoride source may be used. In certain embodiments, the fluoride source is TBAF. In certain embodiments, the fluoride source is TASF.

In the following step, the compound of formula viii is cross-coupled under suitable coupling conditions to form a compound of formula ix. In certain embodiments, the suitable conditions include a catalyzed cross-coupling reaction using a suitable ester. In certain embodiments, an exemplary catalyst comprises palladium. In certain embodiments, the suitable ester includes suitable ethenyl esters. In certain embodiments, the suitable ethenyl ester is vinyl boronic ester.

In the following step, the compound of formula ix is modified to form a compound of formula x, which is then cyclized, followed by a transannular etherification reaction to form a compound of formula xi. In certain embodiments, the cyclization is performed in the presence of a suitable Lewis acid, a suitable amine, and a suitable solvent. In certain embodiments, the suitable Lewis acid is zinc bromide. In certain embodiments, the suitable amine is dimethylamine. In certain embodiments, the suitable solvent is a polar, aprotic solvents. In certain embodiments, the polar, aprotic solvent includes acetonitrile.

In the following step, the compound of formula xi is converted to a compound of formula xii under suitable conditions. In certain embodiments, the suitable conditions include deprotection, followed by oxidation, deacetylation, hydrazone formation, conversion to an appropriate iodide compound, and Stille cross-coupling with an appropriate isoquinolinyl compound. In certain embodiments, the oxidation is performed in the presences of a suitable oxidizing agent. In certain embodiments, the oxidizing agent is TPAP/NMO.

Using methods described herein, the compound of formula xii is finally converted to cortistatin A and various analogs thereof.

In certain embodiments, the invention provides a process for preparing a compound of the formula:

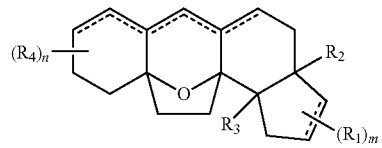

comprising steps of:

(a) cyclizing a compound of formula:

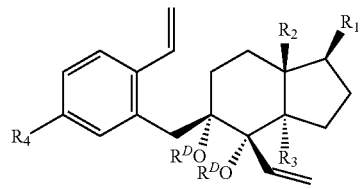

under suitable conditions using a Grubbs catalyst to form a compound of formula:

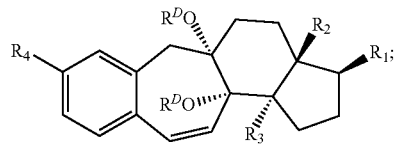

(b) reducing the compound of formula:

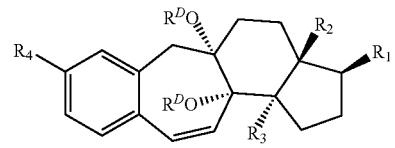

to form a compound of formula:

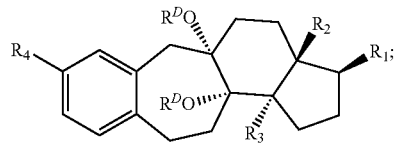

(c) reacting the compound of formula:

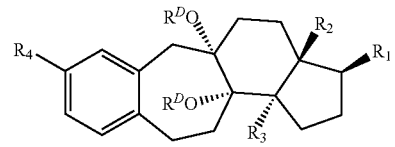

to form a compound of formula:

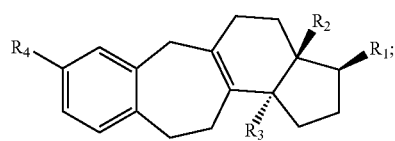

(d) epoxidizing the compound of formula:

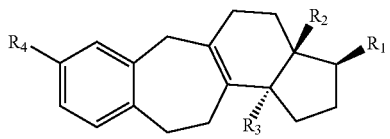

to form an epoxide compound of formula:

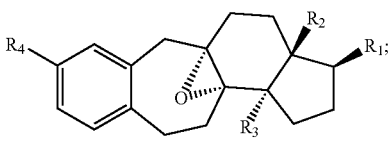

(e) converting the epoxide of formula:

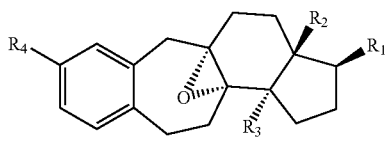

to form an alcohol of formula:

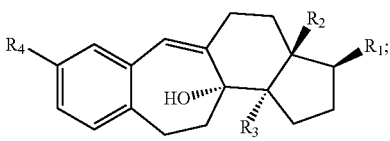

(f) deprotecting the alcohol of formula:

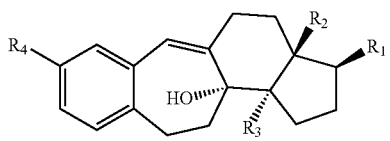

to form a compound of formula:

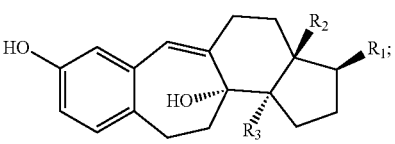

(g) cyclizing the compound of formula:

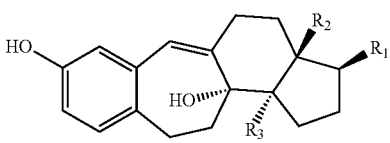

to the compound of formula:

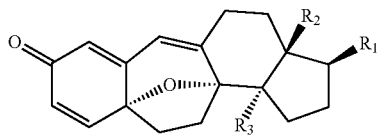

wherein:

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic;

each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N_3$; —$N(R_D)_2$; —$NHC(=O)R_D$; —$NR_AC(=O)N(R_D)_2$; —$OC(=O)OR_D$; —$OC(=O)R_D$; —$OC(=O)N(R_D)_2$; —$NR_DC(=O)OR_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

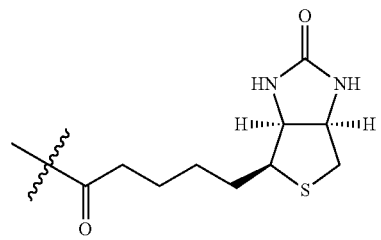 [SMILES: *C(=O)CCCC[C@@H]1SC[C@@H]2NC(=O)N[C@@H]21]

moiety; or a

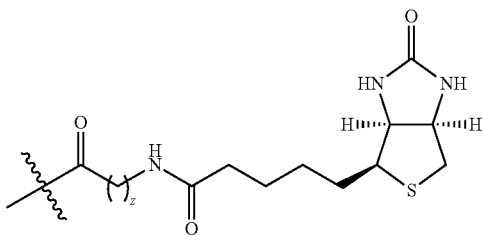

moiety wherein z is an integer between 2 and 10, inclusive; and salts thereof.

In some embodiments, the invention provides a process for preparing a compound of formula:

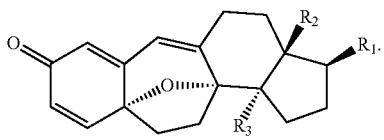

In other embodiments, the present invention is directed to a process for preparing a compound of formula:

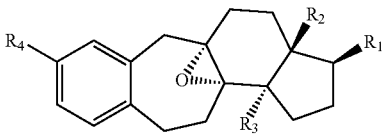

comprising steps of:
(a) coupling compounds of formulae:

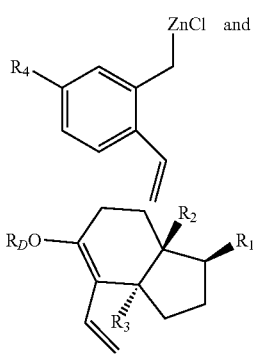

under suitable coupling conditions to form a compound of formula:

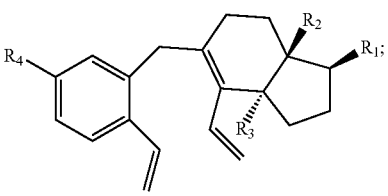

(b) cyclizing the compound of formula:

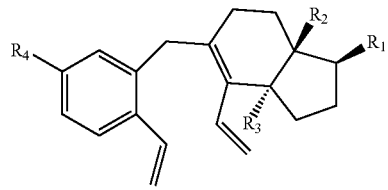

under suitable conditions using an olefin metathesis catalyst to form a compound of formula:

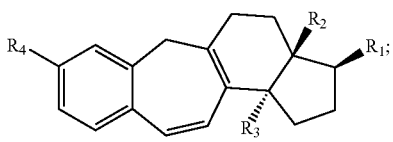

(c) epoxidizing the compound of formula:

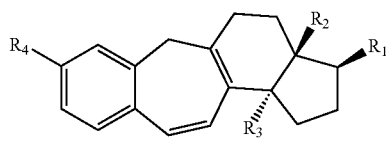

to form an epoxide compound of formula:

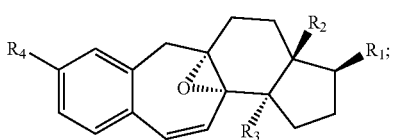

(d) reducing the compound of formula:

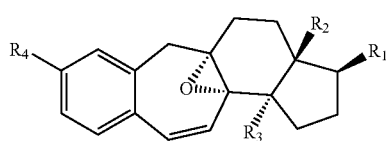

to form a compound of formula:

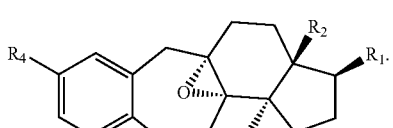

wherein:
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N$_3$; =O; =N(R$_A$); =S; —N(R$_A$)$_2$; —NHC(=O)R$_A$; —NR$_A$C(=O)N(R$_A$)$_2$; —OC(=O)OR$_A$; —OC(=O)R$_A$; —OC(=O)N(R$_A$)$_2$; —NR$_A$C(=O)OR$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_2$ is hydrogen or C$_1$-C$_6$ aliphatic;

R$_3$ is hydrogen or C$_1$-C$_6$ aliphatic;

each occurrence of R$_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO$_2$R$_D$; —CN; —SCN; —SR$_D$; —SOR$_D$; —SO$_2$R$_D$; —NO$_2$; —N$_3$; —N(R$_D$)$_2$; —NHC(=O)R$_D$; —NR$_A$C(=O)N(R$_D$)$_2$; —OC(=O)OR$_D$; —OC(=O)R$_D$; —OC(=O)N(R$_D$)$_2$; —NR$_D$C(=O)OR$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

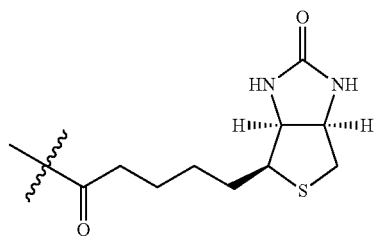 [SMILES: *C(=O)CCCC[C@@H]1SC[C@@H]2NC(=O)N[C@@H]21]

moiety; or a

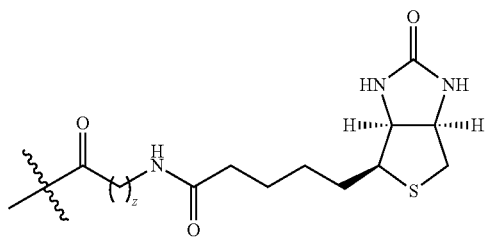

moiety wherein z is an integer between 2 and 10, inclusive; and salts thereof.

In some embodiments, the invention provides a process for preparing a compound of formula:

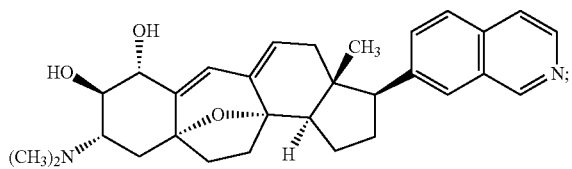

comprising steps of:

(a) reducing and α-halogenating a compound of formula:

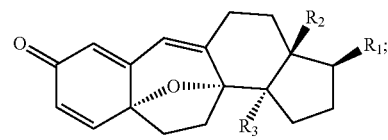

to form a compound of formula:

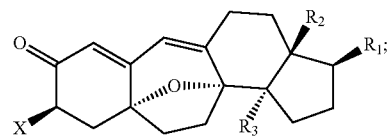

(b) reducing a compound of formula:

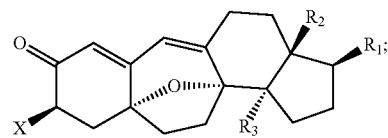

to form a compound of formula:

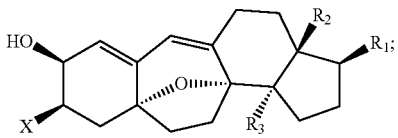

(c) displacing with azide the substituent X of a compound of formula:

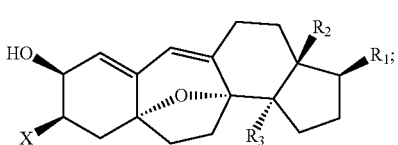

to form a compound of formula:

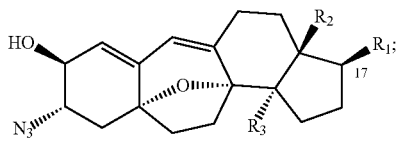

(d) adding alkoxy and halogen equivalents across the diene substituent of a compound of formula:

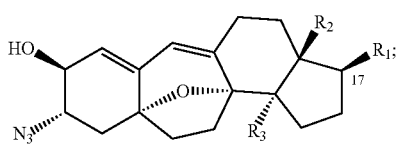

to form a compound of formula:

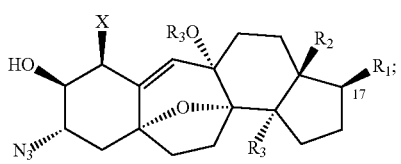

(e) displacing with a hydroxyl group the substituent X from a compound of formula:

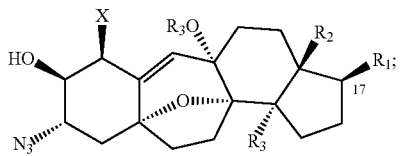

to form a compound of formula:

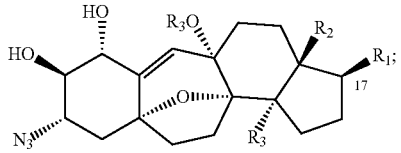

(f) protecting the diol substituents of a compound of formula:

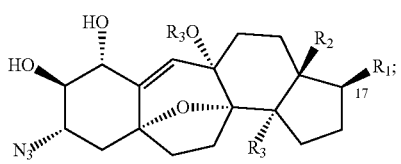

to form a compound of formula:

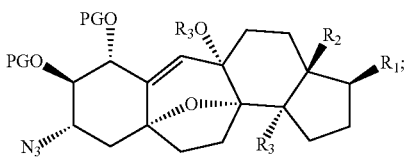

(g) generating a diene from the compound of formula:

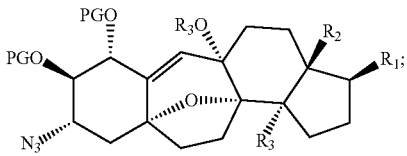

to form a compound of formula:

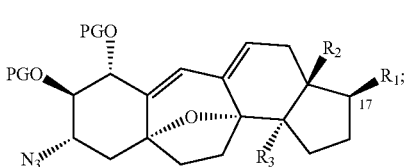

(h) oxidizing $R_1$ of a compound of formula:

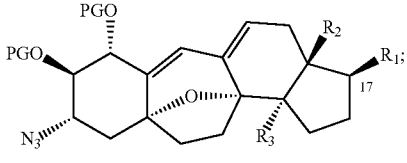

to form a compound of formula:

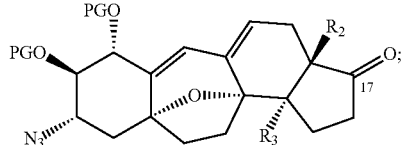

(i) reductively aminating a compound of formula:

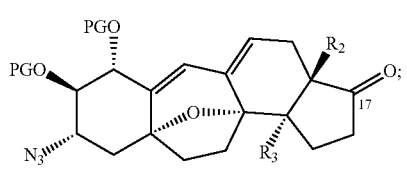

to form a compound of formula:

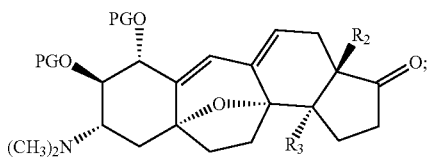

(j) adding an aromatic organolithium reagent to the ketone of a compound of formula:

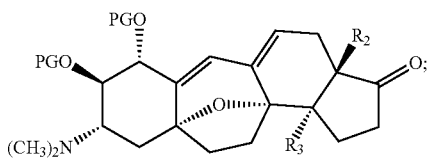

to form a compound of formula:

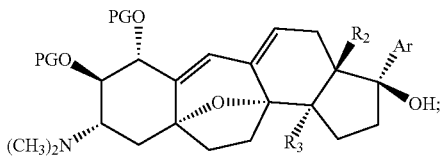

(k) reducing the tertiary alcohol of a compound of formula:

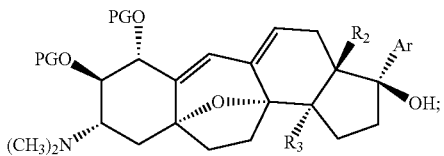

to form a compound of formula:

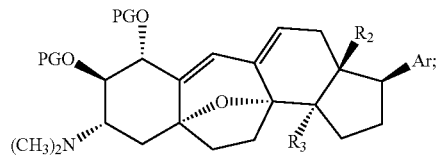

(l) deprotecting the diol substituents of a compound of formula:

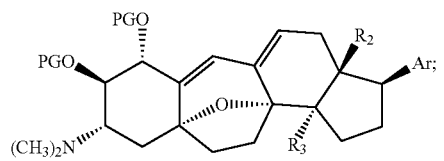

to form a compound of formula:

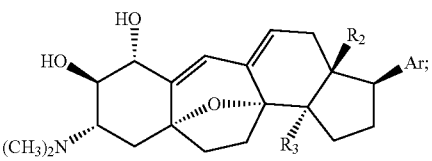

wherein:

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic; and

X is a halogen; and salts thereof.

In other embodiments, the invention provides a process for preparing a compound of formula:

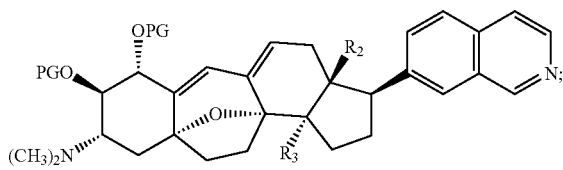

comprising steps of:

(a) reducing and x-halogenating a compound of formula:

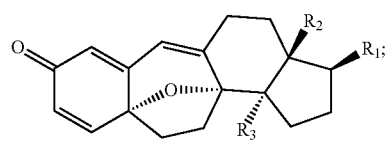

to form a compound of formula:

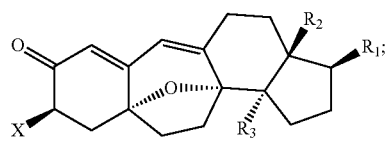

(b) reducing a compound of formula:

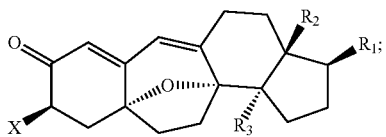

to form a compound of formula:

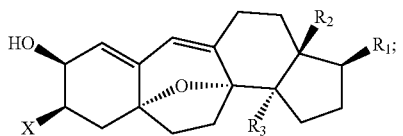

(c) protecting the alcohol of a compound of formula:

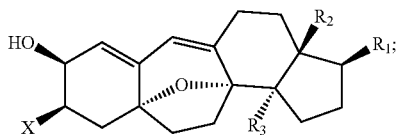

to form a compound of formula:

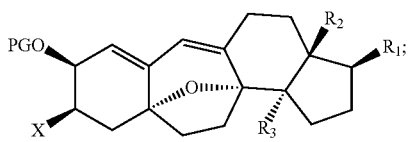

(d) oxidizing the diene of a compound of formula:

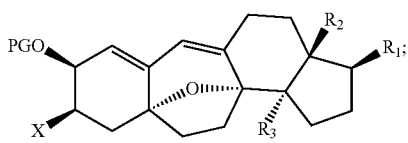

to form a compound of formula:

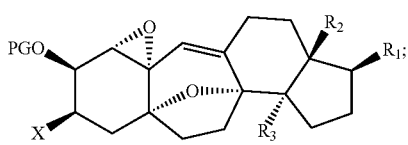

(e) opening the allylic epoxide of a compound of formula:

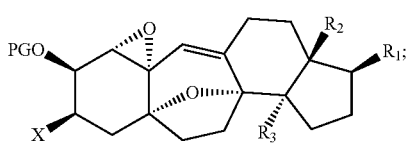

to form a compound of formula:

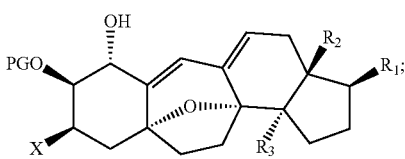

(f) displacing with azide the substituent (X) of a compound of formula:

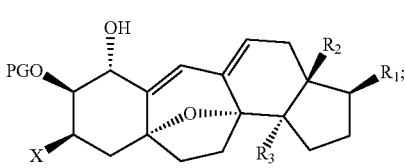

to form a compound of formula:

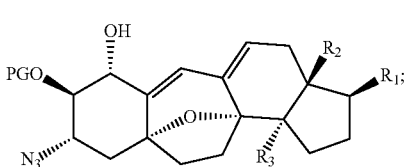

(g) deprotecting the alcohol of a compound of formula:

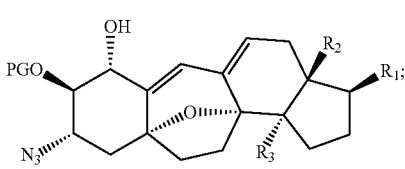

to form a compound of formula:

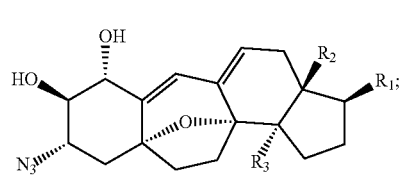

(h) reductively aminating a compound of formula:

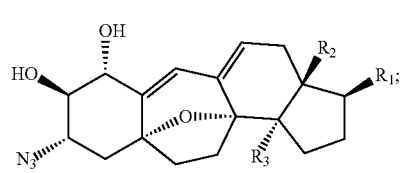

to form a compound of formula:

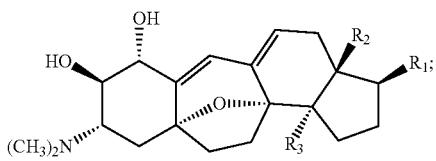

and (i) protecting the diol of a compound of formula:

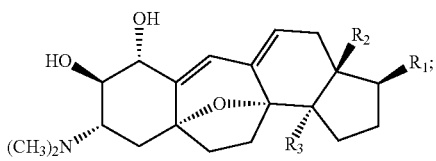

to form a compound of formula:

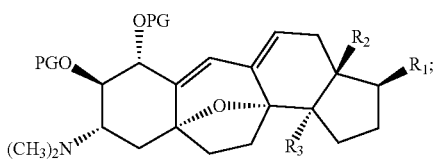

wherein:

each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic; and

X is a halogen; and salts thereof.

In still other embodiments, the invention provides a process for preparing a compound of formula:

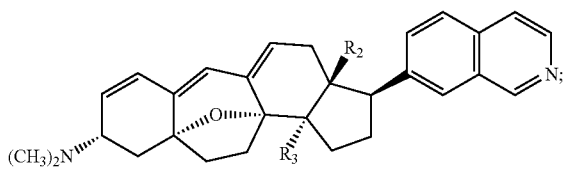

comprising steps of:

(a) reducing and ca-halogenating a compound of formula:

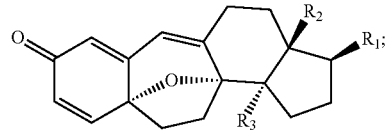

to form a compound of formula:

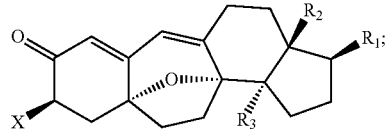

(b) reducing a compound of formula:

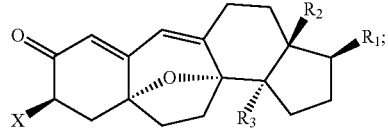

to form a compound of formula:

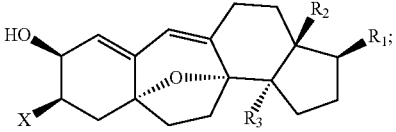

(c) displacing with azide the halogen substituent (X) of the compound of formula

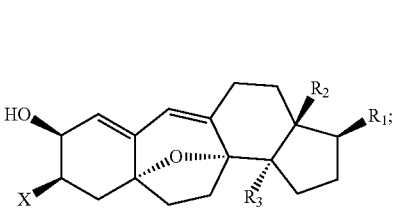

to form a compound of formula:

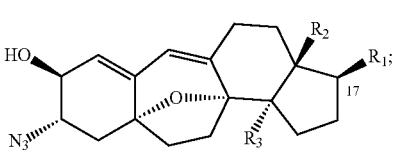

(d) reductively aminating the compound of formula:

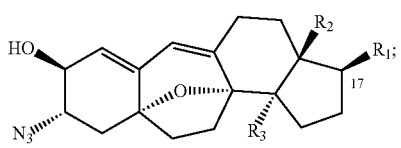

to form a compound of formula:

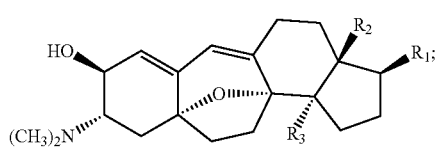

(e) dehydrating the compound of formula:

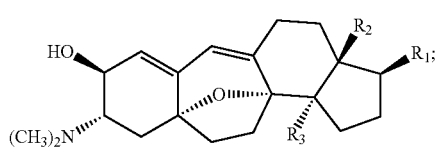

to form a compound of formula:

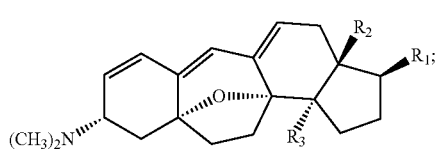

(f) oxidizing the $R_1$ substituent from the compound of formula:

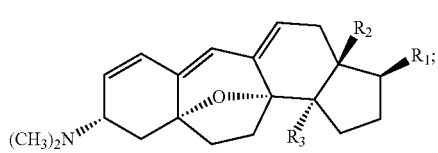

to form a compound of formula:

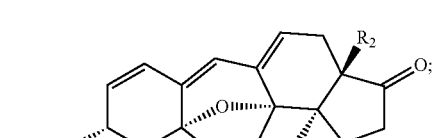

(g) adding an aromatic organolithium reagent to the compound of formula:

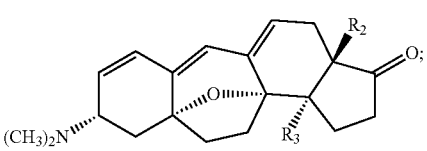

to form a compound of formula:

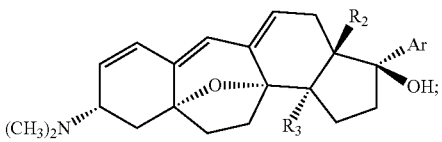

(h) reducing the alcohol of formula:

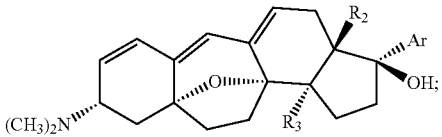

to form a compound of formula:

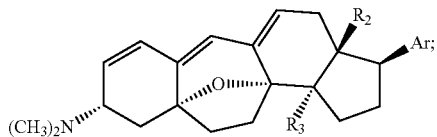

wherein each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic; and

X is a halogen; and salts thereof.

In some embodiments, the invention provides a process for preparing a compound of the formula:

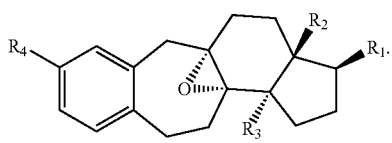

In certain embodiments, the invention provides a process for preparing a compound of formula:

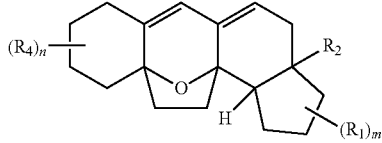

comprising steps of:
(a) converting a compound of formula:

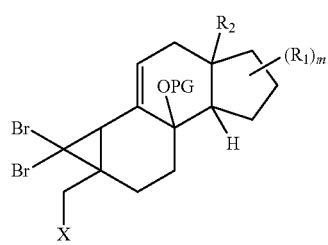

under suitable conditions to form a compound of formula:

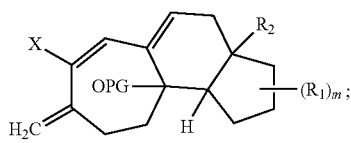

(b) cross-coupling a compound of formula:

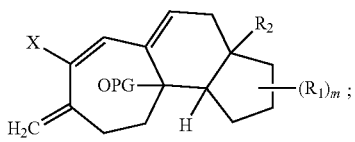

under suitable conditions to form a compound of formula:

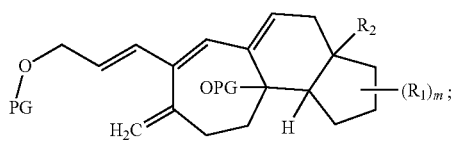

(c) cyclizing and performing a transannular etherification reaction on the compound of formula:

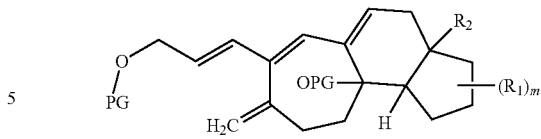

under suitable conditions to form a compound of formula:

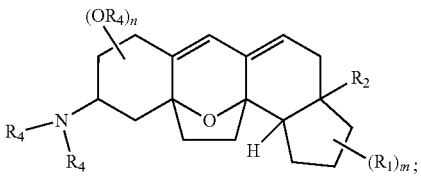

(d) converting the compound of formula:

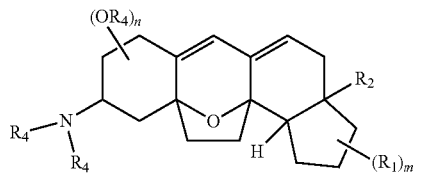

under suitable conditions to form a compound of formula:

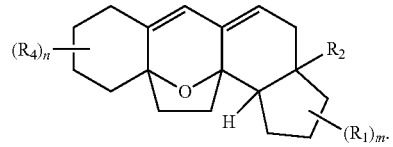

Intermediates

The present invention also provides intermediates useful in the synthesis of cortistatin A or analogs thereof. Typically, the intermediates are useful in the synthetic approaches described herein. In certain embodiments, the intermediates may also have biological activity (e.g. anti-angiogenic activity).

In certain embodiments, the present invention provides compounds of the formula:

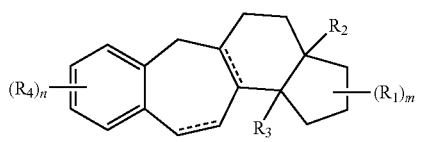

wherein:
each of the dashed lines independently represents the presence or absence of a bond;
m is an integer between 0 and 6, inclusive;
n is an integer between 0 and 4, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; =O; =$N(R_A)$; =S; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen or $C_1$-$C_6$ aliphatic;

$R_3$ is hydrogen or $C_1$-$C_6$ aliphatic;

each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N_3$; —$N(R_D)_2$; —$NHC(=O)R_D$; —$NR_AC(=O)N(R_D)_2$; —$OC(=O)OR_D$; —$OC(=O)R_D$; —$OC(=O)N(R_D)_2$; —$NR_DC(=O)OR_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

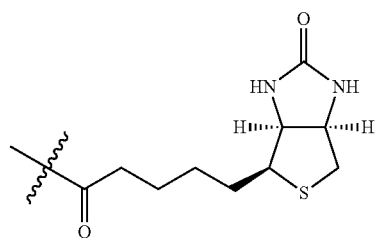 [SMILES: *C(=O)CCCC[C@@H]1SC[C@@H]2NC(=O)N[C@@H]21]

moeity; or a

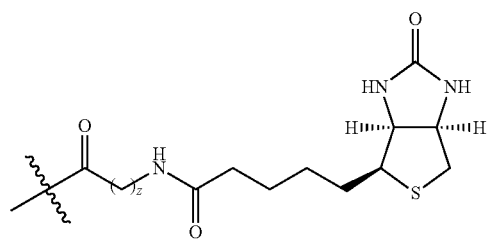

moeity wherein z is an integer between 2 and 10, inclusive; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4.

In certain embodiments, at least one $R_1$ is hydrogen. In certain embodiments, at least one $R_1$ is substituted or unsubstituted aliphatic. In some embodiments, at least one $R_1$ is substituted or unsubstituted alkyl. In certain embodiments, at least one $R_1$ is $C_1$-$C_6$ alkyl. In certain embodiments, at least one $R_1$ is methyl. In certain embodiments, at least one $R_1$ is ethyl. In certain embodiments, at least one $R_1$ is propyl. In certain embodiments, at least one $R_1$ is substituted or unsubstituted aryl. In certain embodiments, at least one $R_1$ is substituted or unsubstituted phenyl. In certain embodiments, at least one $R_1$ is substituted phenyl. In certain embodiments, at least one $R_1$ is unsubstituted phenyl. In certain embodiments, at least one $R_1$ is substituted or unsubstituted naphthyl. In certain embodiments, at least one $R_1$ is substituted naphthyl. In certain embodiments, at least one $R_1$ is unsubstituted naphthyl. In certain embodiments, at least one $R_1$ is substituted or unsubstituted heteroaryl. In certain embodiments, at least one $R_1$ is substituted or unsubstituted isoquinolinyl. In certain embodiments, at least one $R_1$ is substituted isoquinolinyl. In certain embodiments, at least one $R_1$ is unsubstituted isoquinolinyl. In certain embodiments, at least one $R_1$ is unsubstituted 5-isoquinolinyl. In certain embodiments, at least one $R_1$ is unsubstituted 6-isoquinolinyl. In certain embodiments, at least one $R_1$ is substituted or unsubstituted indolyl. In certain embodiments, at least one $R_1$ is substituted or unsubstituted indolyl isoindolyl. In certain embodiments, at least one $R_1$ is substituted or unsubstituted indolyl benzothienyl. In certain embodiments, at least one $R_1$ is substituted or unsubstituted indolyl benzofuranyl. In certain embodiments, at least one $R_1$ is substituted or unsubstituted indolyl dibenzofuranyl. In certain embodiments, at least one $R_1$ is substituted or unsubstituted indolyl. In certain embodiments, at least one $R_1$ is substituted or unsubstituted indolyl indazolyl. In certain embodiments, at least one $R_1$ is substituted or unsubstituted indolyl benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, at least one $R_1$ is —$OR_A$. In certain embodiments, at least one $R_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_4$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ is substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, at least one $R_4$ is hydrogen. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ is $C_1$-$C_6$ alkyl substituted with an aryl group. In certain embodiments, at least one $R_4$ comprises biotin or a biotin derivative. In certain embodiments, at least one $R_4$ is a

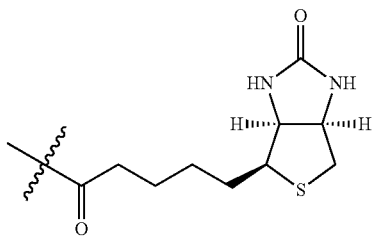 [SMILES: *C(=O)CCCC[C@@H]1SC[C@@H]2NC(=O)N[C@@H]21]

moiety. In some embodiments, at least one $R_4$ is

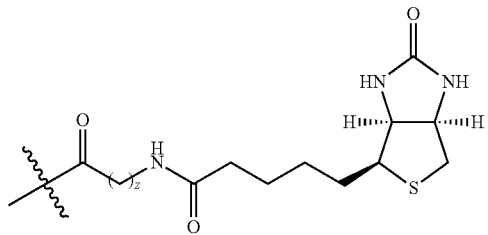

moiety wherein z is an integer between 2 and 10, inclusive. In certain embodiments, at least one $R_4$ is a benzyl group. In certain embodiments, at least one $R_4$ is —$OR_D$ wherein each $R_D$ is hydrogen. In certain embodiments, at least one $R_4$ is —$OR_D$ wherein $R_D$ is $C_1$-$C_6$ alkyl. In certain embodiments, at least one $R_4$ is —$OR_D$ wherein $R_D$ is methyl. In certain embodiments, at least one $R_4$ is —$OR_D$ wherein $R_D$ is ethyl. In certain embodiments, at least one $R_4$ is —$OR_D$ wherein $R_D$ is propyl. In certain embodiments, at least one $R_4$ is —$N(R_D)_2$ wherein each $R_D$ is hydrogen or $C_1$-$C_6$ alkyl. In certain embodiments, at least one $R_4$ is —$N(R_D)_2$ wherein each $R_D$ is $C_1$-$C_6$ alkyl. In certain embodiments, at least one $R_4$ is —$N(R_D)_2$ wherein each $R_D$ is methyl. In certain embodiments, at least one $R_4$ is —$N(R_D)_2$ wherein each $R_D$ is ethyl. In certain embodiments, at least one $R_4$ is —$N(R_D)_2$ wherein each $R_D$ is propyl. In certain embodiments, at least one $R_4$ is —$N(R_D)_2$ wherein each $R_D$ is butyl. In certain embodiments, at least one $R_4$ is —$N(R_D)_2$ wherein each $R_D$ is pentyl. In certain embodiments, at least one $R_4$ is —$N(R_D)_2$ wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, at least one $R_4$ is —$OR_D$. In certain embodiments, at least one $R_D$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_D$ is an alkylaryl group. In certain embodiments, the alkylaryl group is a benzyl group. In certain embodiments, the oxygen protecting group is triisopropylsilyl (TIPS).

In certain embodiments, the compound is of formula:

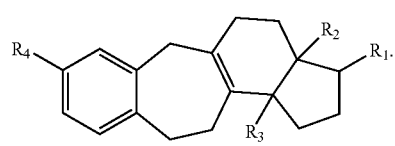

In certain embodiments, the compound is of formula:

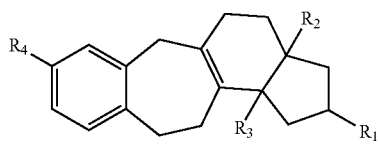

In certain embodiments, the compound is of formula:

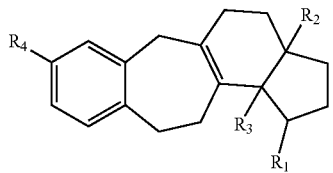

In certain embodiments, the compound is of formula:

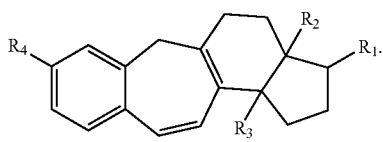

In certain embodiments, the compound is of formula:

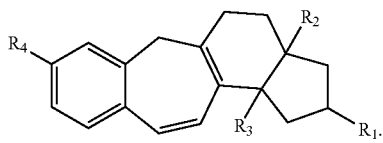

In certain embodiments, the compound is of formula:

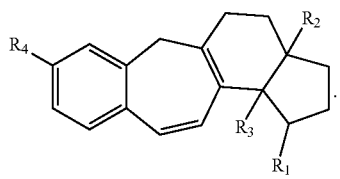

In certain embodiments, the compound is of formula:

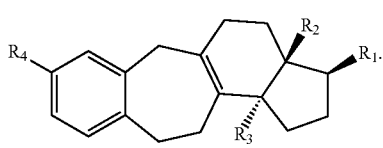

In certain embodiments, the compound is of formula:

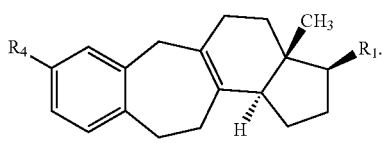

In certain embodiments, the compound is of formula:

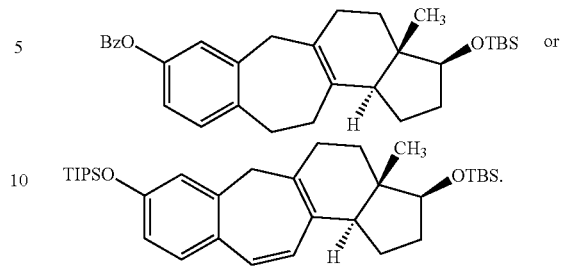

In certain embodiments, the present invention provides compounds of the formula:

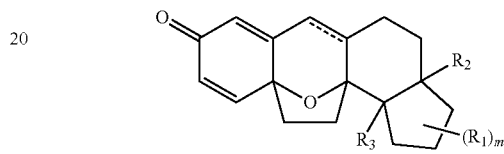

wherein:
the dashed line represents the presence or absence of a bond;
m is an integer between 0 and 6, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; =O; =N($R_A$); =S; —N($R_A$)$_2$; —NHC(=O)$R_A$; —$NR_A$C(=O)N($R_A$)$_2$; —OC(=O)$OR_A$; —OC(=O)$R_A$; —OC(=O)N($R_A$)$_2$; —$NR_A$C(=O)$OR_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R_2$ is hydrogen or $C_1$-$C_6$ aliphatic;
$R_3$ is hydrogen or $C_1$-$C_6$ aliphatic; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, at least one $R_1$ is hydrogen. In certain embodiments, at least one $R_1$ is substituted or unsubstituted aliphatic. In some embodiments, at least one $R_1$ is substituted or unsubstituted alkyl. In certain embodiments, at least one $R_1$ is $C_1$-$C_6$ alkyl. In certain embodiments, at least one $R_1$ is methyl. In certain embodiments, at least one $R_1$ is ethyl. In certain embodiments, at least one $R_1$ is propyl. In certain embodiments, at least one $R_1$ is substituted or unsubstituted aryl. In certain embodiments, at least one $R_1$ is substituted or unsubstituted phenyl. In certain embodiments, at least one $R_1$ is substituted phenyl. In certain embodiments, at least one $R_1$ is unsubstituted phenyl. In certain embodiments, at least one $R_1$ is substituted or unsubstituted naphthyl. In certain embodiments, at least one $R_1$ is substituted naphthyl. In certain embodiments, at least one $R_1$ is unsubstituted naphthyl. In certain embodiments, at least one $R_1$ is substituted or unsubstituted heteroaryl. In certain embodiments, at least one $R_1$ is substituted or unsubstituted isoquinolinyl. In certain embodiments, at least one $R_1$ is substituted isoquinolinyl. In certain embodiments, at least one $R_1$ is unsubstituted isoquinolinyl. In certain embodiments, at least one $R_1$ is unsubstituted 5-isoquinolinyl. In certain embodiments, at least one $R_1$ is unsubstituted 6-isoquinolinyl.

In certain embodiments, at least one $R_1$ is substituted or unsubstituted indolyl. In certain embodiments, at least one $R_1$ is substituted or unsubstituted indolyl isoindolyl. In certain embodiments, at least one $R_1$ is substituted or unsubstituted indolyl benzothienyl. In certain embodiments, at least one $R_1$ is substituted or unsubstituted indolyl benzofuranyl. In certain embodiments, at least one $R_1$ is substituted or unsubstituted indolyl dibenzofuranyl. In certain embodiments, at least one $R_1$ is substituted or unsubstituted indolyl. In certain embodiments, at least one $R_1$ is substituted or unsubstituted indolyl indazolyl. In certain embodiments, at least one $R_1$ is substituted or unsubstituted indolyl benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, at least one $R_1$ is $-OR_A$. In certain embodiments, at least one $R_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_A$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ is substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, the compound is of formula:

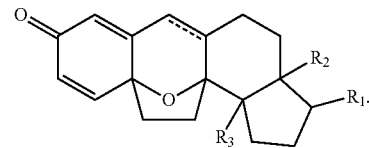

In certain embodiments, the compound is of formula:

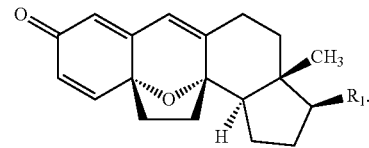

In certain embodiments, the compound is of formula:

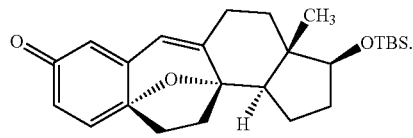

In certain embodiments, the present invention provides compounds of the formula:

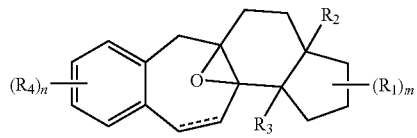

wherein
m is an integer between 0 and 6, inclusive;
n is an integer between 0 and 4, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_A$; $-C(=O)R_A$; $-CO_2R_A$; $-CN$; $-SCN$; $-SR_A$; $-SOR_A$; $-SO_2R_A$; $-NO_2$; $-N_3$; $=O$; $=N(R_A)$; $=S$; $-N(R_A)_2$; $-NHC(=O)R_A$; $-NR_AC(=O)N(R_A)_2$; $-OC(=O)OR_A$;

—OC(=O)R$_A$; —OC(=O)N(R$_A$)$_2$; —NR$_A$C(=O)OR$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_2$ is hydrogen or C$_1$-C$_6$ aliphatic;

R$_3$ is hydrogen or C$_1$-C$_6$ aliphatic;

each occurrence of R$_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO$_2$R$_D$; —CN; —SCN; —SR$_D$; —SOR$_D$; —SO$_2$R$_D$; —NO$_2$; —N$_3$; —N(R$_D$)$_2$; —NHC(=O)R$_D$; —NR$_A$C(=O)N(R$_D$)$_2$; —OC(=O)OR$_D$; —OC(=O)R$_D$; —OC(=O)N(R$_D$)$_2$; —NR$_D$C(=O)OR$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

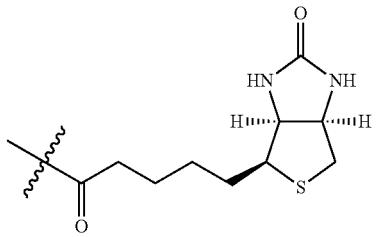 [SMILES: *C(=O)CCCC[C@@H]1SC[C@@H]2NC(=O)N[C@@H]21]

moiety; or a

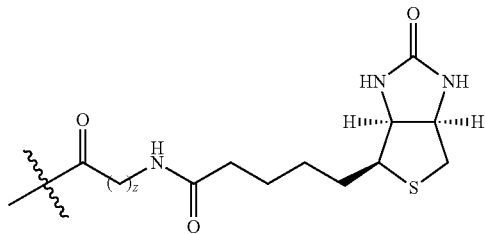

moiety wherein z is an integer between 2 and 10, inclusive; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4.

In certain embodiments, at least one R$_1$ is hydrogen. In certain embodiments, at least one R$_1$ is substituted or unsubstituted aliphatic. In some embodiments, at least one R$_1$ is substituted or unsubstituted alkyl. In certain embodiments, at least one R$_1$ is C$_1$-C$_6$ alkyl. In certain embodiments, at least one R$_1$ is methyl. In certain embodiments, at least one R$_1$ is ethyl. In certain embodiments, at least one R$_1$ is propyl. In certain embodiments, at least one R$_1$ is substituted or unsubstituted aryl. In certain embodiments, at least one R$_1$ is substituted or unsubstituted phenyl. In certain embodiments, at least one R$_1$ is substituted phenyl. In certain embodiments, at least one R$_1$ is unsubstituted phenyl. In certain embodiments, at least one R$_1$ is substituted or unsubstituted naphthyl. In certain embodiments, at least one R$_1$ is substituted naphthyl. In certain embodiments, at least one R$_1$ is unsubstituted naphthyl. In certain embodiments, at least one R$_1$ is substituted or unsubstituted heteroaryl. In certain embodiments, at least one R$_1$ is substituted or unsubstituted isoquinolinyl. In certain embodiments, at least one R$_1$ is substituted isoquinolinyl. In certain embodiments, at least one R$_1$ is unsubstituted isoquinolinyl. In certain embodiments, at least one R$_1$ is unsubstituted 5-isoquinolinyl. In certain embodiments, at least one R$_1$ is unsubstituted 6-isoquinolinyl. In certain embodiments, at least one R$_1$ is substituted or unsubstituted indolyl. In certain embodiments, at least one R$_1$ is substituted or unsubstituted indolyl isoindolyl. In certain embodiments, at least one R$_1$ is substituted or unsubstituted indolyl benzothienyl. In certain embodiments, at least one R$_1$ is substituted or unsubstituted indolyl benzofuranyl. In certain embodiments, at least one R$_1$ is substituted or unsubstituted indolyl dibenzofuranyl. In certain embodiments, at least one R$_1$ is substituted or unsubstituted indolyl. In certain embodiments, at least one R$_1$ is substituted or unsubstituted indolyl indazolyl. In certain embodiments, at least one R$_1$ is substituted or unsubstituted indolyl benzimidazolyl. In certain embodiments, at least one R$_1$ is substituted or unsubstituted benzthiazolyl. In certain embodiments, at least one R$_1$ is substituted or unsubstituted quinolyl. In certain embodiments, at least one R$_1$ is substituted or unsubstituted isoquinolyl. In certain embodiments, at least one R$_1$ is substituted or unsubstituted cinnolinyl. In certain embodiments, at least one R$_1$ is substituted or unsubstituted phthalazinyl. In certain embodiments, at least one R$_1$ is substituted or unsubstituted quinazolinyl. In certain embodiments, at least one R$_1$ is substituted or unsubstituted quinoxalinyl. In certain embodiments, at least one R$_1$ is substituted or unsubstituted 4H-quinolizinyl. In certain embodiments, at least one R$_1$ is substituted or unsubstituted carbazolyl. In certain embodiments, at least one R$_1$ is substituted or unsubstituted acridinyl. In certain embodiments, at least one R$_1$ is substituted or unsubstituted phenazinyl. In certain embodiments, at least one R$_1$ is substituted or unsubstituted phenothiazinyl. In certain embodiments, at least one R$_1$ is substituted or unsubstituted phenoxazinyl. In certain embodiments, at least one R$_1$ is substituted or unsubstituted tetrahydroquinolinyl. In certain embodiments, at least one R$_1$ is substituted or unsubstituted tetrahydroisoquinolinyl. In certain embodiments, at least one R$_1$ is substituted or unsubstituted pyrido[2,3-b]-1,4-oxazin-3(4H)-one.

In certain embodiments, at least one R$_1$ is —OR$_A$. In certain embodiments, at least one R$_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted C$_1$-C$_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_4$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ is substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, $R_4$ is hydrogen. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ comprises biotin or a biotin derivative. In certain embodiments, at least one $R_4$ is a

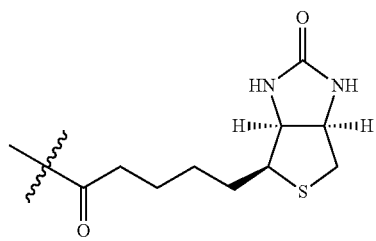 [SMILES: *C(=O)CCCC[C@@H]1SC[C@@H]2NC(=O)N[C@@H]21]

moiety. In some embodiments, at least one $R_4$ is a

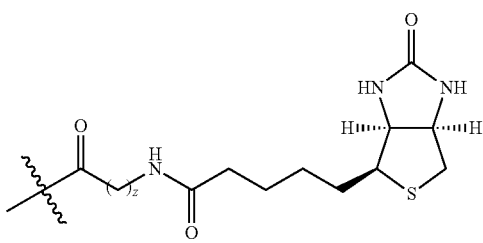

moiety wherein z is an integer between 2 and 10, inclusive. In certain embodiments, at least one $R_4$ is $C_1$-$C_6$ alkyl substituted with an aryl group. In certain embodiments, at least one $R_4$ is a benzyl group. In certain embodiments, at least one $R_4$ is —$OR_D$ wherein $R_D$ is hydrogen. In certain embodiments, at least one $R_4$ is —$OR_D$ wherein $R_D$ is $C_1$-$C_6$ alkyl. In certain embodiments, at least one $R_4$ is —$OR_D$ wherein $R_D$ is methyl. In certain embodiments, at least one $R_4$ is —$OR_D$ wherein $R_D$ is ethyl. In certain embodiments, at least one $R_4$ is —$OR_D$ wherein $R_D$ is propyl. In certain embodiments, at least one $R_4$ is —$N(R_D)_2$ wherein each $R_D$ is hydrogen or $C_1$-$C_6$ alkyl. In certain embodiments, at least one $R_4$ is —$N(R_D)_2$ wherein each $R_D$ is $C_1$-$C_6$ alkyl. In certain embodiments, at least one $R_4$ is —$N(R_D)_2$ wherein each $R_D$ is methyl. In certain embodiments, at least one $R_4$ is —$N(R_D)_2$ wherein each $R_D$ is ethyl. In certain embodiments, at least one $R_4$ is —$N(R_D)_2$ wherein each $R_D$ is propyl. In certain embodiments, at least one $R_4$ is e —$N(R_D)_2$ wherein each $R_D$ is butyl. In certain embodiments, at least one $R_4$ is —$N(R_D)_2$ wherein each $R_D$ is pentyl. In certain embodiments, at least one $R_4$ is —$N(R_D)_2$ wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, at least one $R_4$ is —$OR_D$. In certain embodiments, at least one $R_D$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_D$ is an alkylaryl group. In certain embodiments, the alkylaryl group is a benzyl group. In certain embodiments, the oxygen protecting group is triisopropylsilyl (TIPS).

In certain embodiments, the compound is of formula:

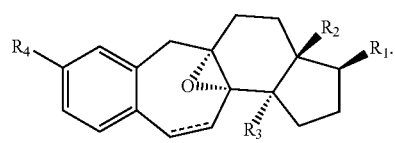

In certain embodiments, the compound is of formula:

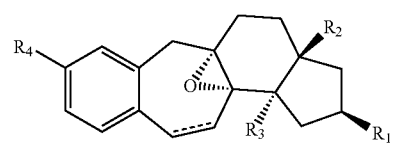

In certain embodiments, the compound is of formula:

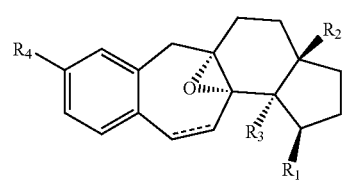

In certain embodiments, the compound is of formula:

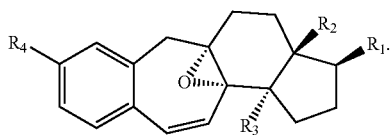

In certain embodiments, the compound is of formula:

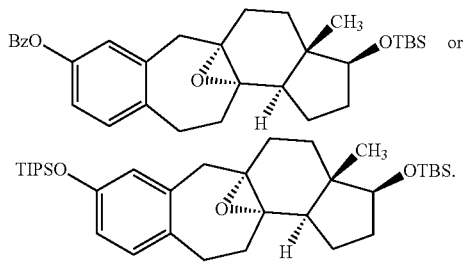

In certain embodiments, the present invention provides compounds of the formula:

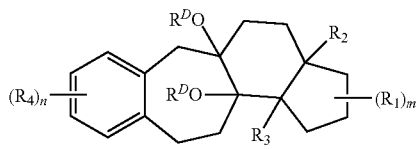

wherein:
m is an integer between 0 and 6, inclusive;
n is an integer between 0 and 4, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; =O; =N($R_D$); =S; —N($R_A$)$_2$; —NHC(=O)$R_A$; —$NR_A$C(=O)N($R_A$)$_2$; —OC(=O)$OR_A$; —OC(=O)$R_A$; —OC(=O)N($R_A$)$_2$; —$NR_A$C(=O)$OR_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R_2$ is hydrogen or $C_1$-$C_6$ aliphatic;
$R_3$ is hydrogen or $C_1$-$C_6$ aliphatic;
each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —C(=O)$R_D$; —$CO_2R_D$; —CN; —SCN; —$SR_D$; —$SOR_D$; —$SO_2R_D$; —$NO_2$; —$N_3$; —N($R_D$)$_2$; —NHC(=O)$R_D$; —$NR_A$C(=O)N($R_D$)$_2$; —OC(=O)$OR_D$; —OC(=O)$R_D$; —OC(=O)N($R_D$)$_2$; —$NR_D$C(=O)$OR_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

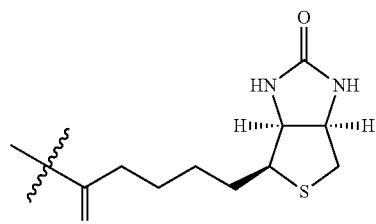

moiety; or a

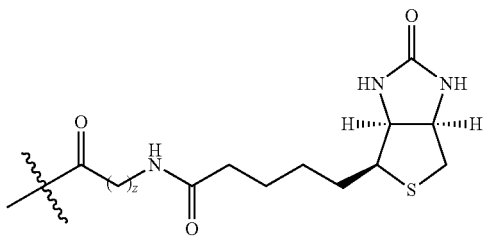

moiety wherein z is an integer between 2 and 10, inclusive; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4.

In certain embodiments, $R_1$ is hydrogen. In certain embodiments, $R_1$ is substituted or unsubstituted aliphatic. In some embodiments, $R_1$ is substituted or unsubstituted alkyl. In certain embodiments, $R_1$ is $C_1$-$C_6$ alkyl. In certain embodiments, $R_1$ is methyl. In certain embodiments, $R_1$ is ethyl. In certain embodiments, $R_1$ is propyl. In certain embodiments, $R_1$ is substituted or unsubstituted aryl. In certain embodiments, $R_1$ is substituted or unsubstituted phenyl. In certain embodiments, $R_1$ is substituted phenyl. In certain embodiments, $R_1$ is unsubstituted phenyl. In certain embodiments, $R_1$ is substituted or unsubstituted naphthyl. In certain embodiments, $R_1$ is substituted naphthyl. In certain embodiments, $R_1$ is unsubstituted naphthyl. In certain embodiments, $R_1$ is substituted or unsubstituted heteroaryl. In certain embodiments, $R_1$ is substituted or unsubstituted isoquinolinyl. In certain embodiments, $R_1$ is substituted isoquinolinyl. In certain embodiments, $R_1$ is unsubstituted isoquinolinyl. In certain embodiments, $R_1$ is unsubstituted 5-isoquinolinyl. In certain embodiments, $R_1$ is unsubstituted 6-isoquinolinyl. In certain embodiments, at least one $R_1$ is substituted or unsubstituted indolyl. In certain embodiments, at least one $R_1$ is substituted or unsubstituted indolyl isoindolyl. In certain embodiments, at least one $R_1$ is substituted or unsubstituted indolyl benzothienyl. In certain embodiments, at least one $R_1$ is substituted or unsubstituted indolyl benzofuranyl. In certain embodiments, at least one $R_1$ is substituted or unsubstituted indolyl dibenzofuranyl. In certain embodiments, at least one $R_1$ is substituted or unsubstituted indolyl. In certain embodiments, at least one $R_1$ is substituted or unsubstituted indolyl indazolyl. In certain embodiments, at least one $R_1$ is substituted or unsubstituted indolyl benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one. In certain embodiments, $R_1$ is not isoquinoline.

In certain embodiments, at least one $R_1$ is —$OR_A$. In certain embodiments, at least one $R_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_A$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, $R_4$ is hydrogen. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ is $C_1$-$C_6$ alkyl substituted with an aryl group. In certain embodiments, at least one $R_4$ comprises biotin or a biotin derivative. In certain embodiments, at least one $R_4$ is a

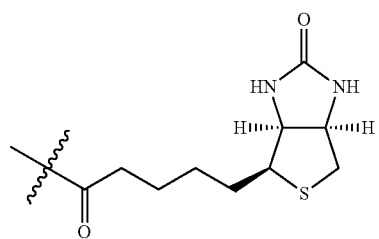 [SMILES: *C(=O)CCCC[C@@H]1SC[C@@H]2NC(=O)N[C@@H]21]

moiety. In certain embodiments, at least one $R_4$ is a

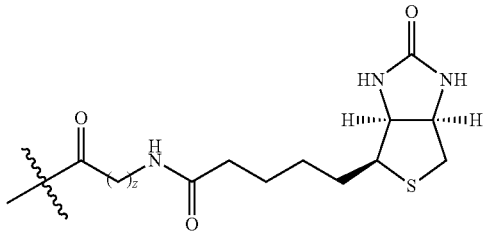

moiety wherein z is an integer between 2 and 10, inclusive. In certain embodiments, at least one $R_4$ is a benzyl group. In certain embodiments, at least one $R_4$ is —$OR_D$ wherein each $R_D$ is hydrogen. In certain embodiments, at least one $R_4$ is —$OR_D$ wherein each $R_D$ is $C_1$-$C_6$ alkyl. In certain embodiments, at least one $R_4$ is —$OR_D$ wherein each $R_D$ is methyl. In certain embodiments, at least one $R_4$ is —$OR_D$ wherein each $R_D$ is ethyl. In certain embodiments, at least one $R_4$ is —$OR_D$ wherein each $R_D$ is propyl. In certain embodiments, at least one $R_4$ is —$N(R_D)_2$ wherein each $R_D$ is hydrogen or $C_1$-$C_6$ alkyl. In certain embodiments, at least one $R_4$ is —$N(R_D)_2$ wherein each $R_D$ is $C_1$-$C_6$ alkyl. In certain embodiments, at least one $R_4$ is —$N(R_D)_2$ wherein each $R_D$ is methyl. In certain embodiments, at least one $R_4$ is —$N(R_D)_2$ wherein each $R_D$ is ethyl. In certain embodiments, at least one $R_4$ is —$N(R_D)_2$ wherein each $R_D$ is propyl. In certain embodiments, at least one $R_4$ is —$N(R_D)_2$ wherein each $R_D$ is butyl. In certain embodiments, at least one $R_4$ is —$N(R_D)_2$ wherein each $R_D$ is pentyl. In certain embodiments, at least one $R_4$ is —$N(R_D)_2$ wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, at least one $R_4$ is —$OR_D$. In certain embodiments, $R_D$ is an acyl moiety. In certain embodiments, the acyl moiety is a $C_1$-$C_3$ acyl moiety. In certain embodiments, the acyl moiety is —$C(=O)CH_3$. In certain embodiments, the acyl moiety is —C(=O)CH₂CH₃. In certain embodiments, the acyl moiety is —C(=O)CH₂CH₂CH₃.

In certain embodiments, the compound is of formula:

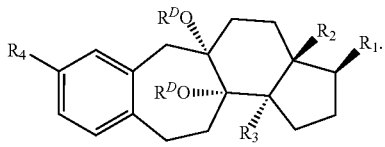

In certain embodiments, the compound is of formula:

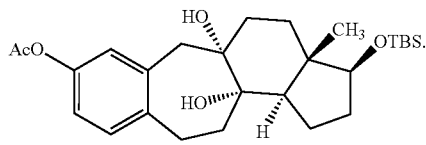

In certain embodiments, the present invention provides compounds of the formula:

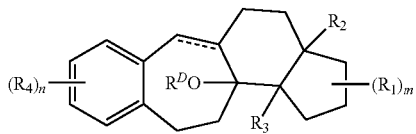

wherein:
the dashed line represents the presence or absence of a bond;
m is an integer between 0 and 6, inclusive;
n is an integer between 0 and 4, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO₂R$_A$; —CN; —SCN; —SR$_A$; —SOR$_A$; —SO₂R$_A$; —NO₂; —N₃; =O; =N(R$_A$); =S; —N(R$_A$)₂; —NHC(=O)R$_A$; —NR$_A$C(=O)N(R$_A$)₂; —OC(=O)OR$_A$; —OC(=O)R$_A$; —OC(=O)N(R$_A$)₂; —NR$_A$C(=O)OR$_A$; or —C(R$_A$)₃; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R_2$ is hydrogen or $C_1$-$C_6$ aliphatic;
$R_3$ is hydrogen or $C_1$-$C_6$ aliphatic;
each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO₂R$_D$; —CN; —SCN; —SR$_D$; —SOR$_D$; —SO₂R$_D$; —NO₂; —N₃; —N(R$_D$)₂; —NHC(=O)R$_D$; —NR$_A$C(=O)N(R$_D$)₂; —OC(=O)OR$_D$; —OC(=O)R$_D$; —OC(=O)N(R$_D$)₂; —NR$_D$C(=O)OR$_D$; or —C(R$_D$)₃; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

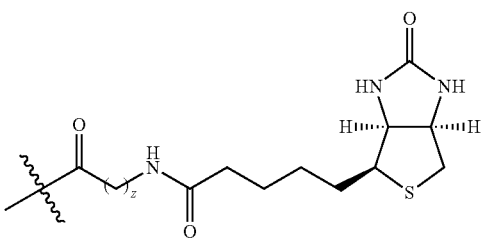

moiety; or a moiety wherein z is an integer between 2 and 10, inclusive; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4.

In certain embodiments, $R_1$ is hydrogen. In certain embodiments, $R_1$ is substituted or unsubstituted aliphatic. In some embodiments, $R_1$ is substituted or unsubstituted alkyl. In certain embodiments, $R_1$ is $C_1$-$C_6$ alkyl. In certain embodiments, $R_1$ is methyl. In certain embodiments, $R_1$ is ethyl. In certain embodiments, $R_1$ is propyl. In certain embodiments, $R_1$ is substituted or unsubstituted aryl. In certain embodiments, $R_1$ is substituted or unsubstituted phenyl. In certain embodiments, $R_1$ is substituted phenyl. In certain embodiments, $R_1$ is unsubstituted phenyl. In certain embodiments, $R_1$ is substituted or unsubstituted naphthyl. In certain embodiments, $R_1$ is substituted naphthyl. In certain embodiments, $R_1$ is unsubstituted naphthyl. In certain embodiments, $R_1$ is substituted or unsubstituted heteroaryl. In certain embodiments, $R_1$ is substituted or unsubstituted isoquinolinyl. In certain embodiments, $R_1$ is substituted isoquinolinyl. In certain embodiments, $R_1$ is unsubstituted isoquinolinyl. In certain embodiments, $R_1$ is unsubstituted 5-isoquinolinyl. In certain embodiments, $R_1$ is unsubstituted 6-isoquinolinyl. In certain embodiments, at least one $R_1$ is substituted or unsubstituted indolyl. In certain embodiments, at least one $R_1$ is substituted or unsubstituted indolyl isoindolyl. In certain embodiments, at least one $R_1$ is substituted or unsubstituted indolyl benzothienyl. In certain embodiments, at least one $R_1$ is substituted or unsubstituted indolyl benzofuranyl. In certain embodiments, at least one $R_1$ is substituted or unsubstituted indolyl dibenzofuranyl. In certain embodiments, at least one $R_1$ is substituted or unsubstituted indolyl. In certain embodiments, at least one $R_1$ is substituted or unsubstituted indolyl indazolyl. In certain embodiments, at least one $R_1$ is substituted or unsubstituted indolyl benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, at least one $R_1$ is $-OR_A$. In certain embodiments, at least one $R_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_A$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, $R_4$ is hydrogen. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ is $C_1$-$C_6$ alkyl substituted with an aryl group. In certain embodiments, at least one $R_4$ comprises biotin or a biotin derivative. In certain embodiments, at least one $R_4$ is a

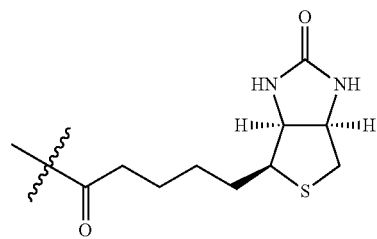 [SMILES: *C(=O)CCCC[C@@H]1SC[C@@H]2NC(=O)N[C@@H]21]

moiety. In certain embodiments, at least one $R_4$ is a

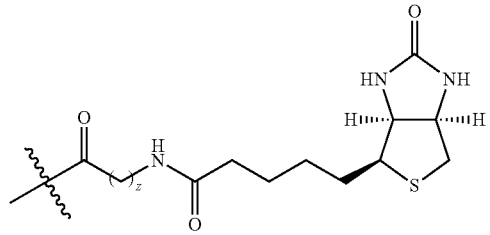

moiety wherein z is an integer between 2 and 10, inclusive. In certain embodiments, at least one $R_4$ is a benzyl group. In certain embodiments, at least one $R_4$ is $-OR_D$ wherein each $R_D$ is hydrogen. In certain embodiments, at least one $R_4$ is $-OR_D$ wherein each $R_D$ is $C_1$-$C_6$ alkyl. In certain embodiments, at least one $R_4$ is $-OR_D$ wherein each $R_D$ is methyl. In certain embodiments, at least one $R_4$ is $-OR_D$ wherein each $R_D$ is ethyl. In certain embodiments, at least one $R_4$ is $-OR_D$ wherein each $R_D$ is propyl. In certain embodiments, at least one $R_4$ is $-N(R_D)_2$ wherein each $R_D$ is hydrogen or $C_1$-$C_6$ alkyl. In certain embodiments, at least one $R_4$ is $-N(R_D)_2$ wherein each $R_D$ is $C_1$-$C_6$ alkyl. In certain embodiments, at least one $R_4$ is $-N(R_D)_2$ wherein each $R_D$ is methyl. In certain embodiments, at least one $R_4$ is $-N(R_D)_2$ wherein each $R_D$ is ethyl. In certain embodiments, at least one $R_4$ is $-N(R_D)_2$ wherein each $R_D$ is propyl. In certain embodiments, at least one $R_4$ is $-N(R_D)_2$ wherein each $R_D$ is butyl. In certain embodiments, at least one $R_4$ is $-N(R_D)_2$ wherein each $R_D$ is pentyl. In certain embodiments, at least one $R_4$ is $-N(R_D)_2$ wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, at least one $R_4$ is $-OR_D$. In certain embodiments, $R_D$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_D$ is an alkylaryl group. In certain embodiments, the alkylaryl group is a benzyl group.

In certain embodiments, the compound is of formula:

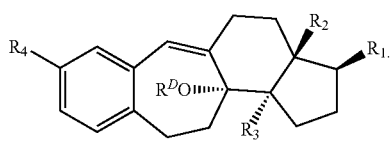

In certain embodiments, the compound is of formula:

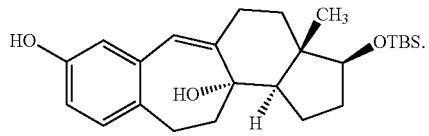

In certain embodiments, the present invention provides compounds of the formula:

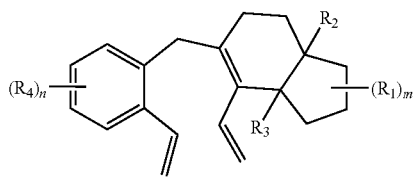

wherein
m is an integer between 0 and 6, inclusive;
n is an integer between 0 and 4, inclusive;
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; =O; =N($R_A$); =S; —N($R_A$)$_2$; —NHC(=O)$R_A$; —$NR_A$C(=O)N($R_A$)$_2$; —OC(=O)$OR_A$; —OC(=O)$R_A$; —OC(=O)N($R_A$)$_2$; —$NR_A$C(=O)$OR_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R_2$ is hydrogen or $C_1$-$C_6$ aliphatic;
$R_3$ is hydrogen or $C_1$-$C_6$ aliphatic;
each occurrence of $R_4$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —C(=O)$R_D$; —$CO_2R_D$; —CN; —SCN; —$SR_D$; —$SOR_D$; —$SO_2R_D$; —$NO_2$; —$N_3$; —N($R_D$)$_2$; —NHC(=O)$R_D$; —$NR_A$C(=O)N($R_D$)$_2$; —OC(=O)$OR_D$; —OC(=O)$R_D$; —OC(=O)N($R_D$)$_2$; —$NR_D$C(=O)$OR_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; heteroarylthio; a

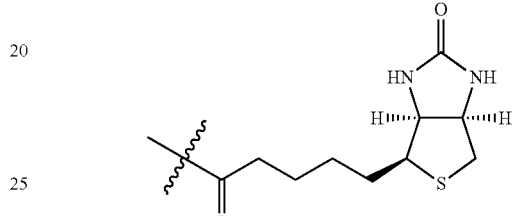

moiety; or a

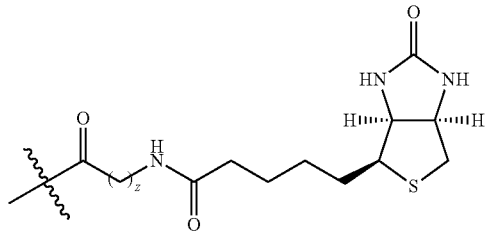

moiety wherein z is an integer between 2 and 10, inclusive; and salts thereof.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6.

In certain embodiments, n is 0. In certain embodiments, n is 1. In certain embodiments, n is 2. In certain embodiments, n is 3. In certain embodiments, n is 4.

In certain embodiments, $R_1$ is hydrogen. In certain embodiments, $R_1$ is substituted or unsubstituted aliphatic. In some embodiments, $R_1$ is substituted or unsubstituted alkyl. In certain embodiments, $R_1$ is $C_1$-$C_6$ alkyl. In certain embodiments, $R_1$ is methyl. In certain embodiments, $R_1$ is ethyl. In certain embodiments, $R_1$ is propyl. In certain embodiments, $R_1$ is substituted or unsubstituted aryl. In certain embodiments, $R_1$ is substituted or unsubstituted phenyl. In certain embodiments, $R_1$ is substituted phenyl. In certain embodiments, $R_1$ is unsubstituted phenyl. In certain embodiments, $R_1$ is substituted or unsubstituted naphthyl. In certain embodiments, $R_1$ is substituted naphthyl. In certain embodiments, $R_1$ is unsubstituted naphthyl. In certain embodiments, $R_1$ is substituted or unsubstituted heteroaryl. In certain embodiments, $R_1$ is substituted or unsubstituted isoquinolinyl. In certain embodiments, $R_1$ is substituted isoquinolinyl. In certain embodiments, $R_1$ is unsubstituted isoquinolinyl. In certain embodiments, $R_1$ is unsubstituted 5-isoquinolinyl. In certain embodiments, $R_1$ is unsubstituted 6-isoquinolinyl. In certain embodiments, at least one $R_1$ is substituted or unsubstituted indolyl. In certain embodiments, at least one $R_1$ is substituted or unsubstituted indolyl isoindolyl. In certain embodiments, at least one $R_1$ is substituted or unsubstituted indolyl benzothienyl. In certain embodiments, at least one $R_1$ is substituted or unsubstituted indolyl benzofuranyl. In certain embodiments, at least one $R_1$ is substituted or unsubstituted indolyl dibenzofuranyl. In certain embodiments, at least one $R_1$ is substituted or unsubstituted indolyl. In certain embodiments, at least one $R_1$ is substituted or unsubstituted indolyl indazolyl. In certain embodiments, at least one $R_1$ is substituted or unsubstituted indolyl benzimidazolyl. In certain embodiments, at least one $R_1$ is substituted or unsubstituted benzthiazolyl. In certain embodiments, at least one $R_1$ is substituted or unsubstituted quinolyl. In certain embodiments, at least one $R_1$ is substituted or unsubstituted isoquinolyl. In certain embodiments, at least one $R_1$ is substituted or unsubstituted cinnolinyl. In certain embodiments, at least one $R_1$ is substituted or unsubstituted phthalazinyl. In certain embodiments, at least one $R_1$ is substituted or unsubstituted quinazolinyl. In certain embodiments, at least one $R_1$ is substituted or unsubstituted quinoxalinyl. In certain embodiments, at least one $R_1$ is substituted or unsubstituted 4H-quinolizinyl. In certain embodiments, at least one $R_1$ is substituted or unsubstituted carbazolyl. In certain embodiments, at least one $R_1$ is substituted or unsubstituted acridinyl. In certain embodiments, at least one $R_1$ is substituted or unsubstituted phenazinyl. In certain embodiments, at least one $R_1$ is substituted or unsubstituted phenothiazinyl. In certain embodiments, at least one $R_1$ is substituted or unsubstituted phenoxazinyl. In certain embodiments, at least one $R_1$ is substituted or unsubstituted tetrahydroquinolinyl. In certain embodiments, at least one $R_1$ is substituted or unsubstituted tetrahydroisoquinolinyl. In certain embodiments, at least one $R_1$ is substituted or unsubstituted pyrido[2,3-b]-1,4-oxazin-3(4H)-one.

In certain embodiments, at least one $R_1$ is —$OR_A$. In certain embodiments, at least one $R_A$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_A$ is an alkylaryl group. In certain embodiments, the alkylaryl group is a benzyl group. In certain embodiments, the oxygen protecting group is TBS (tert-butyldimethylsilyl).

In certain embodiments, $R_2$ is hydrogen. In certain embodiments, $R_2$ is or $C_1$-$C_6$ aliphatic. In some embodiments, $R_2$ is substituted or unsubstituted alkyl. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is pentyl. In certain embodiments, $R_2$ is hexyl.

In certain embodiments, $R_3$ is hydrogen. In certain embodiments, $R_3$ is $C_1$-$C_6$ aliphatic. In some embodiments, $R_3$ is substituted or unsubstituted $C_1$-$C_6$ alkyl. In certain embodiments, $R_3$ is unsubstituted $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is pentyl. In certain embodiments, $R_3$ is hexyl.

In certain embodiments, $R_4$ is hydrogen. In certain embodiments, at least one $R_4$ is substituted or unsubstituted aliphatic. In some embodiments, at least one $R_4$ is substituted or unsubstituted alkyl. In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is substituted alkyl. In certain embodiments, at least one $R_4$ is substituted $C_1$-$C_6$ alkyl. In certain embodiments, at least one $R_4$ is substituted $C_1$-$C_6$ alkyl. In certain embodiments, at least one $R_4$ is $C_1$-$C_6$ alkyl substituted with an aryl group. In certain embodiments, at least one $R_4$ comprises biotin or a biotin derivative. In certain embodiments, at least one $R_4$ is a

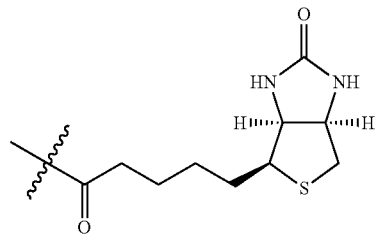 [SMILES: *C(=O)CCCC[C@@H]1SC[C@@H]2NC(=O)N[C@@H]21]

moiety. In certain embodiments, at least one $R_4$ is a

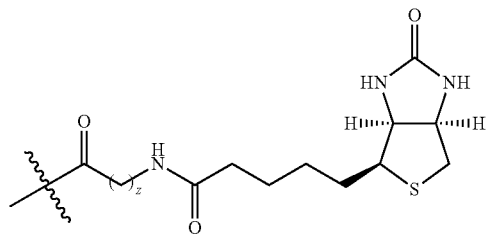

moiety wherein z is an integer between 2 and 10, inclusive. In certain embodiments, at least one $R_4$ is a benzyl group. In certain embodiments, at least one $R_4$ is —$OR_D$ wherein each $R_D$ is hydrogen. In certain embodiments, at least one $R_4$ is —$OR_D$ wherein each $R_D$ is $C_1$-$C_6$ alkyl. In certain embodiments, at least one $R_4$ is —$OR_D$ wherein each $R_D$ is methyl. In certain embodiments, at least one $R_4$ is —$OR_D$ wherein each $R_D$ is ethyl. In certain embodiments, at least one $R_4$ is —$OR_D$ wherein each $R_D$ is propyl. In certain embodiments, at least one $R_4$ is —$N(R_D)_2$ wherein each $R_D$ is hydrogen or $C_1$-$C_6$ alkyl. In certain embodiments, at least one $R_4$ is —$N(R_D)_2$ wherein each $R_D$ is $C_1$-$C_6$ alkyl. In certain embodiments, at least one $R_4$ is —$N(R_D)_2$ wherein each $R_D$ is methyl. In certain embodiments, at least one $R_4$ is —$N(R_D)_2$ wherein each $R_D$ is ethyl. In certain embodiments, at least one $R_4$ is —$N(R_D)_2$ wherein each $R_D$ is propyl. In certain embodiments, at least one $R_4$ is —$N(R_D)_2$ wherein each $R_D$ is butyl. In certain embodiments, at least one $R_4$ is —$N(R_D)_2$ wherein each $R_D$ is pentyl. In certain embodiments, at least one $R_4$ is —$N(R_D)_2$ wherein each $R_D$ is hexyl. As will be appreciated by one of skill in this art, any two combinations of the above $(R_4)_n$ substituents may concurrently be present on the same ring, or any three combinations of the above $(R_4)_n$ substituents may concurrently be present on the same ring.

In certain embodiments, at least one $R_4$ is $—OR_D$. In certain embodiments, at least one $R_D$ is a protecting group. In certain embodiments, the protecting group is an oxygen protecting group. In certain embodiments, the oxygen protecting group is a silyl group. Exemplary oxygen protecting groups include TBS, TMS, TES, TIPS, Ac, Bz, and substituted or unsubstituted $C_1$-$C_6$ alkyl, and others as described herein. In certain embodiments, the oxygen protecting group is methyl. In certain embodiments, the oxygen protecting group is ethyl. In certain embodiments, the oxygen protecting group is propyl. In certain embodiments, the oxygen protecting group is butyl. In certain embodiments, the oxygen protecting group is pentyl. In certain embodiments, the oxygen protecting group is hexyl. In certain embodiments, $R_D$ is an alkylaryl group. In certain embodiments, the alkylaryl group is a benzyl group. In certain embodiments, the oxygen protecting group is triisopropylsilyl (TIPS).

In certain embodiments, the compound is of formula:

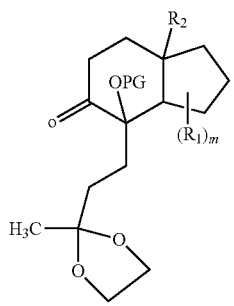

wherein $R_1$, $R_2$, PG, and m are defined as described herein.

In certain embodiments, the compound is of formula:

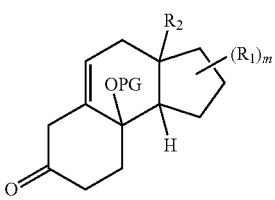

wherein $R_1$, $R_2$, PG, and m are defined as described herein.

In certain embodiments, the compound is of formula:

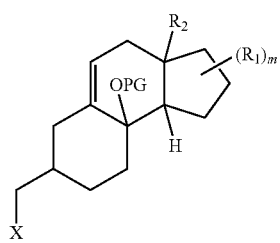

wherein $R_1$, $R_2$, PG, X, and m are defined as described herein.

In certain embodiments, the compound is of formula:

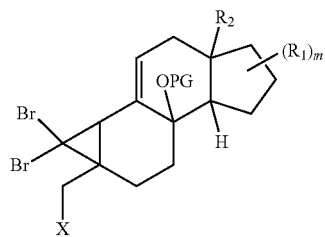

wherein $R_1$, $R_2$, PG, X, and m are defined as described herein.

In certain embodiments, the compound is of formula:

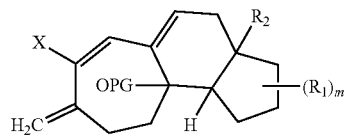

wherein $R_1$, $R_2$, PG, X, and m are defined as described herein.

In certain embodiments, the compound is of formula:

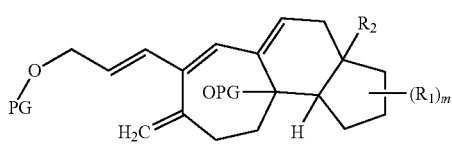

wherein $R_1$, $R_2$, PG, and m are defined as described herein.

In certain embodiments, the compound is of formula:

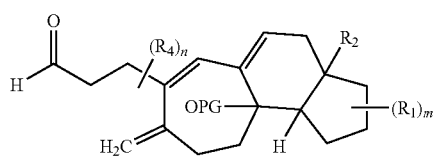

wherein $R_1$, $R_2$, $R_4$, PG, n, and m are defined as described herein.

In certain embodiments, the compound is of formula:

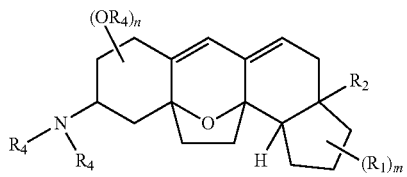

wherein $R_1$, $R_2$, $R_4$, PG, n, and m are defined as described herein.

Exemplary Methods

Provided below are certain exemplary methods for the synthesis of cortistatin A and analogs thereof. The schemes depicted below provide exemplary methods for preparing cortistatin A via Intermediates 2 and 22.

Method for Preparing Cortistatin A from Intermediate 2

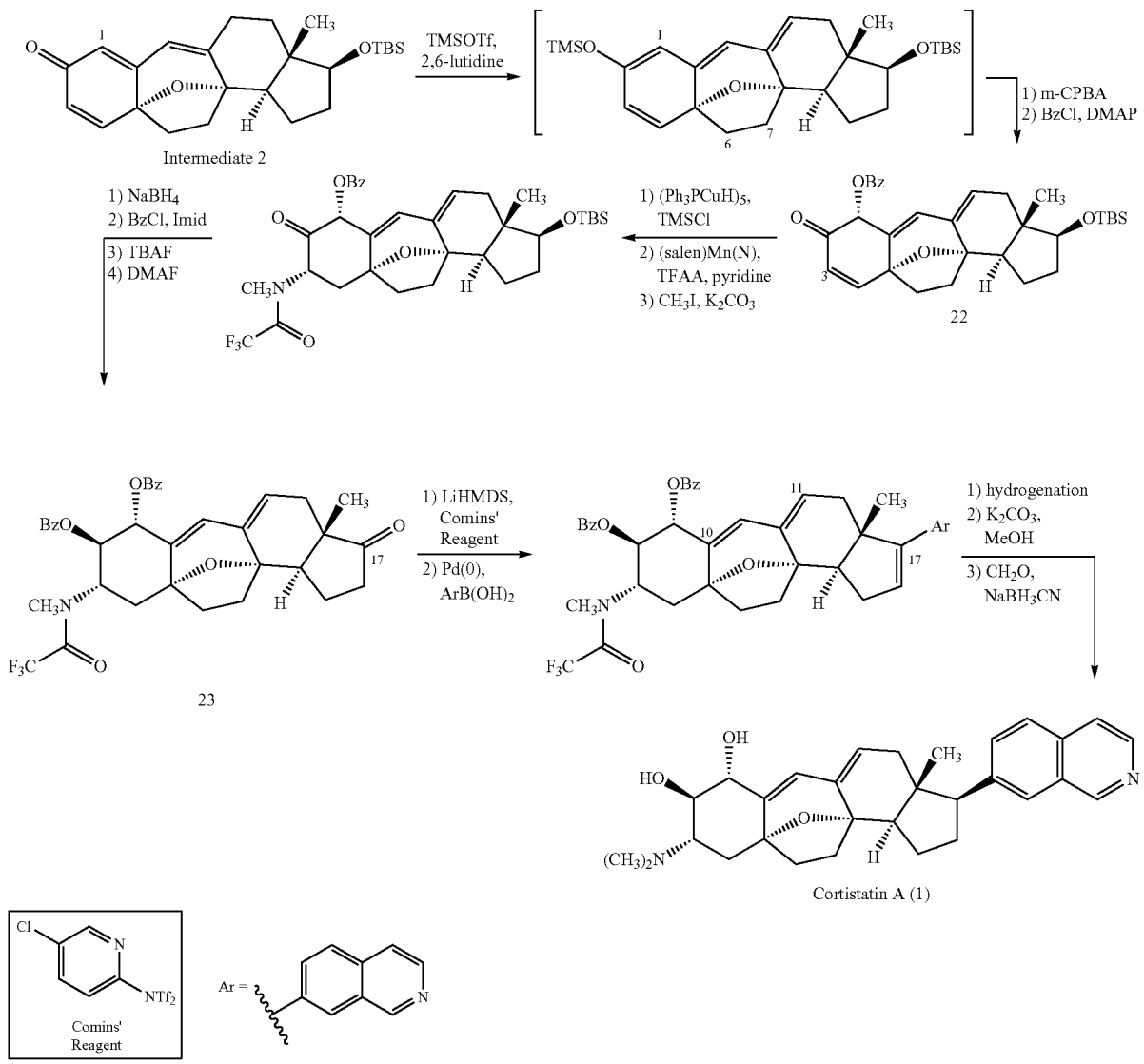

Without wishing to be bound by any particular theory, a trimethylsilyl enol ether intermediate is thought to be formed upon exposure of 2 to trimethylsilyl triflate and 2,6-lutidine, and this intermediate undergoes selective oxidation at position 1 upon treatment with m-chloroperbenzoic acid. It is expected that the hydroxyl group will be introduced with the necessary α-diastereoselectivity, as the C6-C7 carbon bridge should sterically shield the 0-face of the molecule. After hydroxyl protection, the C3 amino group is introduced by enone reductive silylation and electrophilic amination (see Du Bois et al., Nitrogen Transfer from a Nitridomanganese(V) Complex: Amination of Silyl Enol Ethers. *J. Am. Chem. Soc.* 1996, 118, (4), 915-916) of the resulting silyl enol ether; we anticipate that this reaction may also be diastereoselective as a consequence of the C6-C7 carbon bridge. Reduction of the C2 ketone will be followed by several basic functional group manipulations leading to compound 23, which contains a C17 carbonyl group. Literature precedent in similar steroid systems indicates that both the Stille or Suzuki conditions are likely to be effective for carbon-carbon bond formation via the C17 enol triflate intermediate. See Liu et al., 5-(Trimethylstannyl)-2H-pyran-2-one and 3-(Trimethylstannyl)-2H-pyran-2-one: New 2H-Pyran-2-one Synthons. *The Journal of Organic Chemistry* 1996, 61, (19), 6693-6699; and Ottow et al., Highly diastereoselective synthesis of 11 beta, 17 beta-diaryl-18a-homo-19-nor steroids. *Journal Fur Praktische Chemie-Chemiker-Zeitung* 1997, 339, (4), 365-370. Diastereoselective hydrogenation followed by global deprotection and reductive amination is proposed to provide cortistatin A.

An alternative method for preparing cortistatin A from intermediate 22 as shown in the scheme below utilizes different α-amination methodology in which the dimethylamine group is introduced earlier in the synthetic sequence. See Magnus et al, Oxidative addition of azide anion to triisopropylsilyl enol ethers: Synthesis of [alpha]-azido ketones and 2-amino(methoxycarbonyl)alk-2-en-1-ones. *Tetrahedron* 1995, 51, (41), 11075-11086.

Alternative Method for Preparing Cortistatin A from Intermediate 22

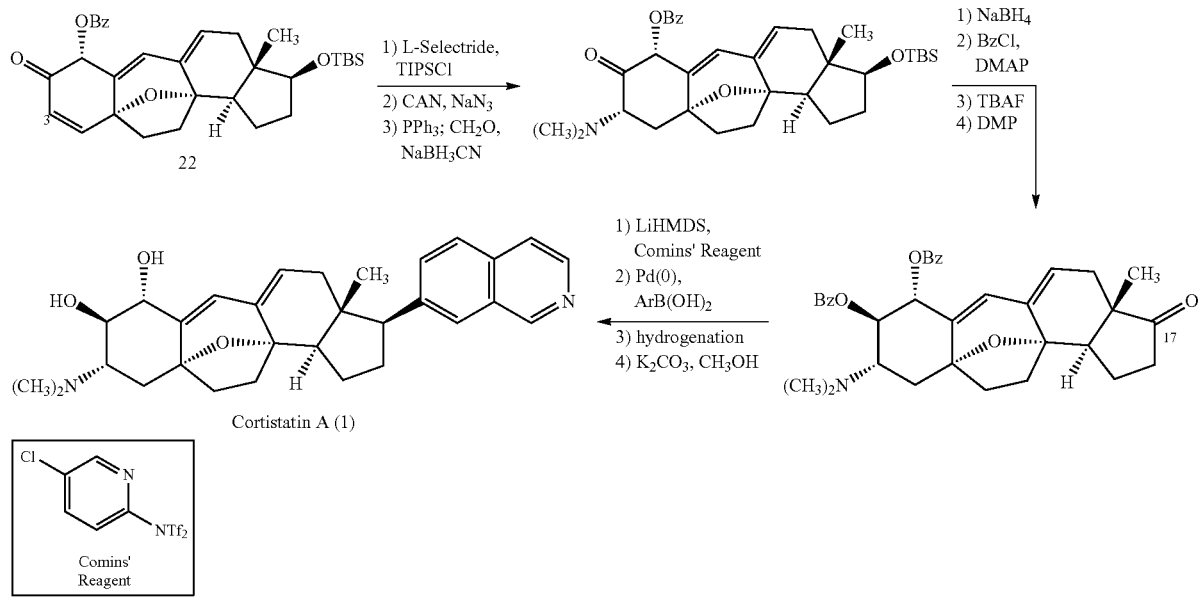

As described above, the synthetic route was designed such that it would be possible to synthesize cortistatin analogues by introducing the A-ring stereotriad or the D-ring isoquinoline group in either order. A synthetic approach based on initial isoquinoline introduction followed by A-ring manipulation is shown in the Scheme below.

Alternative Method for Preparing Cortistatin A from Intermediate 2

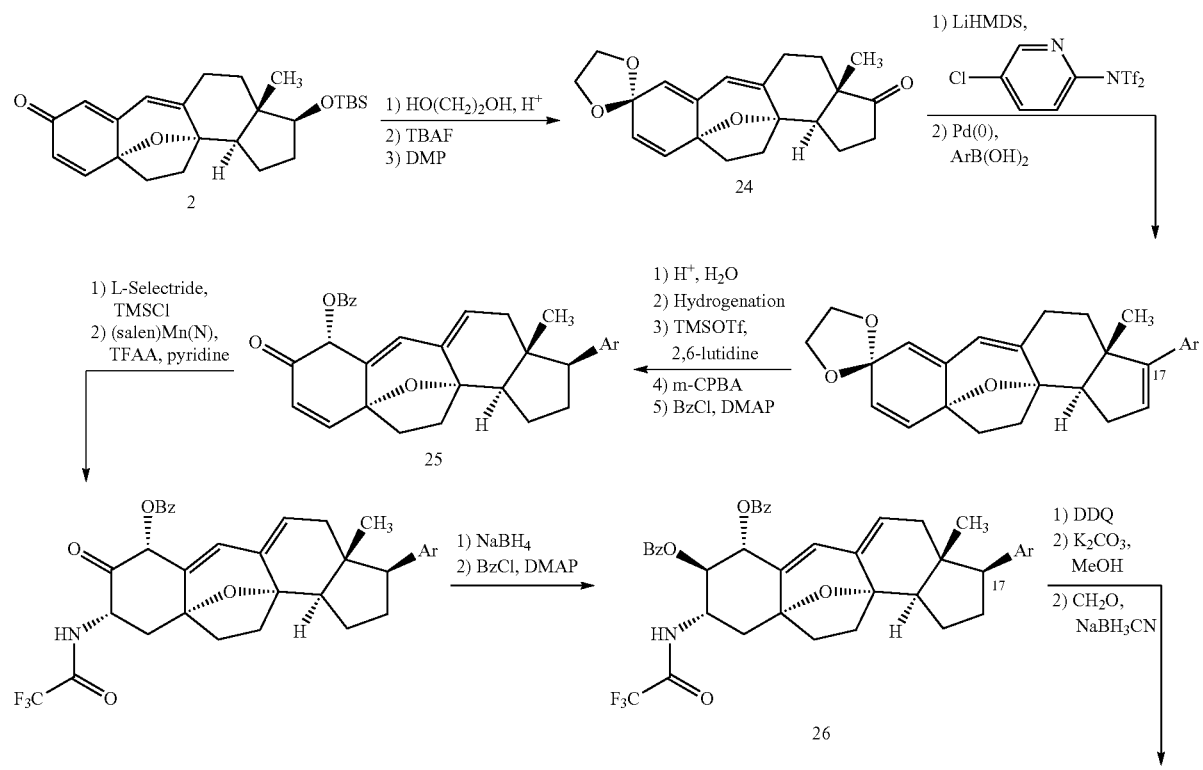

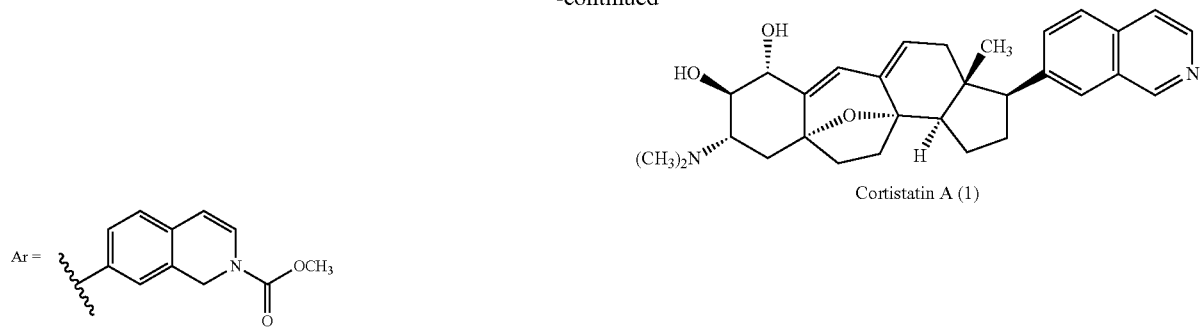

Cortistatin A (1)

In this sequence, ketalization of 2 followed by deprotection and oxidation of the C17 silyl ether is proposed to provide ketone 24. Subsequent enolization with lithium hexamethyldisilazide and trapping of the enolate as the corresponding enol triflate, followed by Suzuki cross-coupling, is proposed to introduce the isoquinoline in protected form. The C17 olefin will be hydrogenated and the C1 and C3 oxidations carried out as previously described to provide intermediate 25. Stereoselective reduction of the ketone and protection of the product alcohol is proposed to provide 26, which will be oxidized, deprotected, and then reductively aminated to furnish cortistatin A. See Williams et al., Isocyanide Addition to Pyridinium Salts. Efficient Entry into Substituted Nicotinonitrile Derivatives. *Org. Lett.* 2006, 8, (25), 5789-5792.

Additional Method for Preparing Cortistatin A from Intermediate 2

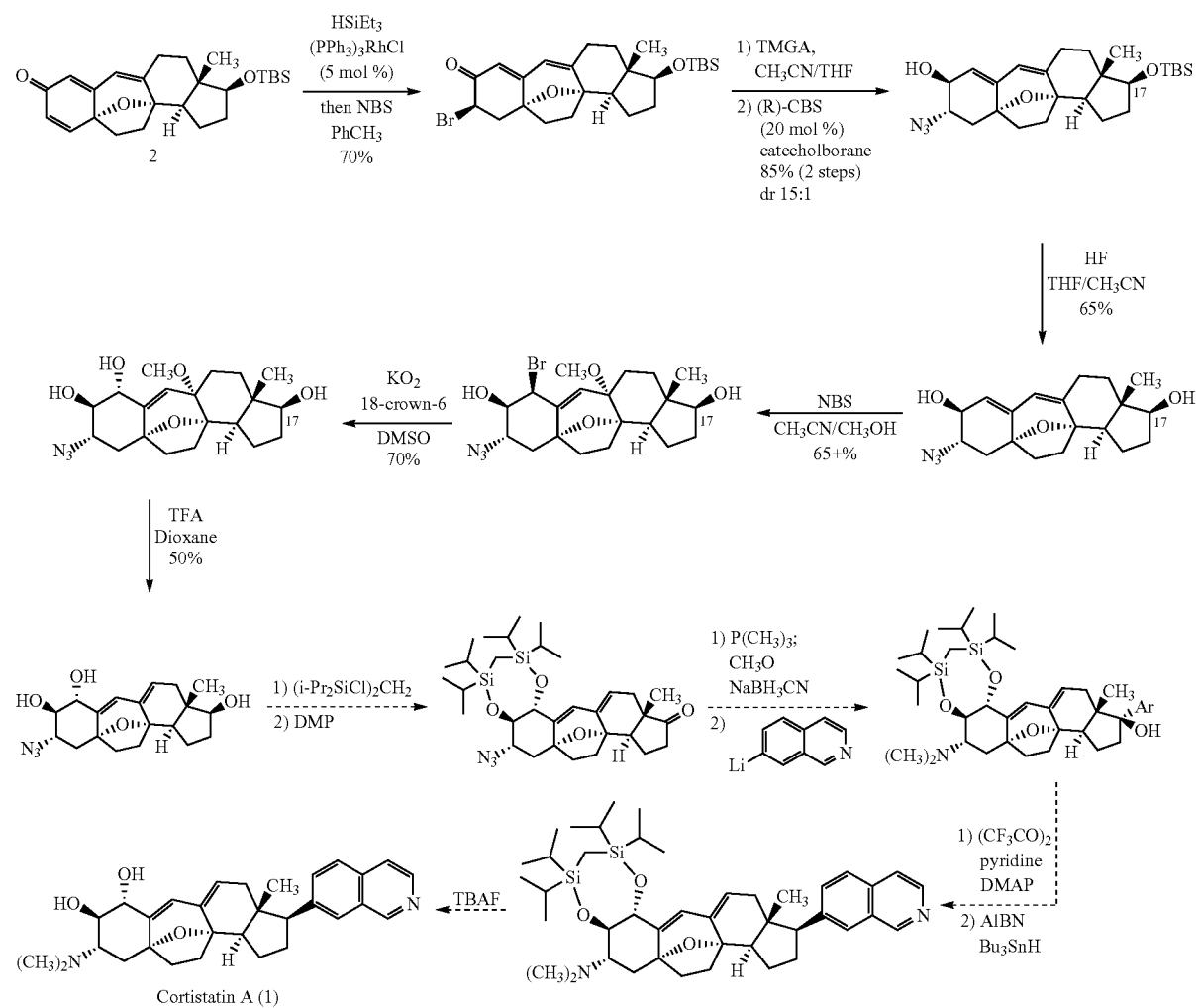

Cortistatin A (1)

An alternative method for preparing cortistatin A from intermediate 2 is shown in the scheme above and utilizes a rhodium-catalyzed Michael addition of hydride to enone 2. Quenching of a proposed enol intermediate with NBS stereoselectively yields the α-bromide product shown. The $S_N2$ displacement of bromide with azide, stereoselective borane reduction, and fluoride-mediated deprotection of the silyl protecting group yield the dihydroxydiene shown. NBS in methanol/acetonitrile stereoselectively adds methoxide and bromide across the diene functionality. Crown ether and potassium superoxide in polar aprotic solvent prompt the $S_N2$ displacement of bromide, resulting in the diol shown which is subsequently converted to the corresponding diene upon the loss of methanol under acidic conditions. Protection of the diol functionality is achieved by conversion to a seven-membered bis-silane ring. Oxidation to the corresponding cyclopentanone is accomplished with Dess-Martin periodinane. Stereoselective 1,2-addition of 7-lithioisoquinoline to the cyclopentanone results in the tertiary alcohol shown, which is converted to the corresponding trifluoroacetate, and deoxygenated with tributyltin hydride and AIBN to the hydrocarbon with inversion of configuration. Fluoride-mediated deprotection of the bis-silane protecting group furnishes cortistatin A.

A method for preparing cortistatin J from intermediate 2 as shown in the scheme above and utilizes a rhodium-catalyzed Michael addition of hydride to cyclohexadienone 2. Quenching of a proposed enol intermediate with NBS stereoselectively yields α-bromide 30. The stereoselective $S_N2$ displacement of bromide is accomplished with tetramethylguanidinium azide (TMGA). Stereoselective borane reduction yields hydroxyazide 31. Reduction of azide 31 to the primary amine and reductive amination to dimethylamine 32 is followed by dehydration of 32 under acidic conditions to yield triene 33. Oxidation to the corresponding cyclopentanone is accomplished with the Dess-Martin periodinane. Stereoselective 1,2-addition of 7-lithioisoquinoline to the cyclopentanone results in the tertiary alcohol shown, which is converted to the corresponding trifluoroacetate, and deoxygenated with inversion of configuration with tributyltin hydride and AIBN to furnish cortistatin J.

Route A: Preparation of the Epoxide

Converting 2-Methylcyclopentaine-1,3-dione to exo-methylene ketone 5

The synthesis of the epoxide begins with synthesizing the Exo-Methylene ketone 5 as shown in the scheme below.

Preparation of Cortistatin J

Synthesis of the exo-methylene ketone 5

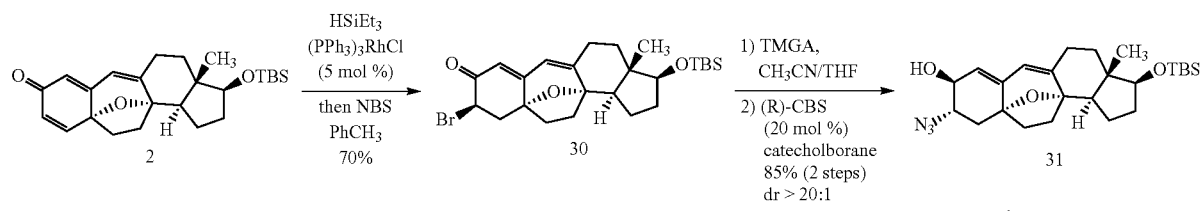

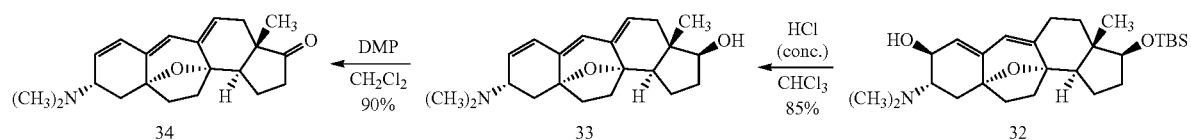

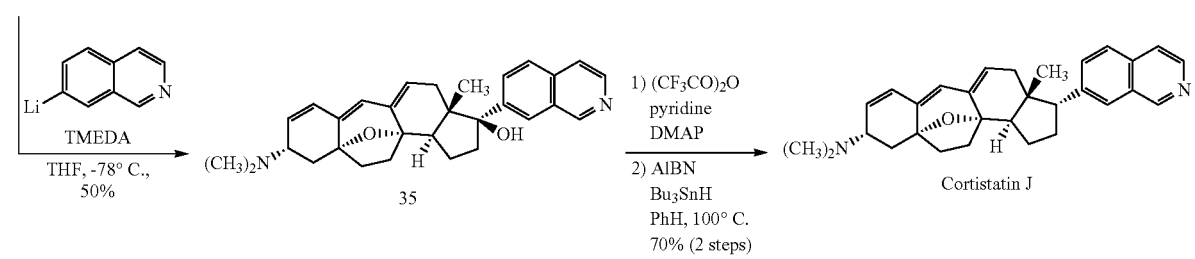

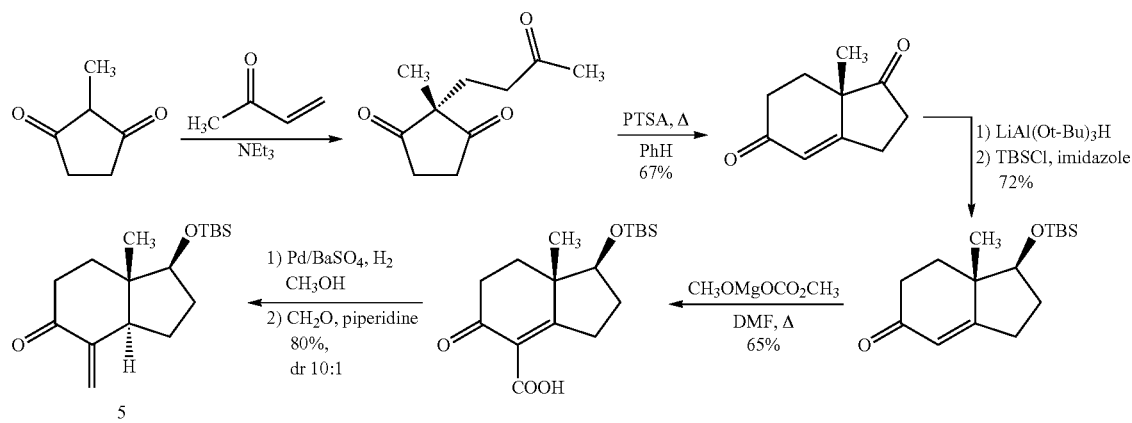

Ketone 5 was converted to the phosphoniosilylated intermediate 6 also depicted in the Scheme below, (see Evans, D. A. et al., New silicon-phosphorus reagents in organic synthesis—carbonyl and conjugate addition-reactions of silicon phosphite esters and related systems. *Journal of the American Chemical Society* 1978, 100, (11), 3467-3477; and Kozikowski et al., Phosphoniosilylation—an efficient and practical method for the beta-functionalization of enones. *Journal of Organic Chemistry* 1986, 51, (17), 3400-3402) and this salt was exposed to n-butyllithium and then paraformaldehyde to achieve a one-carbon Wittig homologation reaction. Rubottom oxidation of silyl enol ether 7 and p-methoxybenzyl protection of the resulting tertiary alcohol 8 provided 4 in 32% overall yield.

Converting exo-methylene ketone 5 to Substituted trans-hydrindane 4

Synthesis of the Substituted trans-hydrindane 4

Converting Substituted trans-hydrindane 4 to the benzyl grignard 3

An exemplary route to the benzylic Grignard reagent 3 is shown in the scheme below. Each step is scalable and high-yielding; this route affords preparation of over 30 grams of benzyl bromide 9, the precursor to Grignard reagent 3. The preparation of o-styryl benzylic Grignard reagents is not well precedented in the literature, and the few related examples that are known were used as polymer initiators or were formed as byproducts during the course of benzyne addition or benzocyclobutenylmethylmagnesium bromide preparation. See Hatada et al., Preparation of PMMA macromers by ortho-vinylbenzylmagnesium chloride and their polymerization. *Polymer Bulletin* 1988, 19, (3), 231-237; Duboudin et al., Evidence for [2+2] and [4+2] cycloadditions of allylic Grignard-reagents to benzyne. *Journal of the Chemical Society-Chemical Communications* 1977, (13), 454-455; and Ernst Peter Künding, C. P., Low temperature Grignard reactions with pure Mg slurries. Trapping of cyclopropylmethyl and benzocyclobutenylmethyl Grignard reagents with $CO_2$. *Helvetica Chimica Acta* 1981, 64, (8), 2606-2613.

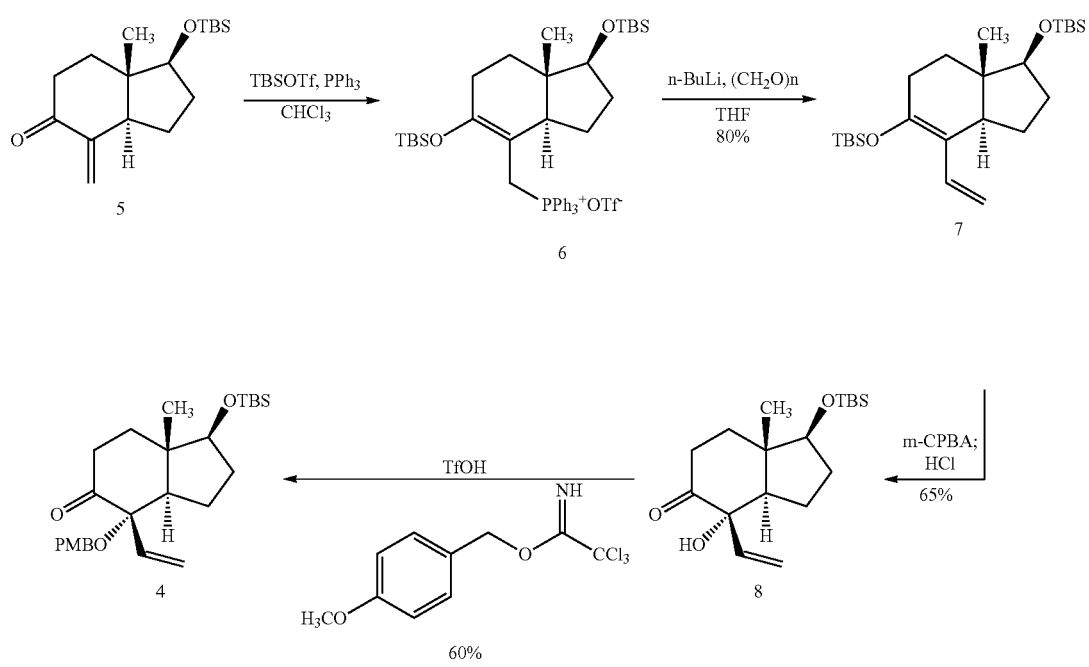

Synthesis of Benzyl Grignard 3

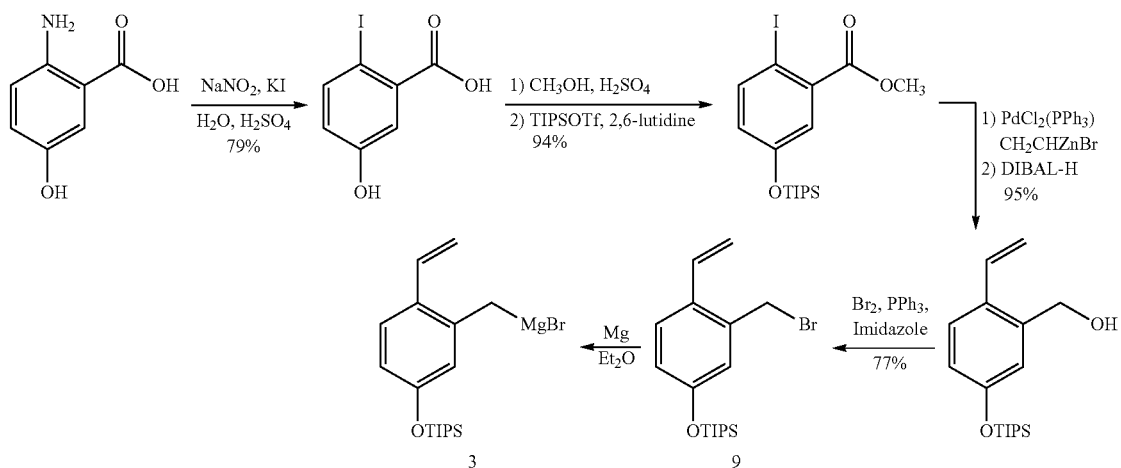

Converting Substituted Trans-Hydrindane 4 to the Epoxide

An exemplary synthesis from the substituted trans-hydrindane 4 to the epoxide (which is en route to Intermediate 2) is shown in the scheme below. As will be appreciated by one of skill in this art, various modifications can be made to the starting materials and reagents used in the scheme to provide the compounds of the present invention.

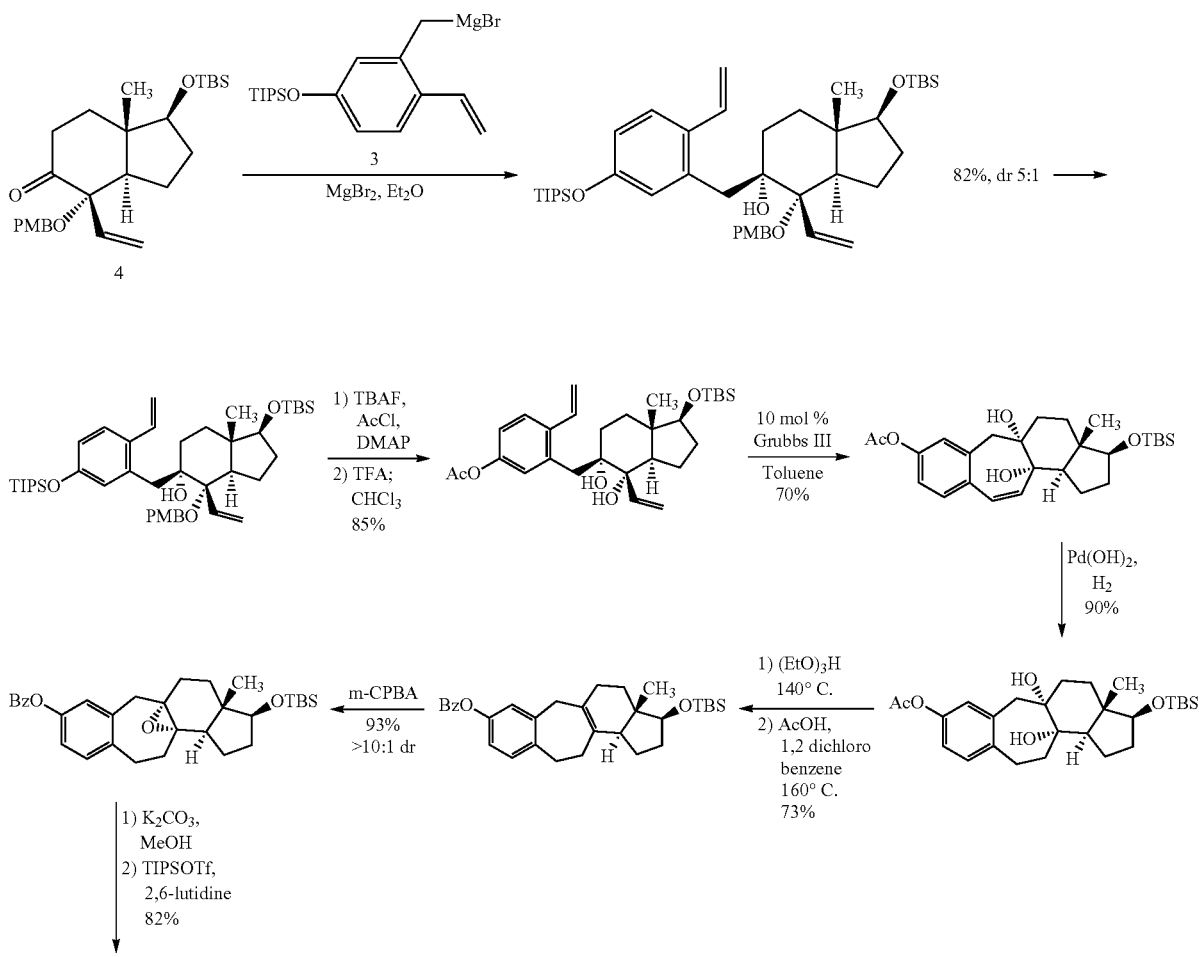

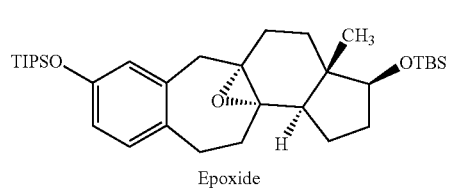
Epoxide
Route B: Preparation of the Epoxide
Converting Exo-Methylene Ketone 5 to the Epoxide
An alternative exemplary synthesis to obtain the epoxide is shown in the scheme below. The synthesis starts with the exo-methylene ketone 5.
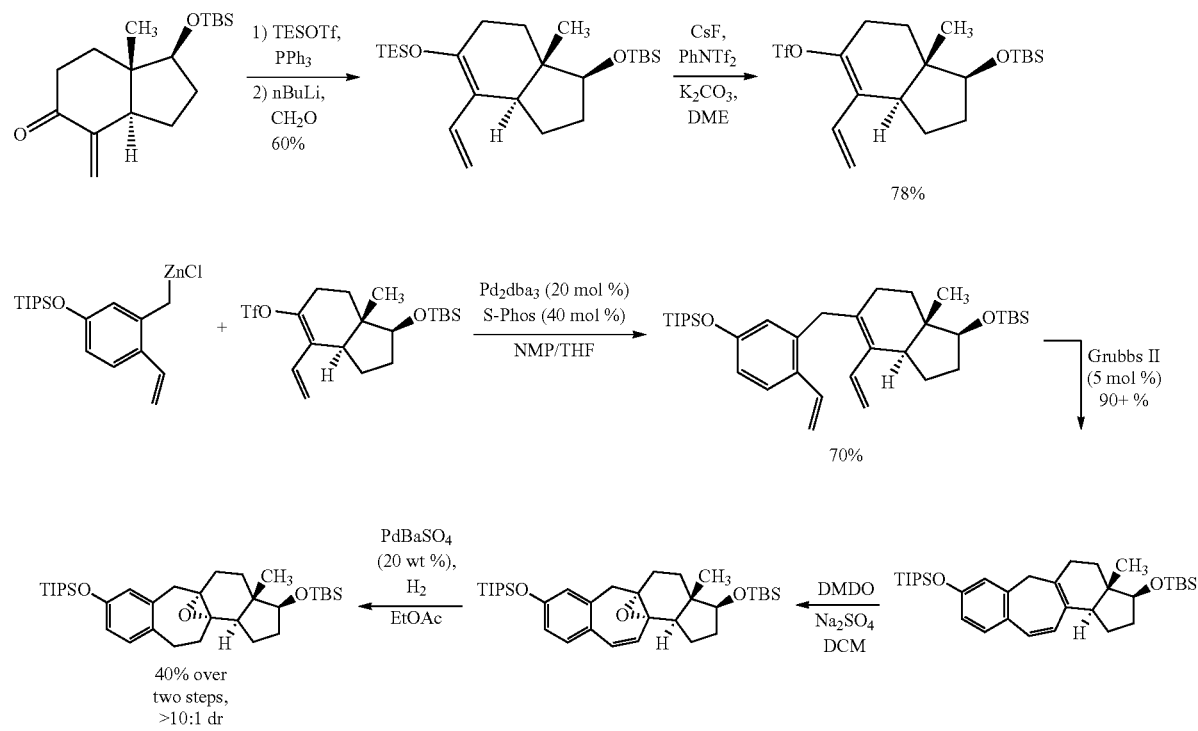
An exemplary synthesis from the epoxide to the Intermediate 2 is shown in the scheme below.
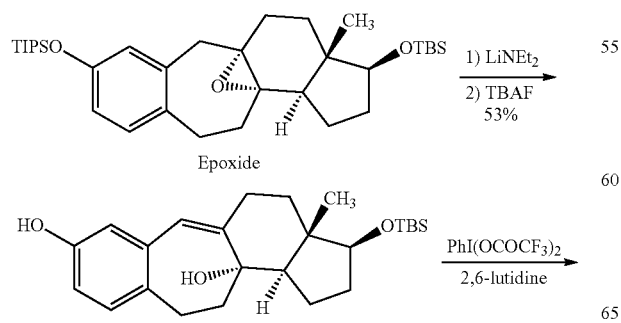
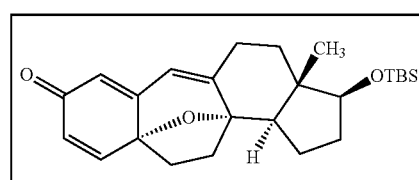
Intermediate 2

Alternative Preparation of Intermediate 2

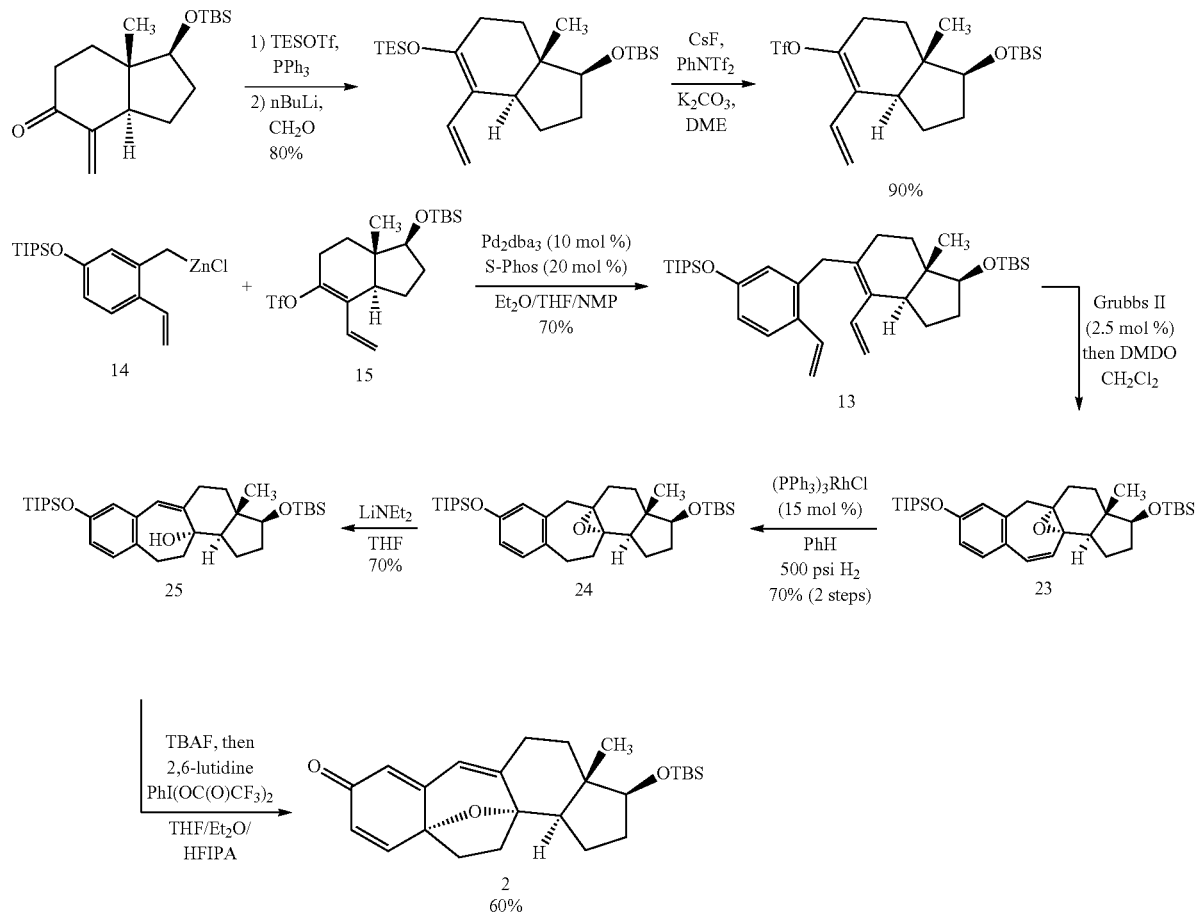

The starting exo-methylene ketone 5 is converted to the silyl-protected dienol shown above upon treatment with triethylsilyltriflate and triphenylphosphine followed by the addition of n-butyllithium, then formaldehyde. Fluoride-mediated deprotection of the silyl ether is followed by reprotection to the corresponding trifluoromethanesulfonate 15 which undergoes palladium-catalyzed Negishi coupling with organozinc derivative 14 to yield the tricyclic derivative 13. Intramolecular olefin metathesis of the terminal alkene units, regio- and stereoselective dimethyldioxirane-mediated epoxidation of the tetrasubstituted olefin, and rhodium-catalyzed reduction of the remaining disubstituted olefin yield the tetracyclic epoxide 24. Regioselective deprotection with $LiNEt_2$ in THF yield tertiary alcohol 25. Fluoride-mediated deprotection of the silyl ether and oxidation of the resulting phenol to cyclohexadienone 2 is mediated with by the Vargolis hypervalent organoiodine reagent and hexafluoro-2-propanol in THF/dimethylether.

Route C: Preparation of Cortistatin Analogs

An exemplary synthesis which in part correlates with Example 3 to obtain cortistatin analogs is shown in the scheme below. The synthesis begins with ketone 5.

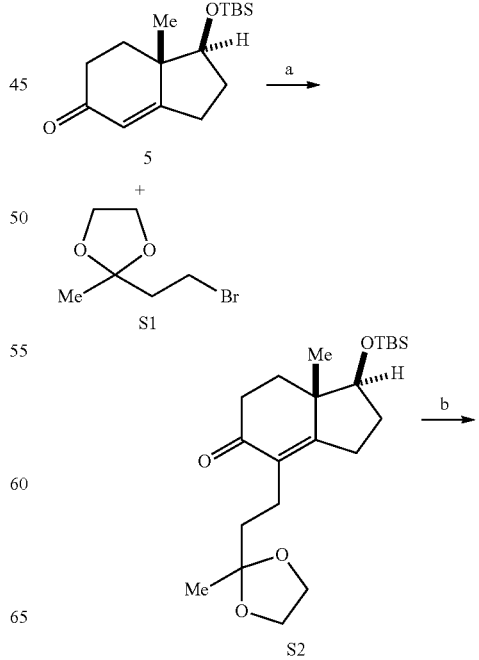

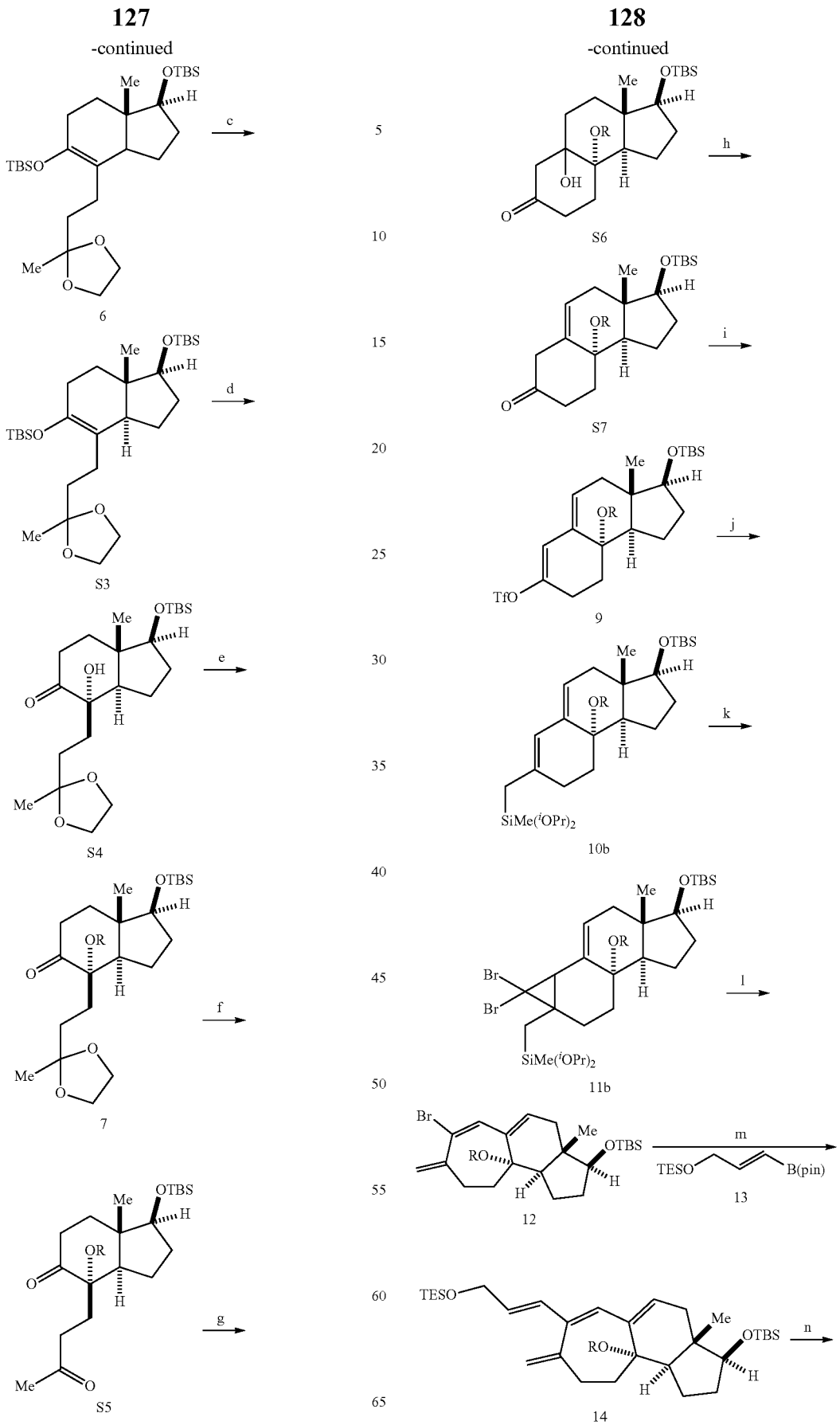

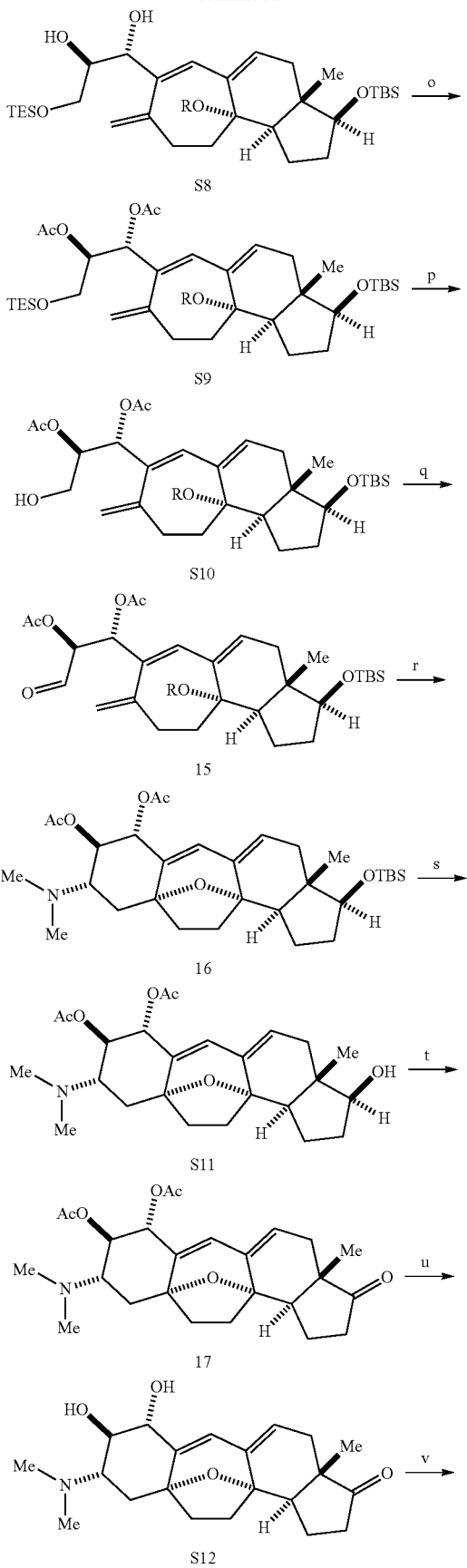
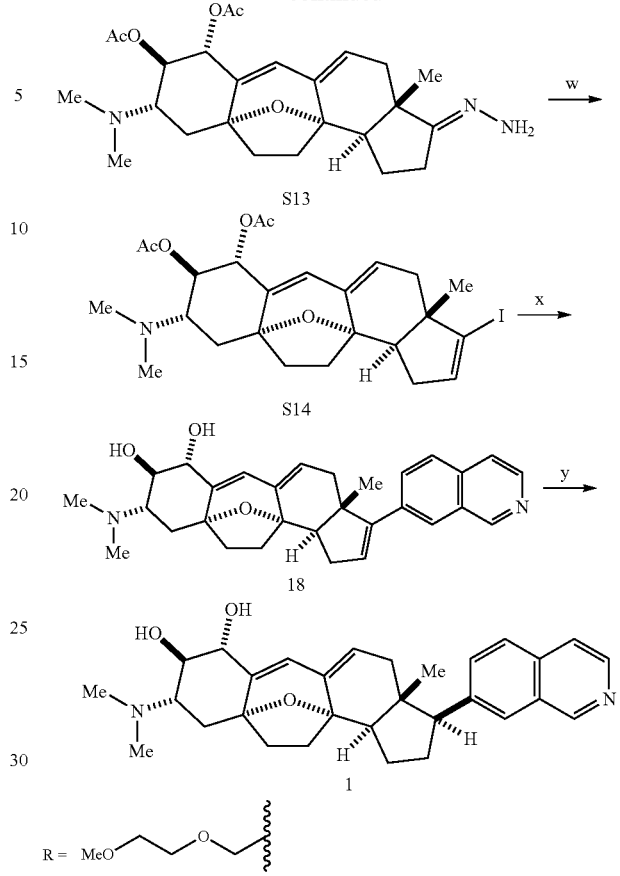

(a) NaH, DMSO, rt, 3 h, 2-(2-bromoethyl)-2-methyl-1,3-dioxolane, rt, 12 h (63%); (b) TBSOTf (1.2 equiv), 2,6-lutidine (2 equiv), $CH_2Cl_2$, 0° C., 2 h; (c) $H_2$ (1 atm), Pd/C (0.08 equiv), EtOAc, rt, 12 h; (d) mCPBA (1.1 equiv), $NaHCO_3$ (10 equiv), toluene, 0° C., 30 min; HF(aq)/THF (1:10), rt, 5 min (66% over 4 steps); (e) MEMCl (2 equiv), iPrNEt$_2$ (4 equiv), 1,2-dichloroethane, 80° C., 18 h (84%); (f) PPTS (0.1 equiv), acetone/water (4:1), 60° C., 4 h; (g) NaOMe (5 equiv), MeOH, 70° C., 1 h (50% over 2 steps); (h) $SOCl_2$ (1.5 equiv), pyridine (3 equiv), $CH_2Cl_2$, −10° C., 30 min; (i) NaHMDS (1.1 equiv), THF, −78 C, 1 h, PhNTf$_2$ (1.05 equiv), 0° C., 2 h; (j) Me(OiPr)$_2$SiCH$_2$MgCl (3 equiv), Pd(PPh$_3$)$_4$ (0.05 equiv), THF, rt, 30 min (62% over 3 steps); (k) CHBr$_3$ (3 equiv), KOtBu (4 equiv), hexane, 0° C., 2 h; (l) TASF (1.2 equiv), DMF, 80° C., 30 min (66% over 2 steps); (m) 13 (2 equiv), Pd(PPh$_3$)$_4$ (0.04 equiv), $K_2CO_3$ (3 equiv), THF/water (5:1), 80° C., 4 h (85%); (n) $K_2OsO_4 \cdot 2H_2O$ (0.02 equiv), (DHQD)$_2$PHAL (0.05 equiv), $K_3Fe(CN)_6$ (3 equiv), $K_2CO_3$ (3 equiv), MeSO$_2$NH$_2$ (1 equiv), tBuOH/water (1:1), 0° C., 2 h; (o) $Ac_2O$ (2.5 equiv), NEt$_3$ (3 equiv), DMAP (0.2 equiv), $CH_2Cl_2$, rt, 18 h (55% over 2 steps); (p) HF/pyr, THF, rt, 5 min; (q) Dess-Martin periodinane (1.2 equiv), $CH_2Cl_2$, rt, 1 h; (r) Me$_2$NH (3 equiv), ZnBr$_2$ (1.5 equiv), $CH_3CN$, 50° C., 40 min (65% over 3 steps); (s) TBAF (1.2 equiv), THF, 70° C., 4 h (70%); (t) TPAP (0.05 equiv), NMO (1.3 equiv), $CH_2Cl_2$, rt, 2.5 h (quant.); (u) $K_2CO_3$ (5 equiv), MeOH, rt, 30 min; (v) $N_2H_4 \cdot H_2O$ (10 equiv), NEt$_3$ (10 equiv), EtOH, 80° C., 6 h; (w) NEt$_3$ (3 equiv), 12 (1 equiv), THF, rt, 5 min; (x) Pd(PPh$_3$)$_4$ (0.5 equiv), 7-isoquinolinestannane (3 equiv), LiCl (10 equiv), CuCl (10 equiv), DMSO, 60° C., 1 h; (y) hydrogenation.

As will be appreciated by one of skill in this art, various modifications can be made to the starting materials and reagents used in the above scheme to provide Intermediate 2, which is then converted to cortistatin A and/or a wide range of cortistatin analogs of the present invention.

Provided below are schemes for certain exemplary methods, Route D and Route E, for the synthesis of analogs of cortistatin A.

Route D

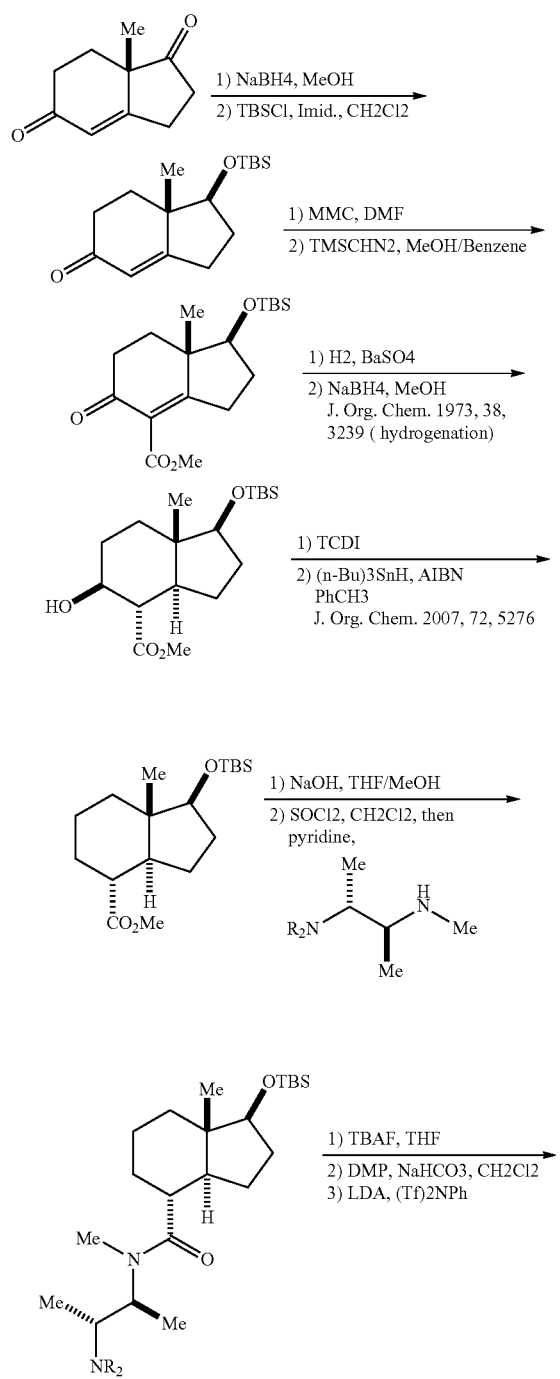

-continued

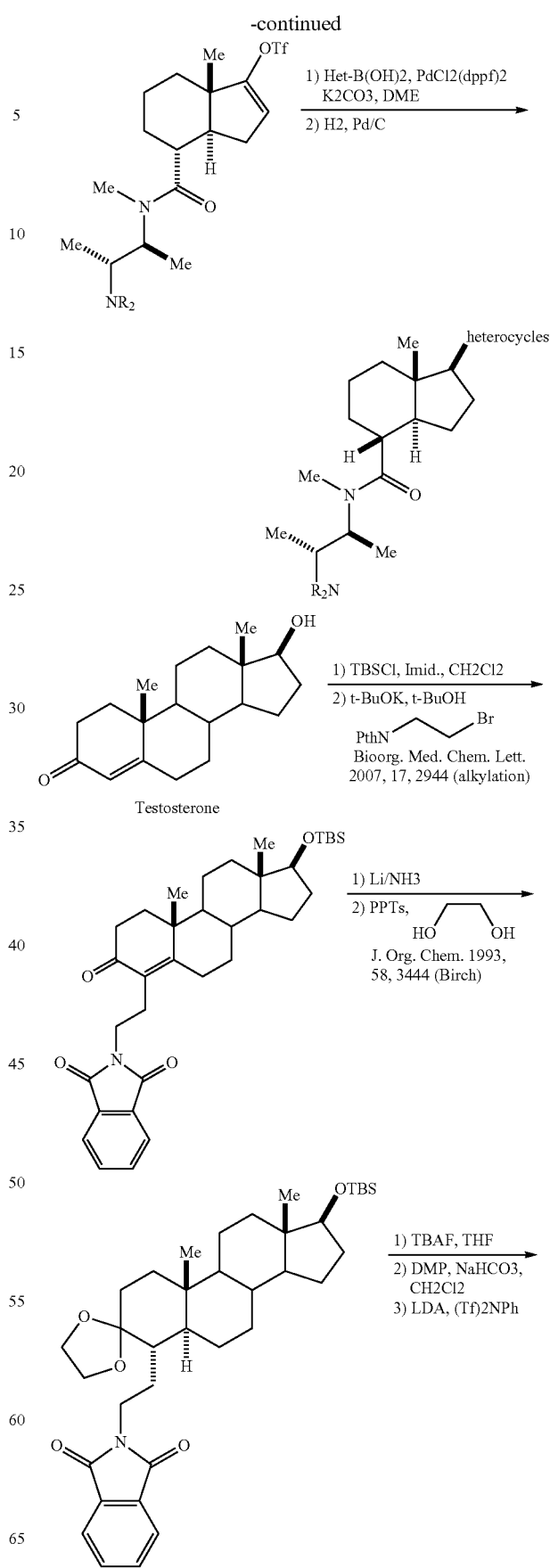

133
-continued
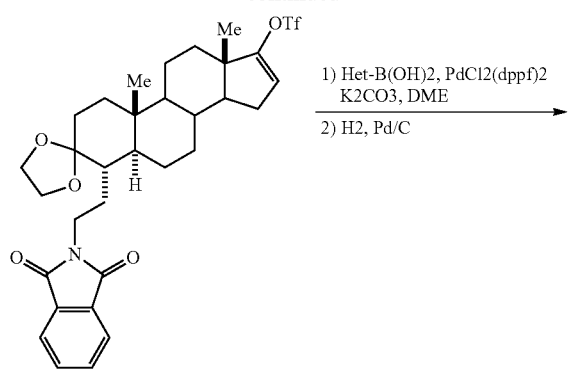
1) Het-B(OH)2, PdCl2(dppf)2
   K2CO3, DME
2) H2, Pd/C
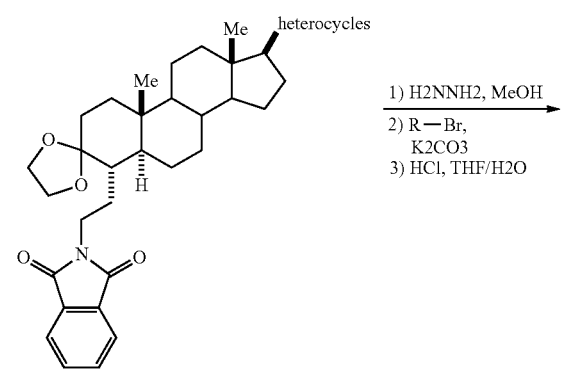
1) H2NNH2, MeOH
2) R—Br, K2CO3
3) HCl, THF/H2O
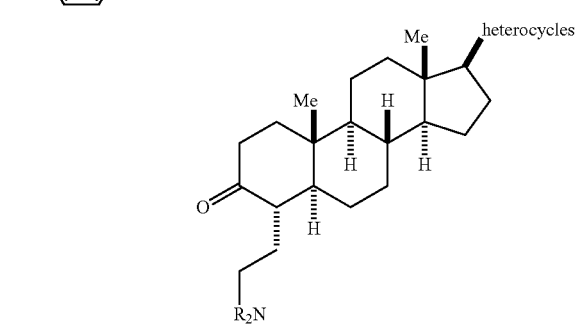
Route E
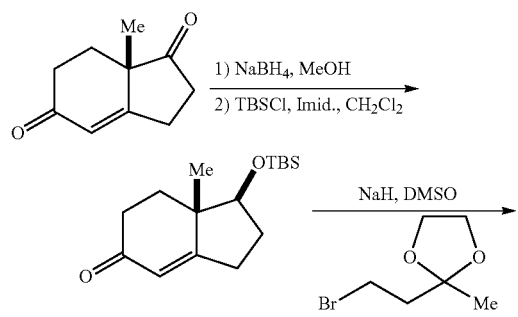
1) NaBH4, MeOH
2) TBSCl, Imid., CH2Cl2
NaH, DMSO
134
-continued
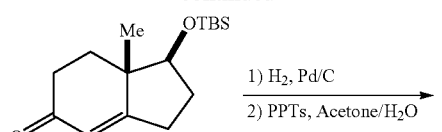
1) H2, Pd/C
2) PPTs, Acetone/H2O
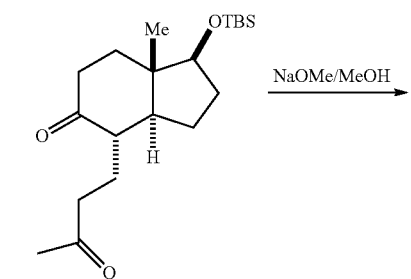
NaOMe/MeOH
1) LDA, PthN—CH2CH2—Br
2) Tf2O, CH2Cl2
*TL*, 2007, 47, 4331 (triflation)
*J. Med. Chem.* 1990, 33, 943 (triflation)
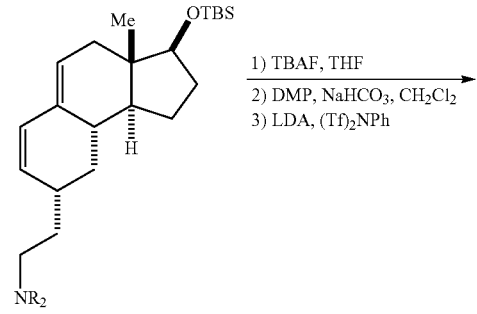
1) (n-Bu)3SnH, Pd(PPh3)4
2) H2NNH2, MeOH
3) R—Br, K2CO3
1) TBAF, THF
2) DMP, NaHCO3, CH2Cl2
3) LDA, (Tf)2NPh

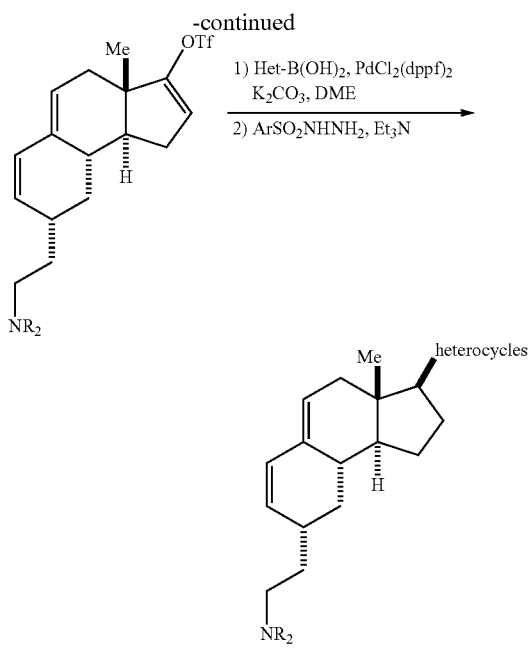

As will be appreciated by one of skill in this art, various modifications can be made to the starting materials and reagents used in the above Route D and Route E scheme to provide cortistatin analogs of the present invention.

Pharmaceutical Compositions and Uses Thereof

This invention also provides pharmaceutical compositions comprising at least one of the compounds as described herein, or a pharmaceutically acceptable salt thereof. In certain embodiments, the compound of the pharmaceutical composition inhibits angiogenesis. Cortistatins have been found to exhibit extremely potent and selective cytostatic activity against human umbilical vein endothelial cells (HUVECs). Therefore, in an embodiment of the invention, cortistatin A and analogs thereof are useful in treating many types of cancer, benign tumors, diabetic retinopathy, rheumatoid arthritis, macular degeneration, atherosclerosis, obesity, and any other diseases or disorders associated with undesired angiogenesis.

As discussed above, the present invention provides novel compounds having anti-angiogenesis activity, and thus the compounds of the present invention provided in the pharmaceutical composition are useful for the treating or preventing any disease or condition associated with aberrant angiogenesis, including a variety of proliferative disorders, such as many types of cancer, benign neoplasms (i.e., tumors), diabetic retinopathy, rheumatoid arthritis, macular degeneration, obesity, and atherosclerosis. Antiangiogenic compounds or compositions of the present invention are administered in therapeutically effective doses to a subject suffering from a proliferative disease. In certain embodiments, the subject suffers from cancer. In certain embodiments, the subject has a benign tumor. In certain embodiments, the subject suffers from diabetic retinopathy. In certain embodiments, the subject suffers from rheumatoid arthritis. In certain embodiments, the subject suffers from macular degeneration. In certain embodiments, the subject suffers from obesity. In certain embodiments, the subject suffers from atherosclerosis. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents, e.g., another antiproliferative agent. In other embodiments, these compositions further comprise an anti-emetic agent, a pain reliever, a multi-vitamin, etc.

It will also be appreciated that certain of the compounds of the present invention can exist in free form for treatment, or where appropriate, as a pharmaceutically acceptable form thereof. According to the present invention, a pharmaceutically acceptable derivative includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof, e.g., a prodrug.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's *Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The invention further provides a method of inhibiting tumor growth. The method involves the administration of a therapeutically effective amount of the compound, a pharmaceutical composition, or a pharmaceutically acceptable form thereof to a subject, including, but not limited to, a human or other mammal (e.g., domesticated animals, cats, dogs, mice, rats). Any method of administration may be used to deliver the compound of pharmaceutical compositions to the animal. In certain embodiments, the compound or pharmaceutical composition is administered orally. In other embodiments, the compound or pharmaceutical composition is administered parenterally.

In certain embodiments, the present invention provides a method of treating a condition associated with abberrant angiogenesis, comprising the step of administering a therapeutically effective amount of the compound, a pharmaceutical composition, or a pharmaceutically acceptable form thereof to a subject. In certain embodiments, the compound or pharmaceutical composition containing the compound is of formula:

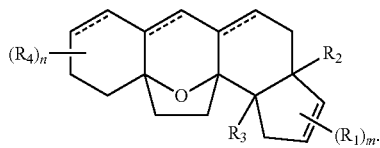

In certain embodiments, the compound or pharmaceutical composition containing the compound is of formula:

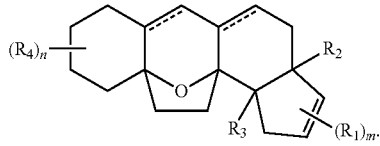

In certain embodiments, the compound is:

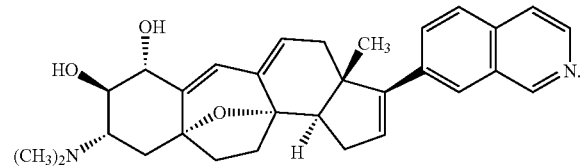

In certain embodiments, the compound or pharmaceutical composition containing the compound is of formula:

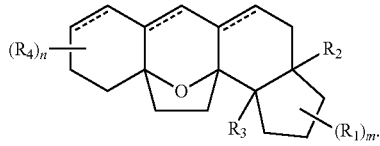

In certain embodiments, the compound or pharmaceutical composition containing the compound is of formula:

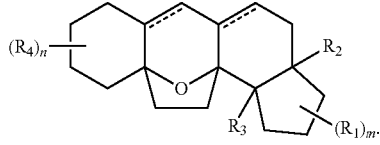

In certain embodiments, the present invention provides a method of treating a proliferative disease, comprising the step of administering a therapeutically effective amount of the compound, a pharmaceutical composition, or a pharmaceutically acceptable form thereof to a subject. In certain embodiments, the compound or pharmaceutical composition containing the compound is of formula

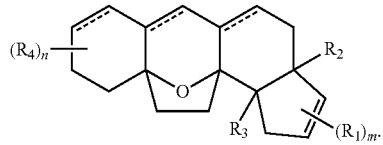

In certain embodiments, the compound or pharmaceutical composition containing the compound is of formula

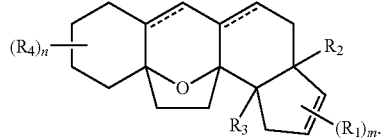

In certain embodiments, the compound is

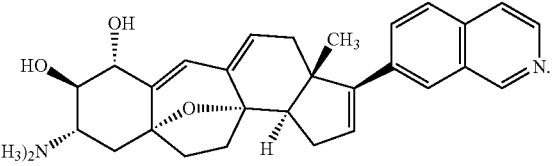

In certain embodiments, the compound or pharmaceutical composition containing the compound is of formula:

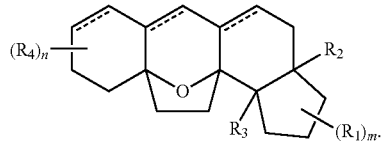

In certain embodiments, the compound or pharmaceutical composition containing the compound is of formula:

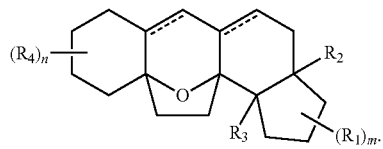

In certain embodiments, the present invention provides a method of inhibiting angiogenesis in a subject, comprising the step of administering an amount of the compound, a pharmaceutical composition, effective to inhibit angiogenesis in a subject. In certain embodiments, the compound or pharmaceutical composition containing the compound is of formula:

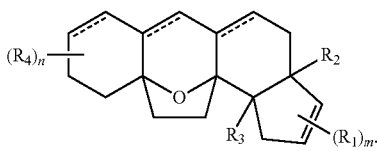

In certain embodiments, the compound or pharmaceutical composition containing the compound is of formula:

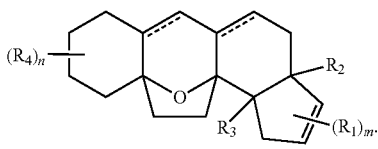

In certain embodiments, the compound is:

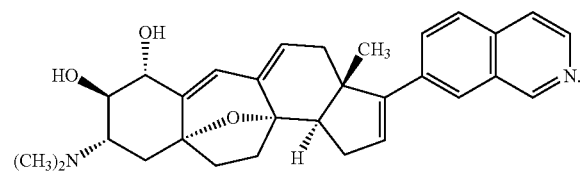

In certain embodiments, the compound or pharmaceutical composition containing the compound is of formula:

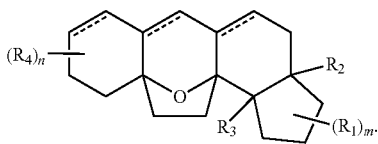

In certain embodiments, the compound or pharmaceutical composition containing the compound is of formula:

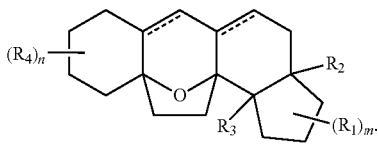

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

143

These and other aspects of the present invention will be further appreciated upon consideration of the following Examples, which are intended to illustrate certain particular embodiments of the invention but are not intended to limit its scope, as defined by the claims.

EXAMPLES

Example 1

The synthesis plan was guided by a desire to produce 1 (cortistatin A), 2 (cortistatin C) and 3 (cortistatin J) for biological and medicinal studies and to generate diverse analogs to systematically determine the structural elements required for anti-angiogenic activity. Eventually, this may enable us to discover molecules less complex than 1 but that maintain its biological activity and that have improved drug properties. The synthesis a shown in the scheme below includes an aza-Prins cyclization via iminium ion 4 with transannular cyclization by a C8 tertiary carbinol. See Simth et al., *Tetrahedron* 1986, 42, 2957-2969. This reaction would simultaneously form the A ring and the oxabicyclo[3.2.1]octene as well as control the C3 N,N-dimethylamine and C5 tertiary ether stereocenters. Substructure matching of 4 suggested that it could be derived from enantiomerically pure Hajos-Parrish ketone. See Hajos et al., *J. Org. Chem.* 1974, 39, 1612-1615. Herein, we report achievement of the aforementioned aza-Prins cyclization reaction and its use in a synthesis of 1.

144

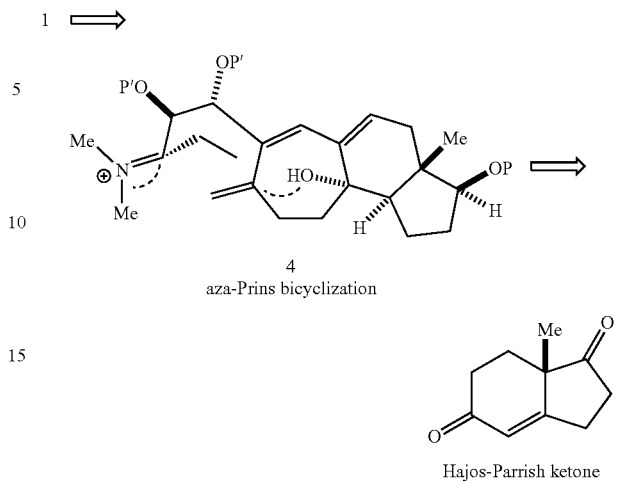

A step of the cortistatin A synthesis is a aza-Prins/transannular etherification reaction. Enantiomerically enriched Hajos-Parrish ketone is the starting material, as depicted above.

Synthesis of Dienes 11a and 11b

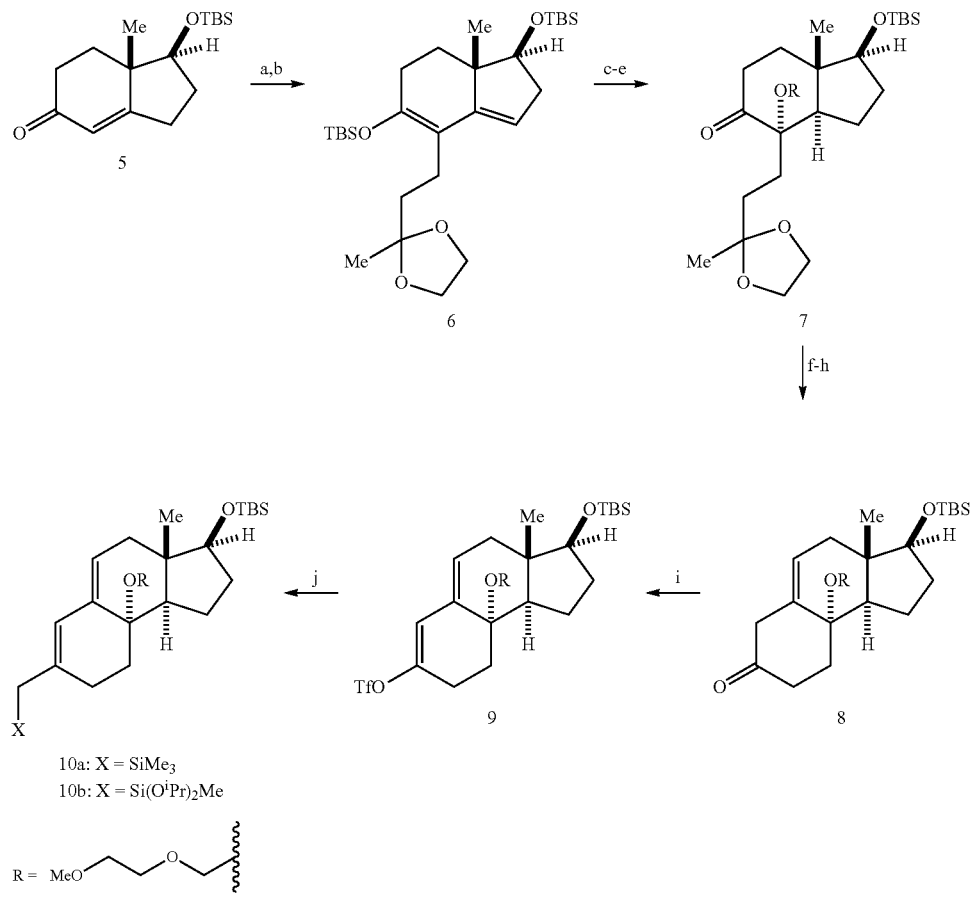

(a) NaH, DMSO, rt, 3 h, 2-(2-bromoethyl)-2-methyl-1,3-dioxolane, rt, 12 h (63%); (b) TBSOTf (1.2 equiv), 2,6-lutidine (2 equiv), $CH_2Cl_2$, 0° C., 2 h; (c) $H_2$ (1 atm), Pd/C (0.08 equiv), EtOAc, rt, 12 h; (d) mCPBA (1.1 equiv), $NaHCO_3$ (10 equiv), toluene, 0° C., 30 min; HF(aq)/THF (1:10), rt, 5 min (66% over 4 steps); (e) MEMCl (2 equiv), $iPrNEt_2$ (4 equiv), 1,2-dichloroethane, 80°, 18 h (84%); (f) PPTS (0.1 equiv), acetone/water (4:1), 60° C., 4 h; (g) NaOMe (5 equiv), MeOH, 70° C., 1 h (50% over 2 steps); (h) $SOCl_2$ (1.5 equiv), pyridine (3 equiv), $CH_2Cl_2$, −10° C., 30 min; (i) NaHMDS (1.1 equiv), THF, −78 C, 1 h, $PhNTf_2$ (1.05 equiv), 0° C., 2 h; (j) $Me_3SiCH_2MgBr$ (3 equiv) for 10a or $Me(OiPr)_2SiCH_2MgCl$ (3 equiv) for 10b, $Pd(PPh_3)_4$ (0.05 equiv), THF, rt, 30 min (62% over 3 steps). Completion of a synthesis of (+)-cortistatin A (1).

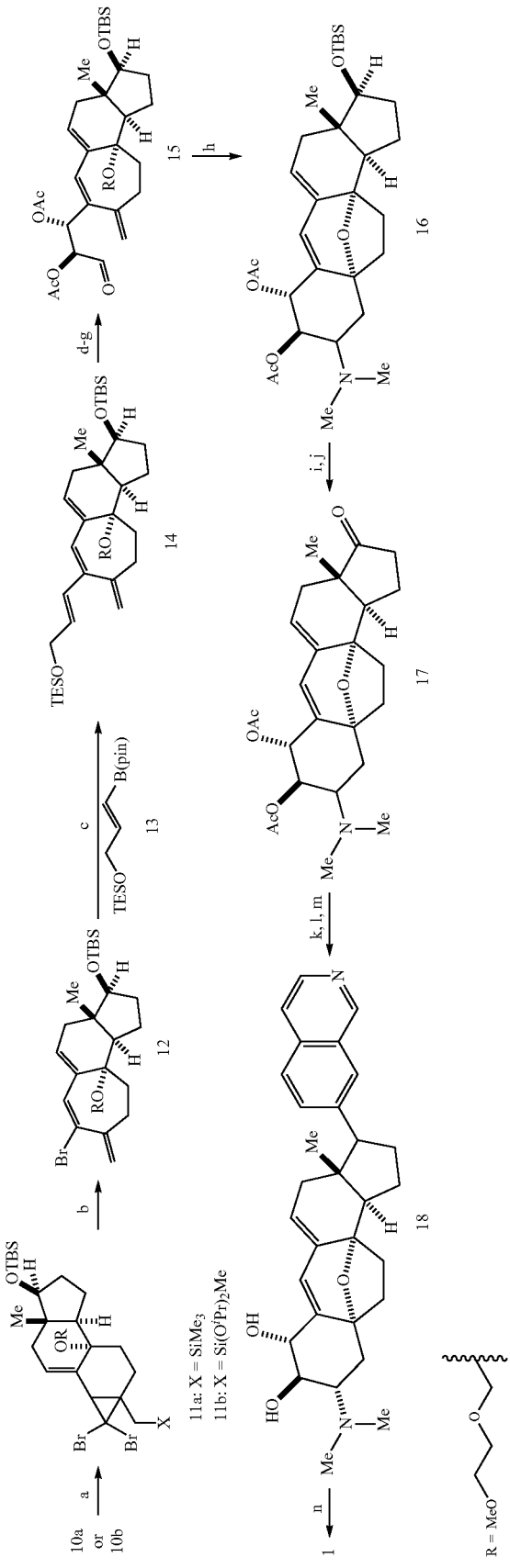

(a) CHBr₃ (3 equiv), KOtBu (4 equiv), hexane, 0° C., 2 h; (b) TASF (1.2 equiv), DMF, 80° C., 30 min (66% over 2 steps); (c) 13 (2 equiv), Pd(PPh₃)₄ (0.04 equiv), K₂CO₃ (3 equiv), THF/water (5:1), 80° C., 4 h (85%); (d) K₂OsO₄·2H₂O (0.02 equiv), (DHQD)₂PHAL (0.05 equiv), K₃Fe(CN)₆ (3 equiv), K₂CO₃ (3 equiv), MeSO₂NH₂ (1 equiv), tBuOH/water (1:1), 0° C., 2 h; (e) Ac₂O (2.5 equiv), NEt₃ (3 equiv), DMAP (0.2 equiv), CH₂Cl₂, rt, 18 h (55% over 2 steps); (f) HF/pyr, THF, rt, 5 min; (g) Dess-Martin periodinane (1.2 equiv), CH₂Cl₂, rt, 1 h; (h) Me₂NH (3 equiv), ZnBr₂ (1.5 equiv), CH₃CN, 50° C., 40 min (65% over 3 steps); (i) TBAF (1.2 equiv), THF, 70° C., 4 h (70%); (j) TPAP (0.05 equiv), NMO (1.3 equiv), CH₂Cl₂, rt, 2.5 h (quant.); (k) K₂CO₃ (5 equiv), MeOH, rt, 30 min; (l) N₂H₄·H₂O (10 equiv), NEt₃ (10 equiv), EtOH, 80° C., 6 h; NEt₃ (3 equiv), 12 (1 equiv), THF, rt, 5 min; (m) Pd(PPh₃)₄ (0.5 equiv), 7-isoquinolinestannane (3 equiv), LiCl (10 equiv), CuCl (10 equiv), DMSO, 60° C., 1 h; (n) hydrogenation.

The synthesis of 1 begins with known enone 5, produced in two steps from enantiomerically pure Hajos-Parrish ketone. See Isaacs et al., *J. Org. Chem.* 1993, 58, 3938-3941. The thermodynamic enolate of 5 was alkylated with the dioxolane of 4-bromo-2-butanone (See Hajos et al., *J. Org. Chem.* 1967, 32, 3008-3010) followed by generation of silyloxydiene 6. Diastereoselective hydrogenation of the cyclopentene of 6, (See Eder et al., *Chem. Ber.* 1975, 108, 2673-2679). Rubottom oxidation of the remaining enolsilane and protection of the tertiary carbinol with MEMCl produced 7. A three-step procedure was used to convert 7 to β,γ-unsaturated enone 9, comprising ketal removal, hydroxide-promoted aldol addition, and SOCl₂-mediated elimination.

In preparation for ring expansion, vinyl triflate 9 was prepared, followed by Pd(0)-catalyzed formation of allylsilane 11. Regioselective and diastereoselective cyclopropanation of 10a with dibromocarbene produced 11a (Scheme 2). See Amice et al., *Synthesis* 1976, 196-197. In the ring expansion reaction, warming of 11a in the presence of fluoride sources [TBAF or TASF (See Tamao et al., *J. Org. Chem.* 1983, 48, 2120-2122)] produced an equal mixture of desired cycloheptadiene 12 and allylsilane 20 in low yields (see Scheme 3). During this reaction, ring opening of 11a and ejection of bromide produces pentadienyl cation 19, which partitions between base-promoted elimination affording 20 and fluoride attack on the TMS group, leading to 12. Attempts to convert 20 to 12 were unsuccessful. We reasoned that the ring opening/elimination reaction might produce more 12 if a disiloxane were used in place of the TMS group since the disiloxane would have a higher propensity for pentacoordinate (or hexacoordinate) fluorosilicate formation (see 21), leading to 12 via silicate-directed elimination. We were pleased to find that exposure of disiloxane 11b (see Tamao et al., *J. Org. Chem.* 1983, 48, 2120-2122) (Scheme 2) to TASF at 80° C. in DMF produced exclusively 12 in 66% yield from 10b (two steps). Pd-catalyzed cross-coupling between 12 and vinyl boronic ester 13 afforded 14 in 85% yield. Although 14 presents four double bonds, the reported rates of catalytic enantioselective dihydroxylation (see Kolb et al., *Chem. Rev.* 1994, 94, 2483-2547) could be used to predict that the 1,2-disubstituted olefin would be dihydroxylated first, which occurred with 10:1 diastereoselectivity, installing the C1-C2 diol. Acetylation of the diol, removal of the TES group and oxidation of the primary alcohol with Dess-Martin periodinane delivered marginally stable aldehyde 15.

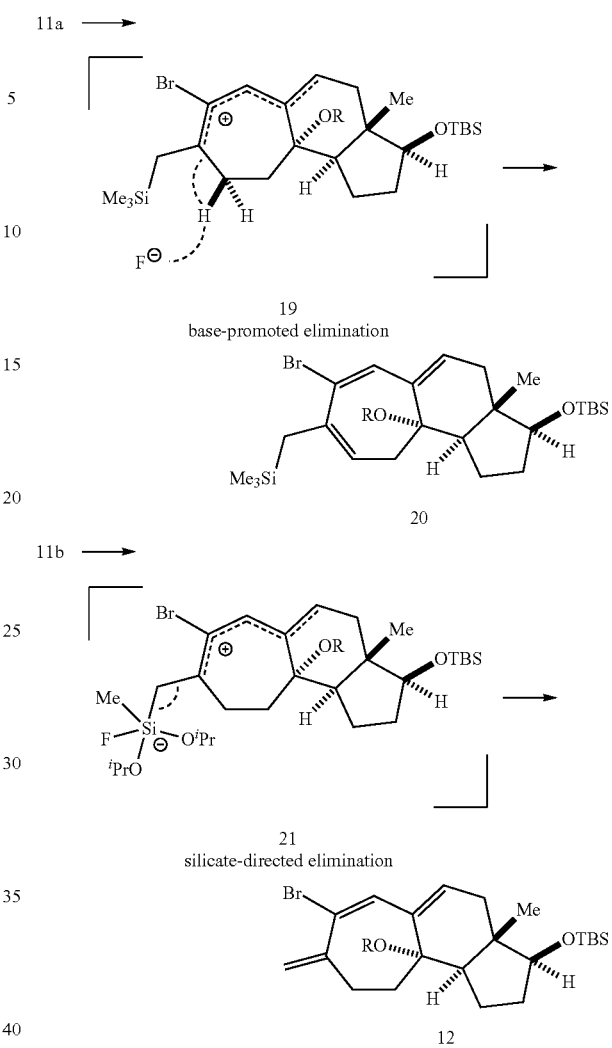

Mechanistic Rationale for Generation of 12 and 20.

A tandem aza-Prins cyclization and transannular etherification was performed by exposing aldehyde 15 to Me₂NH (3.0 eq.) and ZnBr₂ (1.5 eq.) in MeCN at 50° C. for 40 minutes. The aza-Prins cyclization occurred with in-situ removal of the MEM protecting group producing directly 16 in 65% yield over three steps (TES deprotection, oxidation, aza-Prins cyclization), averaging 87% yield per step.

In the aza-Prins cyclization, the C3-amine stereocenter was formed with >95% diastereoselectivity. The high diastereoselectivity in this reaction can be rationalized by examining iminium ion intermediate 22 (see below). According to calculations of 22, the forming A ring exists in a boat conformation. The internal methyl group of the iminium ion and C₂—H are co-planar to avoid A(1,3) strain, while the C₂—OAc blocks addition from the Re-face, guiding addition to the Si-face of the iminium ion. Intermediate 24 is generated by transannular cyclization of the C₈ ether oxygen. Oxonum ion release from 24 affords 16. In support of this sequence of events, rather than MEM deprotection preceeding aza-Prins cyclization, is our observation that exposure of the TES ether precursor of 15 to the aza-Prins reaction conditions does not lead to MEM deprotection.

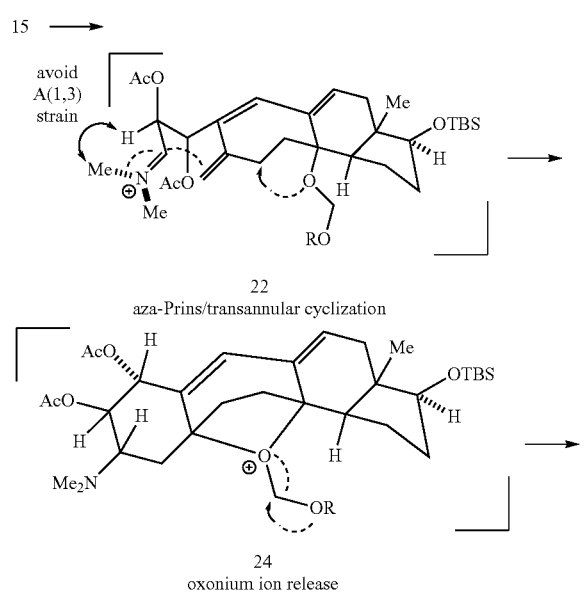

22
aza-Prins/transannular cyclization 24
oxonium ion release

Mechanistic Rationale for the Highly Diastereoselective Aza-Prins Cyclization.

Removal of the silyl protecting group from 16, followed by oxidation of the resulting secondary carbinol with TPAP/NMO delivered ketone 17 in 70% yield over two steps. Deacetylation of 17 followed by hydrazone formation, conversion to the vinyl iodide and Stille cross-coupling with 7-trimethylstannyl isoquinoline delivered $\Delta^{16,17}$-dehydrocortistatin A (18). See Shenvi et al., *J. Am. Chem. Soc.* 2008, 130, 7241-7243. An enantioselective synthesis of cortistatin A has been achieved using a highly diastereoselective aza-Prins cyclization coupled with transannular etherification.

Example 2

General Procedures.

All reactions were performed in oven or flame-dried glassware under a positive pressure of argon unless noted otherwise. Flash column chromatography was performed as described by Still et al., *J. Org. Chem.* 1978, 43, 2923-2925, either employing E. Merck silica gel 60 (230-400 mesh ASTM) or using pre-packaged FLASH columns on a HPFC Biotage system (Biotage Inc.) unless noticed otherwise. Tetrahydrofuran, methylene chloride, toluene, acetonitrile, and dimethylformamide were degassed with argon and passed through a solvent purification system (designed by J.C. Meyer of Glass Contour) utilizing alumina columns. Anhydrous dimethylsulfoxide, 1,2-dichloroethane, and hexane were purchased at the highest quality from Aldrich and used without further purification. Triethylamine and pyridine were freshly distilled upon $CaH_2$ before use. $Pd(PPh_3)_4$ was prepared following a literature procedure (See Coulson, *Inorg. Synth.* 1972, 13, 121-125) and stored under argon at −20° C. protected from light. Dess-Martin periodinane was prepared following a literature procedure (See Boeckman et al., *J. Org. Synth.* 2000, 77, 141-152) and stored at −20° C. in the presence of $CaSO_4$ as a desiccant, protected from light. Other chemicals were purchased from Aldrich and used without further purification unless noticed otherwise. TLC analyses were performed on 250 μm Silica Gel 60F254 plates purchased from EM science.

Instrumentation. Infrared spectra were recorded on a Perkin Elmer Spectrum One FT-IR spectrometer. $^1H$ and $^{13}C$ NMR spectra were recorded on a Varian INOVA600, INOVA500 or Mercury400 spectrometer. Chemical shifts for proton and carbon resonances are reported in ppm (δ) relative to chloroform-d (δ 7.26 ppm, 77.0 ppm respectively). Mass spectra were obtained from the Harvard University Mass Spectrometry Laboratory.

The following are exemplary steps within Route C, supra.

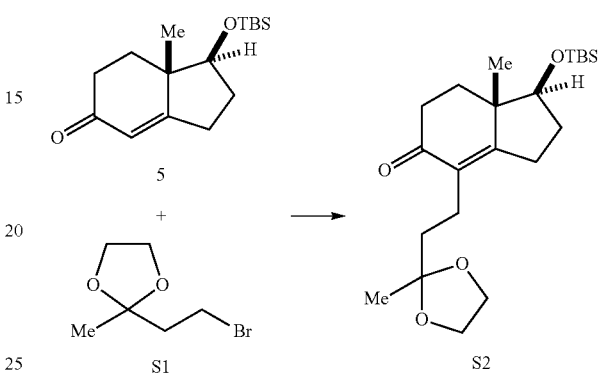

Enone S2

NaH (60 wt % suspension in mineral oil, 1.2 g, 29 mmol, 1.05 equiv) was suspended in DMSO (25 mL) at rt and stirred for 15 min. To this suspension, a solution of 5 (7.8 mg, 28 mmol) (See Isaacs et al., *J. Org. Chem.* 1993, 58, 3938-3941) in DMSO (25 mL) was added. The reaction mixture was stirred at rt for 4 h, and then 2-(2-bromoethyl)-2-methyl-1,3-dioxolane (S1, 6.0 g, 31 mmol, 1.3 equiv) was added (See Rigby et al., *J. Org. Chem.* 1987, 52, 34-44). Reaction mixture was stirred for 17 h. The reaction was quenched by addition of $NH_4Cl$ (aq) sat. solution. The aqueous layer was extracted by EtOAc (3×70 mL). After drying ($Na_2SO_4$) and concentration, the crude was purified on a silica gel column (hexanes:EtOAc 5:1) to provide S2 as a yellow oil (6.9 g, 17.5 mmol, 63% yield) with recovered starting material (680 mg, 2.4 mmol, 9% yield).

$^1H$ NMR (400 MHz, $CDCl_3$) δ 3.93 (ddd, 4H, $J_1$=9.6 Hz, $J_2$=4.0 Hz, $J_3$=2.0 Hz), 3.71 (dd, 1H, $J_1$=10 Hz, $J_2$=7.2 Hz), 2.61-2.48 (m, 2H), 2.45-2.33 (m, 2H), 2.21 (dd, 1H, $J_1$=10 Hz, $J_2$=5.6 Hz), 2.00-1.94 (m, 2H), 1.79 (ddd, 1H, $J_1$=10.4 Hz, $J_2$=10.4 Hz, $J_3$=10.4 Hz), 1.66 (ddd, 1H, $J_1$=13.6 Hz, $J_2$=13.6 Hz, $J_3$=5.2 Hz), 1.63-1.58 (m, 2H), 1.34 (s, 3H), 1.06 (s, 3H), 0.89 (s, 9H), 0.05 (s, 3H), 0.04 (s, 3H);

$^{13}C$ NMR (100 MHz, $CDCl_3$) δ 198.42, 168.02, 133.28, 110.00, 94.55, 81.22, 64.81, 45.66, 37.50, 34.43, 33.79, 30.14, 25.97, 25.28, 23.72, 20.56, 18.24, 15.69, −4.22, −4.65;

FTIR (neat, $cm^{-1}$) 2958, 2931, 2860, 1663;

HRMS (ESI) calcd for $C_{22}H_{39}O_4Si$ $[M+H]^+$ 395.26121, found 395.26197.

Enolsilane S3

Enone S2 (6.8 g, 17.2 mmol) was dissolved in $CH_2Cl_2$ (60 mL) and cooled down to 0° C. To this solution were added 2,6-lutidine (4.0 mL, 34 mmol, 2 equiv) and TBSOTf (5.1 mL, 22.4 mmol, 1.3 equiv). The reaction mixture was stirred for 2 h. The solution was concentrated under reduced pressure and then suspended in EtOAc (50 mL). The insoluble white solid was filtered over a celite pad and washed with EtOAc (50 mL). Evaporation of the filtrate gave the silyloxydiene as a yellow oil. The crude mixture was dissolved in EtOAc (50 mL) and concentrated three times to remove 2,6-lutidine azeotropically (more than 0.5 equiv of 2,6-lutidine can poison Pd/C catalyst and result in slow reaction rate in the next step). The crude product was used in the next step without further purification.

To a solution of 6 (approx. 17.2 mmol) in EtOAc (60 mL) was added Pd/C (10 wt %, 1.4 g). The solution was bubbled with hydrogen gas for 10 min, and the reaction was stirred under $H_2$ balloon at rt for 20 h. The catalyst was filtered off through celite and the filtrate was concentrated to provide S3 as a yellow oil. The crude mixture was used without further purification.

$^1$H NMR (400 MHz, $C_6D_6$) δ 3.64-3.52 (m, 5H), 2.72 (ddd, 1H, $J_1$=12.5 Hz, $J_2$=12.5 Hz, $J_3$=4.6 Hz), 2.24-2.17 (m, 1H), 2.11-1.05 (m, 2H), 1.95-1.82 (m, 2H), 1.74 (dd, 1H, $J_1$=12.2 Hz, $J_2$=6.8 Hz), 1.64-1.35 (m, 4H), 1.42 (s, 3H), 1.22-1.10 (m, 2H), 1.05 (s, 9H), 1.00 (s, 9H), 0.94 (s, 3H), 0.17 (s, 6H), 0.07 (s, 3H), 0.06 (s, 3H).

α-Hydroxyketone S4 mCPBA (77% purchased from Aldrich and purified by washing with pH 7.5 phosphate buffer, 3.1 g, 18 mmol, 1.05 equiv) and $NaHCO_3$ (14.4 g, 172 mmol, 10 equiv) were suspended in toluene (30 mL) at rt and stirred for 5 min. The suspension was cooled down to −10° C., and S3 (17.2 mmol) was added. The reaction mixture was stirred for 30 min at −10° C. After extractive work-up (EtOAc) the crude was dissolved in THF (50 mL) and treated with HF (48% aqueous solution, 10 mL) at 0° C. In 30 min at 0° C., the reaction was quenched by slow addition of $NaHCO_3$ (aq) sat. solution (caution: vigorous gas evolution). The aqueous layer was extracted with EtOAc (3×50 mL). After drying ($Na_2SO_4$) and concentration, the crude was purified by chromatography (Hexanes:EtOAc, 5:1) to provide S4 as a yellow oil (4.7 g, 11.4 mmol, 66% yield over 4 steps).

$^1$H NMR (500 MHz, $CDCl_3$) δ 3.95-3.86 (m, 4H), 3.56 (t, 1H, J=8.6 Hz), 2.72 (ddd, 1H, $J_1$=14.1 Hz, $J_2$=14.1 Hz, $J_3$=5.8 Hz), 2.39 (ddd, 1H, $J_1$=14.1 Hz, $J_2$=2.4 Hz, $J_3$=2.0 Hz), 2.03-1.97 (m, 1H), 1.94-1.73 (m, 3H), 1.81-1.73 (m, 2H), 1.70-1.63 (m, 2H), 1.59 (s, 1H), 1.56-1.51 (m, 1H), 1.38 (ddd, 1H, $J_1$=13.6 Hz, $J_2$=3.0 Hz, $J_3$=3.0 Hz), 1.28 (s, 3H), 1.25-1.18 (m, 1H), 1.21 (s, 3H), 0.88 (s, 9H), 0.01 (s, 3H), 0.00 (s, 3H);

$^{13}$C NMR (125 MHz, $CDCl_3$) δ 215.67, 109.86, 80.89, 80.63, 64.90, 56.72, 43.82, 40.55, 37.16, 34.85, 32.75, 31.31, 27.50, 26.00, 24.10, 19.51, 18.25, 12.30, −4.24, −4.68;

FTIR (neat, $cm^{-1}$) 3490, 2955, 2858, 1710;

HRMS (ESI) calcd for $C_{22}H_{40}O_5SiNa$ $[M+Na]^+$ 435.25372, found 435.25412.

MEM-Protected α-Hydroxyketone 7

To a solution of S4 (4.7 g, 11.4 mmol) in 1,2-dichloroethane (50 mL) were added $iPr_2EtN$ (3.0 mL, 17.2 mmol, 1.5 equiv) and MEMCl (1.3 mL, 11.4 mmol, 1 equiv) were added. The reaction mixture was stirred at 80° C. for 5 h, then $iPr_2EtN$ (3.0 mL, 17.2 mmol, 1.5 equiv) and MEMCl (1.3 mL, 11.4 mmol, 1 equiv) were added again. The reaction mixture was stirred for another 8 h. The solution was diluted with EtOAc (100 mL) and washed with 0.5 M HCl (aq) solution. The aqueous solution was extracted with EtOAc (2×50 mL). The combined organic layer was washed with $NaHCO_3$ (aq) sat. solution, dried over $Na_2SO_4$ and concentrated. After purification on a silica gel column (Hexanes:EtOAc, 5:1) 7 was obtained as a yellow oil (5.0 g, 9.98 mmol, 88% yield).

$^1$H NMR (500 MHz, $CDCl_3$) δ 4.75 (d, 1H, J=8.0 Hz), 4.71 (d, 1H, J=8.0 Hz), 3.93-3.88 (m, 5H), 3.65 (t, 1H, J=8.5 Hz), 3.61-3.50 (m, 3H), 3.73 (s, 3H), 2.59 (ddd, 1H, $J_1$=15 Hz, $J_2$=15 Hz, $J_3$=6.3 Hz), 2.36 (ddd, 1H, $J_1$=11 Hz, $J_2$=2.2 Hz, $J_3$=2.0 Hz), 2.12 (dd, 1H, $J_1$=12 Hz, $J_2$=6.7 Hz), 1.97 (dddd, 1H, $J_1$=14 Hz, $J_2$=9.0 Hz, $J_3$=9.0 Hz, $J_4$=4.5 Hz), 1.89-1.80 (m, 4H), 1.75 (dd, 1H, $J_1$=12 Hz, $J_2$=5.5 Hz), 1.73-1.65 (m, 1H), 1.49 (dddd, 1H, $J_1$=12.5 Hz, $J_2$=12.5 Hz, $J_1$=8.5 Hz, $J_4$=4.2 Hz), 1.38-1.29 (m, 2H), 1.27 (s, 3H), 1.10 (s, 3H), 0.88 (s, 9H), 0.01 (s, 6H);

$^{13}$C NMR (125 MHz, $CDCl_3$) δ 211.60, 110.03, 91.79, 87.55, 80.92, 71.98, 67.60, 64.93, 64.90, 59.20, 50.95, 44.39, 37.35, 35.60, 32.44, 30.96, 27.07, 26.01, 24.29, 19.58, 18.23, 12.57, −4.21, −4.63;

FTIR (neat, $cm^{-1}$) 2953, 2929, 2879, 1716;

HRMS (ESI) calcd for $C_{26}H_{52}NO_7Si$ $[M+NH_4]^+$ 518.35076, found 518.35015.

Diketone S5

To a solution of 7 (4.5 g, 9.0 mmol) in acetone (40 mL)/water (10 mL) was added PPTS (225 mg, 0.90 mmol, 0.1 equiv). The reaction was stirred at 60° C. for 4 h. After cooled to rt, the solution was diluted with EtOAc (50 mL). The organic layer was washed with $NaHCO_3$(aq) sat. solution (50 mL). The aqueous layer was extracted with EtOAc (2×50 mL). The combined organic layer was washed with brine (100 mL), dried over $Na_2SO_4$ and concentrated to provide S5. The diketone was used immediately for the next reaction without further purification.

$^1$H NMR (500 MHz, $CDCl_3$) δ 4.72 (d, 1H, J=7.8 Hz), 4.66 (d, 1H, J=7.8 Hz), 3.86 (ddd, 1H, $J_1$=12.2 Hz, $J_2$=7.3 Hz, $J_3$=2.4 Hz), 3.65 (t, 1H, J=8.5 Hz), 3.57-3.51 (m, 3H), 3.38 (s, 3H), 2.68 (ddd, 1H, $J_1$=16.8 Hz, $J_2$=15.0 Hz, $J_3$=6.3 Hz), 2.53 (ddd, 1H, $J_1$=18.5 Hz, $J_2$=6.6 Hz, $J_3$=6.6 Hz), 2.41 (ddd, 1H, $J_1$=18.5 Hz, $J_2$=6.6 Hz, $J_3$=6.6 Hz), 2.33 (dddd, 1H, $J_1$=15.6 Hz, $J_2$=2.0 Hz, $J_3$=2.0 Hz, $J_4$=2.0 Hz), 2.18 (dd, 1H, $J_1$=14.7 Hz, $J_2$=6.8 Hz), 2.14 (dd, 1H, $J_1$=11.5 Hz, $J_2$=6.8 Hz), 2.09 (s, 3H), 1.97 (dddd, 1H, $J_1$=13.6 Hz, $J_2$=13.6 Hz, $J_3$=5.4 Hz, $J_4$=5.4 Hz), 1.84 (dddd, 1H, $J_1$=12.7 Hz, $J_2$=6.3 Hz, $J_3$=2.0 Hz), 1.77 (dddd, 1H, $J_1$=12.5 Hz, $J_2$=12.5 Hz, $J_3$=12.5 Hz, $J_4$=5.6 Hz), 1.66-1.60 (m, 1H), 1.52 (dddd, 1H, $J_1$=12.7 Hz, $J_2$=12.7 Hz, $J_3$=8.3 Hz, $J_4$=3.9 Hz), 1.35 (ddd, 1H, $J_1$=13.6 Hz, $J_2$=13.6 Hz, $J_3$=4.4 Hz), 1.13 (s, 3H), 0.88 (s, 9H), 0.01 (s, 6H);

$^{13}$C NMR (125 MHz, $CDCl_3$) δ 211.86, 208.67, 91.88, 86.75, 80.97, 71.95, 67.70, 59.23, 50.53, 44.31, 37.42, 37.18, 35.36, 30.90, 30.33, 26.62, 26.03, 19.40, 18.24, 12.43, −4.21, −4.62;

FTIR (neat, $cm^{-1}$) 2954, 2929, 2858, 1716;

HRMS (ESI) calcd for $C_{24}H_{48}NO_6Si$ $[M+NH_4]^+$ 474.32454, found 474.32354.

Aldol Adduct S6

To a solution of S5 (approx. 9.0 mmol) in MeOH (50 mL) was added NaOMe (2.43 g, 45.0 mmol, 5 equiv). The resulting orange solution was heated to 70° C. and stirred for 2 h. The reaction was cooled to rt and quenched by adding $NH_4Cl$(aq) sat. solution (100 mL). The solution was extracted with EtOAc (4×70 mL). The combined organic layer was dried over $Na_2SO_4$ and concentrated. Purification on a silica gel column (hexane:EtOAc, 3:1) provided S6 as a yellow solid (2.0 g, 4.4 mmol, 49% yield over 2 steps). The aldol adduct S6 was stored at −20° C. over 3 months without decomposition.

$^1$H NMR (500 MHz, $CDCl_3$) δ 4.99 (d, 1H, J=7.0 Hz), 4.87 (d, 1H, J=7.0 Hz), 3.86 (d, 1H, J=2.0 Hz), 3.83 (ddd, 1H, $J_1$=10.5 Hz, $J_2$=5.0 Hz, $J_3$=5.0 Hz), 3.76 (ddd, 1H, $J_1$=10.5 Hz, $J_2$=5.0 Hz, $J_3$=5.0 Hz), 3.63 (t, 1H, d=8.5 Hz), 3.55 (t, 2H, d=4.5 Hz), 3.36 (s, 3H), 2.92 (d, 1H, J=13 Hz), 2.76 (ddd, 1H, $J_1$=14 Hz, $J_2$=6.5 Hz, $J_3$=6.5 Hz), 2.35 (dd, 1H, $J_1$=14 Hz, $J_2$=2.0 Hz), 2.26 (dd, 1H, $J_1$=16 Hz, $J_2$=7.0 Hz), 2.18-2.11 (m, 2H), 2.00 (ddd, 1H, $J_1$=14.5 Hz, $J_2$=5.0

Hz, J$_3$=5.0 Hz), 1.91 (dddd, 1H, J$_1$=14 Hz, J$_2$=9.5 Hz, J$_3$=9.0 Hz, J$_4$=4.5 Hz), 1.65-1.48 (m, 5H), 1.39 (ddd, 1H, J$_1$=12.5 Hz, J$_2$=12.5 Hz, J$_3$=4.0 Hz), 1.35-1.32 (m, 1H), 0.87 (s, 9H), 0.81 (s, 3H), 0.00 (s, 6H);

$^{13}$C NMR (125 MHz, CDCl$_3$) δ 209.83, 95.90, 90.25, 81.94, 81.29, 71.87, 68.25, 67.03, 59.27, 53.52, 45.05, 43.97, 36.81, 33.23, 31.50, 30.37, 26.03, 20.40, 18.26, 12.93, −4.29, −4.55;

FTIR (neat, cm$^{-1}$) 3449, 2930, 2858, 1715;

HRMS (ESI) calcd for C$_{24}$H$_{48}$NO$_6$Si [M+NH$_4$]$^+$ 474.32454, found 474.32407.

Ketone S7

To a solution of S6 (1.37 g, 3 mmol) in CH$_2$Cl$_2$ (15 mL) at −10° C. was added pyridine (0.73 mL, 9 mmol, 3 equiv) was added. To this solution, SOCl$_2$ (0.33 mL, 4.5 mmol, 1.5 equiv) was added dropwise. The reaction turned red. The reaction mixture was stirred at −10° C. for 30 min. Extractive work-up (EtOAc/NaHCO$_3$ sat. sol.). The product slowly decomposes at −20° C. under argon, and therefore was immediately used in the next reaction without further purification.

$^1$H NMR (500 MHz, CDCl$_3$) δ 5.72 (ddd, 1H, J$_1$=6.3 Hz, J$_2$=2.0 Hz, J$_3$=2.0 Hz), 4.78 (d, 1H, J=7.0 Hz), 4.70 (d, 1H, J=7.0 Hz), 3.87 (ddd, 1H, J$_1$=10.8 Hz, J$_2$=5.2 Hz, J$_3$=3.2 Hz), 3.73 (t, 1H, J=9.0 Hz), 3.65 (ddd, 1H, J$_1$=10.8 Hz, J$_2$=7.4 Hz, J$_3$=3.2 Hz), 3.59-3.52 (m, 2H), 3.39 (s, 3H), 3.30 (ddd, 1H, J$_1$=15.1 Hz, J$_2$=2.5 Hz, J$_3$=2.5 Hz), 2.84 (dd, 1H, J$_1$=5.0 Hz, J$_2$=1.9 Hz), 2.27 (ddd, 1H, J$_1$=14.8 Hz, J$_2$=2.6 Hz, J$_3$=2.6 Hz), 2.20 (dd, 1H, J$_1$=12.0 Hz, J$_2$=7.6 Hz), 2.06 (dd, 1H, J$_1$=13.8 Hz, J$_2$=6.8 Hz), 1.97 (dd, 1H, J$_1$=16.6 Hz, J$_2$=6.3 Hz), 1.91 (ddd, 1H, J$_1$=18.3 Hz, J$_2$=9.2 Hz, J$_3$=5.8 Hz), 1.87-1.80 (m, 2H), 1.73-1.61 (m, 2H), 1.42 (dddd, 1H, J$_1$=13.2 Hz, J$_2$=13.2 Hz, J$_3$=8.2 Hz, J$_4$=4.4 Hz), 0.87 (s, 9H), 0.71 (s, 3H), 0.01 (s, 3H), 0.00 (s, 3H);

$^{13}$C NMR (125 MHz, CDCl$_3$) δ 209.56, 133.87, 129.20, 90.65, 81.07, 79.11, 72.06, 67.62, 59.26, 47.97, 46.95, 44.69, 38.29, 37.13, 31.06, 30.35, 26.03, 19.02, 18.26, 13.22, −4.21, −4.57;

FTIR (neat, cm$^{-1}$) 2956, 2879, 1719, 1462;

HRMS (ESI) calcd for C$_{24}$H$_{42}$O$_5$SiNa [M+Na]$^+$ 461.26937, found 461.27141.

Dienyl Triflate 9

To a solution of S7 (approx. 3 mmol) in THF (15 mL) at −78° C., NaHMDS (1.0 M in THF, 3.0 mL, 3 mmol, 1 equiv) was added dropwise. The solution turned orange-red. The reaction mixture was stirred at −78° C. for 1 h, and then PhNTf$_2$ (1.6 g, 4.5 mmol, 1.5 equiv) was added. The reaction mixture was stirred 5 min at −78° C., 1 h at 0° C. and 2 h at rt. The reaction was quenched by addition of NH$_4$Cl (aq) sat. solution. The aqueous layer was extracted with EtOAc (3×20 mL). The combined organic layer was washed with brine (50 mL), dried over Na$_2$SO$_4$ and concentrated to provide 9 as an orange-brown solid. The dienyl triflate 9 is unstable on SiO$_2$ and was used in the next reaction without further purification.

$^1$H NMR (500 MHz, CDCl$_3$) δ 6.09 (d, 1H, J=2.0 Hz), 5.95 (d, 1H, J=5.3 Hz), 4.67 (d, 1H, J=7.3 Hz), 4.54 (d, 1H, J=7.3 Hz), 3.77 (ddd, 1H, J$_1$=10.7 Hz, J$_2$=4.7 Hz, J$_3$=4.7 Hz), 3.73 (t, 1H, J=8.3 Hz), 3.57 (ddd, 1H, J$_1$=10.7 Hz, J$_2$=4.7 Hz, J$_3$=4.7 Hz), 3.51 (t, 2H, J=4.7 Hz), 3.37 (s, 3H), 2.80-2.73 (m, 1H), 2.24-2.22 (m, 2H), 2.12 (dd, 1H, J$_1$=17.0 Hz, J$_2$=6.8 Hz), 2.06-2.02 (m, 1H), 1.98-1.91 (m, 2H), 1.72-1.61 (m, 3H), 1.48-1.41 (m, 1H), 0.87 (s, 9H), 0.67 (s, 3H), 0.02 (s, 3H), 0.01 (s, 3H).

Allylsilane 10b

A 50 mL Schlenk flask was charged with magnesium turnings (purchased from Acros, 241 mg, 9.9 mmol, 3.3 equiv) and flame-dried. To the flask was added THF (10 mL), 1,2-dibromoethane (10 μL) and chloromethylmethyldiisopropoxysilane (purchased from Gelest, Inc., 100 μL). The reaction was heated to 50° C. for 3 min, and then cooled down to rt. The mixture was vigorously stirred at rt until the reaction started turning yellow-brown. The rest of the chloromethylmethyldiisopropoxysilane (1.9 g, 9 mmol, 3 equiv combined) was added over a period of 1 h. Once the addition is finished the reaction mixture was stirred for another 2 h at rt. The resulting Grignard solution was clear brown.

The vinyl triflate 9 (approx. 3 mmol) was dissolved in THF along with Pd(PPh$_3$)$_4$ (173.4 mg, 0.15 mmol, 0.05 equiv). To this solution was added the previously prepared Grignard reagent solution in THF (9 mmol, 3 equiv) via cannula, while the reaction was cooled in a cold water bath since the reaction is highly exothermic. The reaction mixture was stirred at rt for 1 h. The reaction was quenched by addition of NH$_4$Cl (aq) sat. solution. The aqueous layer was extracted with EtOAc (3×50 mL). The combined organic layer was washed with brine (100 mL), dried over Na$_2$SO$_4$ and concentrated. Chromatography in Fluorisil (100% hexane) gave 10b as a brown syrup (1.11 g, 1.86 mmol, 62% yield over 3 steps).

$^1$H NMR (500 MHz, CDCl$_3$) δ 5.73 (s, 1H), 5.59 (dd, 1H, J$_1$=6.8 Hz, J$_2$=2.0 Hz), 4.72 (d, 1H, J=7.3 Hz), 4.51 (d, 1H, J=7.3 Hz), 4.12 (dddd, 2H, J$_1$=12.2 Hz, J$_2$=6.3 Hz, J$_3$=6.3 Hz, J$_4$=6.3 Hz), 3.82-3.76 (m, 1H), 3.70 (t, 1H, J=8.3 Hz), 3.54-3.52 (m, 3H), 3.51 (s, 3H), 2.43-2.38 (m, 1H), 2.23 (t, 1H, J=10.0 Hz), 2.04 (dd, 1H, J$_1$=17.0 Hz, J$_2$=7.3 Hz), 1.96-1.86 (m, 4H), 1.67-1.62 (m, 2H), 1.57-1.51 (m, 3H), 1.42 (dddd, 1H, J$_1$=13.2 Hz, J$_2$=7.8 Hz, J$_3$=7.8 Hz, J$_4$=7.8 Hz), 1.19-1.15 (m, 12H), 0.87 (s, 9H), 0.66 (s, 3H), 0.11 (s, 3H), 0.02 (s, 3H), 0.01 (s, 3H);

$^{13}$C NMR (125 MHz, CDCl$_3$) δ 136.17, 136.03, 125.13, 121.99, 91.12, 81.06, 77.27, 72.16, 66.94, 65.15, 65.12, 59.19, 48.01, 45.49, 38.74, 30.76, 30.38, 28.94, 26.22, 26.06, 25.93, 25.91, 25.89, 19.72, 18.28, 12.17, −3.81, −4.23, −4.57;

FTIR (neat, cm$^{-1}$) 2969, 2873;

HRMS (ESI) calcd for C$_{32}$H$_{60}$O$_6$Si$_2$Na [M+Na]$^+$ 619.38206, found 619.38129.

Bromocycloheptene 12

To a solution of 10b (860 mg, 1.44 mmol) in hexane (10 mL) at rt was added KOtBu (646 mg, 5.8 mmol, 4 equiv). The reaction mixture was cooled down to 0° C. and CHBr$_3$ (0.380 mL, 4.3 mmol, 3 equiv) in hexane was added over a period of 2 h using a syringe pump. The reaction was washed with NaHCO$_3$ (aq) sat. solution and the aqueous layer was extracted with EtOAc (2×30 mL). The combined organic layer was dried over Na$_2$SO$_4$ and concentrated to provide 11b as a black oil. The product decomposes at −20° C. overnight, and was used immediately in the next step.

To a solution of 11b (1.44 mmol) in DMF (7 mL) was added a solution of TASF (470 mg, 1.7 mmol, 1.2 equiv) in DMF (7 mL). The reaction mixture was stirred at 80° C. for 30 min ~1 h. The solution was cooled to rt, diluted with EtOAc (30 mL), and washed with NaHCO$_3$ (aq) sat. solution (30 mL). The aqueous layer was extracted with EtOAc (2×30 mL). The combined organic layer was washed with brine (50 mL), dried over Na$_2$SO$_4$ and concentrated. After purification on a Fluorisil column (100% hexane) 12 was isolated as a yellow syrup (500 mg, 0.95 mmol, 66% yield over 2 steps). This compound slowly decomposes at −20° C. under argon and should be used within a week.

$^1$H NMR (500 MHz, CDCl$_3$) δ 6.51 (s, 1H), 6.01-6.00 (m, 1H), 5.36 (s, 1H), 5.18 (s, 1H), 4.56 (d, 1H, J=7.6 Hz), 4.40 (d, 1H, J=7.6 Hz), 3.86-3.82 (m, 1H), 3.72 (t, 1H, J=8.7 Hz), 3.54-3.49 (m, 3H), 3.52 (s, 3H), 2.45-2.42 (m, 2H), 2.24 (ddd, 1H, $J_1$=15.0 Hz, $J_2$=3.9 Hz Hz, $J_3$=3.9 Hz), 2.11-2.05 (m, 2H), 1.96 (d, 1H, J=18.3 Hz), 1.90 (dddd, 1H, $J_1$=13.5 Hz, $J_2$=7.8 Hz, $J_3$=7.8 Hz, $J_4$=7.8 Hz), 1.77 (ddd, 1H, $J_1$=14.2 Hz, $J_2$=9.2 Hz, $J_3$=9.2 Hz), 1.68-1.62 (m, 2H), 1.46 (dddd, 1H, $J_1$=13.0 Hz, $J_2$=8.7 Hz, $J_3$=8.7 Hz, $J_4$=8.7 Hz), 0.88 (s, 9H), 0.78 (s, 3H), 0.02 (s, 3H), 0.01 (s, 3H);

$^{13}$C NMR (125 MHz, CDCl$_3$) δ 146.45, 138.03, 136.68, 132.86, 125.11, 118.99, 90.29, 84.06, 81.69, 72.09, 67.65, 59.18, 47.82, 43.71, 40.24, 36.67, 33.86, 30.67, 26.04, 19.70, 18.27, 13.94, −4.20, −4.57;

FTIR (neat, cm$^{-1}$) 2955, 2929, 2857;

HRMS (ESI) calcd for $C_{26}H_{43}BrO_4SiNa$ [M+Na]$^+$ 549.20062, found 549.20008.

Boronic Ester 13 (See Wang et al., *Tetrahedron Lett.* 2005, 46, 8777-8780)

To a mixture of propagyl triethylsilyl ether (1.5 g, 8.81 mmol) (See Clive et al., *J. Org. Chem.* 2001, 66, 1966-1983) and Et$_3$N (123 μL, 0.88 mmol, 0.1 equiv) was added pinacolborane (1.3 mL, 9.25 mmol, 1.05 equiv) and Cp$_2$ZrHCl (Schwartz reagent, purchased from Strem) (226 mg, 0.88 mmol, 0.1 equiv). The resulting solution was heated to 60° C. and stirred under argon for 8 hr. The mixture was cooled to rt and loaded on a short silica gel column. The column was washed with 10% EtOAc/hexanes solution (150 mL). Concentration of the solution under reduced pressure provided 1.8 g of 13 as a colorless oil (6.03 mmol, 68% yield). This compound was stored at −20° C. under argon for 2 months without decomposition.

$^1$H NMR (500 MHz, CDCl$_3$) δ 6.65 (dt, 1H, $J_1$=17.9 Hz, $J_2$=3.7 Hz), 5.73 (dd, 1H, $J_1$=17.9 Hz, $J_2$=2.0 Hz), 4.22 (dd, 2H, $J_1$=3.7 Hz, $J_2$=2.0 Hz), 1.24 (s, 12H), 0.93 (t, 9H, J=7.8 Hz), 0.58 (q, 6H, J=7.8 Hz);

$^{13}$C NMR (125 MHz, CDCl$_3$) δ 152.20, 83.29, 64.44, 24.94, 6.93, 6.78, 6.02, 4.64 (one carbon missing);

$^{11}$B NMR (96 MHz, CDCl$_3$) δ 29.8;

FTIR (neat, cm$^{-1}$) 2957, 2877, 1645;

HRMS (ESI) calcd for $C_{15}H_{32}BO_3Si$ [M+H]$^+$ 299.22083, found 299.22076.

Tetraene 14

To a solution of 12 (800 mg, 1.52 mmol) in THF (10 mL) was added boronic ester 13 (905 mg, 3.0 mmol, 2 equiv), K$_2$CO$_3$ (630 mg, 4.56 mmol, 3 equiv) and water (2 mL) respectively. To the solution was added Pd(PPh$_3$)$_4$ (70 mg, 0.06 mmol, 0.04 equiv). The resulting solution was heated to 75° C. and stirred for 5 hrs. The reaction slowly turned black. The solution was cooled to rt and diluted with EtOAc (50 mL). The organic layer was washed with brine (50 mL). The aqueous layer was extracted with EtOAc (2×50 mL). Drying the combined organic layer over Na$_2$SO$_4$ and concentration under reduced pressure provided yellow oil. Purification on a Davisil silica gel column (continuous gradient starting with hexanes and ending with 10% EtOAc/hexanes) provided 780 mg of 14 as a yellow syrup (1.28 mmol, 84% yield).

$^1$H NMR (500 MHz, CDCl$_3$) δ 6.24 (d, 1H, J=15.1 Hz), 6.07 (s, 1H), 6.03 (q, 1H, J=2.5 Hz), 5.89 (ddd, 1H, $J_1$=15.1 Hz, $J_2$=5.4 Hz, $J_3$=5.4 Hz), 5.03 (s, 1H), 4.94 (d, 1H, J=1.5 Hz), 4.57 (d, 1H, J=7.8 Hz), 4.32 (d, 1H, J=7.8 Hz), 4.23 (m, 2H), 3.82 (ddd, 1H, $J_1$=10.3 Hz, $J_2$=5.3 Hz, $J_3$=2.4 Hz), 3.72 (t, 1H, J=8.3 Hz), 3.51-3.44 (m, 3H), 3.36 (s, 3H), 2.35 (ddd, 1H, $J_1$=12.7 Hz, $J_2$=5.9 Hz, $J_3$=2.9 Hz), 2.33-2.27 (m, 1H), 2.21 (ddd, 1H, $J_1$=14.1 Hz, $J_2$=5.2 Hz, $J_3$=2.9 Hz), 2.12-2.08 (m, 2H), 2.01 (d, 1H, J=18.1 Hz), 1.94-1.88 (m, 1H), 1.78 (ddd, 1H, $J_1$=13.2 Hz, $J_2$=13.2 Hz, $J_3$=5.9 Hz), 1.69-1.63 (m, 2H), 1.52-1.42 (m, 1H), 0.97 (t, 9H, J=7.8 Hz), 0.88 (s, 9H), 0.79 (s, 3H), 0.62 (q, 6H, J=7.8 Hz), 0.02 (s, 3H), 0.01 (s, 3H);

$^{13}$C NMR (125 MHz, CDCl$_3$) δ 147.33, 139.60, 138.78, 136.20, 132.13, 130.33, 128.10, 113.59, 90.42, 83.99, 81.84, 72.11, 67.44, 63.94, 59.16, 48.17, 43.80, 40.40, 37.18, 34.76, 30.76, 26.06, 19.82, 18.28, 13.97, 7.01, 4.76, −4.20, −4.55;

FTIR (neat, cm$^{-1}$) 2954, 2877, 1645, 1621;

HRMS (ESI) calcd for $C_{35}H_{62}O_5Si_2Na$ [M+Na]$^+$ 641.40280, found 641.40456.

Diol S8

To a solution of 14 (780 mg, 1.28 mmol) in $^t$BuOH (7 mL) was added methylsulfonamide (122 mg, 1.28 mmol, 1 equiv) and (DHQD)$_2$PHAL (50 mg, 0.064 mmol, 0.05 equiv). To this solution was added water (7 mL), K$_3$Fe(CN)$_6$ (1.26 g, 3.83 mmol, 3 equiv) and K$_2$CO$_3$ (531 mg, 3.83 mmol, 3 equiv). The solution was cooled to 0° C. and stirred vigorously. In 5 min, K$_2$OsO$_4$.2H$_2$O (9.4 mmol, 0.025 mmol, 0.02 equiv) was added and the reaction was stirred vigorously at 0° C. for 2 hr. The solution was diluted with EtOAc (50 mL) and washed with brine (50 mL). The aqueous layer was extracted with EtOAc (2×50 mL). The combined organic layer was washed with brine (50 mL), dried over Na$_2$SO$_4$ and concentrated under reduced pressure to provide S8 as a dark purple syrup. This compound is moderately stable on silica gel, therefore used for the next reaction without further purification.

$^1$H NMR (500 MHz, CDCl$_3$) δ 6.14 (s, 1H), 6.07 (d, 1H, J=4.0 Hz), 5.00 (s, 1H), 4.93 (s, 1H), 4.53 (d, 1H, J=6.8 Hz), 4.46 (t, 1H, J=3.6 Hz), 4.40 (d, 1H, J=6.8 Hz), 3.74-3.70 (m, 4H), 3.68-3.58 (m, 2H), 3.50 (t, 2H, J=3.0 Hz), 3.36 (s, 3H), 3.10 (dd, 1H, $J_1$=21.7 Hz, $J_2$=5.1 Hz), 2.37 (ddd, 1H, $J_1$=12.7 Hz, $J_2$=5.2 Hz, $J_3$=5.2 Hz), 2.31 (ddd, 1H, $J_1$=12.7 Hz, $J_2$=4.5 Hz, $J_3$=4.5 Hz), 2.21 (ddd, 1H, $J_1$=14.2 Hz, $J_2$=4.5 Hz, $J_3$=4.5 Hz), 2.11 (dd, 1H, $J_1$=18.6 Hz, $J_2$=5.4 Hz), 2.00 (s, 1H), 1.97-1.87 (m, 2H), 1.76 (ddd, 1H, $J_1$=13.5 Hz, $J_2$=5.2 Hz, $J_3$=5.2 Hz), 1.69-1.60 (m, 2H), 1.51-1.43 (m, 2H), 0.96 (t, 9H, d=7.8 Hz), 0.88 (s, 9H), 0.78 (s, 3H), 0.63 (q, 6H, J=7.8 Hz), 0.02 (s, 3H), 0.01 (s, 3H);

$^{13}$C NMR (125 MHz, CDCl$_3$) δ 147.33, 139.27, 138.00, 136.00, 128.25, 111.46, 90.57, 84.14, 81.86, 73.60, 73.09, 72.03, 68.02, 64.36, 59.16, 48.28, 43.79, 40.34, 36.98, 35.76, 30.71, 26.05, 19.76, 18.28, 13.90, 6.94, 4.56, −4.21, −4.56;

FTIR (neat, cm$^{-1}$) 3384, 2928;

HRMS (ESI) calcd for $C_{35}H_{64}O_7Si_2Na$ [M+Na]$^+$ 675.40828, found 675.40911.

Diacetate S9

To a solution of S8 (approx. 1.28 mmol) in CH$_2$Cl$_2$ (10 mL) was added Ac$_2$O (0.36 mL, 3.84 mmol, 3 equiv), Et$_3$N (0.62 mL, 4.48 mmol, 3.5 equiv) and DMAP (30 mg, 0.26 mmol, 0.2 equiv) at 0° C. In 5 min the reaction was warmed to rt and stirred overnight. In 12-18 hr the starting material was consumed. The solution was diluted with CH$_2$Cl$_2$ (50 mL) and washed with NaHCO$_3$ (aq) sat. solution (50 mL). The aqueous layer was extracted with CH$_2$Cl$_2$ (2×50 mL). The combined organic layer was dried and concentrated under reduced pressure. Purification on a Florisil column (10% EtOAc/hexanes) provided 480 mg of S9 as a yellow syrup (0.650 mmol, 51% yield over 2 steps). This compound slowly decomposes at −20° C. under argon, therefore was used for the next reaction within 12 hr.

$^1$H NMR (500 MHz, CDCl$_3$) δ 6.13 (s, 1H), 6.04 (dd, 1H, $J_1$=4.2 Hz, $J_2$=2.4 Hz), 5.56 (d, 1H, J=8.3 Hz), 5.31 (s, 1H), 5.30 (ddd, 1H, $J_1$=4.2 Hz, $J_2$=4.2 Hz, $J_3$=4.2 Hz), 5.03 (s, 1H), 4.51 (d, 1H, J=7.8 Hz), 4.18 (d, 1H, J=7.8 Hz), 3.85

(ddd, 1H, $J_1$=10.7 Hz, $J_2$=5.2 Hz, $J_3$=3.2 Hz), 3.73 (t, 1H, J=8.6 Hz), 3.65 (dd, 1H, $J_1$=11.2 Hz, $J_2$=3.4 Hz), 3.54 (dd, 1H, $J_1$=11.2 Hz, $J_2$=4.9 Hz), 3.52-3.46 (ddd, 1H $J_1$=10.2 Hz, $J_2$=7.0 Hz, $J_3$=3.4 Hz), 3.43 (ddd, 1H, $J_1$=10.8 Hz, $J_2$=7.0 Hz, $J_3$=3.4 Hz), 3.36 (s, 3H), 2.34-2.30 (m, 1H), 2.26-2.18 (m, 2H), 2.14 (t, 1H, J=10.0 Hz), 2.11-2.01 (m, 1H), 2.05 (s, 3H), 2.03 (s, 3H), 1.91-1.86 (m, 1H), 1.79-1.73 (m, 1H), 1.66-1.62 (m, 2H), 1.49-1.43 (m, 1H), 0.93 (t, 9H, J=7.8 Hz), 0.88 (s, 9H), 0.88 (s, 3H), 0.56 (q, 6H, J=7.8 Hz), 0.02 (s, 3H), 0.01 (s, 3H);

$^{13}$C NMR (125 MHz, CDCl$_3$) δ 170.74, 169.98, 145.68, 137.92, 137.72, 135.37, 133.95, 113.54, 90.44, 84.35, 81.69, 77.15, 74.50, 72.08, 67.34, 61.27, 59.18, 48.04, 43.77, 40.32, 37.16, 36.09, 30.72, 26.06, 21.37, 21.29, 19.79, 18.28, 13.97, 6.92, 4.54, −4.20, −4.55;

FTIR (neat, cm$^{-1}$) 2955, 2877, 1748;

HRMS (ESI) calcd for $C_{39}H_{68}O_9Si_2Na$ [M+Na]$^+$ 759.42941, found 759.42878.

Primary Alcohol S10

To a solution of S9 (430 mg, 0.583 mmol) in THF (20 mL) was added HF/pyridine (3 mL) dropwise at rt. The reaction was completed in 5 min. The reaction was quenched by addition of pH 7 phosphate buffer (40 mL). The aqueous solution was extracted with EtOAc (3×40 mL). The gathered organic layer was washed with NaHCO$_3$(aq) sat. solution (50 mL) and brine (50 mL). Drying over Na$_2$SO$_4$ and concentration under reduced pressure provided S10 as a colorless syrup. The crude product is highly unstable on silica gel and decomposes at −20° C. overnight, therefore was used immediately for the next reaction without further purification.

$^1$H NMR (500 MHz, CDCl$_3$) δ 6.18 (s, 1H), 6.07-6.05 (m, 1H), 5.57 (d, 1H, J=8.8 Hz), 5.34-5.31 (m, 1H), 5.27 (s, 1H), 5.06 (s, 1H), 4.51 (d, 1H, J=7.8 Hz), 4.23 (d, 1H, J=7.8 Hz), 3.84-3.81 (m, 1H), 3.74-3.69 (m, 2H), 3.58-3.53 (m, 1H), 3.52-3.47 (m, 3H), 3.36 (s, 3H), 2.37-2.31 (m, 1H), 2.31-2.28 (m, 1H), 2.24-2.17 (m, 1H), 2.13-2.04 (m, 2H), 2.09 (s, 3H), 2.04 (s, 3H), 1.94-1.88 (m, 2H), 1.76 (ddd, 1H, $J_1$=13.2 Hz, $J_2$=13.2 Hz, $J_3$=5.4 Hz), 1.67-1.62 (m, 2H), 1.50-1.43 (m, 1H), 0.88 (s, 9H), 0.76 (s, 3H), 0.02 (s, 3H), 0.01 (s, 3H).

Diacetoxyaldehyde 15

To a solution of S10 (approx. 0.583 mmol) in CH$_2$Cl$_2$ (8 mL) was added Dess-Martin Periodinane (303 mg, 0.715 mmol, 1.1 equiv) at 0° C. In 5 min the reaction was warmed to rt and stirred for 1 h. The reaction was quenched by adding Na$_2$S$_2$O$_3$ 10% aqueous solution (10 mL)/NaHCO$_3$ (aq) sat. solution mixture (10 mL) and stirring vigorously for 10 min until the reaction turned clear. (Sodium thiosulfate was used to reduce residual hypervalent iodine species to iodobenzoic acid. Iodine byproducts were then washed by a basic aqueous solution. Removal of all iodine compounds is crucial for the reproducibility of the next reaction). The aqueous layer was extracted with EtOAc (3×20 mL). The gathered organic layer was washed with NaHCO$_3$ (aq) sat. solution mixture (50 mL) and brine (50 mL). Drying over Na$_2$SO$_4$ and concentration under reduced pressure provided 15 as a yellow oil. The aldehyde 15 is unstable on silica gel and slowly decomposes at −20° C., therefore was used immediately for the next reaction without further purification.

$^1$H NMR (500 MHz, C$_6$D$_6$) δ 9.35 (s, 1H), 6.17 (s, 1H), 6.03 (d, 1H, J=6.3 Hz), 5.67 (m, 1H), 5.61 (d, 1H, J=6.3 Hz), 5.15 (s, 1H), 4.92 (s, 1H), 4.62 (d, 1H, J=7.4 Hz), 4.41 (d, 1H, J=7.4 Hz), 3.77 (ddd, 1H, $J_1$=10.7 Hz, $J_2$=5.8 Hz, $J_3$=3.9 Hz), 3.58 (t, 1H, J=8.6 Hz), 3.35 (ddd, 1H, $J_1$=10.7 Hz, $J_2$=5.8 Hz, $J_3$=3.9 Hz), 3.28-3.22 (m, 3H), 3.05 (s, 3H), 2.29-2.19 (m, 3H), 2.05-1.86 (m, 4H), 1.84-1.71 (m, 2H), 1.78 (s, 3H), 1.64 (s, 3H), 1.53-1.46 (m, 1H), 1.36-1.31 (m, 1H), 0.89 (s, 9H), 0.76 (s, 3H), −0.02 (s, 3H), −0.04 (s, 3H).

Compound 16

A mixture of ZnBr$_2$ (176 mg, 0.780 mmol, 1.5 equiv) in CH$_3$CN (3 mL) was heated to 50° C. for 10-15 min, until the reaction became homogeneous. To the solution was added Me$_2$NH (2M solution in THF, 0.78 mL, 1.56 mmol, 3.0 equiv) was added to provide slightly yellow solution. This mixture was added to a 50 mL flask charged with a solution of 15 (approx. 0.583 mmol) in CH$_3$CN (4 mL). The flask was sealed using 14/20 glass stopper and the reaction was heated to 50° C. for 40 min. The reaction slowly turned orange/red. The solution was diluted with EtOAc (20 mL) and washed with NaHCO$_3$ (aq) sat. solution (20 mL). The aqueous layer was extracted with EtOAc (2×20 mL). The combined organic layer was washed with brine (50 mL). Drying over Na$_2$SO$_4$ and concentration under reduced pressure provided a deep purple syrup. Purification on a Davisil silica gel column (continuous gradient starting with 25% EtOAc/hexanes and ending with 50% EtOAc/hexanes, with 1% Et$_3$N) provided 210 mg of 16 as a yellow foam (0.375 mmol, 65% yield over 3 steps).

$^1$H NMR (500 MHz, CDCl$_3$) δ 5.74 (d, 1H, J=2.4 Hz), 5.54 (d, 1H, J=9.8 Hz), 5.40 (m, 1H), 5.03 (dd, 1H, $J_1$=10.0 Hz, $J_2$=10.0 Hz), 3.75 (dd, 1H, $J_1$=8.3 Hz, $J_2$=8.3 Hz), 2.72 (ddd, 1H, $J_1$=11.2 Hz, $J_2$=11.2 Hz, $J_3$=5.4 Hz), 2.25 (s, 6H), 2.25-2.21 (m, 2H), 2.14 (s, 3H), 2.23-2.21 (m, 2H), 2.14 (s, 3H), 1.99-1.87 (m, 4H), 1.73-1.61 (m, 2H), 1.56-1.51 (m, 1H), 0.88 (s, 9H), 0.72 (s, 3H), 0.03 (s, 3H), 0.02 (s, 3H);

$^{13}$C NMR (125 MHz, CDCl$_3$) δ 170.45, 170.40, 139.21, 136.22, 123.26, 120.22, 82.17, 81.86, 79.24, 73.82, 72.44, 60.76, 46.50, 43.63, 40.75, 39.54, 39.47, 30.96, 30.92, 30.75, 26.03, 21.34, 20.92, 19.58, 18.28, 13.47, −4.19, −4.60;

FTIR (neat, cm$^{-1}$) 2956, 1747;

HRMS (ESI) calcd for $C_{31}H_{49}NO_6SiNa$ [M+Na]$^+$ 582.32214, found 582.32069.

Sec-Alcohol S11

To a solution of 16 (150 mg, 0.275 mmol) in THF (3 mL) was added TBAF (1M solution in THF, 0.334 mL, 0.334 mmol, 1.2 equiv) (using extra amount of TBAF resulted in deprotection of the acetate groups) at rt. The reaction was heated to 70° C. and stirred for 4 hr. The reaction quickly turned deep purple. After cooling to rt, the solution was diluted with EtOAc (20 mL). The organic layer was washed with NaHCO$_3$(aq) sat. solution (10 mL)/brine (10 mL) mixture. The aqueous layer was extracted with EtOAc (2×20 mL). The gathered organic layer was dried over Na$_2$SO$_4$ and concentrated under reduced pressure provided a deep purple syrup. Purification on a Davisil silica gel column (EtOAc, 1% Et$_3$N) provided 85 mg of S11 as a yellowish solid (0.191 mmol, 70% yield).

$^1$H NMR (500 MHz, CDCl$_3$) δ 5.74 (d, 1H, J=2.0 Hz), 5.54 (d, 1H, J=9.3 Hz), 5.42 (m, 1H), 5.03 (dd, 1H, $J_1$=10.3 Hz, $J_2$=10.3 Hz), 3.86 (dd, 1H, $J_1$=8.8 Hz, $J_2$=8.8 Hz), 2.73 (ddd, 1H, $J_1$=11.3 Hz, $J_2$=11.3 Hz, $J_3$=4.4 Hz), 2.25 (s, 6H), 2.25-2.19 (m, 2H), 2.17-2.13 (m, 2H), 2.14 (s, 3H), 2.10 (s, 1H), 2.05 (s, 3H), 1.94-1.87 (m, 2H), 1.78-1.70 (m, 2H), 1.69-1.61 (m, 3H), 1.55-1.52 (m, 1H), 1.46 (bs, 1H), 0.76 (s, 3H);

$^{13}$C NMR (125 MHz, CDCl$_3$) δ 170.46, 170.40, 139.16, 136.38, 122.85, 120.10, 81.91, 79.28, 73.79, 72.42, 60.74, 46.92, 43.21, 40.75, 39.43, 39.05, 30.91, 30.78, 30.58, 21.34, 20.91, 19.44, 13.11;

FTIR (neat, cm$^{-1}$) 3445, 2960, 1747;

HRMS (ESI) calcd for $C_{25}H_{35}NO_6Na$ [M+Na]$^+$ 468.23566, found 468.23554.

Ketone 17

To a solution of S11 (80 mg, 0.180 mmol) in CH$_2$Cl$_2$ (2 mL) was added N-methylmorpholine N-oxide (27 mg, 0.248 mmol, 1.3 equiv) and 4 Å molecular sieves (85 mg). After stirring for 5 min at rt, TPAP (3.0 mg, 0.0095 mmol, 0.05 equiv) (oxidation using Dess-Martin periodinane resulted in slower reaction with lower yield) was added and the reaction was stirred at rt for 2.5 hr. The reaction was filtered over a celite pad to remove molecular sieves. The filtrate was concentrated under reduced pressure. Purification on a Davisil column (EtOAC, 1% Et$_3$N) provided 80 mg of 17 as a white solid (0.180 mmol, quantitative yield).

$^1$H NMR (500 MHz, CDCl$_3$) δ 5.75 (d, 1H, J=2.5 Hz), 5.55 (d, 1H, J=9.8 Hz), 5.43 (dd, 1H, J$_1$=4.7 Hz, J$_2$=2.5 Hz), 5.05 (t, 1H, J=10.0 Hz), 2.75 (ddd, 1H, J$_1$=12.2 Hz, J$_2$=10.7 Hz, J$_3$=4.4 Hz), 2.52 (dd, 1H, J$_1$=19.3 Hz, J$_2$=8.8 Hz), 2.38 (dd, J$_1$=12.7 Hz, J$_2$=5.9 Hz), 2.26 (s, 6H), 2.26-2.22 (m, 4H), 2.19-2.12 (m, 2H), 2.14 (s, 3H), 2.06 (s, 3H), 2.04-1.93 (m, 2H), 1.93-1.85 (m, 1H), 1.84-1.78 (m, 1H), 1.74-1.71 (m, 1H), 0.91 (s, 3H);

$^{13}$C NMR (125 MHz, CDCl$_3$) δ 220.39, 170.43, 170.37, 139.30, 136.87, 121.96, 119.87, 81.72, 79.55, 73.69, 72.31, 60.72, 48.00, 47.35, 40.77, 39.41, 36.09, 34.18, 31.52, 30.97, 21.33, 20.89, 19.06, 17.11;

FTIR (neat, cm$^{-1}$) 2960, 1747;

HRMS (ESI) calcd for C$_{25}$H$_{34}$NO$_6$ [M+H]$^+$ 444.23806, found 444.23858.

Aminodiol S12

To a solution of S11 (30 mg, 0.068 mmol) in MeOH (0.5 mL) was added K$_2$CO$_3$ (40 mg, 0.146 mmol, 5 equiv) at rt. The reaction was vigorously stirred for 30 min as the solution turned yellow. The solution was diluted with EtOAc (10 mL) and washed with 0.1M NaOH(aq) solution (10 mL). The aqueous layer was extracted with EtOAc (3×10 mL). The combined organic layer was dried over Na$_2$SO$_4$ and concentrated. Purification on a silica gel column (CH$_2$Cl$_2$:MeOH (saturated with ammonia) (prepared by bubbling ammonia gas into MeOH at 0 C for 5 min=10:1) provided 20 mg of S12 as a white solid (0.056 mmol, 82% yield). The $^1$H NMR spectrum matches with one reported by Baran et al. [α]$_D$=183° (c, 0.61, CH$_2$Cl$_2$);

$^1$H NMR (500 MHz, CDCl$_3$) δ

Hydrazone S13

The hydrazone S13 was prepared following the procedure developed by Baran et al. (see Shenvi et al., *J. Am. Chem. Soc.* 2008, 130, 7241-7243) with modification. To a solution of S12 (10 mg, 0.028 mmol) in EtOH (0.3 mL, degassed by bubbling nitrogen into absolute EtOH for 10 min) in a 5 mL vial was added NEt$_3$ (38 μL, 0.273 mmol, 10 equiv) and hydrazine monohydrate (13 μL, 0.273 mmol, 10 equiv) under argon. The vial was quickly capped with a teflon cap and the reaction was heated to 80° C. and stirred for 6 h. The solution was cooled to rt, transferred to a 10 mL round-bottom flask and concentrated under reduced pressure to provide S13. The product was considered to be metastable (Furrow et al., *J. Am. Chem. Soc.* 2004, 126, 5436-5445) and used for the next reaction immediately.

$^1$H NMR (500 MHz, CDCl$_3$) δ 6.25 (s, 1H), 5.49 (m, 1H), 4.84 (s, br, 2H), 4.08 (d, 1H, J=9.3 Hz), 3.32 (t, 1H, J=9.3 Hz), 2.46-2.38 (m, 2H), 2.32-2.14 (m, 6H), 2.28 (s, 6H), 2.09-2.04 (m, 1H), 1.90 (dd, 1H, J$_1$=12.7 Hz, J$_2$=3.4 Hz), 1.85-1.74 (m, 3H), 1.66-1.62 (m, 1H), 0.93 (s, 3H).

Vinyl Iodide S14

The vinyl iodide S14 was prepared following the procedure developed by Baran et al. See Shenvi et al., *J. Am. Chem. Soc.* 2008, 130, 7241-7243. To a solution of S13 (approx. 0.028 mmol) in THF (0.5 mL) was added NEt$_3$ (12 μL, 0.084 mmol, 3 equiv). To the solution was added a solution of 12 (15 mg, 0.059 mmol, 2 equiv) in THF (0.2 mL) dropwise, until purple color persists for more than 30 sec (this took approximately 1 equiv of iodide). The reaction was quenched by addition of Na$_2$S$_2$O$_3$(aq) sat solution (1 mL) and 0.1 M NaOH(aq) solution (1 mL). The aqueous layer was extracted with EtOAc (4×5 mL). The combined organic layer was dried over Na$_2$SO$_4$ and concentrated to provide S14 as a colorless syrup. The product was used for the next reaction without further purification.

$^1$H NMR (500 MHz, CDCl$_3$) δ 6.24 (d, 1H, J=2.0 Hz), 6.17 (m, 1H), 5.48 (dd, 1H, J$_1$=4.9 Hz, J$_2$=2.0 Hz), 4.06 (d, 1H, J=9.3 Hz), 3.32 (t, 1H, J=9.3 Hz), 2.60 (dd, 1H, J$_1$=10.8 Hz, J$_2$=6.6 Hz), 2.43-2.28 (m, 1H), 2.35 (ddd, 1H, J$_1$=15.2 Hz, J$_2$=6.3 Hz, J$_3$=2.9 Hz), 2.28 (s, 6H), 2.28-2.12 (m, 4H), 2.02-1.96 (m, 1H), 1.95-1.87 (m, 2H), 1.82 (t, 1H, J=12.6 Hz), 1.68-1.60 (m, 1H), 0.78 (s, 3H).

Vinylisoquinoline 18

The vinylisoquinoline 18 was prepared following the procedure developed by Baran et al. See Shenvi et al., *J. Am. Chem. Soc.* 2008, 130, 7241-7243. To a solution of S14 (approx. 0.028 mmol) in DMSO (0.3 mL) was added LiCl (12 mg, 0.28 mmol, 10 equiv), CuCl (28 mg, 0.28 mmol, 10 equiv), 7-isoquinolinetrimethylstannane (24 mg, 0.084 mmol, 3 equiv) (see Shenvi et al., *J. Am. Chem. Soc.* 2008, 130, 7241-7243), and Pd(PPh$_3$)$_4$ (16 mg, 0.014 mmol, 0.5 equiv). The resulting black solution was heated to 60° C. and stirred for 1 h. The solution was cooled to rt and diluted with EtOAc (10 mL). The organic layer was washed with 5% NH$_4$OH(aq) solution (10 mL). The aqueous layer was extracted with EtOAc (3×5 mL). The combined organic layer was washed with 0.1 M NaOH(aq) solution (2×5 mL), dried over Na$_2$SO$_4$ and concentrated. Purification on a silica gel column (continuous gradient starting with 100% CH$_2$Cl$_2$ and ending with CH$_2$Cl$_2$:MeOH (saturated with ammonia) (prepared by bubbling ammonia gas into MeOH at 0 C for 5 min)=10:1) provided 8 mg of 18 as a yellow syrup (0.017 mmol, 61% yield over 3 steps). The $^1$H NMR spectrum matches with one reported by Baran et al.

Cortistatin A (1)

The procedure developed by Baran et al. (see Shenvi et al., *J. Am. Chem. Soc.* 2008, 130, 7241-7243) was followed with modification.

Example 3

Intermediate

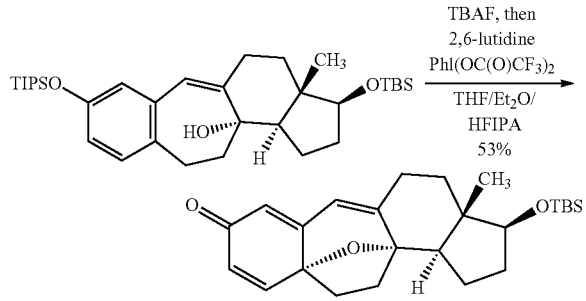

To a solution of the TIPS phenol (4.39 g, 7.69 mmol) in THF/Ether (68 mL each) at 0° C. was added the TBAF (1.0 M in THF) (9.23 ml, 9.23 mmol) over 1 minute. The reaction mixture [rapidly bright golden, then orange] was stirred for 30 minutes at 0° C. 800 μL of TBAF were added, and the mixture further stirred 10 minutes. The 2,6-Lutidine (3.58 ml, 30.8 mmol) was then added, followed by the hexafluoroisopropanol (17 mL) and the BTIB (5.95 g, 13.84 mmol) as a solid in two portions over 5 minutes. The reaction mixture was stirred at 0° C. and monitored by TLC. After 30 minutes, the reaction mixture was diluted with ether (250 mL) and the organic layer washed with dilute aqueous acetic acid (50 mL). The aqueous layer was extracted with ether (2×50 mL), and the combined organic layers were washed with saturated sodium bicarbonate solution (50 mL), and brine solution (50 mL), then dried over sodium sulfate, filtered, and concentrated. The organic residue was purified by flash-column chromatography using deactivated silica (5→17% ethyl acetate-hexanes) to provide the product as an off-white solid (1.68 g, 53%).

$^1$H NMR (500 MHz, benzene) d=6.43 (d, J=9.8 Hz, 1H), 6.20 (dd, J=1.7, 10.0 Hz, 1H), 5.93 (s, 1H), 5.49 (d, J=2.0 Hz, 1H), 3.37 (t, J=7.8 Hz, 1H), 2.11-2.02 (m, 1H), 1.97-1.90 (m, J=1.5, 4.9 Hz, 1H), 1.87-1.82 (m, 1H), 1.80-1.72 (m, 1H), 1.65 (d, J=3.4 Hz, 4H), 1.51-1.39 (m, 3H), 1.20-1.13 (m, 1H), 0.98 (s, 9H), 0.89 (dt, J=4.6, 13.1 Hz, 1H), 0.70 (s, 3H), 0.01 (s, 3H), 0.00 (s, 3H)

$^{13}$C NMR (126 MHz, benzene) d=185.7, 157.4, 154.4, 146.6, 129.9, 119.8, 119.1, 86.2, 81.7, 75.3, 47.7, 43.9, 37.3, 36.2, 30.8, 29.1, 28.9, 26.0, 19.7, 18.3, 11.0, −4.3, −4.7

Bromoether

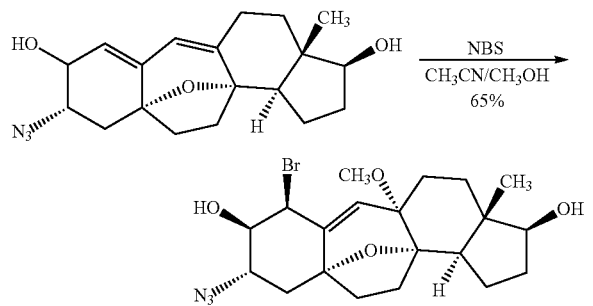

To a solution of the azido allylic alcohol (27 mg, 79 µmol) in acetonitrile (3.5 mL) and methanol (1 mL) at 0° C. was added the NBS (14.27 mg, 80 µmol) dropwise as a solution in acetonitrile (0.5 mL). After 14 minutes, the reaction mixture was quenched at 0° C. with 5 drops of saturated sodium thiosulfate solution and 5 drops of saturated sodium bicarbonate solution and the bulk of the solvent removed on the rotovap. The organic residue was diluted with with ethyl acetate (20 mL) and washed with water (10 mL). The aqueous layer was extracted with ethyl acetate (2×10 mL). The combined organic layers were washed with brine solution (10 mL), then dried over sodium sulfate, filtered, and concentrated. The organic residue was purified by flash-column chromatography using silica deactivated with triethylamine (10$^{-33}$% ethyl acetate-benzene) to give the product as an off-white solid (23.5 mg, 65%).

$^1$H NMR (500 MHz, chloroform) d=5.89 (s, 1H), 5.06 (d, J=3.9 Hz, 1H), 3.83-3.72 (m, 2H), 3.40 (dd, J=3.9, 9.8 Hz, 1H), 3.18 (s, 3H), 2.70-2.61 (m, 1H), 2.42 (dd, J=7.3, 12.2 Hz, 1H), 2.19-2.09 (m, 3H), 2.03-1.94 (m, 1H), 1.81-1.74 (m, 1H), 1.68-1.50 (m, 7H), 1.48-1.41 (m, 3H), 0.86-0.78 (m, 3H)

Triol Methyl Ether

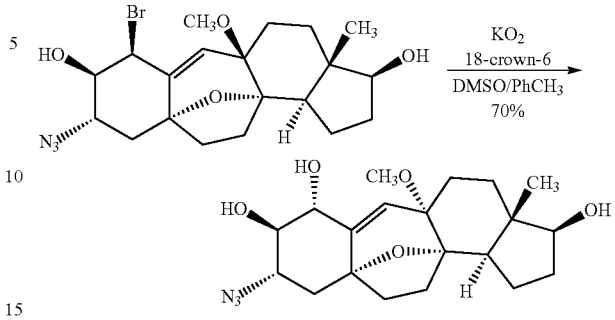

To a vigorously stirred solution of the allylic bromide (21.5 mg, 47.3 µmol) in toluene (3 mL) and DMSO (1 mL) at 0° C. were added the potassium superoxide (13.46 mg, 189 µmol) and the 18-crown-6 (62.5 mg, 237 µmol) as a solution in DMSO (1 mL), and the yellow-orange reaction mixture stirred at 0° C. After 4 minutes the reaction solution was thick and the ice bath was removed. After 3 additional minutes (7 minutes total reaction time1) the reaction mixture was quenched with 0.5 mL of saturated sodium chloride solution and then 0.5 mL of saturated sodium thiosulfate solution. The mixture was poured into ethyl acetate (20 mL), and water (5 mL) and saturated sodium bicarbonate solution (5 mL) were added. The aqueous layer was extracted with ethyl acetate (3×20 mL) and the combined organic layers were washed with brine solution (2×10 mL), then dried over sodium sulfate, filtered, and concentrated. The organic residue was purified by flash-column chromatography (17-33% acetone-benzene) to provide the product (13 mg, 70%).

$^1$H NMR (500 MHz, chloroform) d=5.76 (d, J=2.4 Hz, 1H), 3.94 (d, J=6.8 Hz, 1H), 3.83-3.78 (m, 1H), 3.44-3.37 (m, 2H), 3.20 (s, 3H), 2.49 (dd, J=7.3, 12.2 Hz, 1H), 2.16-2.02 (m, 5H), 1.88-1.78 (m, 2H), 1.66-1.40 (m, 10H), 0.80 (s, 3H)

Diene Triol

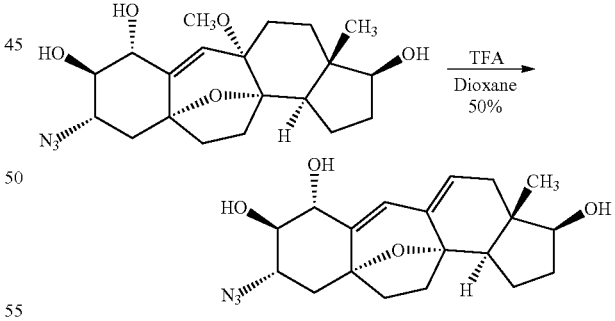

To a solution of the triol methyl ether (15 mg, 38.3 µmol) in dioxane (1.9 mL) at 23° C. was added the trifluoroacetic acid (89 µl, 1150 µmol) and the clear colorless reaction mixture stirred at room temperature. After 3 hours the mixture was diluted with diethyl ether (2 mL) and concentrated to give an orange film. The organic residue was purified by flash-column chromatography (25-33% acetone-benzene) to give the product as an off-white solid (7.6 mg, 50%).

$^1$H NMR (500 MHz, chloroform) d=6.19 (d, J=2.4 Hz, 1H), 5.47 (dd, J=2.7, 5.1 Hz, 1H), 4.07 (d, J=8.8 Hz, 1H), 3.87 (t, J=8.8 Hz, 1H), 3.46-3.34 (m, 2H), 2.30-2.20 (m, 2H), 2.20-2.04 (m, 8H), 2.02-1.94 (m, 1H), 1.81-1.64 (m, 4H), 0.78 (s, 3H)

Hydroxyazide C2OTBS C17OH

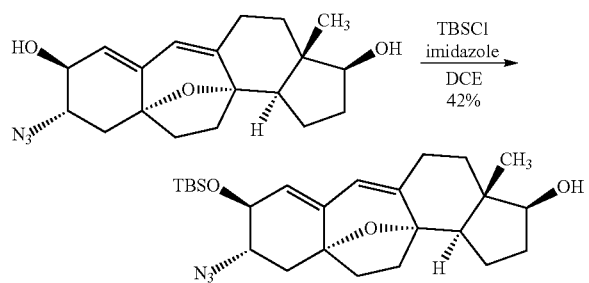

To a solution of the azidodiol (28 mg, 82 µmol), the imidazole (55.5 mg, 815 mol), and the sodium sulfate (463 mg, 3261 µmol) in 1,2-dichloroethane (2 mL) at 23° C. was added the TBSCl (1.0 M in dichloromethane) (163 µl, 163 µmol) and the reaction mixture stirred at that temperature. After 1 hour the reaction mixture was cooled to 0° C. After 1 hour 15 minutes TBSCl solution (80 µl, 80 µmol) was added. After 3 hours TBSCl solution (100 µl, 100 mol) was added. After 1 hour 30 minutes (6 hours 45 minutes total reaction time), the reaction mixture was quenched with 0.2 mL of methanol and stirred for 5 minutes at room temperature. The mixture was then diluted with of ethyl acetate (30 mL) and washed with 0.1 N HCl (10 mL). The aqueous layer was extracted with ethyl acetate (20 mL), and the combined organic layers were washed with brine solution (20 mL), then dried over sodium sulfate, filtered, and concentrated. The organic residue was purified by flash-column chromatography (5-33% ethyl acetate-hexanes) to give the product (16 mg, 42%).

$^1$H NMR (600 MHz, chloroform) d=5.70 (s, 1H), 5.05 (s, 1H), 4.20 (d, J=7.9 Hz, 1H), 3.71 (t, J=8.6 Hz, 1H), 3.46 (ddd, J=4.4, 8.1, 12.4 Hz, 1H), 2.50-2.41 (m, 1H), 2.30 (dd, J=3.5, 16.7 Hz, 1H), 2.19-2.06 (m, 2H), 2.06-1.90 (m, 6H), 1.90-1.76 (m, 4H), 1.73-1.60 (m, 3H), 1.21 (dt, J=4.7, 13.0 Hz, 1H), 0.92 (s, 9H), 0.83 (s, 3H), 0.16 (s, 3H), 0.14-0.11 (m, 3H)

Bromoketone

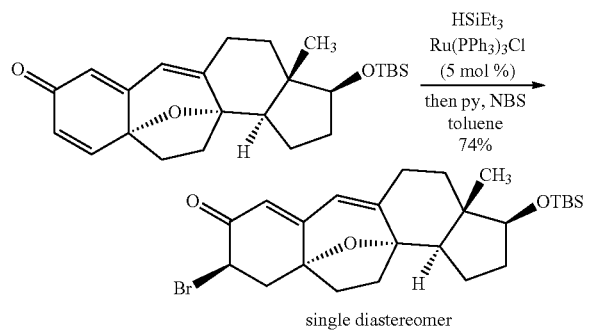

single diastereomer

To a flame-dried flask charged with the Key Intermediate (230 mg, 0.557 mmol, azeotropically dried from toluene) was added triethylsilane (178 µl, 1.12 mmol, allowed to pass through a neutral alumina pipette column right before use) followed by a solution of Wilkinson's catalyst (26 mg, 0.0279 mmol) in toluene (11 mL, degassed by freeze-pump-thaw five times) via cannula. The reaction mixture was heated to 50° C. under argon. After 4 hours, the reaction was cooled down to room temperature and pyridine (2.2 mL) was then added. After 1 hour the reaction mixture was cooled to −78° C. and a solution of NBS (248 mg, 1.39 mmol) in THF (3 mL) was added via cannula. After 1 hour, the cooling bath was removed and the reaction mixture was allowed to warm up to room temperature slowly over 0.5 hour. The mixture was then diluted with ethyl acetate (100 mL) and washed with saturated sodium thiosulfate solution (20 mL). The aqueous layer was extracted with ethyl acetate (3×15 mL), and the combined organic layers were washed with brine solution (20 mL), then dried over sodium sulfate, filtered, and concentrated. The organic residue was purified by flash-column chromatography (5-13% ethyl acetate-hexanes) to give the product as a white solid (204 mg as a single diastereomer, 74%).

$^1$H NMR (500 MHz, chloroform) d=5.92 (d, J=2.3 Hz, 1H), 5.61 (s, 1H), 4.59 (ddd, J=1.1, 2.3, 4.6 Hz, 1H), 3.64 (t, J=8.2 Hz, 1H), 2.93 (dd, J=4.7, 15.0 Hz, 1H), 2.56-2.36 (m, 4H), 2.31 (ddd, J=6.0, 9.3, 13.6 Hz, 1H), 2.09 (dt, J=5.6, 11.4 Hz, 1H), 2.03-1.94 (m, 1H), 1.90 (dd, J=8.9, 10.8 Hz, 1H), 1.84-1.76 (m, 2H), 1.67-1.49 (m, 3H), 1.24-1.19 (m, J=5.0 Hz, 1H), 0.92-0.86 (m, 9H), 0.84 (s, 3H), 0.02 (s, 6H)

$^{13}$C NMR (126 MHz, chloroform) d=191.2, 160.3, 158.9, 119.4, 116.5, 83.4, 81.4, 75.9, 47.7, 44.7, 43.9, 41.1, 37.2, 36.1, 30.5, 29.9, 29.7, 29.2, 25.8, 19.4, 18.0, 10.9, −4.5, −4.9

Hydroxyazide

To a solution of the bromoketone (167 mg, 0.338 mmol) in acetonitrile (8 mL) and THF (4 mL) at 23° C. was added tetramethylguanidinium azide (107 mg, 0.677 mmol) as a solid and the reaction mixture was stirred at that temperature. After 5 hours, the solvents were removed by vacuum, and the residue was dissolved in a mixture of ethyl acetate (30 mL) and diethyl ether (60 mL). The insoluable salt was filtered away and washed with diethyl ether (3×50 mL). The filtrate was concentrated, azeotropically dried from toluene and then dissolved in toluene (7 mL). To this solution was added (R)—CBS catalyst solution (1.0 M in tolune) (67.7 µl, 0.0677 mmol). The reaction mixture was then cooled down to −20° C. and the catecholborane solution (1.0M in tolune) (677 µl, 0.677 mmol) was added dropwise over 5 minutes, and the reaction mixture was stirred at that temperature. After 1 hour, the reaction mixture was quenched by adding methanol (0.2 mL). The solution was warmed up to room temperature and then diluted with ethyl acetate (80 mL), and washed with buffer (pH=13, 1N NaOH/saturated NaHCO$_3$ 2/1) until the aqueous washings were colorless (3×10 mL). The aqueous layers ware extracted with ethyl acetate (3×15 mL), and the combined organic layers were washed with brine solution (20 mL), then dried over sodium sulfate, filtered, and concentrated. The organic residue was purified by flash-column chromatography (11→33% diethyl ether-hexanes) to give the product as a white foam (130 mg, d.r.=15:1, 85% over two steps).

¹H NMR (500 MHz, benzene) d=5.52 (d, J=2.0 Hz, 1H), 4.94 (d, J=2.0 Hz, 1H), 3.94 (d, J=7.8 Hz, 1H), 3.42 (t, J=8.1 Hz, 1H), 3.31 (ddd, J=3.2, 8.2, 13.6 Hz, 1H), 2.28-2.18 (m, 1H), 2.11 (dd, J=12.2, 13.7 Hz, 1H), 2.04 (dd, J=3.2, 16.4 Hz, 1H), 1.91-1.83 (m, 2H), 1.82-1.61 (m, 6H), 1.57-1.41 (m, 5H), 0.98 (s, 9H), 0.78 (s, 3H), 0.01 (s, 3H), 0.00 (s, 3H)

Dimethylaminodieneol

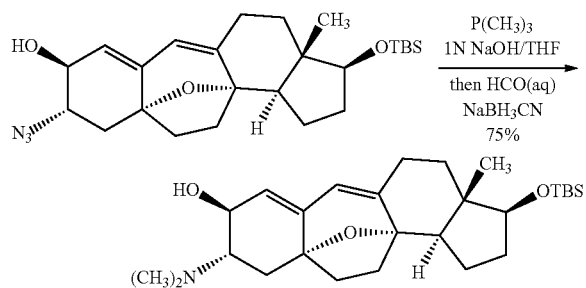

To a solution of the hydroxyazide (38 mg, 0.0830 mmol) in THF (3 mL) and 1N NaOH (0.3 mL) at 23° C. was added trimethylphosphine solution (1.0M in THF) (670 µl, 0.670 mmol) and the reaction mixture was stirred at that temperature. After 3 hours (monitored by TLC), methanol (3.5 mL) was added, followed by trace amount of methyl orange in water as pH indicator. Acetic acid (0.3 mL) was added followed by 1 N HCl dropwisely until the color of the reaction mixture changed from yellow to orange (pH ~4.4) (ca. 0.5 mL 1 N HCl added). HCHO (37% wt in water) (340 µl, 4.15 mmol) and sodium cyanoborohydride (104 mg, 1.66 mmol) were then added. During the reaction, 1N HCl was added as necessary to maintain the orange color of the reaction mixture. After 2 hours, solvents were removed by vacuum. The residue was basified to pH=12 by adding 1N NaOH (20 mL) and the aqueous layer was extracted with ethyl acetate (4×25 mL), and the combined organic layers were washed with brine solution (20 mL), then dried over sodium sulfate, filtered, and concentrated. The organic residue was purified by flash-column chromatography using Davisil® silica(0→50% methanol-ethyl acetate) to give the product as a white solid (29 mg, 75%).

¹H NMR (600 MHz, chloroform) d=5.70 (d, J=2.3 Hz, 1H), 5.30 (d, J=1.8 Hz, 1H), 4.21 (d, J=9.4 Hz, 1H), 3.60 (t, J=8.3 Hz, 1H), 2.58 (ddd, J=2.4, 9.1, 12.6 Hz, 1H), 2.49-2.41 (m, 1H), 2.29 (s, 6H), 2.28-2.23 (m, 1H), 2.10-1.91 (m, 4H), 1.90-1.76 (m, 5H), 1.72 (ddd, J=1.8, 5.3, 12.5 Hz, 1H), 1.68-1.55 (m, 2H), 1.54-1.45 (m, 1H), 1.12 (dt, J=4.5, 13.1 Hz, 1H), 0.88 (s, 9H), 0.79 (s, 3H), 0.01 (s, 3H), 0.01 (s, 3H)

Cortistatin L Dimethylaminoketone

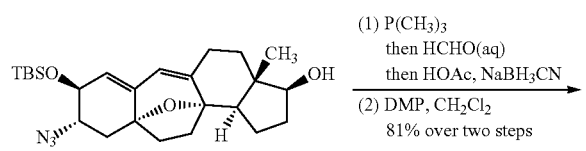

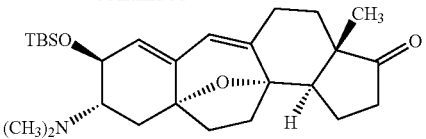

To a solution of the mono-protected hydroxyazide (8.0 mg, 0.0175 mmol) in THF (1.8 mL) at 23° C. was added trimethylphosphine solution (1.0M in THF) (88 µl, 0.0880 mmol) and the reaction mixture was stirred at that temperature. After 20 hours, HCHO (37% wt in water) (140 µl, 1.75 µmol) was added. After another 20 hours, methanol (2 mL) was added, followed by acetic acid (20 µl, 0.350 mmol) and sodium cyanoborohydride (22 mg, 0.350 mmol). After 2 hours, solvents were removed by vacuum. The residue was basified to pH=12 by adding 1 N NaOH (15 mL) and the aqueous layer was extracted with ethyl acetate (4×15 mL), and the combined organic layers were washed with brine solution (10 mL), then dried over sodium sulfate, filtered, and concentrated. The residue was dissolved in dichloromethane (2 mL), cooled down to 0° C. and added DMP (23 mg, 0.0525 mmol) as a solid and the reaction mixture was allowed to warm up to room temperature. After 3 hours, the reaction mixture was diluted with ethyl acetate (10 mL) and quenched by adding a mixture of saturated sodium thiosulfate solution (3 mL), saturated sodium bicarbonate solution (3 mL) and water (3 mL). The mixture was stirred vigorously until the organic layer became clear. The aqueous layer was extracted with ethyl acetate (4×15 mL), and the combined organic layers were washed with 1N NaOH (10 mL) and then brine solution (10 mL), then dried over sodium sulfate, filtered, and concentrated. The organic residue was purified by flash-column chromatography using Davisil® silica(66:33:1 hexane-ethyl acetate-triethylamine) to give the product as a pale yellow oil (6.5 mg, 81% over two steps).

¹H NMR (500 MHz, chloroform) d=5.73 (d, J=2.0 Hz, 1H), 5.14 (d, J=2.4 Hz, 1H), 4.25 (d, J=8.3 Hz, 1H), 2.65-2.57 (m, 1H), 2.56-2.43 (m, 2H), 2.41-2.34 (m, 1H), 2.29 (s, 6H), 2.23-2.00 (m, 5H), 1.95-1.78 (m, 6H), 1.39 (dt, J=4.9, 13.2 Hz, 1H), 0.96 (s, 3H), 0.89 (s, 9H), 0.09 (s, 3H), 0.08 (s, 3H)

Cortistatin J Dimethylamino Ketone

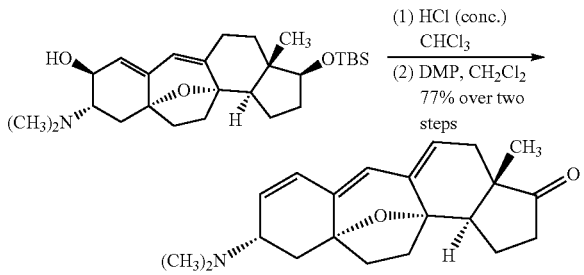

To a solution of dimethylaminodieneol (21 mg, 0.0457 mmol) in chloroform (2.0 mL) at 23° C. was added HCl (conc.) (1.0 mL) and the reaction mixture was stirred at that temperature. After 20 minutes, the reaction mixture was cooled down to 0° C. and then quenched by adding saturated sodium carbonate solution (10 mL). The aqueous layer was basified to pH=12 by adding 1N NaOH (10 mL) and then extracted with ethyl acetate (4×20 mL), and the combined organic layers were washed with brine solution (15 mL), then dried over sodium sulfate, filtered, and concentrated. The residue was dissolved in dichloromethane (4 mL), cooled down to 0° C. and DMP (58 mg, 0.137 mmol) was added as a solid in one portion. The reaction mixture was allowed to warm up to room temperature. After 3 hours, the reaction mixture was diluted with ethyl acetate (10 mL) and quenched by adding a mixture of saturated sodium thiosulfate solution (4 mL), saturated sodium bicarbonate solution (4 mL) and water (4 mL). The mixture was stirred vigorously until the organic layer became clear. The aqueous layer was extracted with ethyl acetate (4×20 mL), and the combined organic layers were washed with 1 N NaOH (10 mL) and then brine solution (15 mL), dried over sodium sulfate, filtered, and concentrated. The organic residue was purified by flash-column chromatography (0→50% methanol-ethyl acetate) to give the product as a pale yellow solid (11.5 mg, 77% over two steps).

$^1$H NMR (500 MHz, chloroform) d=6.13 (dd, J=2.4, 9.8 Hz, 1H), 5.87-5.81 (m, 2H), 5.48-5.43 (m, 1H), 3.57 (d, J=10.3 Hz, 1H), 2.53 (dd, J=8.5, 18.8 Hz, 1H), 2.44 (dd, J=5.6, 12.5 Hz, 1H), 2.36 (s, 6H), 2.30-2.13 (m, 4H), 2.11-2.05 (m, 1H), 2.05-1.87 (m, 4H), 1.86-1.70 (m, 2H), 0.96 (s, 3H)

Example 4

Alternative Route from Intermediate (2) to Intermediate (16)

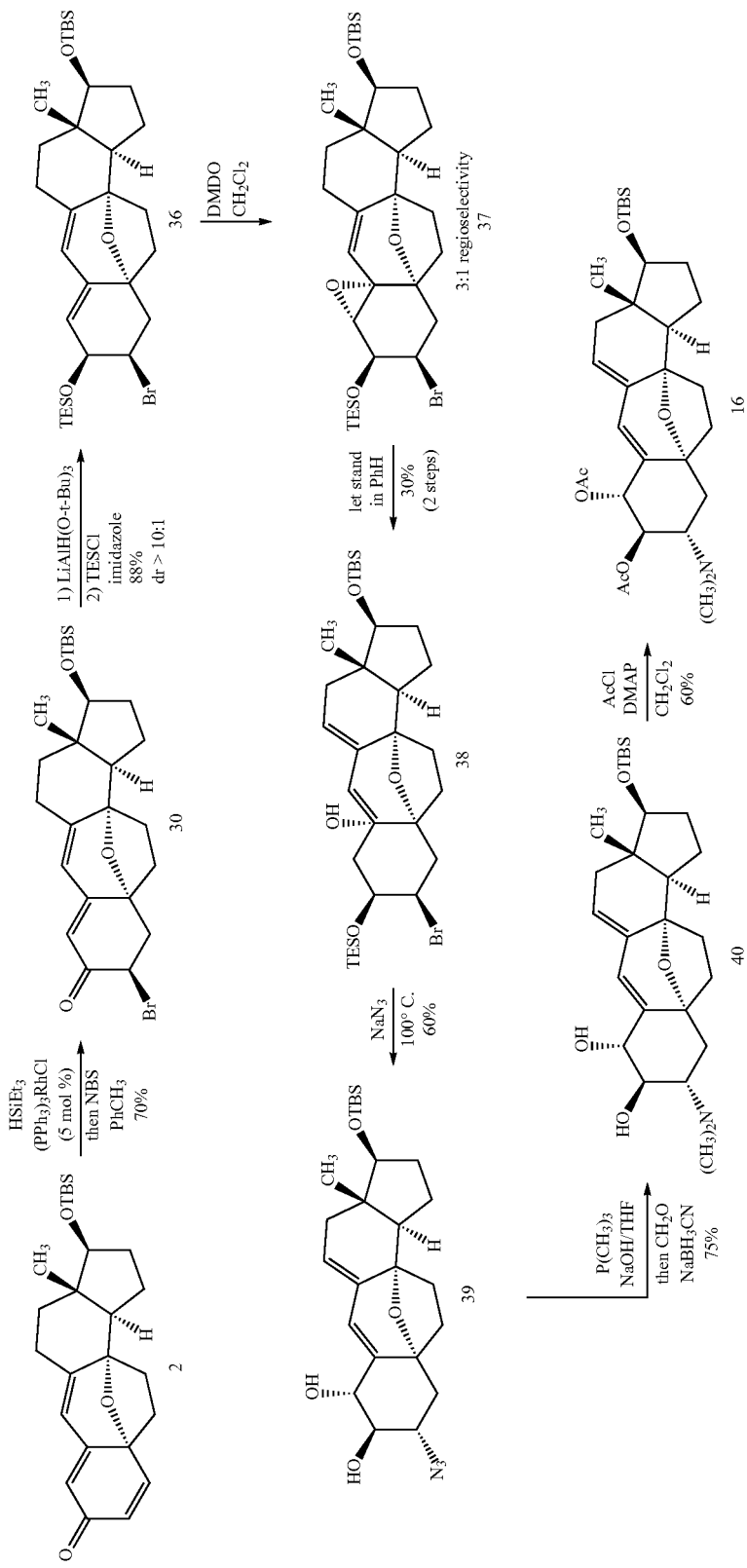

An alternative route from intermediate 2 to (+)-cortistatin A was developed which features the sequence from intermediates 2 to 16 shown above. Cyclohexadienone 2 undergoes a rhodium-catalyzed Michael addition of hydride. Quenching of the proposed enol intermediate with NBS stereoselectively yields α-bromide 30. Stereoselective reduction with tributoxylithium aluminum hydride, followed by protection with triethylsilylchloride yields bromide 36. Dimethyldioxirane-mediated allylic epoxidation of diene 36 to the six-membered epoxide 37 occurs with modest regioselectivity. Rearrangement occurs upon standing in benzene solution to yield dienol 38. Stereoselective $S_N2$ displacement of bromide with azide is accomplished with sodium azide at elevated temperatures. Reduction of azide 39 to the primary amine and reductive amination to dimethylamine 40 is followed by acetylation of the hydroxyl groups to yield intermediate 16, which can be converted to (+)-cortistatin A according to the methods described above.

Example 5

The present invention also provides synthetic approaches to incorporate biological probes, such as biotin and biotin derivatives, onto cortistatins A, J, K, and L, and analogs thereof. For example, the multistep sequence shown below features the reduction of an azide to a primary amine, protection of the primary amine with a BOC group, installation of the isoquinoline functionality, deprotection of the BOC group, and installation of the biotin group via an 6-aminohexanoamide linkage.

Potential Route to Biotinylated Cortistatin J Derivatives

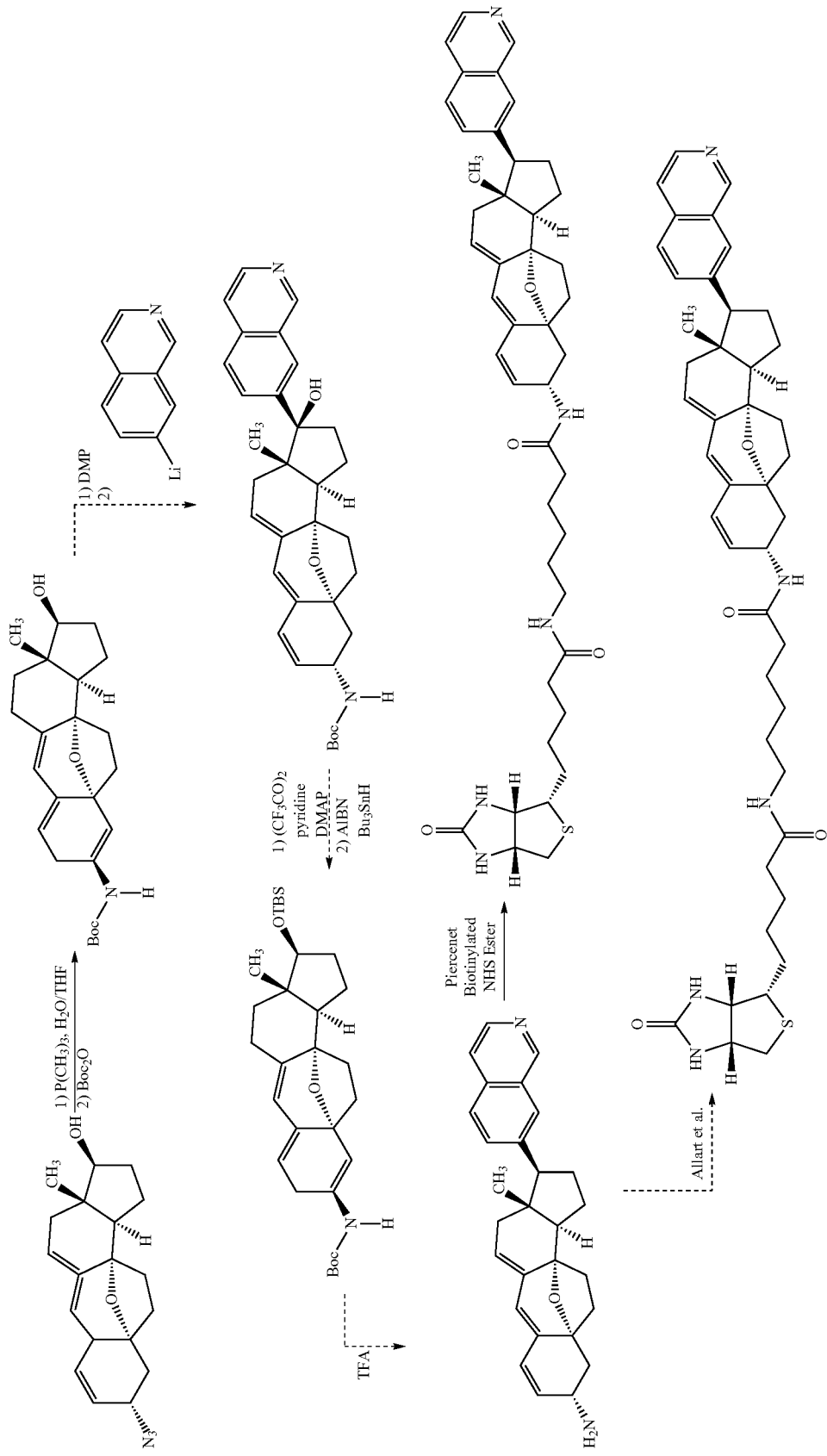

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of treating a disorder selected from benign neoplasm, obesity, macular degeneration, and rheumatoid arthritis, comprising administering a therapeutically effective amount of a compound or a pharmaceutically acceptable salt thereof, to a subject in need thereof, wherein the compound is of formula:

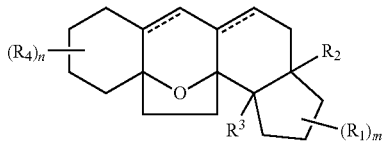

wherein:
 each of the dashed lines independently represents the presence or absence of a bond;
 n is 1;
 m is 1;
 $R_1$ is substituted or unsubstituted heteroaryl;
 $R_2$ is $C_1$-$C_6$ aliphatic;
 $R_3$ is hydrogen;
 $R_4$ is —N($R_D$)$_2$; —NHC(=O)$R_D$; —NR$_A$C(=O)N($R_D$)$_2$; or —NR$_D$C(=O)OR$_D$; and
 $R_A$ is hydrogen, a protecting group, an aliphatic moiety, a heteroaliphatic moiety, an acyl moiety, an aryl moiety, a heteroaryl moiety, alkoxy, aryloxy, alkylthio, arylthio, amino, alkylamino, dialkylamino, heteroaryloxy, or heteroarylthio; and
 each occurrence of $R_D$ is independently hydrogen, a protecting group, aliphatic; heteroaliphatic, acyl, aryl, or heteroaryl.

2. The method of claim 1, wherein the compound is of formula:

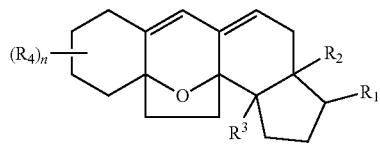

or a pharmaceutically acceptable salt thereof.

3. The method of claim 1, wherein the compound is of formula:

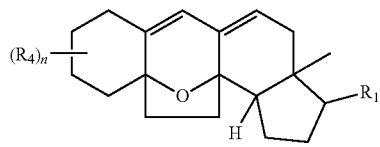

or a pharmaceutically acceptable salt thereof.

4. The method of claim 1, wherein the compound is of formula:

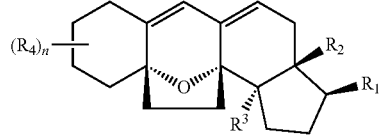

or a pharmaceutically acceptable salt thereof.

5. The method of claim 1, wherein the compound is of formula:

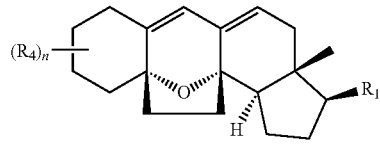

or a pharmaceutically acceptable salt thereof.

6. The method of claim 1, wherein the compound is of formula:

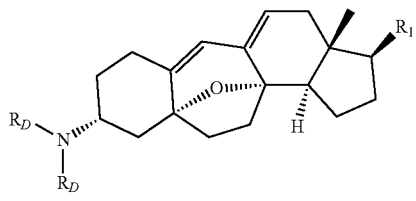

or a pharmaceutically acceptable salt thereof.

7. The method of claim 6, wherein each $R_D$ is independently hydrogen or $C_1$-$C_6$ alkyl.

8. The method of claim 6, wherein each $R_D$ is independently $C_1$-$C_6$ alkyl.

9. The method of claim 6, wherein each $R_D$ is methyl.

10. The method of claim 1, wherein $R_4$ is —N($R_D$)$_2$.

11. The method of claim 1, wherein $R_4$ is —N($R_D$)$_2$ and each $R_D$ is independently hydrogen or $C_1$-$C_6$ alkyl.

12. The method of claim 1, wherein $R_4$ is —N($R_D$)$_2$ and each $R_D$ is methyl.

13. The method of claim 1, wherein $R_2$ is methyl.

14. The method of claim 1, wherein $R_1$ is substituted or unsubstituted isoquinolinyl.

15. The method of claim 14, wherein $R_1$ is substituted isoquinolinyl.

16. The method of claim 14, wherein $R_1$ is unsubstituted isoquinolinyl.

17. The method of claim 1, wherein the compound is

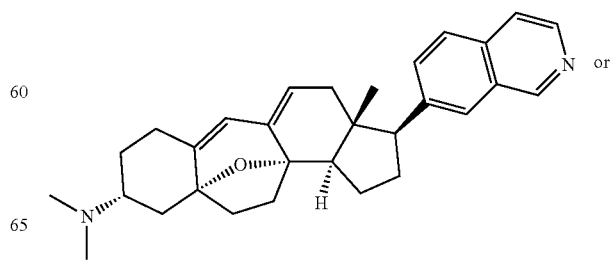

-continued
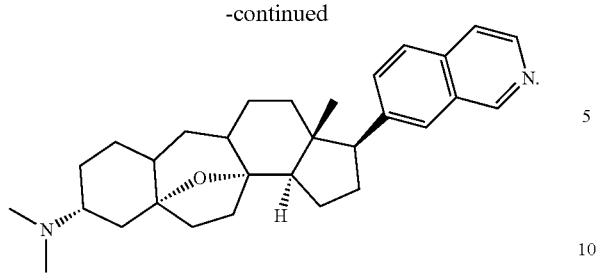
18. The method of claim 1, wherein the disorder is a benign neoplasm.
19. The method of claim 1, wherein the disorder is obesity.
20. The method of claim 1, wherein the disorder is macular degeneration.
21. The method of claim 1, wherein the disorder is rheumatoid arthritis.
* * * * *